United States Patent
Jardin et al.

(10) Patent No.: US 10,519,508 B2
(45) Date of Patent: Dec. 31, 2019

(54) METHODS AND KITS FOR CLASSIFYING DIFFUSE LARGE B-CELL LYMPHOMAS (DLBCLS) INTO GCB-DLBCLS OR INTO ABC-DLBCLS

(71) Applicants: INSERM (Institute National de la Sante et de la Recherche Medicale), Paris (FR); Universite de Rouen, Mont-Saint-Aignan (FR); Centre Henri Becquerel, Rouen (FR)

(72) Inventors: Fabrice Jardin, Rouen (FR); Philippe Ruminy, Rouen (FR); Sylvain Mareschal, Rouen (FR); Vinciane Marchand, Rouen (FR); Cristina Bagacean, Rouen (FR)

(73) Assignees: INSERM (Institut National de la Sante et de la Recherche Medicale), Paris (FR); Universite de Rouen, Mont-Saint-Aignan (FR); Centre Henri Becquerrel, Rouen (FR)

( * ) Notice: Subject to any disclaimer, the term of this patent is extended or adjusted under 35 U.S.C. 154(b) by 0 days.

(21) Appl. No.: 15/124,580

(22) PCT Filed: Mar. 10, 2015

(86) PCT No.: PCT/EP2015/054952
§ 371 (c)(1),
(2) Date: Sep. 8, 2016

(87) PCT Pub. No.: WO2015/135935
PCT Pub. Date: Sep. 17, 2015

(65) Prior Publication Data
US 2017/0016074 A1  Jan. 19, 2017

(30) Foreign Application Priority Data
Mar. 11, 2014 (EP) .................... 14305350

(51) Int. Cl.
*C12Q 1/6886* (2018.01)
(52) U.S. Cl.
CPC ...... *C12Q 1/6886* (2013.01); *C12Q 2600/112* (2013.01); *C12Q 2600/158* (2013.01); *C12Q 2600/16* (2013.01)
(58) Field of Classification Search
None
See application file for complete search history.

(56) References Cited

U.S. PATENT DOCUMENTS 6,955,901 B2  10/2005  Schouten

FOREIGN PATENT DOCUMENTS

EP  1500709 A1 *  1/2005  .......... C12Q 1/6883
WO  2005/024043 A2  3/2005

OTHER PUBLICATIONS

Tromp. Thesis: The microenvironment and treatment resistance in chronic lymphocytic leukemia. 2012. Chapter 4: IL-21 induces proliferation of CD40-stimulated CLL cells and is present in the lymph nodes from CLL patients. (Year: 2012).*
NetAffx. Retrieved on Jan. 29, 2019 from the internet: https://www.affymetrix.com/analysis/netaffx/index.affx. (Year: 2019).*
Promega Corporation; "Product Contents: M-MLVReverse Transcriptase"; Retrieved from the Internet: URL: https://nld.promega.com/resources/protocols/product-information-sheets/g/mmlv-reverse-transcriptase-protocol/ May 1, 2006, entire document.
Rumini et al.; "Accurate Classification of GCB/ABC and MYC/BCL2 Diffuse Large B-Cell Lymphoma With a 14 Genes Expression Signature and a Simple and Robust RT-MLPA Assay"; Blood, vol. 122, No. 21, Nov. 2013, p. 84.
Mrc-Holland B.V.; "RT-MLPA General Protocol—Instructions for Use"; Retrieved from the Internet: https://www.mlpa.com/WebForms/WebFormMain.aspx?Tag=_wl2zCji-rCGANQgZPuTixtCpICA1mmwJoFo_xHPnTgc, Aug. 8, 2013, entire document.
Mrc-Holland B.V.; "Designing synthetic MLPA Probes"; Retrieved from the Internet: https://www.mlpa.com/WebForms/WebFormMain.aspx?Tag=_zjCZBtdOUyAt3KF3EwRZhAPz9QEm7akikAm7AOEGw1vtZvffaZPOiSig8uqel7Yd, Jan. 13, 2012, entire document.
Visco et al.; "Comprehensive gene expression profiling and immunohistochemical studies support application of immunophenotypic algorithm for molecular subtype classification in diffuse large B-cell lymphoma: a report from the International DLBCL Rituximab-CHOP Consortium Program Study"; Leukemia, vol. 26, No. 9, Mar. 22, 2012, pp. 2103-2113.
Gutierrez-Garcia et al.; "Gene-expression profiling and not immunophenotypic algorithms predicts prognosis in patients with diffuse large B-cell lymphoma treated with immunochemotherapy"; Blood, vol. 117, No. 18, May 5, 2011, pp. 4836-4743.
Blenk et al.; "Germinal Center B Cell-Like (GCB) and Activated B Cell-Like (ABC) Type of Diffuse Large B Cell Lymphoma (DLBCL): Analysis of Molecular Predictors, Signatures, Cell Cycle State and Patient Survival"; Cancer Informatics, vol. 3, Dec. 12, 2007, pp. 399-420.

* cited by examiner

Primary Examiner — Joseph G. Dauner
(74) Attorney, Agent, or Firm — W & C IP

(57) ABSTRACT

The present invention relates to a method for classifying a diffuse large B-cell lymphoma (DLBCL) of a subject into a GCB-DLBCL or into a ABC-DLBCL comprising the step of determining the expression level of 10 genes in a tumor tissue sample obtained from the subject by performing a Reverse Transcriptase Multiplex Ligation dependent Probe Amplification (RT-MLPA) assay wherein the 10 genes are NEK6, IRF4, IGHM, LMO2, FOXP1, TNFRSF9, BCL6, TNFRSF13B, CCND2 and MYBL1.

7 Claims, 11 Drawing Sheets

Figures 1A, 1B:
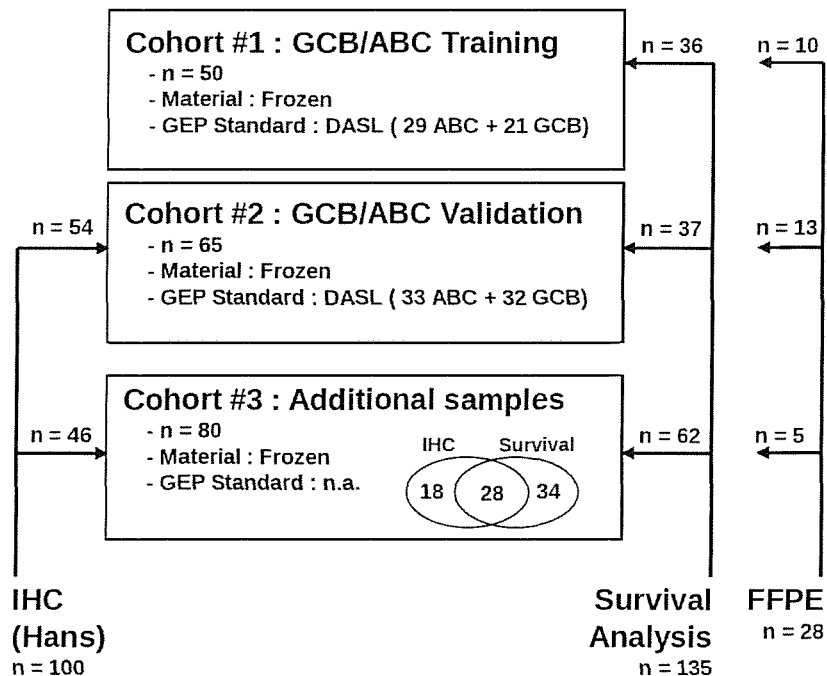

Specification includes a Sequence Listing.

Lysa series : n=64
(independent)

Cohort #4 : Affymetrix Validation
- n = 64
- Material : Frozen
- GEP Standard : Affymetrix
( 25 ABC + 28 GCB + 11 Other)

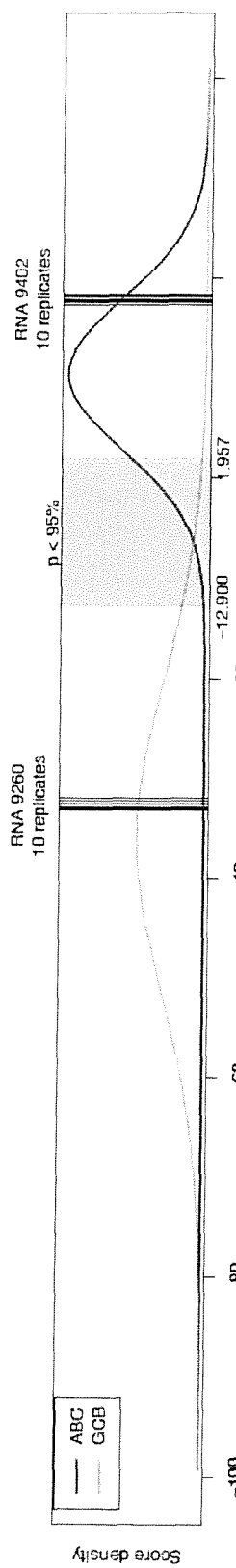
Figure 9A
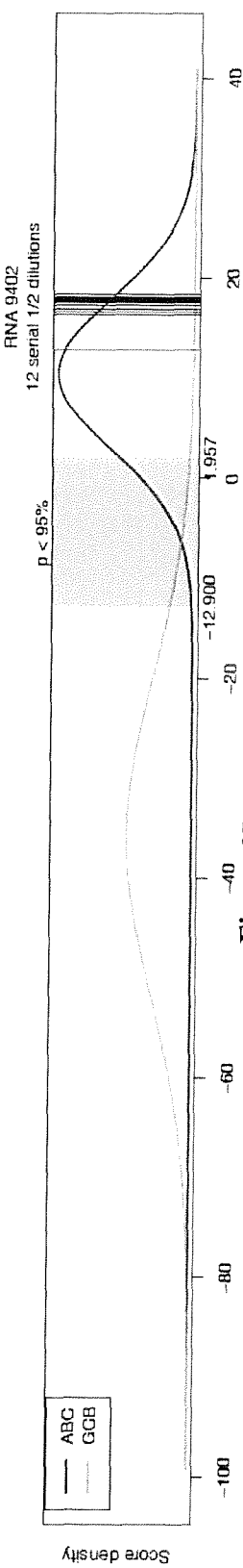
Figure 9B
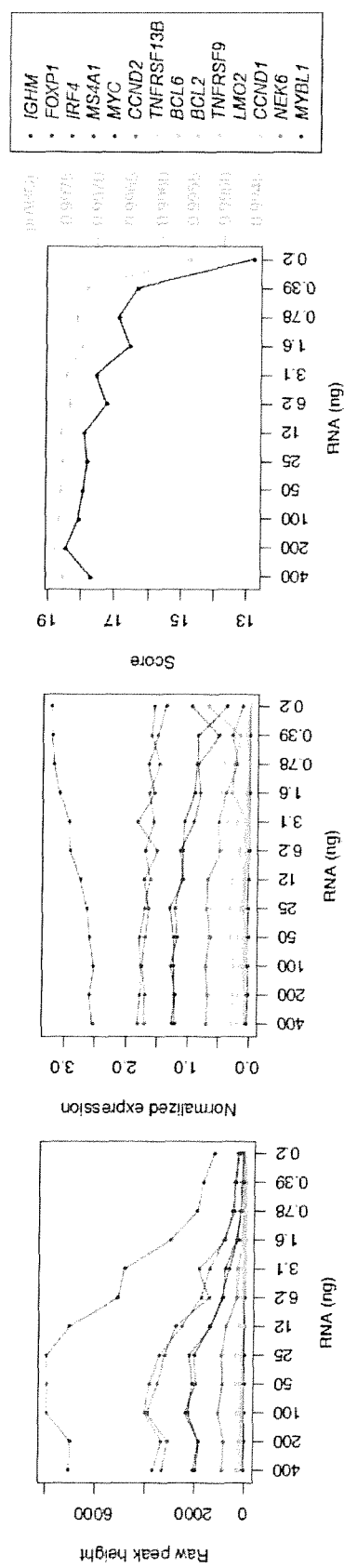
Figure 9C
Figure 9D
Figure 9E

SEQUENCE LISTING

```
<160> NUMBER OF SEQ ID NOS: 85

<210> SEQ ID NO 1
<211> LENGTH: 3619
<212> TYPE: DNA
<213> ORGANISM: Homo sapiens

<400> SEQUENCE: 1
ggcggaaccg agctgacggg cgtgcggccg ctgcgccgca aactcgtgtg ggacgcaccg      60
ctccagccgc ccgcgggcca gcgcaccggt ccccagcgg cagccgagcc cgcccgcgcg     120
ccggagaaga agacacatga attagagaca gcacggggga gcaggctgtg gagctgggag     180
tgacggggtg agtccaggaa ggctgcctgg aggagatgcc caggagagaa gtttgctggg     240
aggcagctca tttccggcag gaggagcaga gcctgccaag gcctcgagtt cgtgccctcg     300
tgaggctggc atgcaggatg gcaggacagc ccggccacat gccccatgga gggagttcca     360
acaacctctg ccacaccctg gggcctgtgc atcctcctga cccacagagg catcccaaca     420
cgctgtcttt tcgctgctcg ctggcggact tccagatcga aaagaagata ggccgaggac     480
agttcagcga ggtgtacaag gccacctgcc tgctggacag gaagacagtg gctctgaaga     540
aggtgcagat ctttgagatg atggacgcca aggcgaggca ggactgtgtc aaggagatcg     600
gcctcttgaa gcaactgaac cacccaaata tcatcaagta tttggactcg tttatcgaag     660
acaacgagct gaacattgtg ctggagttgg ctgacgcagg ggacctctcg cagatgatca     720
agtactttaa gaagcagaag cggctcatcc cggagaggac agtatggaag tactttgtgc     780
agctgtgcag cgccgtggag cacatgcatt cacgcccggt gatgcaccga gacatcaagc     840
ctgccaacgt gttcatcaca gccacgggcg tcgtgaagct cggtgacctt ggtctgggcc     900
gcttcttcag ctctgagacc accgcagccc actccctagt ggggacgccc tactacatgt     960
caccggagag gatccatgag aacggctaca acttcaagtc cgacatctgg tccctgggct    1020
gtctgctgta cgagatggca gcctccaga gccccttcta tggagataag atgaatctct    1080
tctccctgtg ccagaagatc gagcagtgtg actaccccc actccccggg gagcactact    1140
ccgagaagtt acgagaactg gtcagcatgt gcatctgccc tgaccccac cagagacctg    1200 acatcggata cgtgcaccag gtggccaagc agatgcacat ctggatgtcc agcacctgag    1260
cgtggatgca ccgtgcctta tcaaagccag caccactttg ccttacttga gtcgtcttct    1320
cttcgagtgg ccacctggta gcctagaaca gctaagacca cagggttcag caggttcccc    1380
aaaaggctgc ccagccttac agcagatgct gaaggcagag cagctgaggg aggggcgctg    1440
gccacatgtc actgatggtc agattccaaa gtcctttctt tatactgttg tggacaatct    1500
cagctgggtc aataagggca ggtggttcag cgagccacgg cagcccctg tatctggatt    1560 gtaatgtgaa tctttagggt aattcctcca gtgacctgtc aaggcttatg ctaacaggag    1620
acttgcagga gaccgtgtga tttgtgtagt gagcctttga aaatggttag taccgggttc    1680
```

```
agtttagttc ttagtatctt ttcaatcaag ctgtgtgctt aatttactct gttgtaaagg     1740
gataaagtgg aaatcatttt tttccgtgga gtggtgattc tgctaacatt tttatctacg     1800
ttttataact tggtgagtga cgatgagagc cctgcacctg ccagagtgt cacaggcaaa      1860 aggcatcggg aagcaggagc atcttcttgg cagccaggct gggccatctt ctcctggaca     1920
cctgctgtgt accaggaact tcgtcacctc cttgaatgct ggcggttcat ttcatgatca     1980
gtgttaagca ttttcctcca tgggaaggaa gcatgggata tagaaaagcg aagggctgtc    2040
ctttacaaat tctggttctg caacttccta gcgtgacttt gggcttgggc aagtttctta    2100
gccgttctga gccttcattt cctcatctgt acaatgagat taatagtacc tatcatctac    2160
cttcaggatt gctgacagac agaatttgaa ataaatatg caagttagct aatacaaaaa      2220
gtagatgatc caaaaatggt agccactcac ccttcacaaa ctgaagtcca tggaccacgg    2280
aagtcgagaa ttaatgtaca cctgtatcat gtgtaggaaa ccagaaatgt gttccttatt    2340
tcttgttccc aaacaggatt aactgtgaag actaatttat aaatgtgaac ctaagaaaac    2400
tccacctctg aaggaaatca tttgaatttt gttttgtac gtaaagttaa ccttccaatt     2460
gtctgagctg tcgtcactga cttcatgaca gtctggccct ccagacaaga gcagcgctgg    2520
catcgggcag gtgattcctg acacctgctg cctgcaggca ttcactgacc aggcctttcc    2580
tggaggaaac acccagggcc gggcggctgc tgtttccaca cgtggactcg gatctgctgt    2640
gacaccgtca gcccgacagt ctctccatat gcagcctttc ctctgtactt ttctccatgg    2700
ttgaaataaa acagggtgac tgggagttac ttagaattca tgaagatttt aaaatggctt    2760
tggagatttt gcttttaaac cagtagattc aaaacttaaa cagcgtctgc agcacaattt    2820
cttgaggaac cttgaaaaac acaacttccc aggccccatt cagtaatccc aggatttctt    2880
taagctcccc aaataatttt gaaactcatc atcagccgag tttctgccct catgaggtaa    2940
ttccatcgtt ctccccagcc tgcccctggc agctgtaaca caggagctgg cctgagagca    3000 gattcacccct ggaatgttct ctccacagaa caatcaagtc cctgtcgcct gcctagtgct    3060
taccactgaa gatttttctg attccagacc aacttttttgc caacattctg cttccagctc    3120
tctgagcccc tgccgtgtct ccccaacact gccagcccca gcacgcaatc aacctacttt    3180
gtgcatgcca cccgctttcc acactgtgag aacaatctgc ccaactggac cctctggagg    3240
cgcacgatct cagccactca ccaggcctga gtgtttgtga aatgatcatg tcctacttat    3300
tacaaaaccg taaccccaaa acattccttt tatttctgtg aaaccggcca aagtgaggtc    3360
cacccacctt cacacagctc tggcggtgca cctgctcacc ttctcttggt tctcagaact    3420
gagctgggct tgagaacaca gctttggctt tgccattttt ttcctacttg gctgctgagg    3480
tggagggtgt gctgcactta tcaccccatt tcaaaaccaa accaaacctg aggccacccc    3540
aaacaaattc agccagcaaa aagggtaggt atcgatggtc acctgaagcc tcaagggagt    3600
ccactctgac ttctgacag                                                 3619
```

<210> SEQ ID NO 2
<211> LENGTH: 5331
<212> TYPE: DNA
<213> ORGANISM: Homo sapiens

<400> SEQUENCE: 2

```
acctcgcact ctcagtttca ccgctcgatc ttgggaccca ccgctgccct cagctccgag      60
tccagggcga gtgcagagca gagcgggcgg aggaccccgg gcgcgggcgc ggacggcacg     120
```

```
cggggcatga acctggaggg cggcggccga ggcggagagt tcggcatgag cgcggtgagc       180
tgcggcaacg ggaagctccg ccagtggctg atcgaccaga tcgacagcgg caagtacccc       240
gggctggtgt gggagaacga ggagaagagc atcttccgca tccccctgga gcacgcgggc       300
aagcaggact acaaccgcga ggaggacgcc gcgctcttca aggcttgggc actgtttaaa       360
ggaaagttcc gagaaggcat cgacaagccg gaccctccca cctggaagac gcgcctgcgg       420
tgcgctttga acaagagcaa tgactttgag gaactggttg agcggagcca gctggacatc       480
tcagacccgt acaaagtgta caggattgtt cctgagggag ccaaaaaagg agccaagcag       540
ctcaccctgg aggacccgca gatgtccatg agccacccct acaccatgac aacgccttac       600
ccttcgctcc cagcccagca ggttcacaac tacatgatgc caccctcga ccgaagctgg       660 agggactacg tcccggatca gccacacccg gaaatcccgt accaatgtcc catgacgttt       720
ggaccccgcg gccaccactg gcaaggccca gcttgtgaaa atggttgcca ggtgacagga       780 acctttatg cttgtgcccc acctgagtcc caggctcccg gagtcccac agagccaagc       840 ataaggtctg ccgaagcctt ggcgttctca gactgccggc tgcacatctg cctgtactac       900
cgggaaatcc tcgtgaagga gctgaccacg tccagccccg agggctgccg gatctcccat       960
ggacatacgt atgacgccag caacctggac caggtcctgt tccctaccc agaggacaat      1020 ggccagagga aaacattga gaagctgctg agccacctgg agagggcgt ggtcctctgg      1080 atggcccccg acgggctcta tgcgaaaaga ctgtgccaga gcaggatcta ctgggacggg      1140
cccctggcgc tgtgcaacga ccggcccaac aaactggaga gagaccagac ctgcaagctc      1200
tttgacacac agcagttctt gtcagagctg caagcgtttg ctcaccacgg ccgctccctg      1260
ccaagattcc aggtgactct atgctttgga gaggagtttc cagaccctca gaggcaaaga      1320
aagctcatca cagctcacgt agaacctctg ctagccagac aactatatta ttttgctcaa      1380
caaaacagtg acatttcct gaggggctac gatttaccag aacacatcag caatccagaa      1440
gattaccaca gatctatccg ccattcctct attcaagaat gaaaaatgtc aagatgagtg      1500
gttttctttt tccttttttt tttttttttt ttgatacggg gatacggggt cttgctctgt      1560
ctcccaggct ggagtgcagt gacacaatct cagctcactg tgacctccgc ctcctgggtt      1620
caagagactc tcctgcctca gcctccctgg tagctgggat tacaggtgtg agccactgca      1680
cccacccaag acaagtgatt ttcattgtaa atatttgact ttagtgaaag cgtccaattg      1740
actgccctct tactgttttg aggaattcag aagtggagat ttcagttcag cggttgagga      1800
gaattgcggc gagacaagca tggaaaatca gtgacatctg attggcagat gagcttattt      1860
caaaaggaag ggtggctttg catttcttgt gttctgtaga ctgccatcat tgatgatcac      1920
tgtgaaaatt gaccaagtga tgtgtttaca tttactgaaa tgcgctcttt aatttgttgt      1980
agattaggtc ttgctggaag acagagaaaa cttgcctttc agtattgaca ctgactagag      2040
tgatgactgc ttgtaggtat gtctgtgcca tttctcaggg aagtaagatg taaattgaag      2100
aagcctcaca cgtaaaagaa atgtattaat gtatgtagga gctgcagttc ttgtggaaga      2160
cacttgctga gtgaaggaaa tgaatctttg actgaagccg tgcctgtagc cttggggagg      2220
cccatccccc acctgccagc ggtttcctgg tgtgggtccc tctgccccgc cctccttccc      2280
attggctttc tctccttggc cttttcctgga agccagttag taaacttcct attttcttga      2340
gtcaaaaaac atgagcgcta ctcttggatg ggacattttt gtctgtccta caatctagta      2400
atgtctaagt aatggttaag ttttcttgtt tctgcatctt tttgaccctc attctttaga      2460
gatgctaaaa ttcttcgcat aaagaagaag aaattaagga acataaatct taatacttga      2520
```

```
actgttgccc ttctgtccaa gtacttaact atctgttccc ttcctctgtg ccacgctcct    2580
ctgtttgttt ggctgtccag cgatcagcca tggcgacact aaaggaggag gagccgggga    2640
ctcccaggct ggagagcact gccaggaccc accactggaa gcaggatgga gctgactacg    2700
gaactgcaca ctcagtgggc tgtttctgct tatttcatct gttctatgct tcctcgtgcc    2760
aattatagtt tgacagggcc ttaaaattac ttggcttttt ccaaatgctt ctatttatag    2820
aatcccaaag acctccactt gcttaagtat acctatcact tacatttttg tggttttgag    2880
aaagtacagc agtagactgg ggcgtcacct ccaggccgtt tctcatacta caggatattt    2940
actattactc ccaggatcag cagaagattg cgtagctctc aaatgtgtgt tcctgctttt    3000
ctaatggata tttttaaattc attcaacaag cacctagtaa gtgcctgctg tatccctaca    3060
ttacacagtt cagcctttat caagcttagt gagcagtgag cactgaaaca ttattttta     3120
atgtttaaaa agtttctaat attaaagtca gaatattaat acaattaata ttaatattaa    3180
ctacagaaaa gacaaacagt agagaacagc aaaaaaataa aaaggatctc cttttttccc    3240
agcccaaatt ctcctctcta aaagtgtcca caagaagggg tgtttattct tccaacacat    3300
ttcactttc tgtaaatata cataaactta aaaagaaaac ctcatggagt catcttgcac     3360
acactttcat gcagtgctct ttgtagctaa cagtgaagat ttacctcgtt ctgctcagag    3420
gccttgctgt ggagctccac tgccatgtac ccagtagggt ttgacatttc attagccatg    3480
caacatggat atgtattggg cagcagactg tgtttcgtga actgcagtga tgtatacatc    3540
ttatagatgc aaagtatttt ggggtatatt atcctaaggg aagataaaga tgatattaag    3600
aactgctgtt tcacggggcc cttacctgtg accctctttg ctgaagaata tttaacccca    3660
cacagcactt caaagaagct gtcttggaag tctgtctcag gagcaccctg tcttcttaat    3720
tctccaagcg gatgctccat ttcaattgct ttgtgacttc ttcttctttg ttttttttaaa   3780
tattatgctg ctttaacagt ggagctgaat tttctggaaa atgcttcttg gctggggcca    3840
ctacctcctt tcctatctt acatctatgt gtatgttgac tttttaaaat tctgagtgat     3900
ccagggtatg acctagggaa tgaactagct atgaaatact cagggttagg aatcctagca    3960
cttgtctcag gactctgaaa aggaacggct tcctcattcc ttgtcttgat aaagtggaat    4020
tggcaaacta gaatttagtt tgtactcagt ggacagtgct gttgaagatt tgaggacttg    4080
ttaaagagca ctgggtcata tggaaaaaat gtatgtgtct cccaggtgca tttcttggtt    4140
tatgtcttgt tcttgagatt ttgtatattt aggaaaacct caagcagtaa ttaatatctc    4200
ctggaacact atagagaacc aagtgaccga ctcatttaca actgaaacct aggaagcccc    4260
tgagtcctga gcgaaaacag gagagttagt cgccctacag aaaacccagc tagactattg    4320
ggtatgaact aaaagagac tgtgccatgg tgagaaaaat gtaaatcct acagtgaaat       4380
gagcagccct tacagtattg ttaccaccaa gggcaggtag gtattagtgt tgaaaaagc     4440
tggtctttga gcgagggcat aaatacagct agccccaggg gtggaacaac tctgggagtc    4500
ttgggtactc gcacctcttg gctttgttga tgctccgcca ggaaggccac ttgtgtgtgc    4560
gtgtcagtta ctttttagt aacaattcag atccagtgta aacttccgtt cattgctctc     4620
cagtcacatg ccccccacttc cccacaggtg aaagtttttc tgaaagtgtt gggattggtt   4680
aaggtcttta tttgtattac gtatctcccg aagtcctctg tggccagctg catctgtctg    4740
aatggtgcgt gaaggctctc agaccttaca caccattttg taagttatgt tttacatgcc    4800
ccgttttga gactgatctc gatgcaggtg gatctccttg agatcctgat agcctgttac     4860
```

```
aggaatgaag taaaggtcag ttttttttg tattgatttt cacagctttg aggaacatgc    4920
ataagaaatg tagctgaagt agaggggacg tgagagaagg gccaggccgg caggccaacc    4980
ctcctccaat ggaaattccc gtgttgcttc aaactgagac agatgggact taacaggcaa    5040
tggggtccac ttcccctct tcagcatccc ccgtacccca ctttctgctg aaagaactgc    5100
cagcaggtag gaccccagag gcccccaaat gaaagcttga atttcccta ctggctctgc    5160 gttttgctga gatctgtagg aaaggatgct tcacaaactg aggtagataa tgctatgctg    5220
tcgttggtat acatcatgaa tttttatgta aattgctctg caaagcaaat tgatatgttt    5280
gataaattta tgttttagg taaataaaaa cttttaaaaa tttgttatgg a              5331
```

<210> SEQ ID NO 3
<211> LENGTH: 1461
<212> TYPE: DNA
<213> ORGANISM: Homo sapiens

<400> SEQUENCE: 3

```
gggagtgcat ccgccccaac ccttttcccc ctcgtctcct gtgagaattc cccgtcggat      60
acgagcagcg tggccgttgg ctgcctcgca caggacttcc ttcccgactc catcactttc     120
tcctggaaat acaagaacaa ctctgacatc agcagcaccc ggggcttccc atcagtcctg     180 agaggggca agtacgcagc cacctcacag gtgctgctgc cttccaagga cgtcatgcag     240
ggcacagacg aacacgtggt gtgcaaagtc cagcacccca acggcaacaa agaaaagaac     300
gtgcctcttc cagtgattgc cgagctgcct cccaaagtga gcgtcttcgt cccaccccgc     360
gacggcttct tcggcaaccc ccgcaagtcc aagctcatct gccaggccac gggtttcagt     420
ccccggcaga ttcaggtgtc ctggctgcgc gaggggaagc aggtggggtc tggcgtcacc     480
acggaccagg tgcaggctga ggccaaagag tctgggccca cgacctacaa ggtgaccagc     540
acactgacca tcaaagagag cgactggctc agccagagca tgttcacctg ccgcgtggat     600
cacaggggcc tgaccttcca gcagaatgcg tcctccatgt gtggccccga tcaagacaca     660
gccatccggg tcttcgccat ccccccatcc tttgcagca tcttcctcac caagtccacc     720
aagttgacct gcctggtcac agacctgacc acctatgaca gcgtgaccat ctcctggacc     780
cgccagaatg gcgaagctgt gaaaacccac accaacatct ccgagagcca ccccaatgcc     840
actttcagcg ccgtgggtga ggccagcatc tgcgaggatg actggaattc cggggagagg     900
ttcacgtgca ccgtgaccca cacagacctg ccctcgccac tgaagcagac catctcccgg     960 cccaagggg tggccctgca caggcccgat gtctacttgc tgccaccagc ccgggagcag    1020
ctgaacctgc gggagtcggc caccatcacg tgcctggtga cgggcttctc tcccgcggac    1080
gtcttcgtgc agtggatgca gagggggcag ccttgtccc cggagaagta tgtgaccagc    1140
gccccaatgc ctgagcccca ggcccaggc cggtacttcg cccacagcat cctgaccgtg    1200
tccgaagagg aatggaacac gggggagacc tacacctgcg tggtggccca tgaggccctg    1260
cccaacaggg tcaccgagag gaccgtggac aagtccaccg gtaaacccac cctgtacaac    1320
gtgtccctgg tcatgtccga cacagctggc acctgctact gaccctgctg gcctgcccac    1380
aggctcgggg cggctggccg ctctgtgtgt gcatgcaaac taaccgtgtc aacggggtga    1440
gatgttgcat cttataaat t                                              1461
```

<210> SEQ ID NO 4
<211> LENGTH: 4307
<212> TYPE: DNA
<213> ORGANISM: Homo sapiens

<400> SEQUENCE: 4

```
gcttaacaac agtaacgtca cacggactac aggggagttt tgttgaagtt gcaaagtcct      60
ggagcctcca gagggctgtc ggcgcagtag cagcgagcag cagagtccgc acgctccggc     120
gaggggcaga agagcgcgag ggagcgcggg gcagcagaag cgagagccga gcgcggaccc     180
agccaggacc cacagccctc cccagctgcc caggaagagc cccagccatg aacaccagc      240
tcctgtgctg cgaagtggaa accatccgcc gcgcgtaccc cgatgccaac ctcctcaacg     300
accgggtgct gcgggccatg ctgaaggcgg aggagacctg cgcgccctcg gtgtcctact     360
tcaaatgtgt gcagaaggag gtcctgccgt ccatgcggaa gatcgtcgcc acctggatgc     420
tggaggtctg cgaggaacag aagtgcgagg aggaggtctt cccgctggcc atgaactacc     480
tggaccgctt cctgtcgctg agcccgtga aaaagagccg cctgcagctg ctgggggcca     540
cttgcatgtt cgtggcctct aagatgaagg agaccatccc cctgacggcc gagaagctgt     600
gcatctacac cgacaactcc atccggcccg aggagctgct gcaaatggag ctgctcctgg     660
tgaacaagct caagtggaac ctggccgcaa tgaccccgca cgatttcatt gaacacttcc     720
tctccaaaat gccagaggcg gaggagaaca acagatcat ccgcaaacac gcgcagacct     780
tcgttgccct ctgtgccaca gatgtgaagt tcatttccaa tccgccctcc atggtggcag     840
cggggagcgt ggtggccgca gtgcaaggcc tgaacctgag gagccccaac aacttcctgt     900
cctactaccg cctcacacgc ttcctctcca gagtgatcaa gtgtgacccg gactgcctcc     960
gggcctgcca ggagcagatc gaagccctgc tggagtcaag cctgcgccag gcccagcaga    1020
acatggaccc caaggccgcc gaggaggagg aagaggagga ggaggaggtg gacctggctt    1080
gcacacccac cgacgtgcgg gacgtggaca tctgagggcg ccaggcaggc gggcgccacc    1140
gccacccgca gcgagggcgg agccggcccc aggtgctccc ctgacagtcc ctcctctccg    1200
gagcattttg ataccagaag ggaaagcttc attctccttg ttgttggttg ttttttcctt    1260
tgctctttcc cccttccatc tctgacttaa gcaaaagaaa aagattaccc aaaaactgtc    1320
tttaaagag agagagagaa aaaaaaaata gtatttgcat aaccctgagc ggtgggggag     1380
gagggttgtg ctacagatga tagaggattt tataccccaa taatcaactc gtttttatat    1440
taatgtactt gtttctctgt tgtaagaata ggcattaaca caaaggaggc gtctcgggag    1500
aggattaggt tccatccttt acgtgtttaa aaaaaagcat aaaaacattt taaaaacata    1560
gaaaaattca gcaaaccatt tttaaagtag aagagggttt taggtagaaa aacatattct    1620
tgtgcttttc ctgataaagc acagctgtag tggggttcta ggcatctctg tactttgctt    1680
gctcatatgc atgtagtcac tttataagtc attgtatgtt attatattcc gtaggtagat    1740
gtgtaacctc ttcaccttat tcatggctga agtcacctct tggttacagt agcgtagcgt    1800
gcccgtgtgc atgtcctttg cgcctgtgac caccacccca acaaaccatc cagtgacaaa    1860
ccatccagtg gaggtttgtc gggcaccagc cagcgtagca gggtcgggaa aggccacctg    1920
tcccactcct acgatacgct actataaaga gaagacgaaa tagtgacata atatattcta    1980
tttttatact cttcctattt ttgtagtgac ctgtttatga gatgctggtt ttctacccaa    2040
cggccctgca gccagctcac gtccaggttc aacccacagc tacttggttt gtgttcttct    2100
tcatattcta aaaccattcc atttccaagc actttcagtc caataggtgt aggaaatagc    2160
gctgtttttg ttgtgtgtgc agggagggca gttttctaat ggaatggttt gggaatatcc    2220
atgtacttgt ttgcaagcag gactttgagg caagtgtggg ccactgtggt ggcagtggag    2280
```

```
gtggggtgtt tgggaggctg cgtgccagtc aagaagaaaa aggtttgcat tctcacattg      2340
ccaggatgat aagttccttt ccttttcttt aaagaagttg aagtttagga atcctttggt      2400
gccaactggt gtttgaaagt agggacctca gaggtttacc tagagaacag gtgggttttta     2460 agggttatct tagatgtttc acaccggaag gttttaaaac actaaatat ataatttata      2520 gttaaggcta aaaagtatat ttattgcaga ggatgttcat aaggccagta tgatttataa      2580
atgcaatctc cccttgattt aaacacacag atacacacac acacacacac acacacaaac      2640
cttctgcctt tgatgttaca gatttaatac agtttatttt aaagatgga tccttttata       2700 ggtgagaaaa aaacaatctg gaagaaaaaa accacacaaa gacattgatt cagcctgttt      2760
ggcgtttccc agagtcatct gattggacag gcatgggtgc aaggaaaatt agggtactca      2820
acctaagttc ggttccgatg aattcttatc ccctgcccct tcctttaaaa aacttagtga      2880
caaaatagac aatttgcaca tcttggctat gtaattcttg taattttat ttaggaagtg       2940 ttgaagggag gtggcaagag tgtggaggct gacgtgtgag ggaggacagg cgggaggagg      3000
tgtgaggagg aggctcccga ggggaagggg cggtgcccac accggggaca ggccgcagct      3060 ccatttctt attgcgctgc taccgttgac ttccaggcac ggtttggaaa tattcacatc       3120
gcttctgtgt atctctttca cattgtttgc tgctattgga ggatcagttt tttgttttac      3180
aatgtcatat actgccatgt actagtttta gttttctctt agaacattgt attacagatg      3240 cctttttttgt agtttttttt tttttatgt gatcaatttt gacttaatgt gattactgct      3300
ctattccaaa aaggttgctg tttcacaata cctcatgctt cacttagcca tggtggaccc      3360
agcgggcagg ttctgcctgc tttggcgggc agacacgcgg gcgcgatccc acacaggctg      3420 gcggggccg gccccgaggc cgcgtgcgtg agaaccgcgc cggtgtcccc agagaccagg       3480
ctgtgtccct cttctcttcc ctgcgcctgt gatgctgggc acttcatctg atcggggcg       3540 tagcatcata gtagtttta cagctgtgtt attctttgcg tgtagctatg gaagttgcat      3600
aattattatt attattatta taacaagtgt gtcttacgtg ccaccacggc gttgtacctg      3660
taggactctc attcgggatg attggaatag cttctggaat ttgttcaagt tttgggtatg      3720
tttaatctgt tatgtactag tgttctgttt gttattgttt tgttaattac accataatgc     3780
taatttaaag agactccaaa tctcaatgaa gccagctcac agtgctgtgt gccccggtca      3840
cctagcaagc tgccgaacca aaagaatttg caccccgctg cgggcccacg tggttggggc      3900
cctgccctgg cagggtcatc ctgtgctcgg aggccatctc gggcacaggc ccaccccgcc      3960 ccaccctcc agaacacggc tcacgcttac ctcaaccatc ctggctgcgg cgtctgtctg       4020
aaccacgcgg gggccttgag ggacgctttg tctgtcgtga tggggcaagg gcacaagtcc      4080
tggatgttgt gtgtatcgag aggccaaagg ctggtggcaa gtgcacgggg cacagcggag      4140
tctgtcctgt gacgcgcaag tctgagggtc tgggcggcgg gcggctgggt ctgtgcattt      4200
ctggttgcac cgcggcgctt cccagcacca acatgtaacc ggcatgtttc cagcagaaga      4260
caaaaagaca aacatgaaag tctagaaata aaactggtaa aaccccca                   4307
```

<210> SEQ ID NO 5
<211> LENGTH: 2294
<212> TYPE: DNA
<213> ORGANISM: Homo sapiens

<400> SEQUENCE: 5

```
gaattcgtcc aaactgagga tcacaagtct ccacattctg agtaggagga tgagggtctg       60
agttaggatt tgggtcctgc agggcttgct aaggaatccc ctgatggcct aggattccac      120
```

```
gcagagcaca tctggtgtga gagagctcgc tgcaagggtg aaggctccgc cctatcagat      180
agacaaccag gccaccaaga ggcccagccc tccaaaccct ggatttgcaa catcctcaaa      240
gaacagcaac gggccttgag cagaattgag aaggaaatac ccccacctgc cctcagccgt      300
taagtgggct ttgctattca caagggcctc tgggtgtcct ggcagagagg ggagatggca      360
caggcaccag gtgctagggt gccagggcct cccgagaagg aacaggtgca aagcaggcaa      420
ttagcccaga aggtatccgt ggggcaggca gcctagatct gatggggaa gccaccagga       480 ttacatcatc tgctgtaaca actgctctga aaagaagata ttttttcaacc tgaacttgca     540 gtagctagtg gagaggcagg aaaaaggaaa tgaaaccaga gacagaggga agctgagcga      600
aaatagacct tcccgagaga ggaggaagcc cggagagaga cgcacggtcc cctccccgcc      660
cctaggccgc cgcccctct ctgcctcgg cggcgagcag cgcgccgcga cccgggccga       720
aggtgcgagg ggctccgggc ggccgggcgg gcgcacacca tccccgcggg cggcgcggag      780
ccggcgacag cgcgcgagag ggaccgggcg gtggcggcgg cgggaccggg atggaaggga     840
gcgcggtgac tgtccttgag cgcggagggg cgagctcgcc ggcggagcgc cggagcaagc     900
ggaggcgcag gagcggcggc gacggcgcg cggcggcgg cgcccgagca ccgaggggg        960 tccgagcccc ggcagccggc cagccccgcg ccacaaaggg agcgccccg ccgcccggca      1020 ccccgcctcc ctccccaatg tcctcggcca tcgaaggaa gagcctggac ccttcagagg      1080
aaccagtgga tgaggtgctg cagatccccc catccctgct gacatgcggc ggctgccagc     1140
agaacattgg ggaccgctac ttcctgaagg ccatcgacca gtactggcac gaggactgcc     1200
tgagctgcga cctctgtggc tgccggctgg gtgaggtggg gcggcgcctc tactacaaac     1260
tgggccggaa gctctgccgg agagactatc tcaggctttt tgggcaagac ggtctctgcg     1320
catcctgtga caagcggatt cgtgcctatg agatgacaat gcgggtgaaa gacaaagtgt     1380
atcacctgga atgttttcaaa tgcgccgcct gtcagaagca tttctgtgta ggtgacagat     1440
acctcctcat caactctgac atagtgtgcg aacaggacat ctacgagtgg actaagatca     1500
atgggatgat ataggcccga gtccccgggc atctttgggg aggtgttcac tgaagacgcc     1560
gtctccatgg catcttcgtc ttcactctta ggcactttgg gggtttgagg gtggggtaag     1620
ggatttctta ggggatggta gacctttatt gggtatcaag acatagcatc caagtggcat     1680
aattcagggg ctgacacttc aaggtgacag aaggaccagc ccttgaggga gaacttatgg     1740
ccacagccca tccatagtaa ctgacatgat tagcagaaga aggaacatt taggggcaag     1800 caggcgctgt gctatcatga tggaatttca tatctacaga tagagagttg ttgtgtacag     1860
acttgttgtg actttgacgc ttgcgaacta gagatgtgca attgatttct tttcttcctg     1920 gcttttaac tccctgtttt caatcactgt cctccacaca agggaaggac agaaaggaga      1980
gtggccattc tttttttctt ggccccttc ccaaggcctt aagctttgga cccaaggaaa     2040
actgcatgga gacgcatttc ggttgagaat ggaaccaca acttttaacc aaacaattat     2100
ttaaagcaat gctgatgaat cactgttttt agacaccttc attttgaggg gaggagttcc     2160
acagattgtt tctatacaaa tataaatctt aaaaagttgt tcaactattt tattatccta     2220
gattatatca agtatttgt cgtgtgtaga aaaaaaaaca gctctgcagg cttaataaaa     2280
atgacagact gaaa                                                       2294

<210> SEQ ID NO 6
<211> LENGTH: 7114
<212> TYPE: DNA
```

<213> ORGANISM: Homo sapiens

<400> SEQUENCE: 6

```
gggggggtggg cgccagcgcc ccggcgaacg gcaaagaggg agccgctccc gctcgggggg      60
ccgctggagt gcccagcggg aacccgaaag tttgtaagag gaagagagcg cgcggcgagc     120
gagcgagcgg gccggggggca gcggcagcgg cgccggggac catggtgctg ccggcgcctc     180
ctccgcgggc gtgaaggcgg cgctcctact ccctccccgg actccgcggt gtcccagaag     240
cttttgttga caattccagt ttccgaacaa aacatttcgg caatggtgag ggcttcgatc     300
ccttctctga tttgctgtca gccatgaacg gatggatgtg atgcctgcta gccaaaaggc     360
ttccctctgt gtgttgcagt cctgtggcat tatgcatgcc ccctcccagt gaccccaggc     420
tttttatggc tgtgagacac gttaaaattt caggggtaag acgtgacctt ttgaggtgac     480
tataactgaa gattgctttta cagaagccaa aaaaggttttt tgagtcatga tgcaagaatc     540
tgggactgag acaaaaagta acggttcagc catccagaat gggtcgggcg gcagcaacca     600
cttactagag tgcggcggtc ttcgggaggg gcggtccaac ggagagacgc cggccgtgga     660
catcggggca gctgacctcg cccacgccca gcagcagcag caacaggcac ttcaggtggc     720
aagacagctc cttcttcagc agcaacagca gcagcaagtc agtggattaa aatctcccaa     780
gaggaatgac aaacaaccag ctcttcaggt tcccgtgtca gtggctatga tgacacctca     840
agttatcact ccccagcaaa tgcagcagat cctccagcaa caagtgctga ccctcagca     900
gctccaggtt ctcctccagc agcagcaggc cctcatgctt caacagcagc agcttcaaga     960
gttttataaa aaacaacagg aacagttgca gcttcaactt ttacaacaac aacatgctgg    1020
aaaacagcct aaagagcaac agcaggtggc tacccagcag ttggcttttc agcagcagct    1080
tttacagatg cagcagttac agcagcagca cctcctgtct ttgcagcgcc aaggccttct    1140
gacaattcag cccgggcagc ctgcccttcc ccttcaacct cttgctcaag gcatgattcc    1200
aacagaactg cagcagctct ggaaagaagt gacaagtgct catactgcag aagaaaccac    1260
aggcaacaat cacagcagtt tggatctgac cacgacatgt gtctcctcct ctgcaccttc    1320
caagacctcc ttaataatga acccacatgc ctctaccaat ggacagctct cagtccacac    1380
tcccaaaagg gaaagtttgt cccatgagga gcaccccccat agccatcctc tctatggaca    1440
tggtgtatgc aagtggccag gctgtgaagc agtgtgcgaa gatttccaat catttctaaa    1500
acatctcaac agtgagcatg cgctggacga tagaagtaca gcccaatgta gagtacaaat    1560
gcaggttgta cagcagttag agctacagct tgcaaaagac aaagaacgcc tgcaagccat    1620
gatgacccac ctgcatgtga agtctacaga acccaaagcc gccctcagc ccttgaatct    1680
ggtatcaagt gtcactctct ccaagtccgc atcggaggct tctccacaga gcttacctca    1740
tactccaacg accccaaccg ccccctgac tcccgtcacc caaggcccct ctgtcatcac    1800
aaccaccagc atgcacacgg tgggacccat ccgcaggcgg tactcagaca aatcaacgt    1860
gcccatttcg tcagcagata ttgcgcagaa ccaagaattt tataagaacg cagaagttag    1920
accaccattt acatatgcat ctttaattag gcaggccatt ctcgaatctc cagaaaagca    1980
gctaacacta aatgagatct ataactggtt cacacgaatg tttgcttact tccgacgcaa    2040
cgcggccacg tggaagaatg cagtgcgtca taatcttagt cttcacaagt gttttgtgcg    2100
agtagaaaac gttaaggggg cagtatggac agtggatgaa gtagaattcc aaaaacgaag    2160
gccacaaaag atcagtggta acccttccct tattaaaaac atgcagagca gccacgccta    2220
ctgcacacct ctcaatgcag ctttacaggc ttcaatggct gagaatagta tacctctata    2280
```

```
cactaccgct tccatgggaa atcccactct gggcaactta gccagcgcaa tacgggaaga    2340
gctgaacggg gcaatggagc ataccaacag caacagagt gacagcagtc caggcagatc     2400
tcctatgcaa gccgtgcatc ctgtacacgt caaagaagag ccctcgatc cagaggaagc     2460 tgaagggccc ctgtccttag tgacaacagc caaccacagt ccagattttg accatgacag   2520
agattacgaa gatgaaccag taaacgagga catggagtga ctatcggggc gggccaaccc   2580
cgagaatgaa gattggaaaa aggaaaaaaa aaaaacacg tcaaaagtta gcagtgaaat    2640
tgttctccat ttgttgtaca gtctggagga ttttcactac gttttgacaa ctctgaaatg    2700
tgttaactct tagtgccatc aagaacccca tttgggagta ttttgattt ttctactttt     2760 tgttgaaaaa aggaatttgt actctgtgca ttggatggac ttgtttggta cttgggattt    2820
tcctctctta accgtcaaca tcagtgttgt aaatttgcta aactgattca cttttagcag   2880
cagactttga actgcagtcc tgccaacgtt ggacactgag gacgcccgac agagcttgtg   2940
cacctaagct gcagaccaag cctttgccca gaatttaagg attccaatgg acgacctatt  3000
tgcacagtac tgcatgttga ttatcactgc ctttactcct tttttttttt tttttttttt   3060
tttttttttg cttccagttg ggatggggaa ggcctttgtg tgtgtattgg ggggagggggt  3120 taaaaaataa ttatcccaaa cttttaatg tattgctttt tttttttttt ttttccttc     3180 tactatacca ttttaagttc tgacctcagg cctccatttg ggccgatggc ctcttggagg   3240
cttaaagttt tctgtacctt gtgatgaatg ttaataggtg ttttattat acaaagctga    3300 atgtcatttc tcgtttgtag cttctgtca ctcattccat cttccttcag acatcaccac    3360
gtttctctaa agtcagaaaa cattccgttt tggtcttttt caaaaggtc ccaaatgctg    3420 cactctacac atgaaggccc tctcacacag acgtgacgtc ctgccagaaa gagaatgaat  3480
gacagaaaaa aaaagagag acaaactcta ggaacaatgc cgattcattc cacgcagcag   3540
tattgggggt ggttcggggg aggggtgttt cggattttct tttttcttt tcttttcttt    3600 tttttttttt gcagcaacca ttaataaatg ccaccacatt ctaccagcac aaggaaacat  3660
aggcagcact gaaaaaaaaa aaaaagctca tattaattag actgacaata tggccttgga  3720
aggctctccc ttgtggaacc aagttgccat gggccttggg tgctctgcga taacgggtgt   3780
gggttggttt tgtttgcaaa atggccaaaa aaaaaaccg gcttccccga gcagctgccc   3840
tgaaagtagg ggtggcggcg gcggcgctga gtttatacat tagttcagac ctacttggtg  3900
gcattaaact gtttgaatgc aaattcgatt tcagattgaa cttgttaagg gagttaacga   3960
gggctgagtt cagcaaatgc taaagtgtta atttcaaata tgcaaatttg gtactgcagt  4020 tgttatgca atattatatc accaacccag tatcacaaaa actcatagaa gatatcatgt   4080
aggccctggg ctttgggggg gtcccaaaca tggtatgcag aaatgtgatg gttacaggtc  4140
agtacaacct cagtccttag aaccctcca cacttcagct ctgcacccac tttcctgtca   4200
tttatttata taggactgta gttttttta gttcgagagc ctttcgaagc ttaattata    4260 ttctttctt gtacctttt tctaaaatta ccaaagatat tacacaaagg taaattatgt   4320
tctctgtttt atgctttatc tgatgaagcc aaatatcctc ttattgttga tcaaaggagg  4380
caaaagaatt tagaggcaaa tgacaagcga taggctattg caacctgaga aagagaactg  4440
ctccttcatc gtaaatttag aagaccaagt agataatgga accaaagttg ttactttttt   4500
ctagtagtta ttttttcctt tcttttttgt gtacctctac agagaccaaa actcattctc   4560
ttaaagagat tttatggggc tactgcagat aaaaatagga cacaatatta aaggagctac   4620
```

| | |
|---|---|
| agaaggaagg gagtcccatc tcaaaaaaaa aatgaatgta tgccactgca attagagtat | 4680 |
| ccaataaagg agacagttta gagtcaggac agaaaagctt ccataattga actagattac | 4740 |
| ataatagtat ttctagaaaa agagatattt ttagattgta tgccactttt gtttaagaac | 4800 |
| tgtgctgtga tcactgtatt aattttggtt tatcttggca tatatccttc agtttgtttt | 4860 |
| tattttaat ttttccttt tttccgatta ggctttggtc agcattttc atttaaagaa | 4920 |
| aagtaacact cccatccact cataagcttg gtacaaaaac ttctctggca gttacttttg | 4980 |
| aagcttcact ctgctttctg tataaagggc agtctgtggt cacgcaagac tttaaaaaaa | 5040 |
| aaaaaaaaaa aaaaaaaaaa aaaaaaaaaa aaaactttc caggcagctt catgatgtgc | 5100 |
| aggcagtagc cagacagggt catgggaagg gggccctgtg cttctaaact gagtggttgc | 5160 |
| tggttagttt ggtattcaaa agaggataaa aatctggtag attagttcat tctcagcatg | 5220 |
| tgtagctaga catgagtaaa gataacagca tgagaaactg ttagtacgca tacctcagtt | 5280 |
| caaacccttta gggaatgatt aaaatttaaa aaaaaaacat ttcactcagt tgcacttagt | 5340 |
| cgtatgtctt gcatgcttag tctaaagact gtagcaaaaa aaaaaaaaaa agaaaaatta | 5400 |
| gattttacat atctttgcag gtatcacagc cttgcagaag aaccaactga aaaaaaaatt | 5460 |
| ctcaggcttt acagcaagca aacttcacta tgattttac aattctgatt ctgtatcccc | 5520 |
| tgggggttat cccagttgct tctttaggat ggggtttatt acgttgtaca tatatcccga | 5580 |
| tgtgtctgtg tgaatctttg tcttttttgg gggagggcag agggcggttc tttttttaga | 5640 |
| tattgttcct aaaaaggaat aaatgcatac acctgtttgt caaaacacct ttgcttttg | 5700 |
| tgcaactgct ttatattaac gatactaaaa aaaaatagct ttggaaaaaa aactactgta | 5760 |
| tgtaacggaa ttgcagaata tgctgcacat gtatttatt tagttatcct tgctttaaga | 5820 |
| atattggatg acatttcctg acatgtggga gggagaaact ccctaactt ttttttctgc | 5880 |
| ttttaaactg taacatagtt gaagatttct ttttctgtt ctcattgatt ggagcatttt | 5940 |
| gtacaggttt tgtgtgtgtg tgtgtgtgtg tgtgcgcgcg tgcgtgtgtg ttaatctgtt | 6000 |
| ttttgataca ttcctatccc ttgtgtttat cctaccactg ccttcctggc tatcttaaac | 6060 |
| aagttcatac atttgaaaag aaaaaaaaat gttgtttaaa aaatgttttc tcctgctgca | 6120 |
| gtaaatattt tgcatgatga aattccaggg tcacactttt ccaagtttat cagtgaagta | 6180 |
| gtgattaaca atgggagtg tcaaaactat tgaacttttg tataaaaaaa aaaaaacttt | 6240 |
| acaaggtgcc aagatgtaaa gaaaatctgt tacttttttt ttctcaaaga aaagcataca | 6300 |
| ttagggaggt agtcccgtgt gtcagacaaa tgcactgtca ggaatgagga tccaacctac | 6360 |
| ctgtccctag agtccgtctt gtaagatgag ttaggctgcc ccttggacca gccacaaaat | 6420 |
| ggaatatcaa ggcttatgta catacgtgaa gagttaccac cagtcctgcc acctttggac | 6480 |
| agctctaaca ccatccccag catccagtca gacctagtaa agaaaacctt ggattcttaa | 6540 |
| cccaagatag gctgtaaatc actagctttt ttttcctcat gaaaaaaaat agagttaaaa | 6600 |
| aatatttcct ctcttttcca tattccagct gaactccgtt tccaaaggca caagaagag | 6660 |
| tgtgcttatt cagatttga atcttttgg taccttttgg ttaatgacat agcctcctga | 6720 |
| aattctggat gtcttcaaag tcagttttgc ttctttatcc tgaaaatcag atttacaatg | 6780 |
| ctgaaggcat ttcttgggcc cagtgtagct cacgcaatct ctgctaccca taagccttga | 6840 |
| tgaagatgat acagtccgga ctgtgagcat ggtgcttcat gtatatgtgc tgccagtaac | 6900 |
| aagaattttt ttgttttgtt ttgttttgtt ttgataaggc ataaagaaa ctcattcctt | 6960 |
| gacatcaact gtaattccat cattccatgt ctgcggatac agacaataaa aaaaatgttg | 7020 |

-continued

```
tgtagtcagt actaattact gacattataa gcattctcaa atgcaataaa aatgctggtt    7080
gttcacgctg gtagtaaaag ttgccacagc ctaa                                7114

<210> SEQ ID NO 7
<211> LENGTH: 1923
<212> TYPE: DNA
<213> ORGANISM: Homo sapiens

<400> SEQUENCE: 7
gtgtttgacc tgaagtcctc tcgagctgca gaagcctgaa gaccaaggag tggaaagttc      60
tccggcagcc ctgagatctc aagagtgaca tttgtgagac cagctaattt gattaaaatt     120
ctcttggaat cagctttgct agtatcatac ctgtgccaga tttcatcatg ggaaacagct     180
gttacaacat agtagccact ctgttgctgg tcctcaactt tgagaggaca agatcattgc     240
aggatccttg tagtaactgc ccagctggta cattctgtga taataacagg aatcagattt     300
gcagtccctc tcctccaaat agtttctcca gcgcaggtgg acaaaggacc tgtgacatat     360
gcaggcagtg taaggtgtt tcaggacca ggaaggagtg ttcctccacc agcaatgcag       420
agtgtgactg cactccaggg tttcactgcc tgggggcagg atgcagcatg tgtgaacagg     480
attgtaaaca aggtcaagaa ctgacaaaaa aaggttgtaa agactgttgc tttgggacat     540
ttaacgatca gaaacgtggc atctgtcgac cctggacaaa ctgttctttg gatgaaagt      600
ctgtgcttgt gaatgggacg aaggagaggg acgtggtctg tggaccatct ccagccgacc    660
tctctccggg agcatcctct gtgacccgc ctgcccctgc gagagagcca ggacactctc      720
cgcagatcat ctccttcttt cttgcgctga cgtcgactgc gttgctcttc ctgctgttct     780
tcctcacgct ccgtttctct gttgttaaac ggggcagaaa gaaactcctg tatatattca    840
aacaaccatt tatgagacca gtacaaacta ctcaagagga gatggctgt agctgccgat      900
ttccagaaga agaagaagga ggatgtgaac tgtgaaatgg aagtcaatag gctgttggg      960
actttcttga aagaagcaa ggaaatatga gtcatccgct atcacagctt tcaaaagcaa     1020
gaacaccatc ctacataata cccaggattc ccccaacaca cgttcttttc taaatgccaa    1080
tgagttggcc tttaaaaatg caccactttt ttttttttt tgacagggtc tcactctgtc    1140
acccaggctg gagtgcagtg caccaccat ggctctctgc agccttgacc tctgggagct     1200
caagtgatcc tcctgcctca gtctcctgag tagctggaac tacaaggaag gccaccaca     1260
cctgactaac ttttttgttt tttgtttggt aaagatggca tttcaccatg ttgtacaggc    1320
tggtctcaaa ctcctaggtt cactttggcc tcccaaagtg ctgggattac agacatgaac    1380
tgccaggccc ggccaaaata atgcaccact tttaacagaa cagacagatg aggacagagc    1440
tggtgataaa aaaaaaaaa aaaaagcatt ttctagatac cacttaacag gtttgagcta    1500
gttttttga aatccaaaga aaattatagt ttaaattcaa ttacatagtc cagtggtcca    1560
actataatta taatcaaaat caatgcaggt ttgttttttg gtgctaatat gacatatgac    1620
aataagccac gaggtgcagt aagtacccga ctaaagtttc cgtgggttct gtcatgtaac    1680
acgacatgct ccaccgtcag gggggagtat gagcagagtg cctgagttta gggtcaagga    1740
caaaaaacct caggcctgga ggaagttttg gaaagagttc aagtgtctgt atatcctatg    1800
gtcttctcca tcctcacacc ttctgccttt gtcctgctcc cttttaagcc aggttacatt    1860
ctaaaaattc ttaactttta acataatatt ttataccaaa gccaataaat gaactgcata    1920
tga                                                                  1923
```

<210> SEQ ID NO 8
<211> LENGTH: 3569
<212> TYPE: DNA
<213> ORGANISM: Homo sapiens

<400> SEQUENCE: 8

```
ataccatcgt cttgggcccg gggagggaga gccaccttca ggcccctcga gcctcgaacc      60
ggaacctcca aatccgagac gctctgctta tgaggacctc gaaatatgcc ggccagtgaa     120
aaaatcttgt ggcttttgagg gcttttggtt ggccaggggc agtaaaaatc tcggagagct    180
gacaccaagt cctcccctgc cacgtagcag tggtaaagtc cgaagctcaa attccgagaa    240
ttgagctctg ttgattctta gaactggggt tcttagaagt ggtgatgcaa gaagtttcta    300
ggaaaggccg gacaccaggt tttgagcaaa attttggact gtgaagcaag gcattggtga    360
agacaaaatg gcctcgccgg ctgacagctg tatccagttc acccgccatg ccagtgatgt    420
tcttctcaac cttaatcgtc tccggagtcg agacatcttg actgatgttg tcattgttgt    480
gagccgtgag cagtttagag cccataaaac ggtcctcatg gcctgcagtg gcctgttcta    540
tagcatcttt acagaccagt tgaaatgcaa ccttagtgtg atcaatctag atcctgagat    600
caaccctgag ggattctgca tcctcctgga cttcatgtac acatctcggc tcaatttgcg    660
ggagggcaac atcatggctg tgatggccac ggctatgtac ctgcagatgg agcatgttgt    720
ggacacttgc cggaagttta ttaaggccag tgaagcagag atggtttctg ccatcaagcc    780
tcctcgtgaa gagttcctca acagccggat gctgatgccc aagacatca tggcctatcg    840
gggtcgtgag gtggtggaga caacctgcc actgaggagc gcccctgggt gtgagagcag    900
agcctttgcc cccagcctgt acagtggcct gtccacaccg ccagcctctt attccatgta    960
cagccacctc cctgtcagca gcctcctctt ctccgatgag gagtttcggg atgtccggat   1020
gcctgtggcc aaccccttcc ccaaggagcg ggcactccca tgtgatagtg ccaggccagt   1080
ccctggtgag tacagccggc cgactttgga ggtgtccccc aatgtgtgcc acagcaatat   1140
ctattcaccc aaggaaacaa tcccagaaga ggcacgaagt gatatgcact acagtgtggc   1200
tgagggcctc aaacctgctg cccccctcagc ccgaaatgcc ccctacttcc cttgtgacaa   1260
ggccagcaaa gaagaagaga gaccctcctc ggaagatgag attgccctgc atttcgagcc   1320
ccccaatgca ccctgaacc ggaagggtct ggttagtcca cagagccccc agaaatctga    1380
ctgccagccc aactcgccca cagagtcctg cagcagtaag aatgcctgca tcctccaggc   1440
ttctggctcc cctccagcca agagcccac tgacccaaa gcctgcaact ggaagaaata   1500
caagttcatc gtgctcaaca gcctcaacca gaatgccaaa ccagagggc ctgagcaggc   1560
tgagctgggc cgccttttcc cacgagccta acggcccca cctgcctgcc agccacccat   1620
ggagcctgag aaccttgacc tccagtcccc aaccaagctg agtgccagcg ggaggactc   1680
caccatccca caagccagcc ggctcaataa catcgttaac aggtccatga cgggctctcc   1740
ccgcagcagc agcgagagcc actcaccact ctacatgcac ccccgaagt gcacgtcctg   1800
cggctctcag tccccacagc atgcagagat gtgcctccac accgctggcc ccacgttccc   1860
tgaggagatg ggagagaccc agtctgagta ctcagattct agctgtgaga acggggcctt   1920
cttctgcaat gagtgtgact gccgcttctc tgaggaggcc tcactcaaga ggcacacgct   1980
gcagacccac agtgacaaac cctacaagtg tgaccgctgc caggcctcct tccgctacaa   2040
gggcaacctc gccagccaca gaccgtcca taccggtgag aaaccctatc gttgcaacat   2100
ctgtgggcc cagttcaacc ggccagccaa cctgaaaacc cacactcgaa ttcactctgg   2160
```

```
agagaagccc tacaaatgcg aaacctgcgg agccagattt gtacaggtgg cccacctccg    2220
tgcccatgtg cttatccaca ctggtgagaa gccctatccc tgtgaaatct gtggcacccg    2280
tttccggcac cttcagactc tgaagagcca cctgcgaatc cacacaggag agaaaccttta   2340 ccattgtgag aagtgtaacc tgcatttccg tcacaaaagc cagctgcgac ttcacttgcg    2400
ccagaagcat ggcgccatca ccaacaccaa ggtgcaatac cgcgtgtcag ccactgacct    2460
gcctccggag ctccccaaag cctgctgaag catggagtgt tgatgctttc gtctccagcc    2520
ccttctcaga atctacccaa aggatactgt aacactttac aatgttcatc ccatgatgta    2580
gtgcctcttt catccactag tgcaaatcat agctgggggt tggggtggt gggggtcggg     2640 gcctgggga ctgggagccg cagcagctcc cctccccca ctgccataaa acattaagaa       2700
aatcatattg cttcttctcc tatgtgtaag gtgaaccatg tcagcaaaaa gcaaatcat      2760 tttatatgtc aaagcagggg agtatgcaaa agttctgact tgactttagt ctgcaaaatg    2820
aggaatgtat atgttttgtg ggaacagatg tttcttttgt atgtaaatgt gcattctttt    2880
aaaagacaag acttcagtat gttgtcaaag agagggcttt aattttttta accaaaggtg    2940
aaggaatata tggcagagtt gtaaatatat aaatatatat atatataaaa taaatatata    3000
taaacctaaa aagatatat taaaaatata aaactgcgtt aaaggctcga ttttgtatct     3060
gcaggcagac acggatctga aatctttat tgagaaagag cacttaagag aatatttta      3120 gtattgcatc tgtataagta agaaaatatt ttgtctaaaa tgcctcagtg tatttgtatt    3180
tttttgcaag tgaaggttta caatttacaa agtgtgtatt aaaaaaaaca aaaagaacaa    3240
aaaaatctgc agaaggaaaa atgtgtaatt ttgttctagt tttcagtttg tatatacccg    3300
tacaacgtgt cctcacggtg cctttttca cggaagtttt caatgatggg cgagcgtgca    3360
ccatcccttt ttgaagtgta ggcagacaca gggacttgaa gttgttacta actaaactct   3420
ctttgggaat gtttgtctca tcccattctg cgtcatgctt gtgttataac tactccggag    3480
acagggtttg gctgtgtcta aactgcatta ccgcgttgta aaatatagct gtacaaatat    3540
aagaataaaa tgttgaaaag tcaaactgg                                      3569
```

<210> SEQ ID NO 9
<211> LENGTH: 1357
<212> TYPE: DNA
<213> ORGANISM: Homo sapiens

<400> SEQUENCE: 9

```
agcatcctga gtaatgagtg gcctgggccg gagcaggcga ggtggccgga gccgtgtgga     60
ccaggaggag cgcttccac agggcctgtg gacggggtg gctatgagat cctgccccga     120
agagcagtac tgggatcctc tgctgggtac ctgcatgtcc tgcaaaacca tttgcaacca    180
tcagagccag cgcacctgtg cagccttctg caggtcactc agctgccgca aggagcaagg    240
caagttctat gaccatctcc tgagggactg catcagctgt gcctccatct gtggacagca    300
ccctaagcaa tgtgcatact tctgtgagaa caagctcagg agcccagtga accttccacc    360
agagctcagg agacagcgga gtggagaagt tgaaaacaat tcagacaact cgggaaggta    420
ccaaggattg gagcacagag gctcagaagc aagtccagct ctcccggggc tgaagctgag    480
tgcagatcag gtggccctgg tctacagcac gctgggctc tgcctgtgtg ccgtcctctg     540
ctgcttcctg gtgcggtgg cctgcttcct caagaagagg gggatccct gctcctgcca      600 gccccgctca aggccccgtc aaagtccggc caagtcttcc caggatcacg cgatggaagc    660
```

| | |
|---|---|
| cggcagccct gtgagcacat ccccgagcc agtggagacc tgcagcttct gcttccctga | 720 |
| gtgcagggcg cccacgcagg agagcgcagt cacgcctggg accccgacc ccacttgtgc | 780 |
| tggaaggtgg gggtgccaca ccaggaccac agtcctgcag ccttgcccac acatcccaga | 840 |
| cagtggcctt ggcattgtgt gtgtgcctgc ccaggagggg ggcccaggtg cataaatggg | 900 |
| ggtcagggag ggaaaggagg agggagagag atggagagga ggggagagag aaagagaggt | 960 |
| ggggagaggg gagagagata tgaggagaga gagacagagg aggcagagag ggagagaaac | 1020 |
| agaggagaca gagagggaga gagagacaga gggagagaga gacagagggg aagagaggca | 1080 |
| gagagggaaa gaggcagaga aggaaagaga caggcagaga aggagagagg cagagaggga | 1140 |
| gagaggcaga gagggagaga ggcagagaga cagagaggga gagagggaca gagagagata | 1200 |
| gagcaggagg tcggggcact ctgagtccca gttcccagtg cagctgtagg tcgtcatcac | 1260 |
| ctaaccacac gtgcaataaa gtcctcgtgc ctgctgctca cagccccga gagcccctcc | 1320 |
| tcctggagaa taaaaccttt ggcagctgcc cttcctc | 1357 |

<210> SEQ ID NO 10
<211> LENGTH: 6480
<212> TYPE: DNA
<213> ORGANISM: Homo sapiens

<400> SEQUENCE: 10

| | |
|---|---|
| agagcgagca ggggagagcg agaccagttt taaggggagg accggtgcga gtgaggcagc | 60 |
| cccgaggctc tgctcgccca ccacccaatc ctcgcctccc ttctgctcca ccttctctct | 120 |
| ctgccctcac ctctcccccg aaaacccct atttagccaa aggaaggagg tcaggggaac | 180 |
| gctctccct cccttccaa aaacaaaaa cagaaaaacc ttttccagg ccggggaaag | 240 |
| caggaggag aggggccgcc gggctggcca tggagctgct gtgccacgag gtggacccgg | 300 |
| tccgcagggc cgtgcgggac cgcaacctgc tccgagacga ccgcgtcctg cagaacctgc | 360 |
| tcaccatcga ggagcgctac cttccgcagt gctcctactt caagtgcgtg cagaaggaca | 420 |
| tccaacccta catgcgcaga atggtggcca cctggatgct ggaggtctgt gaggaacaga | 480 |
| agtgcgaaga agaggtcttc cctctggcca tgaattacct ggaccgtttc ttggctgggg | 540 |
| tcccgactcc gaagtcccat ctgcaactcc tgggtgctgt ctgcatgttc ctggcctcca | 600 |
| aactcaaaga gaccagcccg ctgaccgcgg agaagctgtg catttacacc gacaactcca | 660 |
| tcaagcctca ggagctgctg gagtgggaac tggtggtgct ggggaagttg aagtggaacc | 720 |
| tggcagctgt cactcctcat gacttcattg agcacatctt gcgcaagctg cccagcagc | 780 |
| gggagaagct gtctctgatc cgcaagcatg ctcagacctt cattgctctg tgtgccaccg | 840 |
| actttaagtt tgccatgtac ccaccgtcga tgatcgcaac tggaagtgtg ggagcagcca | 900 |
| tctgtgggct ccagcaggat gaggaagtga gctcgctcac ttgtgatgcc ctgactgagc | 960 |
| tgctggctaa gatcaccaac acagacgtgg attgtctcaa agcttgccag gagcagatto | 1020 |
| aggcggtgct cctcaatagc ctgcagcagt accgtcagga ccaacgtgac ggatccaagt | 1080 |
| cggaggatga actggaccaa gccagcaccc ctacagacgt gcgggatatc gacctgtgag | 1140 |
| gatgccagtt gggccgaaag agagagacgc gtccataatc tggtctcttc ttctttctgg | 1200 |
| ttgtttttgt tctttgtgtt ttagggtgaa acttaaaaaa aaaattctgc ccccacctag | 1260 |
| atcatattta aagatctttt agaagtgaga gaaaaaggtc ctacgaaaac ggaataataa | 1320 |
| aaagcatttg gtgcctattt gaagtacagc ataagggaat cccttgtata tgcgaacagt | 1380 |
| tattgtttga ttatgtaaaa gtaatagtaa aatgcttaca ggaaaacctg cagagtagtt | 1440 |

-continued

| | |
|---|---|
| agagaatatg tatgcctgca atatgggaac aaattagagg agacttttt ttttcatgtt | 1500 |
| atgagctagc acatacaccc ccttgtagta taatttcaag gaactgtgta cgccatttat | 1560 |
| ggcatgatta gattgcaaag caatgaactc aagaaggaat tgaaataagg agggacatga | 1620 |
| tggggaagga gtacaaaaca atctctcaac atgattgaac catttgggat ggagaagcac | 1680 |
| cttttgctctc agccacctgt tactaagtca ggagtgtagt tggatctcta cattaatgtc | 1740 |
| ctcttgctgt ctacagtagc tgctacctaa aaaagatgt tttatttgc cagttggaca | 1800 |
| caggtgattg gctcctgggt ttcatgttct gtgacatcct gcttcttctt ccaaatgcag | 1860 |
| ttcattgcag acaccaccat attgctatct aatggggaaa tgtagctatg gccataacc | 1920 |
| aaaactcaca tgaaacggag gcagatggag accaagggtg ggatccagaa tggagtcttt | 1980 |
| tctgttattg tatttaaaag ggtaatgtgg ccttggcatt tcttcttaga aaaaaactaa | 2040 |
| ttttggtgc tgattggcat gtctggttca cagtttagca ttgttataaa ccattccatt | 2100 |
| cgaaaagcac tttgaaaaat tgttcccgag cgatagatgg gatggttat gcaagtcatg | 2160 |
| ctgaatactc ctcccctctt ctcttttgcc ccctccttc ctgccccag tctgggttac | 2220 |
| tcttcgcttc tggtatctgg cgttcttggg tacacagttc tggtgttcct accaggactc | 2280 |
| aagagacacc ccttcctgct gacattccca tcacaacatt cctcagacaa gcctgtaaac | 2340 |
| taaaatctgt taccattctg atggcacaga aggatcttaa ttcccatctc tatacttctc | 2400 |
| ctttggacat ggaaagaaaa gttattgctg gtgcaaagat agatggctga acatcagggt | 2460 |
| gtggcatttt gttccctttt ccgtttttt ttttttattg ttgttgttaa ttttattgca | 2520 |
| aagttgtatt cagcgtactt gaattttct tcctctccac ttcttagagg cattcagtta | 2580 |
| gcaaagaggt tggagcaaca acttttttt tttttttgc acaattgtaa ttgacaggta | 2640 |
| atgaagctat ttgttaaaat atttgccttt ttaagtaaaa aagaaaaatc agaacagggc | 2700 |
| tatttgaaga attattttat acacagattc tgccttgttt catagtatga gggttgaaga | 2760 |
| cggaaaacaa tctaagggtc tctcattttt ttaattttgt tttgttcagt ttggttttt | 2820 |
| tttttttttg cgctgctaag aagctaaagt catccatcct tattcacgtt gacagtacct | 2880 |
| agctgtaatg tttcacagag tgtgctgcta tttataaac atttttataa tatattattt | 2940 |
| tactgcttaa attccaagtc ctgaagtaga tggttgagat atgagttctt cgtactggaa | 3000 |
| aagcccttcc gtagtttgtt ttcttctggt agcatattca tggttgtttt ttttttctt | 3060 |
| ttttggtttt ttggtttttt tttttcctc tgatcacatt cttcaaagac ggagtattct | 3120 |
| ttacctcagg tttactggac aaaatcaata actacaaaag gcaatgattc acgcttttgt | 3180 |
| tttcataata cctcacaacc gtacagtttc tgcttgggag cccattcgca tgaggaatac | 3240 |
| agaagcagtg tgagcagggc tgactcctc tcaggtggaa ggcagggcgg tctcactccc | 3300 |
| agggaccttt ttggtcatgg aggccatcgg gctcccagtt agaccctggt atcctcatca | 3360 |
| tgatggaaaa aatacattga accaagggat cctccctccc cttcaaggca gacgttcagt | 3420 |
| acaaacattt atgcggtagg ctcagatgtc gtaatttgca cttaggtacc aggtgtcagg | 3480 |
| aaacagacta aaaagaattc caccaggctg tttggagatc ctcatcttgg agctttttca | 3540 |
| aaagcggggc ttcatctgca aagggccctt tcatcttgaa gttttccc tccgtctttc | 3600 |
| ccctcccctg gcatggacac cttgtgttta ggatcatctc tgcaggtttc ctaggtctga | 3660 |
| atctgcgagt agatgaacct gcagcaagca gcgtttatgg tgcttccttc tcctcctct | 3720 |
| gtctcaaact gcgcaggcaa gcactatgca agcccaggcc ctctgctgag cggtactaaa | 3780 |

```
cggtcgggtt ttcaatcaca ctgaattggc aggataagaa aaataggtca gataagtatg   3840
ggatgatagt tgaagggagg tgaagaggct gcttctctac agaggtgaaa ttccagatga   3900
gtcagtctct tgggaagtgt gtttagaagg gttcaggact ttgtgagtta gcatgaccct   3960
aaaattctag gggatttctg gtgggacaat gggtggtgaa ttctgaagtt ttggagaggg   4020
aagtggagca gccagcaagt aagctagcca gagttttctc aagagccagc tttgctcagc   4080
acactctcct gggccccaag gagtcccacg gaatggggaa agcgggaacc ctggagttct   4140
tgggaatctt ggagcctaaa gagaaaccga ggtgcaaatt catttcatgg tgactgaccc   4200
ttgagcttaa acagaagcag caaatgaaag aaccggacaa ataaggaagg gcacaagcct   4260
acccgactct atttacagtc tgtaactttc cactcttcct gtagtcccga ggcccctggg   4320
tccttctagc ttttctcttt cccatccttg gggccttgtg tgatgatggg tgtggggctg   4380
ccgatgggaa agtcggdggt tgttaggctt ttctgcctgc tcctgcttaa acacaagaag   4440
gaatcctgga ttttgccctc tccttagctc ttagtctctt tggtaggagt tttgttccag   4500
aggagctctc ccccttggat ttgaacttgc tcttttttgtt gttgttgttc tttctcttct   4560
ttttcttacc tcccactaaa ggggttccaa attatcctgg tctttttcta ccttgttgtg   4620
tttctatctc gtctttactt ccatctgttt gtttttttct ccatcagtgg gggccgagtt   4680
gttcccccag cctgccaaat tttgatcctt cccctctttt ggccaaatcc taggggaag   4740 aaatcctagt atgccaaaaa tatatgctaa gcataattaa actccatgcg ggtccataac   4800
agccaagaag cctgcaggag aaagccaagg gcagttccct ccgcagaaca ccccatgcgt   4860
gctgagaggc gagctccttg aagaaggggc tgttcttcca ggaggcctta ttttgaactg   4920
cctcaggacc ccactggaga gcacagcatg ccttactact gggtcatcct tggtctatgt   4980
gctctgtact ggaggctctg ttctgcctct tatcagccag gtcaggggca cacatggctt   5040
aagtgacaaa gccagaggag aagacaaccc tgacagcatc acgctgcatc ccattgctag   5100
caggattggc aactcttcag acggagctgc gcttccctgc agtctagcac ctctagggcc   5160
tctccagact gtgccctggg agctctggga ctgaaaggtt aagaacataa ggcaggatca   5220
gatgactctc tccaagaggg caggggaatt ttctctccat gggccacagg gacagggct   5280 gggagaagaa atagacttgc accttatgtc atgtaaataa ttgattttct agttcaagaa   5340
gataatattg gtagtgtggg aattggaggt aggaaggga ggaagtctga gtaagccagt   5400
tggcttctaa gccaaaagga ttcctctttg tttatctctg agacagtcca accttgagaa   5460
tagctttaaa agggaaatta atgctgagat gataaagtcc ccttaagcca acaaaccctc   5520
tgtagctata gaatgagtgc aggtttctat tggtgtggac tcagagcaat ttacaagagc   5580
tgttcatgca gccatccatt tgtgcaaaat agggtaagaa gattcaagag gatatttatt   5640
acttcctcat accacatggc ttttgatgat tctggattct aaacaaccca gaatggtcat   5700
ttcaggcaca acgatactac attcgtgtgt gtctgctttt aaacttggct gggctatcag   5760
accctattct cggctcaggt tttgagaagc catcagcaaa tgtgtacgtg catgctgtag   5820
ctgcagcctg catcccttcg cctgcagcct actttgggga aataaagtgc cttactgact   5880
gtagccatta cagtatccaa tgtcttttga caggtgcctg tccttgaaaa acaaagtttc   5940
tatttttatt tttaattggt ttagttctta actgctggcc aactcttaca tccccagcaa   6000
atcatcgggc cattggattt tttccattat gttcatcacc cttatatcat gtacctcaga   6060
tctctctctc tctcctctct ctcagttatg tagtttcttg tcttggactt tttttttct   6120 tttctttttc tttttttttt tgctttaaaa caagtgtgat gccatatcaa gtccatgtta   6180
```

| | | | | |
|---|---|---|---|---|
| ttctctcaca | gtgtactcta | taagaggtgt | gggtgtctgt | ttggtcagga tgttagaaag | 6240 |
| tgctgataag | tagcatgatc | agtgtatgcg | aaaaggtttt | taggaagtat ggcaaaaatg | 6300 |
| ttgtattggc | tatgatggtg | acatgatata | gtcagctgcc | ttttaagagg tcttatctgt | 6360 |
| tcagtgttaa | gtgatttaaa | aaataataa | cctgttttct | gactagttta aagatggatt | 6420 |
| tgaaaatggt | tttgaatgca | attaggttat | gctatttgga | caataaactc accttgacct | 6480 |

<210> SEQ ID NO 11
<211> LENGTH: 2345
<212> TYPE: DNA
<213> ORGANISM: Homo sapiens

<400> SEQUENCE: 11

| | | | | |
|---|---|---|---|---|
| ctgctcgcgg | ccgccaccgc | cgggccccgg | ccgtccctgg | ctcccctcct gcctcgagaa | 60 |
| gggcagggct | tctcagaggc | ttggcgggaa | aaagaacgga | gggagggatc gcgctgagta | 120 |
| taaaagccgg | ttttcggggc | tttatctaac | tcgctgtagt | aattccagcg agaggcagag | 180 |
| ggagcgagcg | ggcggccggc | tagggtggaa | gagccgggcg | agcagagctg cgctgcgggc | 240 |
| gtcctgggaa | gggagatccg | gagcgaatag | ggggcttcgc | ctctggccca gccctcccgc | 300 |
| tgatccccca | gccagcggtc | cgcaacccct | gccgcatcca | cgaaactttg cccatagcag | 360 |
| cgggcgggca | ctttgcactg | gaacttacaa | caccccgagca | aggacgcgac tctcccgacg | 420 |
| cggggaggct | attctgccca | tttggggaca | cttccccgcc | gctgccagga cccgcttctc | 480 |
| tgaaaggctc | tccttgcagc | tgcttagacg | ctggattttt | ttcgggtagt ggaaaaccag | 540 |
| cagcctcccg | cgacgatgcc | cctcaacgtt | agcttcacca | caggaactca tgacctcgac | 600 |
| tacgactcgg | tgcagccgta | tttctactgc | gacgaggagg | agaacttcta ccagcagcag | 660 |
| cagcagagcg | agctgcagcc | cccggcgccc | agcgaggata | tctggaagaa attcgagctg | 720 |
| ctgcccaccc | cgcccctgtc | cctagccgc | cgctccgggc | tctgctcgcc ctcctacgtt | 780 |
| gcggtcacac | ccttctccct | tcggggagac | aacgacggcg | gtggcgggag cttctccacg | 840 |
| gccgaccagc | tggagatggt | gaccgagctg | ctgggaggag | acatggtgaa ccagagtttc | 900 |
| atctgcgacc | cggacgacga | gaccttcatc | aaaaacatca | tcatccagga ctgtatgtgg | 960 |
| agcggcttct | cggccgccgc | caagctcgtc | tcagagaagc | tggcctccta ccaggctgcg | 1020 |
| cgcaaagaca | gcggcagccc | gaaccccgcc | cgcggccaca | gcgtctgctc cacctccagc | 1080 |
| ttgtacctgc | aggatctgag | cgccgccgcc | tcagagtgca | tcgacccctc ggtggtcttc | 1140 |
| ccctacccte | tcaacgacag | cagctcgccc | aagtcctgcg | cctcgcaaga ctccagcgcc | 1200 |
| ttctctccgt | cctcggattc | tctgctctcc | tcgacggagt | cctccccgca gggcagcccc | 1260 |
| gagcccctgg | tgctccatga | ggagacaccg | cccaccacca | gcagcgactc tgaggaggaa | 1320 |
| caagaagatg | aggaagaaat | cgatgttgtt | tctgtggaaa | agaggcaggc tcctggcaaa | 1380 |
| aggtcagagt | ctggatcacc | ttctgctgga | ggccacagca | aacctcctca cagcccactg | 1440 |
| gtcctcaaga | ggtgccacgt | ctccacacat | cagcacaact | acgcagcgcc tccctccact | 1500 |
| cggaaggact | atcctgctgc | caagagggtc | aagttggaca | gtgtcagagt cctgagacag | 1560 |
| atcagcaaca | accgaaaatg | caccagcccc | aggtcctcgg | acaccgagga gaatgtcaag | 1620 |
| aggcgaacac | acaacgtctt | ggagcgccag | aggaggaacg | agctaaaacg gagctttttt | 1680 |
| gccctgcgtg | accagatccc | ggagttggaa | aacaatgaaa | aggcccccaa ggtagttatc | 1740 |
| cttaaaaaag | ccacagcata | catcctgtcc | gtccaagcag | aggagcaaaa gctcatttct | 1800 |

| | |
|---|---:|
| gaagaggact tgttgcggaa acgacgagaa cagttgaaac acaaacttga acagctacgg | 1860 |
| aactcttgtg cgtaaggaaa agtaaggaaa acgattcctt ctaacagaaa tgtcctgagc | 1920 |
| aatcacctat gaacttgttt caaatgcatg atcaaatgca acctcacaac cttggctgag | 1980 |
| tcttgagact gaaagattta gccataatgt aaactgcctc aaattggact ttgggcataa | 2040 |
| aagaactttt ttatgcttac catctttttt ttttctttaa cagatttgta tttaagaatt | 2100 |
| gttttaaaa aattttaaga tttacacaat gtttctctgt aaatattgcc attaaatgta | 2160 |
| aataacttta ataaaacgtt tatagcagtt acacagaatt tcaatcctag tatatagtac | 2220 |
| ctagtattat aggtactata aaccctaatt tttttatt aagtacattt tgcttttaa | 2280 |
| agttgatttt tttctattgt ttttagaaaa aataaaataa ctggcaaata tatcattgag | 2340 |
| ccaaa | 2345 |

<210> SEQ ID NO 12
<211> LENGTH: 5192
<212> TYPE: DNA
<213> ORGANISM: Homo sapiens

<400> SEQUENCE: 12

| | |
|---|---:|
| ggacaaaacc ctgcaggaga ctgcgagccc tgcagaactg ctagctgcgg gggagagggc | 60 |
| aggggtcggg cgcctgtggc ggagccgggc tggggccagg gcaggaggc tgacaagcgg | 120 |
| cgggagaagc cggcggaggg cgggatcgcg cctcctgaca tgttgggggt atccctggcc | 180 |
| gggccgggcc ggggctaaga gcggcgctgc gggccggggt cggggtcggg tcgcggtccg | 240 |
| cccccgctgt ccctccgtcc tgccctgtcg aggacgtgcg ttccgcactc ggccgcctcc | 300 |
| agagggagcg agggaagcgg ctagaggatc ggggagaagg agcattcgcc ggaggctgga | 360 |
| ggaggctgac ccgcgtcccc gcccagcctg ctcctatgcg gtacttgaag gatggcgaag | 420 |
| aggtcgcgca gtgaggatga ggatgatgac cttcagtatg ccgatcatga ttatgaagta | 480 |
| ccacaacaaa aaggactgaa gaaactctgg aacagagtaa aatggacaag ggacgaggat | 540 |
| gataaattaa agaagttggt tgaacaacat ggaactgatg attggactct aattgctagt | 600 |
| catcttcaaa atcgctctga ttttcagtgc cagcatcgat ggcagaaagt tttaaatcct | 660 |
| gaattgataa agggtccttg gactaaagaa gaagatcaga gggttattga attagttcag | 720 |
| aaatatgggc caaaagatg gtctttaatt gcaaaacatt taaaggaag aataggcaag | 780 |
| cagtgtagag aaagatggca taatcatctg aatcctgagg taaagaaatc ttcctggaca | 840 |
| gaagaggagg acaggatcat ctatgaagca cataagcggt tgggaaatcg ttgggcagaa | 900 |
| attgccaaac tacttccagg aaggactgat aattctatca aaaatcattg gaattctact | 960 |
| atgcgaagaa aagtggaaca ggagggctat ttacaagatg gaataaaatc agaacgatct | 1020 |
| tcatctaaac ttcaacacaa accttgtgca gctatggatc atatgcaaac ccagaatcag | 1080 |
| ttttacatac ctgttcagat ccctgggtat cagtatgtgt cacctgaagg caattgtata | 1140 |
| gaacatgttc agcctacttc tgcctttatt cagcaaccct tcattgatga agatcctgat | 1200 |
| aaggaaaaga aaataaagga acttgagatg cttcttatgt cagctgagaa tgaagttaga | 1260 |
| agaaagcgaa ttccatcaca gcctggaagt tttttctagct ggtctggtag tttcctcatg | 1320 |
| gatgataaca tgtctaatac tctaaatagc cttgacgagc acactagtga gttttacagt | 1380 |
| atggatgaaa atcagcctgt gtctgctcag cagaattcac ccacaaagtt cctggccgtg | 1440 |
| gaggcaaacg ctgtgttatc ctctttgcag accatcccag aatttgcaga gactctagaa | 1500 |
| cttattgaat ctgatcctgt agcatggagt gacgttacca gttttgatat ttctgatgct | 1560 |

```
gctgcttctc ctatcaaatc caccccagtt aaattaatga gaattcagca caatgaagga    1620
gccatggaat gccaatttaa cgtcagtctt gtacttgaag ggaaaaaaaa cacttgtaat    1680
ggtggcaaca gtgaagctgt tcctttaaca tccccaaata tagccaagtt tagcactcca    1740
ccagccatcc tcagaaagaa gagaaaaatg cgagtgggtc attccccagg cagcgaactt    1800
agggatggct cattgaacga tggtggtaat atggcgctaa acatacacc actgaaaaca      1860 ctaccatttt ctccttcaca gttttcaac acatgtcctg gtaatgaaca acttaatata     1920
gaaaatcctt catttacatc aaccctatt tgtgggcaga aagctctcat tacaactcct     1980
cttcataagg aaacaactcc caaagatcaa aaggaaaatg tagggtttag aacacctact    2040
attagaagat ctatactggg taccacacca agaactccta ctccttttaa gaatgcgctt    2100
gctgctcagg agaaaaaata tggacctctt aaaattgtgt cccagccact tgctttcttg    2160
gaagaagata ttcgggaagt tttaaaagaa gaaactggaa cagacctatt cctcaaagag    2220
gaagatgaac ctgcttacaa agctgcaaa caagagaata ccgcttctgg gaagaaagtc     2280
agaaaatcac tagtcttaga taattgggaa aaagaagaat caggcactca actgttgact    2340
gaagacattt cagacatgca gtcagaaaat agatttacta catccttatt aatgatacca    2400
ttattggaaa tacatgacaa taggtgcaac ttgattcctg aaaaacaaga tataaattca    2460
accaacaaaa catatacact tactaaaaag aaaccaaacc ctaacacttc caaagttgtc    2520
aaattggaaa agaatcttca gtcaaattgt gaatgggaaa cagtggttta tgggaagaca    2580
gaagaccaac ttattatgac tgaacaagca agaagatatc tgagtactta cacagctacc    2640
agtagtactt caagagctct catactgtaa ttgttattaa aattgatgaa atgccccact    2700
cccttactgc agtctctact aaattaggtt gcagtgaaat ttttctcaat tagttgtttt    2760
taaagttgta agatagccct tttaatacag catctttttt ctattctata tagtaggcag    2820
aaagctagta agtcacttaa ggggtagata gtttcatagt ttatttttta agagatgaga    2880 ttttaaaaa ttgttttaa agaacaagat gggaaaataa tagaatgttc atggatttct      2940
aaaagtaaat tctcatatat tttcttcaca agatatatgt tgctactctc ttgatgctgc    3000
agttttgtta tagataggtg tatgagtata tatgattct gaaattagtc tatgtatgga     3060
aagcacacat gattttatga agtacttttg cccatgtgct gatttactta ggctaccatt    3120
tacaaagaaa cacattgaaa aggaatttaa aggaaggata gaaagttgca ctactaattt    3180 tttgttttt tttcagaag cagtaaaatt aactacagtg ttaaatgtat ttatttgagc      3240
atagtactga aacaaaaag cattcaaaaa agagttttt ctttattagt aaatagtatt      3300
ttcttaatct cagaggagct gagagttttg ttgaatgtat tgtacagtat gtaggagcag    3360
gagaactttg taaattggaa agaagtctgt ttttataatt tattttattt tttaaagctt    3420
aaatgtagat atttatacgt atacagggtg cctagaagcc aatgttgttt cctgttatta    3480
cagctaacac agtaaagaat aattttgact ttaagtatga aacagtagta agttatagct    3540
gcaaagaata caatatctat actgtatgtc acatctacct aaatgttgca ctatgccctt    3600
taaatcatgc tggttataaa gtagttctaa aaatgtacta ataataatt taatattttc     3660 tttttaaatt atatcggggg tggtcatata cattaatctg gtgatttgta tatgtgtttg    3720 aaattttgc attttgttta aaaataata tggtaccttg gtccctaaaa acagtctgca      3780
cttagaagtt tatattact cagtgtttca gaagtggaga acattatctt ttattttataa    3840 aaatattttg tcctttttta aatgttttgt gtttctctac aggttacaac agttgcttca    3900
```

| | |
|---|---|
| gttgcctgtt ttaggtgttt gcacttattt tatttcttct tgaaagaatt tttatttgct | 3960 |
| tttgtggtag agattatatg taattttttt tcagtcatat aatggtgtgc tgtcaactta | 4020 |
| aacactgaca ggtaaataga attgtacact gtagtttgaa ttatttataa ttgacacact | 4080 |
| ctctccctct ccactcctga agtatgctgc tatagaaaat agcagaatcg cttgctgct | 4140 |
| acgagagaag gaaagagcga ccaccacttg cactgtgtga aaagataaaa aacaaatgat | 4200 |
| ggcaagttct caagttaact aaatggaatc aaccattacc aggcaaattc ttgcaaatac | 4260 |
| caaaatacta ctatgcctta taaaacaaaa tgaaagcagg ttaagatttt ctgctctgtt | 4320 |
| tgtatgttaa tagaaatgga aatactaagt atttaatgc ttagctcttg aacagtagac | 4380 |
| ctaaaagggt tttaagctat ttaaatctac ttgctagttt ttgcatattt tatatatata | 4440 |
| tatatttata tatatatata gtgagaagtg aagaaaatgt atggtactaa gattatgcct | 4500 |
| tattgataaa tagataaacc aatttgaatc ctcttagcat gtttaagtat gttgattgct | 4560 |
| ttctaattaa tgaacttctc acagaaattt cacttagtga aaccaatgat tgtagcaaac | 4620 |
| tcatactgga tcatttcagt taccttgaac taatagcaca taatggtttt ttgttgttgt | 4680 |
| tgttttaat gtagccctta cctggatata catagtctgc aatcaccaaa gtataatatc | 4740 |
| ttgtaaggct atatttttta aagcatattt tttcttgagc attaaattat cctaaatggt | 4800 |
| aatatattgt ggataagtct gggcttattg gacataatac atatttgggt tggtactggt | 4860 |
| tgaatccttc agttaactgc tttgttgctt tttgcaagat ttttatctt aaacatgtca | 4920 |
| ggcatcttaa gtcacctta tactgttttg ttcctctgag tttctttcag tatgttatac | 4980 |
| aaaatgccaga cataacatgt agcagccata cttgcatgga aactgactac acatacataa | 5040 |
| tactgcattt tattgtaagg ttttcacatt aatacagcaa ttaccctgac taaattgagt | 5100 |
| tttgtgatat atggaaaact tcattgtaag agaatcttgc atacaatgtt gacatattaa | 5160 |
| catccaaaat aaagcatctg tgtacaagct ga | 5192 |

<210> SEQ ID NO 13
<211> LENGTH: 3209
<212> TYPE: DNA
<213> ORGANISM: Homo sapiens

<400> SEQUENCE: 13

| | |
|---|---|
| accacctcct tctccccacc cctcgccgca ccacacacag cgcgggcttc tagcgctcgg | 60 |
| caccggcggg ccaggcgcgt cctgccttca tttatccagc agcttttcgg aaaatgcatt | 120 |
| tgctgttcgg agtttaatca gaagaggatt cctgcctccg tccccggctc cttcatcgtc | 180 |
| ccctctcccc tgtctctctc ctggggaggc gtgaagcggt cccgtggata gagattcatg | 240 |
| cctgtgcccg cgcgtgtgtg cgcgcgtgta aattgccgag aaggggaaaa catcacagga | 300 |
| cttctgcgaa taccggactg aaaattgtaa ttcatctgcc gccgccgctg cctttttttt | 360 |
| ttctcgagct cttgagatct ccggttggga ttcctgcgga ttgacatttc tgtgaagcag | 420 |
| aagtctggga atcgatctgg aaatcctcct aatttttact ccctctcccc gcgactcctg | 480 |
| attcattggg aagtttcaaa tcagctataa ctggagagtg ctgaagattg atgggatcgt | 540 |
| tgccttatgc atttgttttg gttttacaaa aaggaaactt gacagaggat catgctgtac | 600 |
| ttaaaaaata caacatcaca gaggaagtag actgatatta acaatactta ctaataataa | 660 |
| cgtgcctcat gaaataaaga tccgaaagga attggaataa aaatttcctg catctcatgc | 720 |
| caaggggaa acaccagaat caagtgttcc gcgtgattga agacacccc tcgtccaaga | 780 |
| atgcaaagca catccaataa aatagctgga ttataactcc tcttctttct ctgggggccg | 840 |

```
tggggtggga gctggggcga gaggtgccgt tggcccccgt tgcttttcct ctgggaagga    900
tggcgcacgc tgggagaaca gggtacgata accgggagat agtgatgaag tacatccatt    960
ataagctgtc gcagaggggc tacgagtggg atgcgggaga tgtgggcgcc gcgccccgg    1020
gggccgcccc cgcaccgggc atcttctcct cccagcccgg gcacacgccc catccagccg   1080
catcccggga cccggtcgcc aggacctcgc cgctgcagac cccggctgcc cccggcgccg   1140
ccgcggggcc tgcgctcagc ccggtgccac ctgtggtcca cctgaccctc cgccaggccg   1200
gcgacgactt ctcccgccgc taccgccgcg acttcgccga gatgtccagc cagctgcacc   1260
tgacgcccct caccgcgcgg ggacgctttg ccacggtggt ggaggagctc ttcagggacg   1320
gggtgaactg ggggaggatt gtggccttct ttgagttcgg tggggtcatg tgtgtggaga   1380
gcgtcaaccg ggagatgtcg cccctggtgg acaacatcgc cctgtggatg actgagtacc   1440
tgaaccggca cctgcacacc tggatccagg ataacggagg ctgggatgcc tttgtggaac   1500
tgtacggccc cagcatgcgg cctctgtttg atttctcctg gctgtctctg aagactctgc   1560
tcagtttggc cctggtggga gcttgcatca ccctgggtgc ctatctgggc cacaagtgaa   1620
gtcaacatgc ctgccccaaa caaatatgca aaaggttcac taaagcagta gaataatat   1680
gcattgtcag tgatgtacca tgaaacaaag ctgcaggctg tttaagaaaa aataacacac   1740
atataaacat cacacacaca gacagacaca cacacacaca acaattaaca gtcttcaggc   1800
aaaacgtcga atcagctatt tactgccaaa gggaaatatc atttattttt tacattatta   1860
agaaaaaaag atttatttat ttaagacagt cccatcaaaa ctcctgtctt tggaaatccg   1920
accactaatt gccaagcacc gcttcgtgtg gctccacctg gatgttctgt gcctgtaaac   1980
atagattcgc tttccatgtt gttggccgga tcaccatctg aagagcagac ggatggaaaa   2040
aggacctgat cattggggaa gctggctttc tggctgctgg aggctgggga aaggtgttc    2100
attcacttgc atttctttgc cctgggggct gtgatattaa cagagggagg gttcctgtgg   2160
ggggaagtcc atgcctccct ggcctgaaga agagactctt tgcatatgac tcacatgatg   2220
catacctggt gggaggaaaa gagttgggaa cttcagatgg acctagtacc cactgagatt   2280
tccacgccga aggacagcga tgggaaaaat gcccttaaat cataggaaag tatttttta   2340
agctaccaat tgtgccgaga aaagcatttt agcaatttat acaatatcat ccagtacctt   2400
aagccctgat tgtgtatatt catatatttt ggatacgcac cccccaactc caatactgg   2460
ctctgtctga gtaagaaaca gaatcctctg gaacttgagg aagtgaacat ttcggtgact   2520
tccgcatcag gaaggctaga gttacccaga gcatcaggcc gccacaagtg cctgcttta   2580
ggagaccgaa gtccgcagaa cctgcctgtg tcccagcttg gaggcctggt cctggaactg   2640
agccggggcc ctcactggcc tcctccaggg atgatcaaca gggcagtgtg gtctccgaat   2700
gtctggaagc tgatggagct cagaattcca ctgtcaagaa agagcagtag aggggtgtgg   2760
ctgggcctgt caccctgggg ccctccaggt aggcccgttt tcacgtggag catgggagcc   2820
acgacccttc ttaagacatg tatcactgta gagggaagga acagaggccc tgggcccttc   2880
ctatcagaag gacatggtga aggctgggaa cgtgaggaga ggcaatggcc acggcccatt   2940
ttggctgtag cacatggcac gttggctgtg tggccttggc ccacctgtga gtttaaagca   3000
aggcttttaaa tgactttgga gagggtcaca aatcctaaaa gaagcattga agtgaggtgt   3060
catggattaa ttgaccccctg tctatggaat tacatgtaaa acattatctt gtcactgtag   3120
tttggtttta tttgaaaacc tgacaaaaaa aaagttccag gtgtgaata tgggggttat   3180
```

```
ctgtacatcc tggggcatta aaaaaaaaa                                              3209
```

<210> SEQ ID NO 14
<211> LENGTH: 928
<212> TYPE: DNA
<213> ORGANISM: Homo sapiens

<400> SEQUENCE: 14

```
accctcccag tgtgcttgag aaacaaactg cacccactga actccgcagc tagcatccaa              60
atcagccctt gagatttgag gccttggaga ctcaggagtt ttgagagcaa aatgacaaca             120
cccagaaatt cagtaaatgg gactttcccg gcagagccaa tgaaaggccc tattgctatg             180
caatctggtc caaaccact cttcaggagg atgtcttcac tggaacttgt aatagctggc              240
atcgttgaga atgaatggaa agaacgtgc tccagaccca aatctaacat agttctcctg              300
tcagcagaag aaaaaaaaga acagactatt gaaataaaag aagaagtggt tgggctaact             360
gaaacatctt cccaaccaaa gaatgaagaa gacattgaaa ttattccaat ccaagaagag             420
gaagaagaag aaacagagac gaactttcca gaacctcccc aagatcagga atcctcacca             480
atagaaaatg acagctctcc ttaagtgatt tcttctgttt tctgtttcct ttttttaaaca            540
ttagtgttca tagcttccaa gagacatgct gactttcatt tcttgaggta ctctgcacat             600
acgcaccaca tctctatctg gcctttgcat ggagtgacca tagctccttc tctcttacat             660
tgaatgtaga gaatgtagcc attgtagcag cttgtgttgt cacgcttctt cttttgagca             720
actttcttac actgaagaaa ggcagaatga gtgcttcaga atgtgatttc ctactaacct             780
gttccttgga taggcttttt agtatagtat ttttttttgt cattttctcc atcaacaacc             840
agggagactg cacctgatgg aaaagatata tgactgcttc atgacattcc taaactatct             900
ttttttatt ccacatctac gtttttgg                                                 928
```

<210> SEQ ID NO 15
<211> LENGTH: 24
<212> TYPE: DNA
<213> ORGANISM: Artificial
<220> FEATURE:
<223> OTHER INFORMATION: Synthetic NEK6 target specific region (L)

<400> SEQUENCE: 15

```
cctgtgcatc ctcctgaccc acag                                                    24
```

<210> SEQ ID NO 16
<211> LENGTH: 23
<212> TYPE: DNA
<213> ORGANISM: Artificial
<220> FEATURE:
<223> OTHER INFORMATION: Synthetic NEK6 target specific region (R)

<400> SEQUENCE: 16

```
aggcatccca acacgctgtc ttt                                                     23
```

<210> SEQ ID NO 17
<211> LENGTH: 24
<212> TYPE: DNA
<213> ORGANISM: Artificial
<220> FEATURE:
<223> OTHER INFORMATION: Synthetic IRF4 target specific region (L)

<400> SEQUENCE: 17

```
ctgccgaagc cttggcgttc tcag                                                    24
```

```
<210> SEQ ID NO 18
<211> LENGTH: 25
<212> TYPE: DNA
<213> ORGANISM: Artificial
<220> FEATURE:
<223> OTHER INFORMATION: Synthetic IRF4 target specific region (L)

<400> SEQUENCE: 18
actgccggct gcacatctgc ctgta                                              25

<210> SEQ ID NO 19
<211> LENGTH: 22
<212> TYPE: DNA
<213> ORGANISM: Artificial
<220> FEATURE:
<223> OTHER INFORMATION: Synthetic IGHM target specific region (L)

<400> SEQUENCE: 19
gcgtcctcca tgtgtggccc cg                                                 22

<210> SEQ ID NO 20
<211> LENGTH: 26
<212> TYPE: DNA
<213> ORGANISM: Artificial
<220> FEATURE:
<223> OTHER INFORMATION: Synthetic IGHM target specific region (R)

<400> SEQUENCE: 20
atcaagacac agccatccgg gtcttc                                             26

<210> SEQ ID NO 21
<211> LENGTH: 25
<212> TYPE: DNA
<213> ORGANISM: Artificial
<220> FEATURE:
<223> OTHER INFORMATION: Synthetic CCND1 target specific region (L)

<400> SEQUENCE: 21
accttcgttg ccctctgtgc cacag                                              25

<210> SEQ ID NO 22
<211> LENGTH: 27
<212> TYPE: DNA
<213> ORGANISM: Artificial
<220> FEATURE:
<223> OTHER INFORMATION: Synthetic CCND1 target specific region (R)

<400> SEQUENCE: 22
atgtgaagtt catttccaat ccgccct                                            27

<210> SEQ ID NO 23
<211> LENGTH: 29
<212> TYPE: DNA
<213> ORGANISM: Artificial
<220> FEATURE:
<223> OTHER INFORMATION: Synthetic LMO2 target specific region (L)

<400> SEQUENCE: 23
cggaagctct gccggagaga ctatctcag                                          29

<210> SEQ ID NO 24
<211> LENGTH: 25
<212> TYPE: DNA
<213> ORGANISM: Artificial
<220> FEATURE:
<223> OTHER INFORMATION: Synthetic LMO2 target specific region (R)
```

<400> SEQUENCE: 24 gcttttggg caagacggtc tctgc                                                    25

<210> SEQ ID NO 25
<211> LENGTH: 27
<212> TYPE: DNA
<213> ORGANISM: Artificial
<220> FEATURE:
<223> OTHER INFORMATION: Synthetic FOXP1 target specific region (L)

<400> SEQUENCE: 25
cccttcccct tcaacctctt gctcaag                                                 27

<210> SEQ ID NO 26
<211> LENGTH: 27
<212> TYPE: DNA
<213> ORGANISM: Artificial
<220> FEATURE:
<223> OTHER INFORMATION: Synthetic FOXP1 target specific region (R)

<400> SEQUENCE: 26
gcatgattcc aacagaactg cagcagc                                                 27

<210> SEQ ID NO 27
<211> LENGTH: 30
<212> TYPE: DNA
<213> ORGANISM: Artificial
<220> FEATURE:
<223> OTHER INFORMATION: Synthetic TNFRSF9 target specific region (L)

<400> SEQUENCE: 27
ggacctgtga catatgcagg cagtgtaaag                                              30

<210> SEQ ID NO 28
<211> LENGTH: 29
<212> TYPE: DNA
<213> ORGANISM: Artificial
<220> FEATURE:
<223> OTHER INFORMATION: Synthetic TNFRSF9 target specific region (R)

<400> SEQUENCE: 28
gtgttttcag gaccaggaag gagtgttcc                                               29

<210> SEQ ID NO 29
<211> LENGTH: 26
<212> TYPE: DNA
<213> ORGANISM: Artificial
<220> FEATURE:
<223> OTHER INFORMATION: Synthetic BCL6 target specific region (L)

<400> SEQUENCE: 29
cataaaacgg tcctcatggc ctgcag                                                  26

<210> SEQ ID NO 30
<211> LENGTH: 34
<212> TYPE: DNA
<213> ORGANISM: Artificial
<220> FEATURE:
<223> OTHER INFORMATION: Synthetic BCL6 target specific region (R)

<400> SEQUENCE: 30
tggcctgttc tatagcatct ttacagacca gttg                                         34

<210> SEQ ID NO 31
<211> LENGTH: 23

```
<212> TYPE: DNA
<213> ORGANISM: Artificial
<220> FEATURE:
<223> OTHER INFORMATION: Synthetic TNFRSF13B target specific region (L)

<400> SEQUENCE: 31
gcgcacctgt gcagccttct gca                                         23

<210> SEQ ID NO 32
<211> LENGTH: 24
<212> TYPE: DNA
<213> ORGANISM: Artificial
<220> FEATURE:
<223> OTHER INFORMATION: Synthetic TNFRSF13B target specific region (R)

<400> SEQUENCE: 32
ggtcactcag ctgccgcaag gagc                                        24

<210> SEQ ID NO 33
<211> LENGTH: 26
<212> TYPE: DNA
<213> ORGANISM: Artificial
<220> FEATURE:
<223> OTHER INFORMATION: Synthetic CCND2 target specific region (L)

<400> SEQUENCE: 33
gaccttcatt gctctgtgtg ccaccg                                      26

<210> SEQ ID NO 34
<211> LENGTH: 30
<212> TYPE: DNA
<213> ORGANISM: Artificial
<220> FEATURE:
<223> OTHER INFORMATION: Synthetic CCND2 target specific region (R)

<400> SEQUENCE: 34
actttaagtt tgccatgtac ccaccgtcga                                  30

<210> SEQ ID NO 35
<211> LENGTH: 26
<212> TYPE: DNA
<213> ORGANISM: Artificial
<220> FEATURE:
<223> OTHER INFORMATION: Synthetic MYC target specific region (L)

<400> SEQUENCE: 35
tcgggtagtg gaaaaccagc agcctc                                      26

<210> SEQ ID NO 36
<211> LENGTH: 24
<212> TYPE: DNA
<213> ORGANISM: Artificial
<220> FEATURE:
<223> OTHER INFORMATION: Synthetic MYC target specific region (R)

<400> SEQUENCE: 36
ccgcgacgat gccccctcaac gtta                                       24

<210> SEQ ID NO 37
<211> LENGTH: 36
<212> TYPE: DNA
<213> ORGANISM: Artificial
<220> FEATURE:
<223> OTHER INFORMATION: Synthetic MYBL1 target specific region (L)

<400> SEQUENCE: 37
```

```
ccagaatttg cagagactct agaacttatt gaatct                                36

<210> SEQ ID NO 38
<211> LENGTH: 33
<212> TYPE: DNA
<213> ORGANISM: Artificial
<220> FEATURE:
<223> OTHER INFORMATION: Synthetic MYBL1 target specific region (R)

<400> SEQUENCE: 38
gatcctgtag catggagtga cgttaccagt ttt                                   33

<210> SEQ ID NO 39
<211> LENGTH: 26
<212> TYPE: DNA
<213> ORGANISM: Artificial
<220> FEATURE:
<223> OTHER INFORMATION: Synthetic BCL2 target specific region (R)

<400> SEQUENCE: 39
cctggatcca ggataacgga ggctgg                                           26

<210> SEQ ID NO 40
<211> LENGTH: 25
<212> TYPE: DNA
<213> ORGANISM: Artificial
<220> FEATURE:
<223> OTHER INFORMATION: Synthetic BCL2 target specific region (R)

<400> SEQUENCE: 40
gatgcctttg tggaactgta cggcc                                            25

<210> SEQ ID NO 41
<211> LENGTH: 30
<212> TYPE: DNA
<213> ORGANISM: Artificial
<220> FEATURE:
<223> OTHER INFORMATION: Synthetic MS4A1 target specific region (L)

<400> SEQUENCE: 41
ttcttcatga gggaatctaa gactttgggg                                       30

<210> SEQ ID NO 42
<211> LENGTH: 30
<212> TYPE: DNA
<213> ORGANISM: Artificial
<220> FEATURE:
<223> OTHER INFORMATION: Synthetic MS4A1

<400> SEQUENCE: 42
gctgtccaga ttatgaatgg gctcttccac                                       30

<210> SEQ ID NO 43
<211> LENGTH: 23
<212> TYPE: DNA
<213> ORGANISM: Artificial
<220> FEATURE:
<223> OTHER INFORMATION: Synthetic tail region (TL)

<400> SEQUENCE: 43
gtgccagcaa gatccaatct aga                                              23

<210> SEQ ID NO 44
<211> LENGTH: 19
<212> TYPE: DNA
<213> ORGANISM: Artificial
```

```
<220> FEATURE:
<223> OTHER INFORMATION: Synthetic tail region (TR)

<400> SEQUENCE: 44
tccaaccctt agggaaccc                                                    19

<210> SEQ ID NO 45
<211> LENGTH: 3
<212> TYPE: DNA
<213> ORGANISM: Artificial
<220> FEATURE:
<223> OTHER INFORMATION: Synthetic spacer region

<400> SEQUENCE: 45 tac                                                                      3

<210> SEQ ID NO 46
<211> LENGTH: 4
<212> TYPE: DNA
<213> ORGANISM: Artificial
<220> FEATURE:
<223> OTHER INFORMATION: Synthetic spacer region

<400> SEQUENCE: 46 tact                                                                     4

<210> SEQ ID NO 47
<211> LENGTH: 5
<212> TYPE: DNA
<213> ORGANISM: Artificial
<220> FEATURE:
<223> OTHER INFORMATION: Synthetic spacer region

<400> SEQUENCE: 47 tacta                                                                    5

<210> SEQ ID NO 48
<211> LENGTH: 7
<212> TYPE: DNA
<213> ORGANISM: Artificial
<220> FEATURE:
<223> OTHER INFORMATION: Synthetic spacer region

<400> SEQUENCE: 48 tactact                                                                  7

<210> SEQ ID NO 49
<211> LENGTH: 10
<212> TYPE: DNA
<213> ORGANISM: Artificial
<220> FEATURE:
<223> OTHER INFORMATION: Synthetic spacer region

<400> SEQUENCE: 49
tactactact                                                              10

<210> SEQ ID NO 50
<211> LENGTH: 11
<212> TYPE: DNA
<213> ORGANISM: Artificial
<220> FEATURE:
<223> OTHER INFORMATION: Synthetic spacer region

<400> SEQUENCE: 50
tactactact a                                                            11
```

```
<210> SEQ ID NO 51
<211> LENGTH: 12
<212> TYPE: DNA
<213> ORGANISM: Artificial
<220> FEATURE:
<223> OTHER INFORMATION: Synthetic spacer region

<400> SEQUENCE: 51
tactactact ac                                                              12

<210> SEQ ID NO 52
<211> LENGTH: 14
<212> TYPE: DNA
<213> ORGANISM: Artificial
<220> FEATURE:
<223> OTHER INFORMATION: Synthetic spacer region

<400> SEQUENCE: 52
tactactact acta                                                            14

<210> SEQ ID NO 53
<211> LENGTH: 16
<212> TYPE: DNA
<213> ORGANISM: Artificial
<220> FEATURE:
<223> OTHER INFORMATION: Synthetic spacer region

<400> SEQUENCE: 53
tactactact actact                                                          16

<210> SEQ ID NO 54
<211> LENGTH: 47
<212> TYPE: DNA
<213> ORGANISM: Artificial
<220> FEATURE:
<223> OTHER INFORMATION: Synthetic NEK6 first probe

<400> SEQUENCE: 54
gtgccagcaa gatccaatct agacctgtgc atcctcctga cccacag                        47

<210> SEQ ID NO 55
<211> LENGTH: 42
<212> TYPE: DNA
<213> ORGANISM: Artificial
<220> FEATURE:
<223> OTHER INFORMATION: Synthetic NEK6 second probe

<400> SEQUENCE: 55
aggcatccca acacgctgtc ttttccaacc cttagggaac cc                             42

<210> SEQ ID NO 56
<211> LENGTH: 48
<212> TYPE: DNA
<213> ORGANISM: Artificial
<220> FEATURE:
<223> OTHER INFORMATION: Synthetic IRF4 first probe

<400> SEQUENCE: 56
gtgccagcaa gatccaatct agatctgccg aagccttggc gttctcag                       48

<210> SEQ ID NO 57
<211> LENGTH: 44
<212> TYPE: DNA
<213> ORGANISM: Artificial
<220> FEATURE:
<223> OTHER INFORMATION: Synthetic second probe
```

```
<400> SEQUENCE: 57
actgccggct gcacatctgc ctgtatccaa cccttaggga accc                    44

<210> SEQ ID NO 58
<211> LENGTH: 46
<212> TYPE: DNA
<213> ORGANISM: Artificial
<220> FEATURE:
<223> OTHER INFORMATION: Synthetic IGHM first probe

<400> SEQUENCE: 58
gtgccagcaa gatccaatct agatgcgtcc tccatgtgtg gccccg                  46

<210> SEQ ID NO 59
<211> LENGTH: 50
<212> TYPE: DNA
<213> ORGANISM: Artificial
<220> FEATURE:
<223> OTHER INFORMATION: Synthetic IGHM second probe

<400> SEQUENCE: 59
atcaagacac agccatccgg gtcttctact atccaaccct tagggaaccc              50

<210> SEQ ID NO 60
<211> LENGTH: 49
<212> TYPE: DNA
<213> ORGANISM: Artificial
<220> FEATURE:
<223> OTHER INFORMATION: Synthetic CCND1 first probe

<400> SEQUENCE: 60
gtgccagcaa gatccaatct agataccttc gttgccctct gtgccacag               49

<210> SEQ ID NO 61
<211> LENGTH: 50
<212> TYPE: DNA
<213> ORGANISM: Artificial
<220> FEATURE:
<223> OTHER INFORMATION: Synthetic CCND1 second probe

<400> SEQUENCE: 61
atgtgaagtt catttccaat ccgcccttac ttccaaccct tagggaaccc              50

<210> SEQ ID NO 62
<211> LENGTH: 52
<212> TYPE: DNA
<213> ORGANISM: Artificial
<220> FEATURE:
<223> OTHER INFORMATION: Synthetic LMO2 first probe

<400> SEQUENCE: 62
gtgccagcaa gatccaatct agacggaagc tctgccggag agactatctc ag           52

<210> SEQ ID NO 63
<211> LENGTH: 49
<212> TYPE: DNA
<213> ORGANISM: Artificial
<220> FEATURE:
<223> OTHER INFORMATION: Synthetic LMO2 second probe

<400> SEQUENCE: 63 gcttttggg caagacggtc tctgctacta tccaacccct agggaaccc                 49

<210> SEQ ID NO 64
```

```
<211> LENGTH: 50
<212> TYPE: DNA
<213> ORGANISM: Artificial
<220> FEATURE:
<223> OTHER INFORMATION: Synthetic FOXP1 first probe

<400> SEQUENCE: 64
gtgccagcaa gatccaatct agacccttcc ccttcaacct cttgctcaag           50

<210> SEQ ID NO 65
<211> LENGTH: 55
<212> TYPE: DNA
<213> ORGANISM: Artificial
<220> FEATURE:
<223> OTHER INFORMATION: Synthetic FOXP1 second probe

<400> SEQUENCE: 65
gcatgattcc aacagaactg cagcagctac tactactcca acccttaggg aaccc      55

<210> SEQ ID NO 66
<211> LENGTH: 56
<212> TYPE: DNA
<213> ORGANISM: Artificial
<220> FEATURE:
<223> OTHER INFORMATION: Synthetic TNFRSF9 first probe

<400> SEQUENCE: 66
gtgccagcaa gatccaatct agatacggac ctgtgacata tgcaggcagt gtaaag     56

<210> SEQ ID NO 67
<211> LENGTH: 51
<212> TYPE: DNA
<213> ORGANISM: Artificial
<220> FEATURE:
<223> OTHER INFORMATION: Synthetic TNFRSF9 second probe

<400> SEQUENCE: 67
gtgttttcag gaccaggaag gagtgttcct actccaaccc ttagggaacc c          51

<210> SEQ ID NO 68
<211> LENGTH: 56
<212> TYPE: DNA
<213> ORGANISM: Artificial
<220> FEATURE:
<223> OTHER INFORMATION: Synthetic BCL6 first probe

<400> SEQUENCE: 68
gtgccagcaa gatccaatct agatactact cataaaacgg tcctcatggc ctgcag     56

<210> SEQ ID NO 69
<211> LENGTH: 53
<212> TYPE: DNA
<213> ORGANISM: Artificial
<220> FEATURE:
<223> OTHER INFORMATION: Synthetic BCL6 second probe

<400> SEQUENCE: 69
tggcctgttc tatagcatct ttacagacca gttgtccaac ccttagggaa ccc        53

<210> SEQ ID NO 70
<211> LENGTH: 57
<212> TYPE: DNA
<213> ORGANISM: Artificial
<220> FEATURE:
<223> OTHER INFORMATION: Synthetic TNFRSF13B first probe

<400> SEQUENCE: 70
```
gtgccagcaa gatccaatct agatactact actagcgcac ctgtgcagcc ttctgca     57

<210> SEQ ID NO 71
<211> LENGTH: 55
<212> TYPE: DNA
<213> ORGANISM: Artificial
<220> FEATURE:
<223> OTHER INFORMATION: Synthetic TNFRSF13B second probe

<400> SEQUENCE: 71
ggtcactcag ctgccgcaag gagctactac tactactcca acccttaggg aaccc       55

<210> SEQ ID NO 72
<211> LENGTH: 56
<212> TYPE: DNA
<213> ORGANISM: Artificial
<220> FEATURE:
<223> OTHER INFORMATION: Synthetic CCND2 first probe

<400> SEQUENCE: 72
gtgccagcaa gatccaatct agatactact gaccttcatt gctctgtgtg ccaccg      56

<210> SEQ ID NO 73
<211> LENGTH: 57
<212> TYPE: DNA
<213> ORGANISM: Artificial
<220> FEATURE:
<223> OTHER INFORMATION: Synthetic CCND2 second probe

<400> SEQUENCE: 73
actttaagtt tgccatgtac ccaccgtcga tactactatc caaccct tag ggaaccc    57

<210> SEQ ID NO 74
<211> LENGTH: 59
<212> TYPE: DNA
<213> ORGANISM: Artificial
<220> FEATURE:
<223> OTHER INFORMATION: Synthetic MYC first probe

<400> SEQUENCE: 74
gtgccagcaa gatccaatct agatactact acttcgggta gtggaaaacc agcagcctc   59

<210> SEQ ID NO 75
<211> LENGTH: 57
<212> TYPE: DNA
<213> ORGANISM: Artificial
<220> FEATURE:
<223> OTHER INFORMATION: Synthetic MYC second probe

<400> SEQUENCE: 75
ccgcgacgat gccctcaac gttatactac tactactatc caaccctag ggaaccc       57

<210> SEQ ID NO 76
<211> LENGTH: 59
<212> TYPE: DNA
<213> ORGANISM: Artificial
<220> FEATURE:
<223> OTHER INFORMATION: Synthetic MYBL1 first probe

<400> SEQUENCE: 76
gtgccagcaa gatccaatct agaccagaat ttgcagagac tctagaactt attgaatct   59

<210> SEQ ID NO 77
<211> LENGTH: 59
<212> TYPE: DNA

<213> ORGANISM: Artificial
<220> FEATURE:
<223> OTHER INFORMATION: Synthetic MYBL1 second probe

<400> SEQUENCE: 77
gatcctgtag catggagtga cgttaccagt ttttactact tccaacccct agggaaccc    59

<210> SEQ ID NO 78
<211> LENGTH: 61
<212> TYPE: DNA
<213> ORGANISM: Artificial
<220> FEATURE:
<223> OTHER INFORMATION: Synthetic BCL2 first probe

<400> SEQUENCE: 78
gtgccagcaa gatccaatct agatactact actccctgg atccaggata acggaggctg     60
g                                                                    61

<210> SEQ ID NO 79
<211> LENGTH: 60
<212> TYPE: DNA
<213> ORGANISM: Artificial
<220> FEATURE:
<223> OTHER INFORMATION: Synthetic BCL2 second probe

<400> SEQUENCE: 79
gatgcctttg tggaactgta cggcctacta ctactactac ttccaaccct tagggaaccc    60

<210> SEQ ID NO 80
<211> LENGTH: 64
<212> TYPE: DNA
<213> ORGANISM: Artificial
<220> FEATURE:
<223> OTHER INFORMATION: Synthetic MS4A1 first probe

<400> SEQUENCE: 80
gtgccagcaa gatccaatct agatactact actattcttc atgagggaat ctaagacttt    60
gggg                                                                 64

<210> SEQ ID NO 81
<211> LENGTH: 60
<212> TYPE: DNA
<213> ORGANISM: Artificial
<220> FEATURE:
<223> OTHER INFORMATION: Synthetic MS4A1 second probe

<400> SEQUENCE: 81
gctgtccaga ttatgaatgg gctcttccac tactactact atccaaccct tagggaaccc    60

<210> SEQ ID NO 82
<211> LENGTH: 23
<212> TYPE: DNA
<213> ORGANISM: Artificial
<220> FEATURE:
<223> OTHER INFORMATION: Synthetic NEK6 competitor probe

<400> SEQUENCE: 82
aggcatccca acacgctgtc ttt                                            23

<210> SEQ ID NO 83
<211> LENGTH: 26
<212> TYPE: DNA
<213> ORGANISM: Artificial
<220> FEATURE:
<223> OTHER INFORMATION: Synthetic IGHM competitor probe

```
<400> SEQUENCE: 83
atcaagacac agccatccgg gtcttc                                          26

<210> SEQ ID NO 84
<211> LENGTH: 19
<212> TYPE: DNA
<213> ORGANISM: Artificial
<220> FEATURE:
<223> OTHER INFORMATION: Synthetic ILLU1 primer

<400> SEQUENCE: 84
gggttcccta agggttgga                                                  19

<210> SEQ ID NO 85
<211> LENGTH: 23
<212> TYPE: DNA
<213> ORGANISM: Artificial
<220> FEATURE:
<223> OTHER INFORMATION: Synthetic ILLU2 primer

<400> SEQUENCE: 85
gtgccagcaa gatccaatct aga                                             23
```

METHODS AND KITS FOR CLASSIFYING DIFFUSE LARGE B-CELL LYMPHOMAS (DLBCLS) INTO GCB-DLBCLS OR INTO ABC-DLBCLS

FIELD OF THE INVENTION

The present invention relates to methods and kits for classifying a diffuse large B-cell lymphoma (DLBCL) of a subject into a GCB-DLBCL or into a ABC-DLBCL.

BACKGROUND OF THE INVENTION

Diffuse large B-cell lymphoma (DLBCL) is the most frequent non-Hodgkin's lymphoma (NHL), accounting for 30 to 40% of diagnoses[1]. Its prognosis has significantly improved over the last decade, predominantly because of the addition of the Rituximab antibody to chemotherapy regimens[2]. Unfortunately, approximately one third of subjects do not respond to therapies or rapidly relapse, and a majority of them rapidly succumb from the disease[3]. These differences in clinical evolutions can, at least in part, be explained by the heterogeneity of this tumor, which regroups two major subtypes with different outcomes[4]. The first, termed germinal center B cell-like (GCB), develops from germinal center B-cells. It is the most curable, with a 5 years overall survival rate of nearly 75%. The second, termed activated B-Cell like (ABC), develops from late GC-B cells or plasmablasts. It is more aggressive and can only be cured in approximately 30% of subjects[5].

If this GCB/ABC cell of origin (COO) classification has been described more than 10 years ago, it still has little influence on clinical practices. However, recent advances suggest that these tumors could soon benefit from targeted therapies. Signaling through the B-cell receptor (BCR) has for example been shown to be essential for ABC DLBCL cells survival, and specific inhibitors directed against major component of the NFkappaB pathway should rapidly become available in the clinics (ref Roschewski et al, Nature review 2014). Similarly, GCB DLBCLs could soon benefit from inhibitors of the BCL2 or BCL6 oncoproteins, and from therapies targeting their recurrent epigenetic abnormalities. Unfortunately, these lymphomas are morphologically undistinguishable in routine diagnosis, which is a major problem for the development of these therapies. Furthermore, array-based gene expression profiling, which is considered as the "gold standard" to discriminate these tumors, remains poorly transposable to routine diagnosis, and the surrogate immunohistochemical (IHC) algorithms which have been proposed are often considered poorly reliable (ref Ludenburg consortium De Jong J C O 2007 and Salles Blood 2011).

SUMMARY OF THE INVENTION

The inventors developed a robust Reverse Transcriptase Multiplex Ligation dependent Probe Amplification (RT-MLPA) based assay which allows a rapid, parsimonious and accurate classification of GCB and ABC DLBCLs in routine diagnosis. In particular, the present invention is defined by the claims.

DETAILED DESCRIPTION OF THE INVENTION

Diffuse large B-cell lymphoma (DLBCL) is the most common non-Hodgkin lymphoma. It is subdivided into two molecular subtypes, Germinal Center B cell-like (GCB) and Activated B Cell-like (ABC), which derive from mature B-cells at different stages of differentiation. Unfortunately, gene expression profiling methods to distinguish these diseases are not available in routine diagnosis and the surrogate immunohistochemical algorithms are considered poorly reproducible. To address this issue, the inventors have developed a simple and inexpensive gene expression profiling method based on a 14 gene signature and a Reverse Transcriptase Multiplex Ligation dependent Probe Amplification (RT-MLPA) assay. Trained on 50 DLBCL cases, it proved its accuracy as compared to gene-expression profiling performed by Illumina DASL (50 cases) or Affymetrix arrays (64 cases), and to be more reliable than immunochemistry (176 cases). Moreover, RT-MLPA proved to be sensitive enough to obtain satisfactory results from FFPE samples (29 cases) and to be flexible enough to include further prognostic factors like MYC/BCL2 co-expression. Requiring only common molecular biology instruments (a thermocycler and a fragment analyzer), this assay could easily be implemented in routine laboratories and represents an adequate tool for the stratification of patients in prospective clinical trials and guide treatment decision making in clinical practice.

Accordingly, the present invention relates to a method for classifying a diffuse large B-cell lymphoma (DLBCL) of a subject into a GCB-DLBCL or into a ABC-DLBCL comprising the step of determining the expression level of 10 genes in a tumor tissue sample obtained from the subject by performing a Reverse Transcriptase Multiplex Ligation dependent Probe Amplification (RT-MLPA) assay wherein the 10 genes are NEK6, IRF4, IGHM, LMO2, FOXP1, TNFRSF9, BCL6, TNFRSF13B, CCND2 and MYBL1.

In some embodiments, the RT-MPLPA assay of the method of the present invention further comprises means for determining the expression level of CCND1 in the tumor sample. Determining the expression level of CCND1 is particularly suitable for excluding the fact that the B cell lymphoma of the subject is a mantle B cell lymphoma.

In some embodiments, the RT-MPLPA assay of the method of the present invention further comprises means for determining the expression level of MS4A1 in the tumor sample. Determining the expression level of MS4A1 is particularly suitable for determining whether the subject will achieve a response with an anti-CD20 antibody.

In some embodiments, the RT-MPLPA assay of the method of the present invention further comprises means for determining the expression level(s) of MYC and/or BCL2 in the tumor sample. Determining the expression level of MYC and/or BCL2 is particularly suitable for predicting the subject's survival outcome.

In some embodiments, the method of the present invention comprises a step of determining the expression level of 14 genes in a tumor tissue sample obtained from the subject by performing a Reverse Transcriptase Multiplex Ligation dependent Probe Amplification (RT-MLPA) assay wherein the 14 genes are NEK6, IRF4, IGHM, CCND1, LMO2, FOXP1, TNFRSF9, BCL6, TNFRSF13B, CCND2, MYC, MYBL1, BCL2, and MS4A1.

The term "tumor sample" means any tissue sample derived from the tumor of the subject. The tissue sample is obtained for the purpose of the in vitro evaluation and typically results from biopsy performed in a tumour of the subject. The sample can be fresh, frozen, or embedded (e.g., FFPE biopsy).

In the present specification, the name of each of the genes of interest refers to the internationally recognised name of the corresponding gene, as found in internationally recognised gene sequences and protein sequences databases, including the database from the HUGO Gene Nomenclature Committee that is available notably at the following Internet address: gene.ucl.ac.uk/nomenclature/index.html. In the present specification, the name of each of the genes of interest may also refer to the internationally recognised name of the corresponding gene, as found in the internationally recognised gene sequences database Genbank. Through these internationally recognised sequence databases, the nucleic acid to each of the gene of interest described herein may be retrieved by one skilled in the art.

As used herein the term "NEK6" has its general meaning in the art and refers to the NIMA-related kinase 6 gene. A typical cDNA sequence of NEK6 is represented by SEQ ID NO:1.

```
(NEK6_homo sapiens)
                                                                SEQ ID NO: 1
GGCGGAACCGAGCTGACGGGCGTGCGGCCGCTGCGCCGCAAACTCGTGTGGGACGCACCGCTCCAGCCG

CCCGCGGGCCAGCGCACCGGTCCCCCAGCGGCAGCCGAGCCCGCCCGCGCGCCGGAGAAGAAGACACAT

GAATTAGAGACAGCACGGGGGAGCAGGCTGTGGAGCTGGGAGTGACGGGGTGAGTCCAGGAAGGCTGCC

TGGAGGAGATGCCCAGGAGAGAAGTTTGCTGGGAGGCAGCTCATTTCCGGCAGGAGGAGCAGAGCCTGC

CAAGGCCTCGAGTTCGTGCCCTCGTGAGGCTGGCATGCAGGATGGCAGGACAGCCCGGCCACATGCCCC

ATGGAGGGAGTTCCAACAACCTCTGCCACACCCTGGGGCCTGTGCATCCTCCTGACCCACAGAGGCATC

CCAACACGCTGTCTTTTCGCTGCTCGCTGGCGGACTTCCAGATCGAAAAGAAGATAGGCCGAGGACAGT

TCAGCGAGGTGTACAAGGCCACCTGCCTGCTGGACAGGAAGACAGTGGCTCTGAAGAAGGTGCAGATCT

TTGAGATGATGGACGCCAAGGCGAGGCAGGACTGTGTCAAGGAGATCGGCCTCTTGAAGCAACTGAACC

ACCCAAATATCATCAAGTATTTGGACTCGTTTATCGAAGACAACGAGCTGAACATTGTGCTGGAGTTGG

CTGACGCAGGGGACCTCTCGCAGATGATCAAGTACTTTAAGAAGCAGAAGCGGCTCATCCCGGAGAGGA

CAGTATGGAAGTACTTTGTGCAGCTGTGCAGCGCCGTGGAGCACATGCATTCACGCCGGGTGATGCACC

GAGACATCAAGCCTGCCAACGTGTTCATCACAGCCACGGGCGTCGTGAAGCTCGGTGACCTTGGTCTGG

GCCGCTTCTTCAGCTCTGAGACCACCGCAGCCCACTCCCTAGTGGGGACGCCCTACTACATGTCACCGG

AGAGGATCCATGAGAACGGCTACAACTTCAAGTCCGACATCTGGTCCCTGGGCTGTCTGCTGTACGAGA

TGGCAGCCCTCCAGAGCCCCTTCTATGGAGATAAGATGAATCTCTTCTCCCTGTGCCAGAAGATCGAGC

AGTGTGACTACCCCCCACTCCCCGGGGAGCACTACTCCGAGAAGTTACGAGAACTGGTCAGCATGTGCA

TCTGCCCTGACCCCCACCAGAGACCTGACATCGGATACGTGCACCAGGTGGCCAAGCAGATGCACATCT

GGATGTCCAGCACCTGAGCGTGGATGCACCGTGCCTTATCAAAGCCAGCACCACTTTGCCTTACTTGAG

TCGTCTTCTCTTCGAGTGGCCACCTGGTAGCCTAGAACAGCTAAGACCACAGGGTTCAGCAGGTTCCCC

AAAAGGCTGCCCAGCCTTACAGCAGATGCTGAAGGCAGAGCAGCTGAGGGAGGGGCGCTGGCCACATGT

CACTGATGGTCAGATTCCAAAGTCCTTTCTTTATACTGTTGTGGACAATCTCAGCTGGGTCAATAAGGG

CAGGTGGTTCAGCGAGCCACGGCAGCCCCTGTATCTGGATTGTAATGTGAATCTTTAGGGTAATTCCT

CCAGTGACCTGTCAAGGCTTATGCTAACAGGAGACTTGCAGGAGACCGTGTGATTTGTGTAGTGAGCCT

TTGAAAATGGTTAGTACCGGGTTCAGTTTAGTTCTTAGTATCTTTTCAATCAAGCTGTGTGCTTAATTT

ACTCTGTTGTAAAGGGATAAAGTGGAAATCATTTTTTTCCGTGGAGTGGTGATTCTGCTAACATTTTTA

TCTACGTTTTATAACTTGGTGAGTGACGATGAGAGCCCTGCACCTGGCCAGAGTGTCACAGGCAAAAGG

CATCGGGAAGCAGGAGCATCTTCTTGGCAGCCAGGCTGGGCCATCTTCTCCTGGACACCTGCTGTGTAC

CAGGAACTTCGTCACCTCCTTGAATGCTGGCGGTTCATTTCATGATCAGTGTTAAGCATTTTCCTCCAT

GGGAAGGAAGCATGGGATATAGAAAAGCGAAGGGCTGTCCTTTACAAATTCTGGTTCTGCAACTTCCTA

GCGTGACTTTGGGCTTGGGCAAGTTTCTTAGCCGTTCTGAGCCTTCATTTCCTCATCTGTACAATGAGA

TTAATAGTACCTATCATCTACCTTCAGGATTGCTGACAGACAGAATTTGAAATAAAATATGCAAGTTAG

CTAATACAAAAAGTAGATGATCCAAAAATGGTAGCCACTCACCCTTCACAAACTGAAGTCCATGGACCA

CGGAAGTCGAGAATTAATGTACACCTGTATCATGTGTAGGAAACCAGAAATGTGTTCCTTATTTCTTGT
```

-continued

```
TCCCAAACAGGATTAACTGTGAAGACTAATTTATAAATGTGAACCTAAGAAAACTCCACCTCTGAAGGA

AATCATTTGAATTTTGTTTTTGTACGTAAAGTTAACCTTCCAATTGTCTGAGCTGTCGTCACTGACTTC

ATGACAGTCTGGCCCTCCAGACAAGAGCAGCGCTGGCATCGGGCAGGTGATTCCTGACACCTGCTGCCT

GCAGGCATTCACTGACCAGGCCTTTCCTGGAGGAAACACCCAGGGCCGGGCGGCTGCTGTTTCCACACG

TGGACTCGGATCTGCTGTGACACCGTCAGCCCGACAGTCTCTCCATATGCAGCCTTTCCTCTGTACTTT

TCTCCATGGTTGAAATAAAACAGGGTGACTGGGAGTTACTTAGAATTCATGAAGATTTTAAAATGGCTT

TGGAGATTTTGCTTTTAAACCAGTAGATTCAAAACTTAAACAGCGTCTGCAGCACAATTTCTTGAGGAA

CCTTGAAAAACACAACTTCCCAGGCCCCATTCAGTAATCCCAGGATTTCTTTAAGCTCCCCAAATAATT

TTGAAACTCATCATCAGCCGAGTTTCTGCCCTCATGAGGTAATTCCATCGTTCTCCCCAGCCTGCCCCT

GGCAGCTGTAACACAGGAGCTGGCCTGAGAGCAGATTCACCCTGGAATGTTCTCTCCACAGAACAATCA

AGTCCCTGTCGCCTGCCTAGTGCTTACCACTGAAGATTTTTCTGATTCCAGACCAACTTTTTGCCAACA

TTCTGCTTCCAGCTCTCTGAGCCCCTGCCGTGTCTCCCCAACACTGCCAGCCCCAGCACGCAATCAACC

TACTTTGTGCATGCCACCCGCTTTCCACACTGTGAGAACAATCTGCCCAACTGGACCCTCTGGAGGCGC

ACGATCTCAGCCACTCACCAGGCCTGAGTGTTTGTGAAATGATCATGTCCTACTTATTACAAAACCGTA

ACCCCAAAACATTCCTTTTATTTCTGTGAAACCGGCCAAAGTGAGGTCCACCCACCTTCACACAGCTCT

GGCGGTGCACCTGCTCACCTTCTCTTGGTTCTCAGAACTGAGCTGGGCTTGAGAACACAGCTTTGGCTT

TGCCATTTTTTTCCTACTTGGCTGCTGAGGTGGAGGGTGTGCTGCACTTATCACCCCATTTCAAAACCA

AACCAAACCTGAGGCCACCCCAAACAAATTCAGCCAGCAAAAAGGGTAGGTATCGATGGTCACCTGAAG

CCTCAAGGGAGTCCACTCTGACTTCTGACAG
```

As used herein the term "IRF4" has its general meaning in the art and refers to interferon regulatory factor 4 gene. A typical cDNA sequence of IRF4 is represented by SEQ ID NO:2.

(IRF4_homo sapiens)

SEQ ID NO: 2
```
ACCTCGCACTCTCAGTTTCACCGCTCGATCTTGGGACCCACCGCTGCCCTCAGCTCCGAGTCCAGGGCG

AGTGCAGAGCAGAGCGGGCGGAGGACCCCGGGCGCGGGCGCGGACGGCACGCGGGGCATGAACCTGGAG

GGCGGCGGCCGAGGCGGAGAGTTCGGCATGAGCGCGGTGAGCTGCGGCAACGGGAAGCTCCGCCAGTGG

CTGATCGACCAGATCGACAGCGGCAAGTACCCCGGGCTGGTGTGGGAGAACGAGGAGAAGAGCATCTTC

CGCATCCCCTGGAAGCACGCGGGCAAGCAGGACTACAACCGCGAGGAGGACGCCGCGCTCTTCAAGGCT

TGGGCACTGTTTAAAGGAAAGTTCCGAGAAGGCATCGACAAGCCGGACCCTCCCACCTGGAAGACGCGC

CTGCGGTGCGCTTTGAACAAGAGCAATGACTTTGAGGAACTGGTTGAGCGGAGCCAGCTGGACATCTCA

GACCCGTACAAAGTGTACAGGATTGTTCCTGAGGGAGCCAAAAAAGGAGCCAAGCAGCTCACCCTGGAG

GACCCGCAGATGTCCATGAGCCACCCCTACACCATGACAACGCCTTACCCTTCGCTCCCAGCCCAGCAG

GTTCACAACTACATGATGCCACCCCTCGACCGAAGCTGGAGGGACTACGTCCCGGATCAGCCACACCCG

GAAATCCCGTACCAATGTCCCATGACGTTTGGACCCCGCGGCCACCACTGGCAAGGCCCAGCTTGTGAA

AATGGTTGCCAGGTGACAGGAACCTTTTATGCTTGTGCCCCACCTGAGTCCCAGGCTCCCGGAGTCCCC

ACAGAGCCAAGCATAAGGTCTGCCGAAGCCTTGGCGTTCTCAGACTGCCGGCTGCACATCTGCCTGTAC

TACCGGGAAATCCTCGTGAAGGAGCTGACCACGTCCAGCCCCGAGGGCTGCCGGATCTCCCATGGACAT

ACGTATGACGCCAGCAACCTGGACCAGGTCCTGTTCCCCTACCCAGAGGACAATGGCCAGAGGAAAAAC

ATTGAGAAGCTGCTGAGCCACCTGGAGAGGGGCGTGGTCCTCTGGATGGCCCCCGACGGGCTCTATGCG

AAAAGACTGTGCCAGAGCAGGATCTACTGGGACGGGCCCCTGGCGCTGTGCAACGACCGGCCCAACAAA
```

-continued

```
CTGGAGAGAGACCAGACCTGCAAGCTCTTTGACACACAGCAGTTCTTGTCAGAGCTGCAAGCGTTTGCT

CACCACGGCCGCTCCCTGCCAAGATTCCAGGTGACTCTATGCTTTGGAGAGGAGTTTCCAGACCCTCAG

AGGCAAAGAAAGCTCATCACAGCTCACGTAGAACCTCTGCTAGCCAGACAACTATATTATTTTGCTCAA

CAAAACAGTGGACATTTCCTGAGGGGCTACGATTTACCAGAACACATCAGCAATCCAGAAGATTACCAC

AGATCTATCCGCCATTCCTCTATTCAAGAATGAAAAATGTCAAGATGAGTGGTTTTCTTTTTCCTTTTT

TTTTTTTTTTTTTGATACGGGGATACGGGGTCTTGCTCTGTCTCCCAGGCTGGAGTGCAGTGACACAA

TCTCAGCTCACTGTGACCTCCGCCTCCTGGGTTCAAGAGACTCTCCTGCCTCAGCCTCCCTGGTAGCTG

GGATTACAGGTGTGAGCCACTGCACCCACCCAAGACAAGTGATTTTCATTGTAAATATTTGACTTTAGT

GAAAGCGTCCAATTGACTGCCCTCTTACTGTTTTGAGGAATTCAGAAGTGGAGATTTCAGTTCAGCGGT

TGAGGAGAATTGCGGCGAGACAAGCATGGAAAATCAGTGACATCTGATTGGCAGATGAGCTTATTTCAA

AAGGAAGGGTGGCTTTGCATTTCTTGTGTTCTGTAGACTGCCATCATTGATGATCACTGTGAAAATTGA

CCAAGTGATGTGTTTACATTTACTGAAATGCGCTCTTTAATTTGTTGTAGATTAGGTCTTGCTGGAAGA

CAGAGAAAACTTGCCTTTCAGTATTGACACTGACTAGAGTGATGACTGCTTGTAGGTATGTCTGTGCCA

TTTCTCAGGGAAGTAAGATGTAAATTGAAGAAGCCTCACACGTAAAAGAAATGTATTAATGTATGTAGG

AGCTGCAGTTCTTGTGGAAGACACTTGCTGAGTGAAGGAAATGAATCTTTGACTGAAGCCGTGCCTGTA

GCCTTGGGGAGGCCCATCCCCCACCTGCCAGCGGTTTCCTGGTGTGGGTCCCTCTGCCCCGCCCTCCTT

CCCATTGGCTTTCTCTCCTTGGCCTTTCCTGGAAGCCAGTTAGTAAACTTCCTATTTTCTTGAGTCAAA

AAACATGAGCGCTACTCTTGGATGGGACATTTTTGTCTGTCCTACAATCTAGTAATGTCTAAGTAATGG

TTAAGTTTTCTTGTTTCTGCATCTTTTTGACCCTCATTCTTTAGAGATGCTAAAATTCTTCGCATAAAG

AAGAAGAAATTAAGGAACATAAATCTTAATACTTGAACTGTTGCCCTTCTGTCCAAGTACTTAACTATC

TGTTCCCTTCCTCTGTGCCACGCTCCTCTGTTTGTTTGGCTGTCCAGCGATCAGCCATGGCGACACTAA

AGGAGGAGGAGCCGGGGACTCCCAGGCTGGAGAGCACTGCCAGGACCCACCACTGGAAGCAGGATGGAG

CTGACTACGGAACTGCACACTCAGTGGGCTGTTTCTGCTTATTTCATCTGTTCTATGCTTCCTCGTGCC

AATTATAGTTTGACAGGGCCTTAAAATTACTTGGCTTTTTCCAAATGCTTCTATTTATAGAATCCCAAA

GACCTCCACTTGCTTAAGTATACCTATCACTTACATTTTTGTGGTTTTGAGAAAGTACAGCAGTAGACT

GGGGCGTCACCTCCAGGCCGTTTCTCATACTACAGGATATTTACTATTACTCCCAGGATCAGCAGAAGA

TTGCGTAGCTCTCAAATGTGTGTTCCTGCTTTTCTAATGGATATTTTAAATTCATTCAACAAGCACCTA

GTAAGTGCCTGCTGTATCCCTACATTACACAGTTCAGCCTTTATCAAGCTTAGTGAGCAGTGAGCACTG

AAACATTATTTTTTAATGTTTAAAAAGTTTCTAATATTAAAGTCAGAATATTAATACAATTAATATTAA

TATTAACTACAGAAAAGACAAACAGTAGAGAACAGCAAAAAAATAAAAAGGATCTCCTTTTTTCCCAGC

CCAAATTCTCCTCTCTAAAAGTGTCCACAAGAAGGGGTGTTTATTCTTCCAACACATTTCACTTTTCTG

TAAATATACATAAACTTAAAAAGAAAACCTCATGGAGTCATCTTGCACACACTTTCATGCAGTGCTCTT

TGTAGCTAACAGTGAAGATTTACCTCGTTCTGCTCAGAGGCCTTGCTGTGGAGCTCCACTGCCATGTAC

CCAGTAGGGTTTGACATTTCATTAGCCATGCAACATGGATATGTATTGGGCAGCAGACTGTGTTTCGTG

AACTGCAGTGATGTATACATCTTATAGATGCAAAGTATTTTGGGGTATATTATCCTAAGGGAAGATAAA

GATGATATTAAGAACTGCTGTTTCACGGGGCCCTTACCTGTGACCCTCTTTGCTGAAGAATATTTAACC

CCACACAGCACTTCAAAGAAGCTGTCTTGGAAGTCTGTCTCAGGAGCACCCTGTCTTCTTAATTCTCCA

AGCGGATGCTCCATTTCAATTGCTTTGTGACTTCTTCTTCTTTGTTTTTTAAATATTATGCTGCTTTA

ACAGTGGAGCTGAATTTTCTGGAAAATGCTTCTTGGCTGGGGCCACTACCTCCTTTCCTATCTTTACAT

CTATGTGTATGTTGACTTTTTAAAATTCTGAGTGATCCAGGGTATGACCTAGGGAATGAACTAGCTATG
```

-continued
```
AAATACTCAGGGTTAGGAATCCTAGCACTTGTCTCAGGACTCTGAAAAGGAACGGCTTCCTCATTCCTT

GTCTTGATAAAGTGGAATTGGCAAACTAGAATTTAGTTTGTACTCAGTGGACAGTGCTGTTGAAGATTT

GAGGACTTGTTAAAGAGCACTGGGTCATATGGAAAAAATGTATGTGTCTCCCAGGTGCATTTCTTGGTT

TATGTCTTGTTCTTGAGATTTTGTATATTTAGGAAAACCTCAAGCAGTAATTAATATCTCCTGGAACAC

TATAGAGAACCAAGTGACCGACTCATTTACAACTGAAACCTAGGAAGCCCCTGAGTCCTGAGCGAAAAC

AGGAGAGTTAGTCGCCCTACAGAAAACCCAGCTAGACATATTGGGTATGAACTAAAAAGAGACTGTGCCA

TGGTGAGAAAAATGTAAAATCCTACAGTGAAATGAGCAGCCCTTACAGTATTGTTACCACCAAGGGCAG

GTAGGTATTAGTGTTTGAAAAAGCTGGTCTTTGAGCGAGGGCATAAATACAGCTAGCCCCAGGGGTGGA

ACAACTCTGGGAGTCTTGGGTACTCGCACCTCTTGGCTTTGTTGATGCTCCGCCAGGAAGGCCACTTGT

GTGTGCGTGTCAGTTACTTTTTTAGTAACAATTCAGATCCAGTGTAAACTTCCGTTCATTGCTCTCCAG

TCACATGCCCCCACTTCCCCACAGGTGAAAGTTTTTCTGAAAGTGTTGGGATTGGTTAAGGTCTTTATT

TGTATTACGTATCTCCCGAAGTCCTCTGTGGCCAGCTGCATCTGTCTGAATGGTGCGTGAAGGCTCTCA

GACCTTACACACCATTTTGTAAGTTATGTTTTACATGCCCCGTTTTTGAGACTGATCTCGATGCAGGTG

GATCTCCTTGAGATCCTGATAGCCTGTTACAGGAATGAAGTAAAGGTCAGTTTTTTTTGTATTGATTT

TCACAGCTTTGAGGAACATGCATAAGAAATGTAGCTGAAGTAGAGGGGACGTGAGAGAAGGGCCAGGCC

GGCAGGCCAACCCTCCTCCAATGGAAATTCCCGTGTTGCTTCAAACTGAGACAGATGGGACTTAACAGG

CAATGGGGTCCACTTCCCCCTCTTCAGCATCCCCCGTACCCCACTTTCTGCTGAAAGAACTGCCAGCAG

GTAGGACCCCAGAGGCCCCAAATGAAAGCTTGAATTTCCCCTACTGGCTCTGCGTTTTGCTGAGATCT

GTAGGAAAGGATGCTTCACAAACTGAGGTAGATAATGCTATGCTGTCGTTGGTATACATCATGAATTTT

TATGTAAATTGCTCTGCAAAGCAAATTGATATGTTTGATAAATTTATGTTTTTAGGTAAATAAAAACTT

TTAAAAATTTGTTATGGA
```

As used herein the term "IGHM" has its general meaning in the art and refers to immunoglobulin heavy constant mu gene. A typical cDNA sequence of IGHM is represented by SEQ ID NO:3.

```
(IGHM_homo sapiens)
                                    SEQ ID NO: 3
GGGAGTGCATCCGCCCCAACCCTTTTCCCCCTCGTCTCCTGTGAGAATTC

CCCGTCGGATACGAGCAGCGTGGCCGTTGGCTGCCTCGCACAGGACTTCC

TTCCCGACTCCATCACTTTCTCCTGGAAATACAAGAACAACTCTGACATC

AGCAGCACCCGGGGCTTCCCATCAGTCCTGAGAGGGGGCAAGTACGCAGC

CACCTCACAGGTGCTGCTGCCTTCCAAGGACGTCATGCAGGGCACAGACG

AACACGTGGTGTGCAAAGTCCAGCACCCCAACGGCAACAAAGAAAAGAAC

GTGCCTCTTCCAGTGATTGCCGAGCTGCCTCCCAAAGTGAGCGTCTTCGT

CCCACCCCGCGACGGCTTCTTCGGCAACCCCCGCAAGTCCAAGCTCATCT

GCCAGGCCACGGGTTTCAGTCCCCGGCAGATTCAGGTGTCCTGGCTGCGC

GAGGGGAAGCAGGTGGGGTCTGGCGTCACCACGGACCAGGTGCAGGCTGA

GGCCAAAGAGTCTGGGCCCACGACCTACAAGGTGACCAGCACACTGACCA

TCAAAGAGAGCGACTGGCTCAGCCAGAGCATGTTCACCTGCCGCGTGGAT

CACAGGGGCCTGACCTTCCAGCAGAATGCGTCCTCCATGTGTGGCCCCGA

TCAAGACACAGCCATCCGGGTCTTCGCCATCCCCCCATCCTTTGCCAGCA

TCTTCCTCACCAAGTCCACCAAGTTGACCTGCCTGGTCACAGACCTGACC

ACCTATGACAGCGTGACCATCTCCTGGACCCGCCAGAATGGCGAAGCTGT

GAAAACCCACACCAACATCTCCGAGAGCCACCCCAATGCCACTTTCAGCG

CCGTGGGTGAGGCCAGCATCTGCGAGGATGACTGGAATTCCGGGGAGAGG

TTCACGTGCACCGTGACCCACACAGACCTGCCCTCGCCACTGAAGCAGAC

CATCTCCCGGCCCAAGGGGGTGGCCCTGCACAGGCCCGATGTCTACTTGC

TGCCACCAGCCCGGGAGCAGCTGAACCTGCGGGAGTCGGCCACCATCACG

TGCCTGGTGACGGGCTTCTCTCCCGCGGACGTCTTCGTGCAGTGGATGCA

GAGGGGGCAGCCCTTGTCCCCGGAGAAGTATGTGACCAGCGCCCCAATGC

CTGAGCCCCAGGCCCCAGGCCGGTACTTCGCCCACAGCATCCTGACCGTG

TCCGAAGAGGAATGGAACACGGGGGAGACCTACACCTGCGTGGTGGCCCA

TGAGGCCCTGCCCAACAGGGTCACCGAGAGGACCGTGGACAAGTCCACCG

GTAAACCCACCCTGTACAACGTGTCCCTGGTCATGTCCGACACAGCTGGC

ACCTGCTACTGACCCTGCTGGCCTGCCCACAGGCTCGGGGCGGCTGGCCG

CTCTGTGTGTGCATGCAAACTAACCGTGTCAACGGGGTGAGATGTTGCAT

CTTATAAAATT
```

As used herein the term "CCND1" has its general meaning in the art and refers to cyclin D1 gene. A typical cDNA sequence of CCND1 is represented by SEQ ID NO:4.

(CCND1_homo sapiens)

SEQ ID NO: 4

GCTTAACAACAGTAACGTCACACGGACTACAGGGGAGTTTTGTTGAAGTT
GCAAAGTCCTGGAGCCTCCAGAGGGCTGTCGGCGCAGTAGCAGCGAGCAG
CAGAGTCCGACACGCTCCGGCGAGGGGCAGAAGAGCGCGAGGGAGCGCGGG
GCAGCAGAAGCGAGAGCCGAGCGCGGACCCAGCCAGGACCCACAGCCCTC
CCCAGCTGCCCAGGAAGAGCCCCAGCCATGGAACACCAGCTCCTGTGCTG
CGAAGTGGAAACCATCCGCCGCGCGTACCCCGATGCCAACCTCCTCAACG
ACCGGGTGCTGCGGGCCATGCTGAAGGCGGAGGAGACCTGCGCGCCCTCG
GTGTCCTACTTCAAATGTGTGCAGAAGGAGGTCCTGCCGTCCATGCGGAA
GATCGTCGCCACCTGGATGCTGGAGGTCTGCGAGGAACAGAAGTGCGAGG
AGGAGGTCTTCCCGCTGGCCATGAACTACCTGGACCGCTTCCTGTCGCTG
GAGCCCGTGAAAAAGAGCCGCCTGCAGCTGCTGGGGGCCACTTGCATGTT
CGTGGCCTCTAAGATGAAGGAGACCATCCCCCTGACGGCCGAGAAGCTGT
GCATCTACACCGACAACTCCATCCGGCCCGAGGAGCTGCTGCAAATGGAG
CTGCTCCTGGTGAACAAGCTCAAGTGGAACCTGGCCGCAATGACCCCGCA
CGATTTCATTGAACACTTCCTCTCCAAAATGCCAGAGGCGGAGGAGAACA
AACAGATCATCCGCAAACACGCGCAG**ACCTTCGTTGCCCTCTGTGCCACA
GA**TGTGAAGTTCATTTCCAATCCGCCCTCCATGGTGGCAGCGGGGAGCGT
GGTGGCCGCAGTGCAAGGCCTGAACCTGAGGAGCCCCAACAACTTCCTGT
CCTACTACCGCCTCACACGCTTCCTCTCCAGAGTGATCAAGTGTGACCCG
GACTGCCTCCGGGCCTGCCAGGAGCAGATCGAAGCCCTGCTGGAGTCAAG
CCTGCGCCAGGCCCAGCAGAACATGGACCCCAAGGCCGCCGAGGAGGAGG
AAGAGGAGGAGGAGGAGGTGGACCTGGCTTGCACACCCACCGACGTGCGG
GACGTGGACATCTGAGGGCGCCAGGCAGGCGGGCGCCACCGCCACCCGCA
GCGAGGGCGGAGCCGGCCCCAGGTGCTCCCCTGACAGTCCCTCCTCTCCG
GAGCATTTTGATACCAGAAGGGAAAGCTTCATTCTCCTTGTTGTTGGTTG
TTTTTTCCTTTGCTCTTTCCCCCTTCCATCTCTGACTTAAGCAAAAGAAA
AAGATTACCCAAAAACTGTCTTTAAAAGAGAGAGAGAGAAAAAAAAATA
GTATTTGCATAACCCTGAGCGGTGGGGGAGGAGGGTTGTGCTACAGATGA
TAGAGGATTTTATACCCCAATAATCAACTCGTTTTTATATTAATGTACTT
GTTTCTCTGTTGTAAGAATAGGCATTAACACAAAGGAGGCGTCTCGGGAG
AGGATTAGGTTCCATCCTTTACGTGTTTAAAAAAAAGCATAAAAACATTT
TAAAAACATAGAAAATTCAGCAAACCATTTTTAAAGTAGAAGAGGGTTT
TAGGTAGAAAAACATATTCTTGTGCTTTTCCTGATAAAGCACAGCTGTAG
TGGGGTTCTAGGCATCTCTGTACTTTGCTTGCTCATATGCATGTAGTCAC
TTTATAAGTCATTGTATGTTATTATATTCCGTAGGTAGATGTGTAACCTC
TTCACCTTATTCATGGCTGAAGTCACCTCTTGGTTACAGTAGCGTAGCGT
GCCCGTGTGCATGTCCTTTGCGCCTGTGACCACCACCCCAACAAACCATC
CAGTGACAAACCATCCAGTGGAGGTTTGTCGGGCACCAGCCAGCGTAGCA
GGGTCGGGAAAGGCCACCTGTCCCACTCCTACGATACGCTACTATAAAGA
GAAGACGAAATAGTGACATAATATATTCTATTTTTATACTCTTCCTATTT
TTGTAGTGACCTGTTTATGAGATGCTGGTTTTCTACCCAACGGCCCTGCA
GCCAGCTCACGTCCAGGTTCAACCCACAGCTACTTGGTTTGTGTTCTTCT
TCATATTCTAAAACCATTCCATTTCCAAGCACTTTCAGTCCAATAGGTGT
AGGAAATAGCGCTGTTTTTGTTGTGTGTGCAGGGAGGGCAGTTTTCTAAT
GGAATGGTTTGGGAATATCCATGTACTTGTTTGCAAGCAGGACTTTGAGG
CAAGTGTGGGCACTGTGGTGGCAGTGGAGGTGGGGTGTTTGGGAGGCTG
CGTGCCAGTCAAGAAGAAAAAGGTTTGCATTCTCACATTGCCAGGATGAT
AAGTTCCTTTCCTTTTCTTTAAAGAAGTTGAAGTTTAGGAATCCTTTGGT
GCCAACTGGTGTTTGAAAGTAGGGACCTCAGAGGTTTACCTAGAGAACAG
GTGGTTTTAAGGGTTATCTTAGATGTTTCACACCGGAAGGTTTTTAAAC
ACTAAAATATATAATTTATAGTTAAGGCTAAAAAGTATATTTATTGCAGA
GGATGTTCATAAGGCCAGTATGATTTATAAATGCAATCTCCCCTTGATTT
AAACACACAGATACACACACACACACACACACACAAACCTTCTGCCTT
TGATGTTACAGATTTAATACAGTTTATTTTTAAAGATAGATCCTTTTATA
GGTGAGAAAAAACAATCTGGAAGAAAAAAACCACACAAAGACATTGATT
CAGCCTGTTTGGCGTTTCCCAGAGTCATCTGATTGGACAGGCATGGGTGC
AAGGAAAATTAGGGTACTCAACCTAAGTTCGGTTCCGATGAATTCTTATC
CCCTGCCCCTTCCTTTAAAAAACTTAGTGACAAAATAGACAATTTGCACA
TCTTGGCTATGTAATTCTTGTAATTTTTATTTAGGAAGTGTTGAAGGGAG
GTGGCAAGAGTGTGGAGGCTGACGTGTGAGGGAGGACAGGCGGGAGGAGG
TGTGAGGAGGAGGCTCCCGAGGGGAAGGGGCGGTGCCCACACCGGGGACA
GGCCGCAGCTCCATTTTCTTATTGCGCTGCTACCGTTGACTTCCAGGCAC
GGTTTGGAAATATTCACATCGCTTCTGTGTATCTCTTTCACATTGTTTGC
TGCTATTGGAGGATCAGTTTTTTGTTTTACAATGTCATATACTGCCATGT
ACTAGTTTTAGTTTTCTCTTAGAACATTGTATTACAGATGCCTTTTTTGT
AGTTTTTTTTTTTTATGTGATCAATTTTGACTTAATGTGATTACTGCT
CTATTCCAAAAAGGTTGCTGTTTCACAATACCTCATGCTTCACTTAGCCA
TGGTGGACCCAGCGGGCAGGTTCTGCCTGCTTTGGCGGGCAGACACGCGG
GCGCGATCCCACACAGGCTGGCGGGGCCGGCCCCGAGGCCGCGTGCGTG
AGAACCGCGCCGGTGTCCCCAGAGACCAGGCTGTGTCCCTCTTCTCTTCC
CTGCGCCTGTGATGCTGGGCACTTCATCTGATCGGGGGCGTAGCATCATA
GTAGTTTTTACAGCTGTGTTATTCTTTGCGTGTAGCTATGGAAGTTGCAT
AATTATTATTATTATTATAACAAGTGTGTCTTACGTGCCACCACGGC
GTTGTACCTGTAGGACTCTCATTCGGGATGATTGGAATAGCTTCTGGAAT
TTGTTCAAGTTTTGGGTATGTTTAATCTGTTATGTACTAGTGTTCTGTTT
GTTATTGTTTTGTTAATTACACCATAATGCTAATTTAAAGAGACTCCAAA
TCTCAATGAAGCCAGCTCACAGTGCTGTGTGCCCCGGTCACCTAGCAAGC
TGCCGAACCAAAAGAATTTGCACCCCGCTGCGGGCCCACGTGGTTGGGGC
CCTGCCCTGGCAGGGTCATCCTGTGCTCGGAGGCCATCTCGGGCACAGGC
CCACCCCGCCCCACCCCTCCAGAACACGGCTCACGCTTACCTCAACCATC

-continued
```
CTGGCTGCGGCGTCTGTCTGAACCACGCGGGGGCCTTGAGGGACGCTTTG

TCTGTCGTGATGGGGCAAGGGCACAAGTCCTGGATGTTGTGTGTATCGAG

AGGCCAAAGGCTGGTGGCAAGTGCACGGGGCACAGCGGAGTCTGTCCTGT

GACGCGCAAGTCTGAGGGTCTGGGCGGCGGGCGGCTGGGTCTGTGCATTT

CTGGTTGCACCGCGGCGCTTCCCAGCACCAACATGTAACCGGCATGTTTC

CAGCAGAAGACAAAAAGACAAACATGAAAGTCTAGAAATAAAACTGGTAA

AACCCCA
```

As used herein the term "LMO2" has its general meaning in the art and refers to LIM domain only 2 (rhombotin-like 1) gene. A typical cDNA sequence of LMO2 is represented by SEQ ID NO:5.

```
(LMO2_homo sapiens)
                                     SEQ ID NO: 5
GAATTCGTCCAAACTGAGGATCACAAGTCTCCACATTCTGAGTAGGAGGA

TGAGGGTCTGAGTTAGGATTTGGGTCCTGCAGGGCTTGCTAAGGAATCCC

CTGATGGCCTAGGATTCCACGCAGAGCACATCTGGTGTGAGAGAGCTCGC

TGCAAGGGTGAAGGCTCCGCCCTATCAGATAGACAACCAGGCCACCAAGA

GGCCCAGCCCTCCAAACCCTGGATTTGCAACATCCTCAAAGAACAGCAAC

GGGCCTTGAGCAGAATTGAGAAGGAAATACCCCCACCTGCCCTCAGCCGT

TAAGTGGGCTTTGCTATTCACAAGGGCCTCTGGGTGTCCTGGCAGAGAGG

GGAGATGGCACAGGCACCAGGTGCTAGGGTGCCAGGGCCTCCCGAGAAGG

AACAGGTGCAAAGCAGGCAATTAGCCCAGAAGGTATCCGTGGGGCAGGCA

GCCTAGATCTGATGGGGAAGCCACCAGGATTACATCATCTGCTGTAACA

ACTGCTCTGAAAAGAAGATATTTTTCAACCTGAACTTGCAGTAGCTAGTG

GAGAGGCAGGAAAAAGGAAATGAAACCAGAGACAGAGGGAAGCTGAGCGA

AAATAGACCTTCCCGAGAGAGGAGGAAGCCCGGAGAGAGACGCACGGTCC

CCTCCCCGCCCCTAGGCCGCCGCCCCCTCTCTGCCCTCGGCGGCGAGCAG

CGCGCCGCGACCCGGGCCGAAGGTGCGAGGGGCTCCGGGCGGCCGGGCGG

GCGCACACCATCCCCGCGGGCGGCGCGGAGCCGGCGACAGCGCGCGAGAG

GGACCGGGCGGTGGCGGCGGCGGGACCGGGATGGAAGGGAGCGCGGTGAC

TGTCCTTGAGCGCGAGGGGCGAGCTCGCCGGCGGAGCGCCGGAGCAAGC

GGAGGCGCAGGAGCGGCGGCGACGGCGGCGGCGGCGGCGGCGCCCGAGCA

CCCGAGGGGTCCGAGCCCCGGCAGCCGGCCAGCCCCGCGCCACAAAGGG

AGCGCCCCGCCGCCCGGCACCCCGCCTCCCTCCCCAATGTCCTCGGCCA

TCGAAAGGAAGAGCCTGGACCCTTCAGAGGAACCAGTGGATGAGGTGCTG

CAGATCCCCCCATCCCTGCTGACATGCGGCGGCTGCCAGCAGAACATTGG

GGACCGCTACTTCCTGAAGGCCATCGACCAGTACTGGCACGAGGACTGCC

TGAGCTGCGACCTCTGTGGCTGCCGGCTGGGTGAGGTGGGGCGGCGCCTC

TACTACAAACTGGGCCGGAAGCTCTGCCGGAGAGACTATCTCAGGCTTTT

TGGGCAAGACGGTCTCTGCGCATCCTGTGACAAGCGGATTCGTGCCTATG

AGATGACAATGCGGGTGAAAGACAAAGTGTATCACCTGGAATGTTTCAAA

TGCGCCGCCTGTCAGAAGCATTTCTGTGTAGGTGACAGATACCTCCTCAT
```

-continued
```
CAACTCTGACATAGTGTGCGAACAGGACATCTACGAGTGGACTAAGATCA

ATGGGATGATATAGGCCCGAGTCCCCGGGCATCTTTGGGGAGGTGTTCAC

TGAAGACGCCGTCTCCATGGCATCTTCGTCTTCACTCTTAGGCACTTTGG

GGGTTTGAGGGTGGGGTAAGGGATTTCTTAGGGGATGGTAGACCTTTATT

GGGTATCAAGACATAGCATCCAAGTGGCATAATTCAGGGGCTGACACTTC

AAGGTGACAGAAGGACCAGCCCTTGAGGGAGAACTTATGGCCACAGCCCA

TCCATAGTAACTGACATGATTAGCAGAAGAAAGGAACATTTAGGGGCAAG

CAGGCGCTGTGCTATCATGATGGAATTTCATATCTACAGATAGAGAGTTG

TTGTGTACAGACTTGTTGTGACTTTGACGCTTGCGAACTAGAGATGTGCA

ATTGATTTCTTTTCTTCCTGGCTTTTTAACTCCCCTGTTTCAATCACTGT

CCTCCACACAAGGGAAGGACAGAAAGGAGAGTGGCCATTCTTTTTTTCTT

GGCCCCCTTCCCAAGGCCTTAAGCTTTGGACCCAAGGAAAACTGCATGGA

GACGCATTTCGGTTGAGAATGGAAACCACAACTTTTAACCAAACAATTAT

TTAAAGCAATGCTGATGAATCACTGTTTTTAGACACCTTCATTTTGAGGG

GAGGAGTTCCACAGATTGTTTCTATACAAATATAAATCTTAAAAAGTTGT

TCAACTATTTTATTATCCTAGATTATATCAAAGTATTTGTCGTGTGTAGA

AAAAAAACAGCTCTGCAGGCTTAATAAAAATGACAGACTGAAA
```

As used herein the term "FOXP1" has its general meaning in the art and refers to forkhead box P1 gene. A typical cDNA sequence of FOXP1 is represented by SEQ ID NO:6.

```
(FOXP1_homo sapiens)
                                     SEQ ID NO: 6
GGGGGGTGGGCGCCAGCGCCCCGGCGAACGGCAAAGAGGGAGCCGCTCCC

GCTCGGGGGCCGCTGGAGTGCCCAGCGGGAACCCGAAAGTTTGTAAGAG

GAAGAGAGCGCGCGGCGAGCGAGCGAGCGGGCCGGGGGCAGCGGCAGCGG

CGCCGGGACCATGGTGCTGCCGGCGCCTCCTCCGCGGGCGTGAAGGCGG

CGCTCCTACTCCCTCCCCGGACTCCGCGGTGTCCCAGAAGCTTTTGTTGA

CAATTCCAGTTTCCGAACAAAACATTTCGGCAATGGTGAGGGCTTCGATC

CCTTCTCTGATTTGCTGTCAGCCATGAACGGATGGATGTGATGCCTGCTA

GCCAAAAGGCTTCCCTCTGTGTGTTGCAGTCCTGTGGCATTATGCATGCC

CCCTCCCAGTGACCCCAGGCTTTTTATGGCTGTGAGACACGTTAAAATTT

CAGGGGTAAGACGTGACCTTTTGAGGTGACTATAACTGAAGATTGCTTTA

CAGAAGCCAAAAAAGGTTTTTGAGTCATGATGCAAGAATCTGGGACTGAG

ACAAAAAGTAACGGTTCAGCCATCCAGAATGGGTCGGCGGCAGCAACCA

CTTACTAGAGTGCGGCGGTCTTCGGGAGGGGCGGTCCAACGGAGAGACGC

CGGCCGTGGACATCGGGGCAGCTGACCTCGCCCACGCCCAGCAGCAGCAG

CAACAGGCACTTCAGGTGGCAAGACAGCTCCTTCTTCAGCAGCAACAGCA

GCAGCAAGTTAGTGGATTAAAATCTCCCAAGAGGAATGACAAACAACCAG

CTCTTCAGGTTCCCGTGTCAGTGGCTATGATGACACCTCAAGTTATCACT

CCCCAGCAAATGCAGCAGATCCTCCAGCAACAAGTGCTGAGCCCTCAGCA

GCTCCAGGTTCTCCTCCAGCAGCAGCAGGCCCTCATGCTTCAACAGCAGC

AGCTTCAAGAGTTTTATAAAAAACAACAGGAACAGTTGCAGCTTCAACTT
```

```
TTACAACAACAACATGCTGGAAAACAGCCTAAAGAGCAACAGCAGGTGGC
TACCCAGCAGTTGGCTTTTCAGCAGCAGCTTTTACAGATGCAGCAGTTAC
AGCAGCAGCACCTCCTGTCTTTGCAGCGCCAAGGCCTTCTGACAATTCAG
CCCGGGCAGCCTGCCCTTCCCCTTCAACCTCTTGCTCAAGGCATGATTCC
AACAGAACTGCAGCAGCTCTGGAAAGAAGTGACAAGTGCTCATACTGCAG
AAGAAACCACAGGCAACAATCACAGCAGTTTGGATCTGACCACGACATGT
GTCTCCTCCTCTGCACCTTCCAAGACCTCCTTAATAATGAACCCACATGC
CTCTACCAATGGACAGCTCTCAGTCCACACTCCCAAAAGGGAAAGTTTGT
CCCATGAGGAGCACCCCCATAGCCATCCTCTCTATGGACATGGTGTATGC
AAGTGGCCAGGCTGTGAAGCAGTGTGCGAAGATTTCCAATCATTTCTAAA
ACATCTCAACAGTGAGCATGCGCTGGACGATAGAAGTACAGCCCAATGTA
GAGTACAAATGCAGGTTGTACAGCAGTTAGAGCTACAGCTTGCAAAAGAC
AAAGAACGCCTGCAAGCCATGATGACCCACCTGCATGTGAAGTCTACAGA
ACCCAAAGCCGCCCCTCAGCCCTTGAATCTGGTATCAAGTGTCACTCTCT
CCAAGTCCGCATCGGAGGCTTCTCCACAGAGCTTACCTCATACTCCAACG
ACCCCAACCGCCCCCCTGACTCCCGTCACCCAAGGCCCCTCTGTCATCAC
AACCACCAGCATGCACACGGTGGGACCCATCCGCAGGCGGTACTCAGACA
AATACAACGTGCCCATTTCGTCAGCAGATATTGCGCAGAACCAAGAATTT
TATAAGAACGCAGAAGTTAGACCACCATTTACATATGCATCTTTAATTAG
GCAGGCCATTCTCGAATCTCCAGAAAAGCAGCTAACACTAAATGAGATCT
ATAACTGGTTCACACGAATGTTTGCTTACTTCCGACGCAACGCGGCCACG
TGGAAGAATGCAGTGCGTCATAATCTTAGTCTTCACAAGTGTTTTGTGCG
AGTAGAAAACGTTAAAGGGGCAGTATGGACAGTGGATGAAGTAGAATTCC
AAAAACGAAGGCCACAAAAGATCAGTGGTAACCCTTCCCTTATTAAAAAC
ATGCAGAGCAGCCACGCCTACTGCACACCTCTCAATGCAGCTTTACAGGC
TTCAATGGCTGAGAATAGTATACCTCTATACACTACCGCTTCCATGGGAA
ATCCCACTCTGGGCAACTTAGCCAGCGCAATACGGGAAGAGCTGAACGGG
GCAATGGAGCATACCAACAGCAACGAGAGTGACAGCAGTCCAGGCAGATC
TCCTATGCAAGCCGTGCATCCTGTACACGTCAAAGAAGAGCCCCTCGATC
CAGAGGAAGCTGAAGGGCCCCTGTCCTTAGTGACAACAGCCAACCACAGT
CCAGATTTTGACCATGACAGAGATTACGAAGATGAACCAGTAAACGAGGA
CATGGAGTGACTATCGGGGCGGGCCAACCCCGAGAATGAAGATTGGAAGG
AAAAAAAAAAAAAACACGTCAAAAGTTAGCAGTGAAATTGTTCTCCAT
TTGTTGTACAGTCTGGAGGATTTTCACTACGTTTTGACAACTCTGAAATG
TGTTAACTCTTAGTGCCATCAAGAACCCCATTTGGGAGTATTTTGATTT
TTCTACTTTTTGTTGAAAAAGGAATTTGTACTCTGTGCATTGGATGGAC
TTGTTTGGTACTTGGGATTTTCCTCTCTTAACCGTCAACATCAGTGTTGT
AAATTTGCTAAACTGATTCACTTTTAGCAGCAGACTTTGAACTGCAGTCC
TGCCAACGTTGGACACTGAGGACGCCCGACAGAGCTTGTGCACCCTAAGCT
GCAGACCAAGCCTTTGCCCAGAATTTAAGGATTCCAATGGACGACCTATT
TGCACAGTACTGCATGTTGATTATCACTGCCTTTACTCCTTTTTTTTTTTT
TTTTTTTTTTTTTTTTTTGCTTCCAGTTGGGATGGGGAAGGCCTTTGTG
TGTGTATTGGGGGGAGGGGTTAAAAAATAATTATCCCAAACTTTTTAATG
TATTGCTTTTTTTTTTTTTTTTTCCTTCTACTATACCATTTTAAGTTC
TGACCTCAGGCCTCCATTTGGGCCGATGGCCTCTTGGAGGCTTAAAGTTT
TCTGTACCTTGTGATGAATGTTAATAGGTGTTTTTATTATACAAAGCTGA
ATGTCATTTCTCGTTTGTAGCTTTCTGTCACTCATTCCATCTTCCTTCAG
ACATCACCACGTTTCTCTAAAGTCAGAAAACATTCCGTTTTGGTCTTTTT
CAAAAAGGTCCCAAATGCTGCACTCTACACATGAAGGCCCTCTCACACAG
ACGTGACGTCCTGCCAGAAAGAGAATGAATGACAGAAAAAAAAAGAGAG
ACAAACTCTAGGAACAATGCCGATTCATTCCACGCAGCAGTATTGGGGGT
GGTTCGGGGAGGGGTGTTTCGGATTTTCTTTTTTTCTTTTCTTTTCTTT
TTTTTTTTTGCAGCAACCATTAATAAATGCCACCACATTCTACCAGCAC
AAGGAAACATAGGCAGCACTGAAAAAAAAAAAAAGCTCATATTAATTAG
ACTGACAATATGGCCTTGGAAGGCTCTCCCTTGTGGAACCAAGTTGCCAT
GGGCCTTGGGTGCTCTGCGATAACGGGTGTGGGTTGGTTTTGTTTGCAAA
ATGGCCAAAAAAAAAAACCGGCTTCCCCGAGCAGCTGCCCTGAAAGTAGG
GGTGGCGGCGGCGGCGCTGAGTTTATACATTAGTTCAGACCTACTTGGTG
GCATTAAACTGTTTGAATGCAAATTCGATTTCAGATTGAACTTGTTAAGG
GAGTTAACGAGGGCTGAGTTCAGCAAATGCTAAAGTGTTAATTTCAAATA
TGCAAATTTGGTACTGCAGTTTGTTATGCAATATTATATCACCAACCCAG
TATCACAAAAACTCATAGAAGATATCATGTAGGCCCTGGGCTTTGGGGGG
GTCCCAAACATGGTATGCAGAAATGTGATGGTTACAGGTCAGTACAACCT
CAGTCCTTAGAACCCCTCCACACTTCAGCTCTGCACCCACTTTCCTGTCA
TTTATTTATATAGGACTGTAGTTTTTTTAGTTCGAGAGCCTTTCGAAGC
TTAATTTATATTCTTTCTTTGTACCTTTTTTCTAAAATTACCAAAGATAT
TACACAAAGGTAAATTATGTTCTCTGTTTTATGCTTTATCTGATGAAGCC
AAATATCCTCTTATTGTTGATCAAAGGAGGCAAAAGAATTTAGAGGCAAA
TGACAAGCGATAGGCTATTGCAACCTGAGAAAGAGAACTGCTCCTTCATC
GTAAATTTAGAAGACCAAGTAGATAATGGAACCAAAGTTGTTACTTTTTT
CTAGTAGTTATTTTTCCTTTTCTTTTTGTGTACCTCTACAGAGACCAAA
ACTCATTCTCTTAAAGAGATTTTATGGGCTACTGCAGATAAAAATAGGA
CACAATATTAAAGGAGCTACAGAAGGAAGGGAGTCCCATCTCAAAAAAAA
AATGAATGTATGCCACTGCAATTAGAGTATCCAATAAAGGAGACAGTTTA
GAGTCAGGACAGAAAAGCTTCCATAATTGAACTAGATTACATAATAGTAT
TTCTAGAAAAGAGATATTTTTAGATTGTATGCCACTTTTGTTTAAGAAC
TGTGCTGTGATCACTGTATTAATTTTGGTTTATCTTGGCATATATCCTTC
AGTTTGTTTTTATTTTTAATTTTTCCTTTTTTTCCGATTAGGCTTTGGTC
AGCATTTTTCATTTAAAGAAAAGTAACACTCCCATCCACTCATAAGCTTG
GTACAAAAACTTCTCTGGCAGTTACTTTTGAAGCTTCACTCTGCTTTCTG
TATAAAGGGCAGTCTGTGGTCACGCAAGACTTTAAAAAAAAAAAAAAAA
```

-continued

```
AAAAAAAAAAAAAAAAAAAAAAAAACTTTTCCAGGCAGCTTCATGATGTGC
AGGCAGTAGCCAGACAGGGTCATGGGAAGGGGGCCCTGTGCTTCTAAACT
GAGTGGTTGCTGGTTAGTTTGGTATTCAAAAGAGGATAAAAATCTGGTAG
ATTAGTTCATTCTCAGCATGTGTAGCTAGACATGAGTAAAGATAACAGCA
TGAGAAACTGTTAGTACGCATACCTCAGTTCAAACCTTTAGGGAATGATT
AAAATTTAAAAAAAAAACATTTCACTCAGTTGCACTTAGTCGTATGTCTT
GCATGCTTAGTCTAAAGACTGTAGCAAAAAAAAAAAAAAAGAAAAATTA
GATTTTACATATCTTTGCAGGTATCACAGCCTTGCAGAAGAACCAACTGA
AAAAAAAATTCTCAGGCTTTACAGCAAGCAAACTTCACTATGATTTTTAC
AATTCTGATTCTGTATCCCCTGGGGGTTATCCCAGTTGCTTCTTTAGGAT
GGGGTTTATTACGTTGTACATATATCCCGATGTGTCTGTGTGAATCTTTG
TCTTTTTTGGGGGAGGGCAGAGGGCGGTTCTTTTTTTAGATATTGTTCCT
AAAAAGGAATAAATGCATACACCTGTTTGTCAAAACACCTTTGCTTTTTG
TGCAACTGCTTTATATTAACGATACTAAAAAAAAATAGCTTTGGAAAAAA
AACTACTGTATGTAACGGAATTGCAGAATATGCTGCACATGTATTTTATT
TAGTTATCCTTGCTTTAAGAATATTGGATGACATTTCCTGACATGTGGA
GGGAGAAACTCCCTAACTTTTTTTTCTGCTTTTAAACTGTAACATAGTT
GAAGATTCTTTTTTCTGTTCTCATTGATTGGAGCATTTTGTACAGGTTT
TGTGTGTGTGTGTGTGTGTGCGCGTGCGTGTGTTAATCTGTT
TTTTGATACATTCCTATCCCTTGTGTTTATCCTACCACTGCCTTCCTGGC
TATCTTAAACAAGTTCATACATTTGAAAAGAAAAAAAAATGTTGTTTAAA
AATGTTTTCTCCTGCTGCAGTAAATATTTTGCATGATGAAATTCCAGGGT
CACACTTTTCCAAGTTTATCAGTGAAGTAGTGATTAACAATGGGGAGTGT
CAAAACTATTGAACTTTTGTATAAAAAAAAAAAAACTTTACAAGGTGCCA
AGATGTAAAGAAATCTGTTACTTTTTTTTTCTCAAAGAAAAGCATACAT
TAGGGAGGTAGTCCCGTGTGTCAGACAAATGCACTGTCAGGAATGAGGAT
CCAACCTACCTGTCCCTAGAGTCCGTCTTGTAAGATGAGTTAGGCTGCCC
CTTGGACCAGCCACAAAATGGAATATCAAGGCTTATGTACATACGTGAAG
AGTTACCACCAGTCCTGCCACCTTTGGACAGCTCTAACACCATCCCCAGC
ATCCAGTCAGACCTAGTAAAGAAAACCTTGGATTCTTAACCCAAGATAGG
CTGTAAATCACTAGCTTTTTTTCCTCATGAAAAAAAATAGAGTTAAAAA
ATATTTCCTCTCTTTTCCATATTCCAGCTGAACTCCGTTTCCAAAGGCAC
AAAGAAGAGTGTGCTTATTCAGATTTTGAATCTTTTTGGTACCTTTTGGT
TAATGACATAGCCTCCTGAAATTCTGGATGTCTTCAAAGTCAGTTTTGCT
TCTTTATCCTGAAAATCAGATTTACAATGCTGAAGGCATTTCTTGGGCCC
AGTGTAGCTCACGCAATCTCTGCTACCCATAAGCCTTGATGAAGATGATA
CAGTCCGGACTGTGAGCATGGTGCTTCATGTATATGCTGCCAGTAACA
AGAATTTTTTGTTTTGTTTTGTTTTGTTTTGATAAGGCATAAAAGAAAC
TCATTCCTTGACATCAACTGTAATTCCATCATTCCATGTCTGCGGATACA
GACAATAAAAAAATGTTGTGTAGTCAGTACTAATTACTGACATTATAAG
CATTCTCAAATGCAATAAAAATGCTGGTTGTTCACGCTGGTAGTAAAAGT
TGCCACAGCCTAA
```

As used herein the term "TNFRSF9" has its general meaning in the art and refers to tumor necrosis factor receptor superfamily, member 9 gene. A typical cDNA sequence of TNFRSF9 is represented by SEQ ID NO:7.

(TNFRSF9_homo sapiens)
SEQ ID NO: 7
```
GTGTTTGACCTGAAGTCCTCTCGAGCTGCAGAAGCCTGAAGACCAAGGAG
TGGAAAGTTCTCCGGCAGCCCTGAGATCTCAAGAGTGACATTTGTGAGAC
CAGCTAATTTGATTAAAATTCTCTTGGAATCAGCTTTGCTAGTATCATAC
CTGTGCCAGATTTCATCATGGGAAACAGCTGTTACAACATAGTAGCCACT
CTGTTGCTGGTCCTCAACTTTGAGAGGACAAGATCATTGCAGGATCCTTG
TAGTAACTGCCCAGCTGGTACATTCTGTGATAATAACAGGAATCAGATTT
GCAGTCCCTGTCCTCCAAATAGTTTCTCCAGCGCAGGTGGACAAAGGACC
TGTGACATATGCAGGCAGTGTAAAGGTGTTTTCAGGACCAGGAAGGAGTG
TTCCTCCACCAGCAATGCAGAGTGTGACTGCACTCCAGGGTTTCACTGCC
TGGGGGCAGGATGCAGCATGTGTGAACAGGATTGTAAACAAGGTCAAGAA
CTGACAAAAAAGGTTGTAAAGACTGTTGCTTTGGGACATTTAACGATCA
GAAACGTGGCATCTGTCGACCCTGGACAAACTGTTCTTTGGATGGAAAGT
CTGTGCTTGTGAATGGGACGAAGGAGAGGGACGTGGTCTGTGGACCATCT
CCAGCCGACCTCTCTCCGGGAGCATCCTCTGTGACCCCGCCTGCCCCTGC
GAGAGAGCCAGGACACTCTCCGCAGATCATCTCCTTCTTTCTTGCGCTGA
CGTCGACTGCGTTGCTCTTCCTGCTGTTCTTCCTCACGCTCCGTTTCTCT
GTTGTTAAACGGGGCAGAAAGAAACTCCTGTATATATTCAAACAACCATT
TATGAGACCAGTACAAACTACTCAAGAGGAAGATGGCTGTAGCTGCCGAT
TTCCAGAAGAAGAAGAAGGAGGATGTGAACTGTGAAATGGAAGTCAATAG
GGCTGTTGGGACTTTCTTGAAAAGAAGCAAGGAAATATGAGTCATCCGCT
ATCACAGCTTTCAAAAGCAAGAACACCATCCTACATAATACCCAGGATTC
CCCCAACACACGTTCTTTTCTAAATGCCAATGAGTTGGCCTTTAAAAATG
CACCACTTTTTTTTTTTTTTGACAGGGTCTCACTCTGTCACCCAGGCTG
GAGTGCAGTGGCACCACCATGGCTCTCTGCAGCCTTGACCTCTGGGAGCT
CAAGTGATCCTCCTGCCTCAGTCTCCTGAGTAGCTGGAACTACAAGGAAG
GGCCACCACACCTGACTAACTTTTTGTTTTTTGTTTGGTAAAGATGGCA
TTTCACCATGTTGTACAGGCTGGTCTCAAACTCCTAGGTTCACTTTGGCC
TCCCAAAGTGCTGGGATTACAGACATGAACTGCCAGGCCCGGCCAAAATA
ATGCACCACTTTTAACAGAACAGACAGATGAGGACAGAGCTGGTGATAAA
AAAAAAAAAAAAAAGCATTTTCTAGATACCACTTAACAGGTTTGAGCTA
GTTTTTTTGAAATCCAAAGAAAATTATAGTTTAAATTCAATTACATAGTC
CAGTGGTCCAACTATAATTATAATCAAAATCAATGCAGGTTTGTTTTTTG
GTGCTAATATGACATATGACAATAAGCCACGAGGTGCAGTAAGTACCCGA
CTAAAGTTTCCGTGGGTTCTGTCATGTAACACGACATGCTCCACCGTCAG
```

-continued
GGGGGAGTATGAGCAGAGTGCCTGAGTTTAGGGTCAAGGACAAAAAACCT

CAGGCCTGGAGGAAGTTTTGGAAAGAGTTCAAGTGTCTGTATATCCTATG

GTCTTCTCCATCCTCACACCTTCTGCCTTTGTCCTGCTCCCTTTTAAGCC

AGGTTACATTCTAAAAATTCTTAACTTTTAACATAATATTTTATACCAAA

GCCAATAAATGAACTGCATATGA

As used herein the term "BCL6" has its general meaning in the art and refers to B-cell CLL/lymphoma 6 gene. A typical cDNA sequence of BCL6 is represented by SEQ ID NO:8.

(BCL6_homo sapiens)
SEQ ID NO: 8
ATACCATCGTCTTGGGCCCGGGGAGGGAGAGCCACCTTCAGGCCCCTCGA

GCCTCGAACCGGAACCTCCAAATCCGAGACGCTCTGCTTATGAGGACCTC

GAAATATGCCGGCCAGTGAAAAAATCTTGTGGCTTTGAGGGCTTTTGGTT

GGCCAGGGGCAGTAAAAATCTCGGAGAGCTGACACCAAGTCCTCCCCTGC

CACGTAGCAGTGGTAAAGTCCGAAGCTCAAATTCCGAGAATTGAGCTCTG

TTGATTCTTAGAACTGGGGTTCTTAGAAGTGGTGATGCAAGAAGTTTCTA

GGAAAGGCCGGACACCAGGTTTTGAGCAAAATTTTGGACTGTGAAGCAAG

GCATTGGTGAAGACAAAATGGCCTCGCCGGCTGACAGCTGTATCCAGTTC

ACCCGCCATGCCAGTGATGTTCTTCTCAACCTTAATCGTCTCCGGAGTCG

AGACATCTTGACTGATGTTGTCATTGTTGTGAGCCGTGAGCAGTTTAGAG

CCCATAAAACGGTCCTCATGGCCTGCAGTGGCCTGTTCTATAGCATCTTT

ACAGACCAGTTGAAATGCAACCTTAGTGTGATCAATCTAGATCCTGAGAT

CAACCCTGAGGGATTCTGCATCCTCCTGGACTTCATGTACACATCTCGGC

TCAATTTGCGGGAGGGCAACATCATGGCTGTGATGGCCACGGCTATGTAC

CTGCAGATGGAGCATGTTGTGGACACTTGCCGGAAGTTTATTAAGGCCAG

TGAAGCAGAGATGGTTTCTGCCATCAAGCCTCCTCGTGAAGAGTTCCTCA

ACAGCCGGATGCTGATGCCCCAAGACATCATGGCCTATCGGGGTCGTGAG

GTGGTGGAGAACAACCTGCCACTGAGGAGCGCCCCTGGGTGTGAGAGCAG

AGCCTTTGCCCCCAGCCTGTACAGTGGCCTGTCCACACCGCCAGCCTCTT

ATTCCATGTACAGCCACCTCCCTGTCAGCAGCCTCCTCTTCTCCGATGAG

GAGTTTCGGGATGTCCGGATGCCTGTGGCCAACCCCTTCCCCAAGGAGCG

GGCACTCCATGTGATAGTGCCAGGCCAGTCCCTGGTGAGTACAGCCGGC

CGACTTTGGAGGTGTCCCCCAATGTGTGCCACAGCAATATCTATTCACCC

AAGGAAACAATCCCAGAAGAGGCACGAAGTGATATGCACTACAGTGTGGC

TGAGGGCCTCAAACCTGCTGCCCCCTCAGCCCGAAATGCCCCCTACTTCC

CTTGTGACAAGGCCAGCAAAGAAGAAGAGAGACCCTCCTCGGAAGATGAG

ATTGCCCTGCATTTCGAGCCCCCCAATGCACCCCTGAACCGGAAGGGTCT

GGTTAGTCCACAGAGCCCCCAGAAATCTGACTGCCAGCCCAACTCGCCCA

CAGAGTCCTGCAGCAGTAAGAATGCCTGCATCCTCCAGGCTTCTGGCTCC

CCTCCAGCCAAGAGCCCCACTGACCCCAAAGCCTGCAACTGGAAGAAATA

CAAGTTCATCGTGCTCAACAGCCTCAACCAGAATGCCAAACCAGAGGGGC

-continued
CTGAGCAGGCTGAGCTGGGCCGCCTTTCCCCACGAGCCTACACGGCCCCA

CCTGCCTGCCAGCCACCCATGGAGCCTGAGAACCTTGACCTCCAGTCCCC

AACCAAGCTGAGTGCCAGCGGGGAGGACTCCACCATCCCACAAGCCAGCC

GGCTCAATAACATCGTTAACAGGTCCATGACGGGCTCTCCCCGCAGCAGC

AGCGAGAGCCACTCACCACTCTACATGCACCCCCCGAAGTGCACGTCCTG

CGGCTCTCAGTCCCCACAGCATGCAGAGATGTGCCTCCACACCGCTGGCC

CCACGTTCCCTGAGGAGATGGGAGAGACCCAGTCTGAGTACTCAGATTCT

AGCTGTGAGAACGGGGCCTTCTTCTGCAATGAGTGTGACTGCCGCTTCTC

TGAGGAGGCCTCACTCAAGAGGCACACGCTGCAGACCCACAGTGACAAAC

CCTACAAGTGTGACCGCTGCCAGGCCTCCTTCCGCTACAAGGGCAACCTC

GCCAGCCACAAGACCGTCCATACCGGTGAGAAACCCTATCGTTGCAACAT

CTGTGGGGCCCAGTTCAACCGGCCAGCCAACCTGAAAACCCACACTCGAA

TTCACTCTGGAGAGAAGCCCTACAAATGCGAAACCTGCGGAGCCAGATTT

GTACAGGTGGCCCACCTCCGTGCCCATGTGCTTATCCACACTGGTGAGAA

GCCCTATCCCTGTGAAATCTGTGGCACCCGTTTCCGGCACCTTCAGACTC

TGAAGAGCCACCTGCGAATCCACACAGGAGAGAAACCTTACCATTGTGAG

AAGTGTAACCTGCATTTCCGTCACAAAAGCCAGCTGCGACTTCACTTGCG

CCAGAAGCATGGCGCCATCACCAACACCAAGGTGCAATACCGCGTGTCAG

CCACTGACCTGCCTCCGGAGCTCCCCAAAGCCTGCTGAAGCATGGAGTGT

TGATGCTTTCGTCTCCAGCCCCTTCTCAGAATCTACCCAAAGGATACTGT

AACACTTTACAATGTTCATCCCATGATGTAGTGCCTCTTTCATCCACTAG

TGCAAATCATAGCTGGGGGTTGGGGGTGGTGGGGGTCGGGGCCTGGGGGA

CTGGGAGCCGCAGCAGCTCCCCCTCCCCCACTGCCATAAAACATTAAGAA

AATCATATTGCTTCTTCTCCTATGTGTAAGGTGAACCATGTCAGCAAAAA

GCAAAATCATTTTATATGTCAAAGCAGGGGAGTATGCAAAAGTTCTGACT

TGACTTTAGTCTGCAAAATGAGGAATGTATATGTTTTGTGGGAACAGATG

TTTCTTTTGTATGTAAATGTGCATTCTTTTAAAAGACAAGACTTCAGTAT

GTTGTCAAAGAGAGGGCTTTAATTTTTTTAACCAAAGGTGAAGGAATATA

TGGCAGAGTTGTAAATATATAAATATATATATATATAAAATAAATATATA

TAAACCTAAAAAAGATATATTAAAAATATAAAACTGCGTTAAAGGCTCGA

TTTTGTATCTGCAGGCAGACACGGATCTGAGAATCTTTATTGAGAAAGAG

CACTTAAGAGAATATTTTAAGTATTGCATCTGTATAAGTAAGAAAATATT

TTGTCTAAAATGCCTCAGTGTATTTGTATTTTTTGCAAGTGAAGGTTTA

CAATTTACAAAGTGTGTATTAAAAAAAACAAAAGAACAAAAAAATCTGC

AGAAGGAAAATGTGTAATTTTGTTCTAGTTTTCAGTTTGTATATACCCG

TACAACGTGTCCTCACGGTGCCTTTTTTCACGGAAGTTTTCAATGATGGG

CGAGCGTGCACCATCCCTTTTTGAAGTGTAGGCAGACACAGGGACTTGAA

GTTGTTACTAACTAAACTCTCTTTGGGAATGTTTGTCTCATCCCATTCTG

CGTCATGCTTGTGTTATAACTACTCCGGAGACAGGGTTTGGCTGTGTCTA

AACTGCATTACCGCGTTGTAAAATATAGCTGTACAAATATAAGAATAAAA

TGTTGAAAAGTCAAACTGG

As used herein the term "TNFRSF13B" has its general meaning in the art and refers to tumor necrosis factor receptor superfamily, member 13B gene. A typical cDNA sequence of TNFRSF13B is represented by SEQ ID NO:9. TNFRSF13B is also known as TACI.

(TNFRSF13B_homo sapiens)
SEQ ID NO: 9
AGCATCCTGAGTAATGAGTGGCCTGGGCCGGAGCAGGCGAGGTGGCCGGA

GCCGTGTGGACCAGGAGGAGCGCTTTCCACAGGGCCTGTGGACGGGGGTG

GCTATGAGATCCTGCCCCGAAGAGCAGTACTGGGATCCTCTGCTGGGTAC

CTGCATGTCCTGCAAAACCATTTGCAACCATCAGAGCCAGCGCACCTGTG

CAGCCTTCTGCAGGTCACTCAGCTGCCGCAAGGAGCAAGGCAAGTTCTAT

GACCATCTCCTGAGGGACTGCATCAGCTGTGCCTCCATCTGTGGACAGCA

CCCTAAGCAATGTGCATACTTCTGTGAGAACAAGCTCAGGAGCCCAGTGA

ACCTTCCACCAGAGCTCAGGAGACAGCGGAGTGGAGAAGTTGAAAACAAT

TCAGACAACTCGGGAAGGTACCAAGGATTGGAGCACAGAGGCTCAGAAGC

AAGTCCAGCTCTCCCGGGGCTGAAGCTGAGTGCAGATCAGGTGGCCCTGG

TCTACAGCACGCTGGGGCTCTGCCTGTGTGCCGTCCTCTGCTGCTTCCTG

GTGGCGGTGGCCTGCTTCCTCAAGAAGAGGGGGGATCCCTGCTCCTGCCA

GCCCCGCTCAAGGCCCCGTCAAAGTCCGGCCAAGTCTTCCCAGGATCACG

CGATGGAAGCCGGCAGCCCTGTGAGCACATCCCCCGAGCCAGTGGAGACC

TGCAGCTTCTGCTTCCCTGAGTGCAGGGCGCCCACGCAGGAGAGCGCAGT

CACGCCTGGGACCCCCGACCCCACTTGTGCTGGAAGGTGGGGGTGCCACA

CCAGGACCACAGTCCTGCAGCCTTGCCCACACATCCCAGACAGTGGCCTT

GGCATTGTGTGTGTGCCTGCCCAGGAGGGGGCCCAGGTGCATAAATGGG

GGTCAGGGAGGGAAAGGAGGAGGGAGAGAGATGGAGAGGAGGGGAGAGAG

AAAGAGAGGTGGGGAGAGGGGAGAGAGATATGAGGAGAGAGAGACAGAGG

AGGCAGAGAGGGAGAGAAACAGAGGGAGACAGAGAGGGAGAGAGAGACAGA

GGGAGAGAGAGACAGAGGGGAAGAGAGGCAGAGAGGGAAAGAGGCAGAGA

AGGAAAGAGACAGGCAGAGAAGGAGAGAGGCAGAGAGGGAGAGAGGCAGA

GAGGGAGAGAGGCAGAGAGACAGAGAGGGAGAGAGGGACAGAGAGAGATA

GAGCAGGAGGTCGGGGCACTCTGAGTCCCAGTTCCCAGTGCAGCTGTAGG

TCGTCATCACCTAACCACACGTGCAATAAAGTCCTCGTGCCTGCTGCTCA

CAGCCCCCGAGAGCCCCTCCTCCTGGAGAATAAAACCTTTGGCAGCTGCC

CTTCCTC

As used herein the term "CCND2" has its general meaning in the art and refers to cyclin D2 gene. A typical cDNA sequence of CCND2 is represented by SEQ ID NO:10.

(CCND2_homo sapiens)
SEQ ID NO: 10
AGAGCGAGCAGGGGAGAGCGAGACCCAGTTTTAAGGGGAGGACCGGTGCGA

GTGAGGCAGCCCCGAGGCTCTGCTCGCCCACCACCCAATCCTCGCCTCCC

TTCTGCTCCACCTTCTCTCTCTGCCCTCACCTCTCCCCCGAAAACCCCCT

ATTTAGCCAAAGGAAGGAGGTCAGGGGAACGCTCTCCCCTCCCCTTCCAA

AAAACAAAAACAGAAAAACCTTTTTCCAGGCCGGGGAAAGCAGGAGGGAG

AGGGGCCGCCGGGCTGGCCATGGAGCTGCTGTGCCACGAGGTGGACCCGG

TCCGCAGGGCCGTGCGGGACCGCAACCTGCTCCGAGACGACCGCGTCCTG

CAGAACCTGCTCACCATCGAGGAGCGCTACCTTCCGCAGTGCTCCTACTT

CAAGTGCGTGCAGAAGGACATCCAACCCTACATGCGCAGAATGGTGGCCA

CCTGGATGCTGGAGGTCTGTGAGGAACAGAAGTGCGAAGAAGAGGTCTTC

CCTCTGGCCATGAATTACCTGGACCGTTTCTTGGCTGGGGTCCCGACTCC

GAAGTCCCATCTGCAACTCCTGGGTGCTGTCTGCATGTTCCTGGCCTCCA

AACTCAAAGAGACCAGCCCGCTGACCGCGGAGAAGCTGTGCATTTACACC

GACAACTCCATCAAGCCTCAGGAGCTGCTGGAGTGGGAACTGGTGGTGCT

GGGGAAGTTGAAGTGGAACCTGGCAGCTGTCACTCCTCATGACTTCATTG

AGCACATCTTGCGCAAGCTGCCCCAGCAGCGGGAGAAGCTGTCTCTGATC

CGCAAGCATGCTCAGACCTTCATTGCTCTGTGTGCCACCGACTTTAAGTT

TGCCATGTACCCACCGTCGATGATCGCAACTGGAAGTGTGGGAGCAGCCA

TCTGTGGGCTCCAGCAGGATGAGGAAGTGAGCTCGCTCACTTGTGATGCC

CTGACTGAGCTGCTGGCTAAGATCACCAACACAGACGTGGATTGTCTCAA

AGCTTGCCAGGAGCAGATTGAGGCGGTGCTCCTCAATAGCCTGCAGCAGT

ACCGTCAGGACCAACGTGACGGATCCAAGTCGGAGGATGAACTGGACCAA

GCCAGCACCCCTACAGACGTGCGGGATATCGACCTGTGAGGATGCCAGTT

GGGCCGAAAGAGAGACGCGTCCATAATCTGGTCTCTTCTTCTTTCTGG

TTGTTTTTGTTCTTTGTGTTTAGGGTGAAACTTAAAAAAAAAATTCTGC

CCCCACCTAGATCATATTTAAAGATCTTTTAGAAGTGAGAGAAAAAGGTC

CTACGAAAACGGAATAATAAAAAGCATTTGGTGCCTATTTGAAGTACAGC

ATAAGGGAATCCCTTGTATATGCGAACAGTTATTGTTTGATTATGTAAAA

GTAATAGTAAAATGCTTACAGGAAAAACCTGCAGAGTAGTTAGAGAATATG

TATGCCTGCAATATGGGAACAAATTAGAGGAGACTTTTTTTTTTCATGTT

ATGAGCTAGCACATACACCCCCTTGTAGTATAATTTCAAGGAACTGTGTA

CGCCATTTATGGCATGATTAGATTGCAAAGCAATGAACTCAAGAAGGAAT

TGAAATAAGGAGGGACATGATGGGGAAGGAGTACAAAACAATCTCTCAAC

ATGATTGAACCATTTGGGATGGAGAAGCACCTTTGCTCTCAGCCACCTGT

TACTAAGTCAGGAGTGTAGTTGGATCTCTACATTAATGTCCTCTTGCTGT

CTACAGTAGCTGCTACCTAAAAAAAGATGTTTTATTTTGCCAGTTGGACA

CAGGTGATTGGCTCCTGGGTTTCATGTTCTGTGACATCCTGCTTCTTCTT

CCAAATGCAGTTCATTGCAGACACCACCATATTGCTATCTAATGGGAAA

TGTAGCTATGGGCCATAACCAAAACTCACATGAAACGGAGGCAGATGGAG

ACCAAGGGTGGGATCCAGAATGGAGTCTTTTCTGTTATTGTATTTAAAAG

GGTAATGTGGCCTTGGCATTTCTTCTTAGAAAAAAACTAATTTTTGGTGC

TGATTGGCATGTCTGGTTCACAGTTTAGCATTGTTATAAACCATTCCATT

CGAAAAGCACTTTGAAAAATTGTTCCCGAGCGATAGATGGGATGGTTTAT

GCAAGTCATGCTGAATACTCCTCCCCTCTTCTCTTTTGCCCCCTCCCTTC

CTGCCCCCAGTCTGGGTTACTCTTCGCTTCTGGTATCTGGCGTTCTTTGG

-continued

TACACAGTTCTGGTGTTCCTACCAGGACTCAAGAGACACCCCTTCCTGCT
GACATTCCCATCACAACATTCCTCAGACAAGCCTGTAAACTAAAATCTGT
TACCATTCTGATGGCACAGAAGGATCTTAATTCCCATCTCTATACTTCTC
CTTTGGACATGGAAAGAAAAGTTATTGCTGGTGCAAAGATAGATGGCTGA
ACATCAGGGTGTGGCATTTTGTTCCCTTTTCCGTTTTTTTTTTTTATTG
TTGTTGTTAATTTTATTGCAAAGTTGTATTCAGCGTACTTGAATTTTTCT
TCCTCTCCACTTCTTAGAGGCATTCAGTTAGCAAAGAGGTTGGAGCAACA
ACTTTTTTTTTTTTTTGCACAATTGTAATTGACAGGTAATGAAGCTAT
TTGTTAAAATATTTGCCTTTTTAAGTAAAAAGAAAAATCAGAACAGGGC
TATTTGAAGAATTATTTTATACACAGATTCTGCCTTGTTTCATAGTATGA
GGGTTGAAGACGGAAAACAATCTAAGGGTCTCTCATTTTTTTAATTTTGT
TTTGTTCAGTTTGGTTTTTTTTTTTTTTGCGCTGCTAAGAAGCTAAAGT
CATCCATCCTTATTCACGTTGACAGTACCTAGCTGTAATGTTTCACAGAG
TGTGCTGCTATTTTATAAACATTTTTATAATATATTATTTTACTGCTTAA
ATTCCAAGTCCTGAAGTAGATGGTTGAGATATGAGTTCTTCGTACTGGAA
AAGCCCTTCCGTAGTTTGTTTCTTCTGGTAGCATATTCATGGTTGTTTT
TTTTTTTCTTTTTGGTTTTTTGGTTTTTTTTTTTTCCTCTGATCACATT
CTTCAAAGACGGAGTATTCTTTACCTCAGGTTTACTGGACAAAATCAATA
ACTACAAAAGGCAATGATTCACGCTTTTGTTTTCATAATACCTCACAACC
GTACAGTTTCTGCTTGGGAGCCCATTCGCATGAGGAATACAGAAGCAGTG
TGAGCAGGGCTGACTCCCTCTCAGGTGGAAGGCAGGGCGGTCTCACTCCC
AGGGACCTTTTTGGTCATGGAGGCCATCGGGCTCCCAGTTAGACCCTGGT
ATCCTCATCATGATGGAAAAAATACATTGAACCAAGGGATCCTCCCTCCC
CTTCAAGGCAGACGTTCAGTACAAACATTTATGCGGTAGGCTCAGATGTC
GTAATTTGCACTTAGGTACCAGGTGTCAGGAAACAGACTAAAAGAATTC
CACCAGGCTGTTTGGAGATCCTCATCTTGGAGCTTTTTCAAAAGCGGGGC
TTCATCTGCAAAGGGCCCTTTCATCTTGAAGTTTTTCCCCTCCGTCTTTC
CCCTCCCCTGGCATGGACACCTTGTGTTTAGGATCATCTCTGCAGGTTTC
CTAGGTCTGAATCTGCGAGTAGATGAACCTGCAGCAAGCAGCGTTTATGG
TGCTTCCTTCTCCCTCCTCTGTCTCAAACTGCGCAGGCAAGCACTATGCA
AGCCCAGGCCCTCTGCTGAGCGGTACTAAACGGTCGGGTTTTCAATCACA
CTGAATTGGCAGGATAAGAAAAATAGGTCAGATAAGTATGGGATGATAGT
TGAAGGGAGGTGAAGAGGCTGCTTCTCTACAGAGGTGAAATTCCAGATGA
GTCAGTCTCTTGGGAAGTGTGTTTAGAAGGGTTCAGGACTTTGTGAGTTA
GCATGACCCTAAAATTCTAGGGGATTTCTGGTGGGACAATGGGTGGTGAA
TTCTGAAGTTTTGGAGAGGGAAGTGGAGCAGCCAGCAAGTAAGCTAGCCA
GAGTTTTCTCAAGAGCCAGCTTTGCTCAGCACACTCTCCTGGGCCCCAAG
GAGTCCCACGGAATGGGGAAAGCGGGAACCCTGGAGTTCTTGGGAATCTT
GGAGCCTAAAGAGAAACCGAGGTGCAAATTCATTTCATGGTGACTGACCC
TTGAGCTTAAACAGAAGCAGCAAATGAAGAACCGGACAAATAAGGAAGG

-continued

GCACAAGCCTACCCGACTCTATTTACAGTCTGTAACTTTCCACTCTTCCT
GTAGTCCCGAGGCCCCTGGGTCCTTCTAGCTTTTCTCTTTCCCATCCTTG
GGGCCTTGTGTGATGATGGGTGTGGGGCTGCCGATGGGAAAGTCGGGGGT
TGTTAGGCTTTTCTGCCTGCTCCTGCTTAAACACAAGAAGGAATCCTGGA
TTTTGCCCTCTCCTTAGCTCTTAGTCTCTTTGGTAGGAGTTTTGTTCCAG
AGGAGCTCTCCCCCTTGGATTTGAACTTGCTCTTTTTGTTGTTGTTGTTC
TTTCTCTTCTTTTTCTTACCTCCCACTAAAGGGGTTCCAAATTATCCTGG
TCTTTTTCTACCTTGTTGTGTTTCTATCTCGTCTTTACTTCCATCTGTTT
GTTTTTTTCTCCATCAGTGGGGGCCGAGTTGTTCCCCCAGCCTGCCAAAT
TTTGATCCTTCCCCTCTTTTGGCCAAATCCTAGGGGGAAGAAATCCTAGT
ATGCCAAAAATATATGCTAAGCATAATTAAACTCCATGCGGGTCCATAAC
AGCCAAGAAGCCTGCAGGAGAAAGCCAAGGGCAGTTCCCTCCGCAGAACA
CCCCCATGCGTGCTGAGAGGCGAGCTCCTTGAAGAAGGGGCTGTTCTTCCA
GGAGGCCTTATTTTGAACTGCCTCAGGACCCCACTGGAGAGCACAGCATG
CCTTACTACTGGGTCATCCTTGGTCTATGTGCTCTGTACTGGAGGCTCTG
TTCTGCCTCTTATCAGCCAGGTCAGGGGCACACATGGCTTAAGTGACAAA
GCCAGAGGAGAAGACAACCCTGACAGCATCACGCTGCATCCCATTGCTAG
CAGGATTGGCAACTCTTCAGACGGAGCTGCGCTTCCCTGCAGTCTAGCAC
CTCTAGGGCCTCTCCAGACTGTGCCCTGGGAGCTCTGGGACTGAAAGGTT
AAGAACATAAGGCAGGATCAGATGACTCTCTCCAAGAGGGCAGGGGAATT
TTCTCTCCATGGGCCACAGGGGACAGGGCTGGGAGAAGAAATAGACTTGC
ACCTTATGTCATGTAAATAATTGATTTTCTAGTTCAAGAAGATAATATTG
GTAGTGTGGGAATTGGAGGTAGGAAGGGGAGGAAGTCTGAGTAAGCCAGT
TGGCTTCTAAGCCAAAAGGATTCCTCTTTGTTTATCTCTGAGACAGTCCA
ACCTTGAGAATAGCTTTAAAAGGGAAATTAATGCTGAGATGATAAAGTCC
CCTTAAGCCAACAAACCCTCTGTAGCTATAGAATGAGTGCAGGTTTCTAT
TGGTGTGGACTCAGAGCAATTTACAAGAGCTGTTCATGCAGCCATCCATT
TGTGCAAAATAGGGTAAGAAGATTCAAGAGGATATTTATTACTTCCTCAT
ACCACATGGCTTTTGATGATTCTGGATTCTAAACAACCCAGAATGGTCAT
TTCAGGCACAACGATACTACATTCGTGTGTGTCTGCTTTTAAACTTGGCT
GGGCTATCAGACCCTATTCTCGGCTCAGGTTTTGAGAAGCCATCAGCAAA
TGTGTACGTGCATGCTGTAGCTGCAGCCTGCATCCCTTCGCCTGCAGCCT
ACTTTGGGAAATAAAGTGCCTTACTGACTGTAGCCATTACAGTATCCAA
TGTCTTTTGACAGGTGCCTGTCCTTGAAAAACAAAGTTTCTATTTTTATT
TTTAATTGGTTTAGTTCTTAACTGCTGGCCAACTCTTACATCCCCAGCAA
ATCATCGGGCCATTGGATTTTTTCCATTATGTTCATCACCCTTATATCAT
GTACCTCAGATCTCTCTCTCTCCTCTCTCAGTTATGTAGTTTCTTG
TCTTGGACTTTTTTTTTCTTTTCTTTTTCTTTTTTTTTGCTTTAAAA
CAAGTGTGATGCCATATCAAGTCCATGTTATTCTCTCACAGTGTACTCTA
TAAGAGGTGTGGGTGTCTGTTTGGTCAGGATGTTAGAAAGTGCTGATAAG
TAGCATGATCAGTGTATGCGAAAAGGTTTTTAGGAAGTATGGCAAAAATG

TTGTATTGGCTATGATGGTGACATGATATAGTCAGCTGCCTTTTAAGAGG

TCTTATCTGTTCAGTGTTAAGTGATTTAAAAAAATAATAACCTGTTTTCT

GACTAGTTTAAAGATGGATTTGAAAATGGTTTTGAATGCAATTAGGTTAT

GCTATTTGGACAATAAACTCACCTTGACCT

As used herein the term "MYC" has its general meaning in the art and refers to v-myc avian myelocytomatosis viral oncogene homolog gene. A typical cDNA sequence of MYC is represented by SEQ ID NO:11.

(MYC_homo sapiens)
SEQ ID NO: 11
CTGCTCGCGGCCGCCACCGCCGGGCCCCGGCCGTCCCTGGCTCCCCTCCT

GCCTCGAGAAGGGCAGGGCTTCTCAGAGGCTTGGCGGGAAAAAGAACGGA

GGGAGGGATCGCGCTGAGTATAAAAGCCGGTTTTCGGGGCTTTATCTAAC

TCGCTGTAGTAATTCCAGCGAGAGGCAGAGGGAGCGAGCGGGCGGCCGGC

TAGGGTGGAAGAGCCGGGCGAGCAGAGCTGCGCTGCGGGCGTCCTGGGAA

GGGAGATCCGGAGCGAATAGGGGGCTTCGCCTCTGGCCCAGCCCTCCCGC

TGATCCCCCAGCCAGCGGTCCGCAACCCTTGCCGCATCCACGAAACTTTG

CCCATAGCAGCGGGCGGGCACTTTGCACTGGAACTTACAACACCCGAGCA

AGGACGCGACTCTCCCGACGCGGGGAGGCTATTCTGCCCATTTGGGGACA

CTTCCCCGCCGCTGCCAGGACCCGCTTCTCTGAAAGGCTCTCCTTGCAGC

TGCTTAGACGCTGGATTTTTTTCGGGTAGTGGAAAACCAGCAGCCTCCCG

CGACGATGCCCCTCAACGTTAGCTTCACCAACAGGAACTATGACCTCGAC

TACGACTCGGTGCAGCCGTATTTCTACTGCGACGAGGAGGAGAACTTCTA

CCAGCAGCAGCAGCAGAGCGAGCTGCAGCCCCCGGCGCCCAGCGAGGATA

TCTGGAAGAAATTCGAGCTGCTGCCCACCCCGCCCCTGTCCCCTAGCCGC

CGCTCCGGGCTCTGCTCGCCCTCCTACGTTGCGGTCACACCCTTCTCCCT

TCGGGGAGACAACGACGGCGGTGGCGGGAGCTTCTCCACGGCCGACCAGC

TGGAGATGGTGACCGAGCTGCTGGGAGGAGACATGGTGAACCAGAGTTTC

ATCTGCGACCCGGACGACGAGACCTTCATCAAAAACATCATCATCCAGGA

CTGTATGTGGAGCGGCTTCTCGGCCGCCGCCAAGCTCGTCTCAGAGAAGC

TGGCCTCCTACCAGGCTGCGCGCAAAGACAGCGGCAGCCCGAACCCCGCC

CGCGGCCACAGCGTCTGCTCCACCTCCAGCTTGTACCTGCAGGATCTGAG

CGCCGCCGCCTCAGAGTGCATCGACCCCTCGGTGGTCTTCCCCTACCCTC

TCAACGACAGCAGCTCGCCCAAGTCCTGCGCCTCGCAAGACTCCAGCGCC

TTCTCTCCGTCCTCGGATTCTCTGCTCTCCTCGACGGAGTCCTCCCCGCA

GGGCAGCCCCGAGCCCCTGGTGCTCCATGAGGAGACACCGCCCACCACCA

GCAGCGACTCTGAGGAGGAACAAGAAGATGAGGAAGAAATCGATGTTGTT

TCTGTGGAAAAGAGGCAGGCTCCTGGCAAAAGGTCAGAGTCTGGATCACC

TTCTGCTGGAGGCCACAGCAAACCTCCTCACAGCCCACTGGTCCTCAAGA

GGTGCCACGTCTCCACACATCAGCACAACTACGCAGCGCCTCCCTCCACT

CGGAAGGACTATCCTGCTGCCAAGAGGGTCAAGTTGGACAGTGTCAGAGT

CCTGAGACAGATCAGCAACAACCGAAAATGCACCAGCCCCAGGTCCTCGG

ACACCGAGGAGAATGTCAAGAGGCGAACACACAACGTCTTGGAGCGCCAG

AGGAGGAACGAGCTAAAACGGAGCTTTTTTGCCCTGCGTGACCAGATCCC

GGAGTTGGAAAACAATGAAAAGGCCCCCAAGGTAGTTATCCTTAAAAAAG

CCACAGCATACATCCTGTCCGTCCAAGCAGAGGAGCAAAAGCTCATTTCT

GAAGAGGACTTGTTGCGGAAACGACGAGAACAGTTGAAACACAAACTTGA

ACAGCTACGGAACTCTTGTGCGTAAGGAAAAGTAAGGAAAACGATTCCTT

CTAACAGAAATGTCCTGAGCAATCACCTATGAACTTGTTTCAAATGCATG

ATCAAATGCAACCTCACAACCTTGGCTGAGTCTTGAGACTGAAAGATTTA

GCCATAATGTAAACTGCCTCAAATTGGACTTTGGGCATAAAAGAACTTTT

TTATGCTTACCATCTTTTTTTTTTCTTTAACAGATTTGTATTTAAGAATT

GTTTTTAAAAAATTTTAAGATTTACACAATGTTTCTCTGTAAATATTGCC

ATTAAATGTAAATAACTTTAATAAAACGTTTATAGCAGTTACACAGAATT

TCAATCCTAGTATATAGTACCTAGTATTATAGGTACTATAAACCCTAATT

TTTTTTATTTAAGTACATTTTGCTTTTTAAAGTTGATTTTTTCTATTGT

TTTTAGAAAAAATAAAATAACTGGCAAATATATCATTGAGCCAAA

As used herein the term "MYBL1" has its general meaning in the art and refers to v-myb avian myeloblastosis viral oncogene homolog-like 1 gene. A typical cDNA sequence of MYBL1 is represented by SEQ ID NO:12.

(MYBL1_homo sapiens)
SEQ ID NO: 12
GGACAAAACCCTGCAGGAGACTGCGAGCCCTGCAGAACTGCTAGCTGCGG

GGGAGAGGGCAGGGGTCGGGCGCCTGTGGCGGAGCCGGGCTGGGGCCAGG

GCAGGGAGGCTGACAAGCGGCGGGAGAAGCCGGCGGAGGGCGGGATCGCG

CCTCCTGACATGTTGGGGGTATCCCTGGCCGGGCCGGGCCGGGGCTAAGA

GCGGCGCTGCGGGCCGGGGTCGGGGTCGGGTCGCGGTCCGCCCCCGCTGT

CCCTCCGTCCTGCCCTGTCGAGGACGTGCGTTCCGCACTCGGCCGCCTCC

AGAGGGAGCGAGGGAAGCGGCTAGAGGATCGGGGAGAAGGAGCATTCGCC

GGAGGCTGGAGGAGGCTGACCCGCGTCCCCGCCCAGCCTGCTCCTATGCG

GTACTTGAAGGATGGCGAAGAGGTCGCGCAGTGAGGATGAGGATGATGAC

CTTCAGTATGCCGATCATGATTATGAAGTACCACAACAAAAAGGACTGAA

GAAACTCTGGAACAGAGTAAAATGGACAAGGGACGAGGATGATAAATTAA

AGAAGTTGGTTGAACAACATGGAACTGATGATTGGACTCTAATTGCTAGT

CATCTTCAAAATCGCTCTGATTTTCAGTGCCAGCATCGATGGCAGAAAGT

TTTAAATCCTGAATTGATAAAGGGTCCTTGGACTAAAGAAGAAGATCAGA

GGGTTATTGAATTAGTTCAGAAATATGGGCCAAAAAGATGGTCTTTAATT

GCAAAACATTTAAAAGGAAGAATAGGCAAGCAGTGTAGAGAAAGATGGCA

TAATCATCTGAATCCTGAGGTAAAGAAATCTTCCTGGACAGAAGAGGAGG

ACAGGATCATCTATGAAGCACATAAGCGGTTGGGAAATCGTTGGGCAGAA

ATTGCCAAACTACTTCCAGGAAGGACTGATAATTCTATCAAAAATCATTG

GAATTCTACTATGCGAAGAAAAGTGGAACAGGAGGGCTATTTACAAGATG

GAATAAAATCAGAACGATCTTCATCTAAACTTCAACACAAACCTTGTGCA

GCTATGGATCATATGCAAACCCAGAATCAGTTTTACATACCTGTTCAGAT
CCCTGGGTATCAGTATGTGTCACCTGAAGGCAATTGTATAGAACATGTTC
AGCCTACTTCTGCCTTTATTCAGCAACCCTTCATTGATGAAGATCCTGAT
AAGGAAAAGAAAATAAAGGAACTTGAGATGCTTCTTATGTCAGCTGAGAA
TGAAGTTAGAAGAAAGCGAATTCCATCACAGCCTGGAAGTTTTTCTAGCT
GGTCTGGTAGTTTCCTCATGGATGATAACATGTCTAATACTCTAAATAGC
CTTGACGAGCACACTAGTGAGTTTTACAGTATGGATGAAAATCAGCCTGT
GTCTGCTCAGCAGAATTCACCCACAAAGTTCCTGGCCGTGGAGGCAAACG
CTGTGTTATCCTCTTTGCAGACCATCCCAGAATTTGCAGAGACTCTAGAA
CTTATTGAATCTGATCCTGTAGCATGGAGTGACGTTACCAGTTTTGATAT
TTCTGATGCTGCTGCTTCTCCTATCAAATCCACCCCAGTTAAATTAATGA
GAATTCAGCACAATGAAGGAGCCATGGAATGCCAATTTAACGTCAGTCTT
GTACTTGAAGGGAAAAAAAACACTTGTAATGGTGGCAACAGTGAAGCTGT
TCCTTTAACATCCCAAATATAGCCAAGTTTAGCACTCCACCAGCCATCC
TCAGAAAGAAGAGAAAAATGCGAGTGGGTCATTCCCCAGGCAGCGAACTT
AGGGATGGCTCATTGAACGATGGTGGTAATATGGCGCTAAAACATACACC
ACTGAAAACACTACCATTTTCTCCTTCACAGTTTTTCAACACATGTCCTG
GTAATGAACAACTTAATATAGAAAATCCTTCATTTACATCAACCCCTATT
TGTGGGCAGAAAGCTCTCATTACAACTCCTCTTCATAAGGAAACAACTCC
CAAAGATCAAAAGGAAAATGTAGGGTTTAGAACACCTACTATTAGAAGAT
CTATACTGGGTACCACACCAAGAACTCCTACTCCTTTTAAGAATGCGCTT
GCTGCTCAGGAGAAAAAATATGGACCTCTTAAAATTGTGTCCCAGCCACT
TGCTTTCTTGGAAGAAGATATTCGGGAAGTTTTAAAAGAAGAAACTGGAA
CAGACCTATTCCTCAAAGAGGAAGATGAACCTGCTTACAAAAGCTGCAAA
CAAGAGAATACCGCTTCTGGGAAGAAAGTCAGAAAATCACTAGTCTTAGA
TAATTGGGAAAAGAAGAATCAGGCACTCAACTGTTGACTGAAGACATTT
CAGACATGCAGTCAGAAAATAGATTTACTACATCCTTATTAATGATACCA
TTATTGGAAATACATGACAATAGGTGCAACTTGATTCCTGAAAAACAAGA
TATAAATTCAACCAACAAACATATACACTTACTAAAAAGAAACCAAACC
CTAACACTTCCAAAGTTGTCAAATTGGAAAAGAATCTTCAGTCAAATTGT
GAATGGGAAACAGTGGTTTATGGGAAGACAGAAGACCAACTTATTATGAC
TGAACAAGCAAGAAGATATCTGAGTACTTACACAGCTACCAGTAGTACTT
CAAGAGCTCTCATACTGTAATTGTTATTAAAATTGATGAAATGCCCCACT
CCCTTACTGCAGTCTCTACTAAATTAGGTTGCAGTGAATTTTTCTCAAT
TAGTTGTTTTTAAAGTTGTAAGATAGCCCTTTTAATACAGCATCTTTTTT
CTATTCTATATAGTAGGCAGAAAGCTAGTAAGTCACTTAAGGGGTAGATA
GTTTCATAGTTTATTTTTAAGAGATGAGATTTTTAAAAATTGTTTTTAA
AGAACAAGATGGGAAAATAATAGAATGTTCATGGATTTCTAAAAGTAAAT
TCTCATATATTTTCTTCACAAGATATATGTTGCTACTCTCTTGATGCTGC
AGTTTTGTTATAGATAGGTGTATGAGTATATATGATTTCTGAAATTAGTC
TATGTATGGAAAGCACACATGATTTTATGAAGTACTTTTGCCCATGTGCT
GATTTACTTAGGCTACCATTTACAAAGAAACACATTGAAAAGGAATTTAA
AGGAAGGATAGAAAGTTGCACTACTAATTTTTGTTTTTTTTTCAGAAG
CAGTAAAATTAACTACAGTGTTAAATGTATTTATTTGAGCATAGTACTGA
AAACAAAAAGCATTCAAAAAGAGTTTTTTCTTTATTAGTAAATAGTATT
TTCTTAATCTCAGAGGAGCTGAGAGTTTTGTTGAATGTATTGTACAGTAT
GTAGGAGCAGGAGAACTTTGTAAATTGGAAAGAAGTCTGTTTTTATAATT
TATTTTTATTTTTAAAGCTTAAATGTAGATATTTATACGTATACAGGGTG
CCTAGAAGCCAATGTTGTTTCCTGTTATTACAGCTAACACAGTAAAGAAT
AATTTTGACTTTAAGTATGAAACAGTAGTAAGTTATAGCTGCAAAGAATA
CAATATCTATACTGTATGTCACATCTACCTAAATGTTGCACTATGCCCTT
TAAATCATGCTGGTTATAAAGTAGTTCTAAAAATGTACTAAATAATAATT
TAATATTTTCTTTTTAAATTATATCGGGGGTGGTCATATACATTAATCTG
GTGATTTGTATATGTGTTTGAAATTTTTGCATTTTGTTTAAAAAATAATA
TGGTACCTTGGTCCCTAAAAACAGTCTGCACTTAGAAGTTTATATTTACT
CAGTGTTTCAGAAGTGGAGAACATTATCTTTTATTTATAAAAATATTTTG
TCCTTTTTTAAATGTTTTGTGTTTCTCTACAGGTTACAACAGTTGCTTCA
GTTGCCTGTTTTAGGTGTTTGCACTTATTTTATTTCTTCTTGAAAGAATT
TTTATTTGCTTTTGTGGTAGAGATTATATGTAATTTTTTTTCAGTCATAT
AATGGTGTGCTGTCAACTTAAACACTGACAGGTAAATAGAATTGTACACT
GTAGTTTGAATTATTTATAATTGACACACTCTCTCCCTCTCCACTCCTGA
AGTATGCTGCTATAGAAAATAGCAGAATCGGCTTGCTGCTACGAGAGAAG
GAAAGAGCGACCACCACTTGCACTGTGTGAAAAGATAAAAAACAAATGAT
GGCAAGTTCTCAAGTTAACTAAATGGAATCAACCATTACCAGGCAAATTC
TTGCAAATACCAAAATACTACTATGCCTTATAAAACAAAATGAAAGCAGG
TTAAGATTTTCTGCTCTGTTTGTATGTTAATAGAAATGGAAATACTAAGT
ATTTTAATGCTTAGCTCTTGAACAGTAGACCTAAAAGGGTTTTAAGCTAT
TTAAATCTACTTGCTAGTTTTTGCATATTTTATATATATATATATTTATA
TATATATATAGTGAGAAGTGAAGAAAATGTATGGTACTAAGATTATGCCT
TATTGATAAATAGATAAACCAATTTGAATCCTCTTAGCATGTTTAAGTAT
GTTGATTGCTTTCTAATTAATGAACTTCTCACAGAAATTTCACTTAGTGA
AACCAATGATTGTAGCAAACTCATACTGGATCATTTCAGTTACCTTGAAC
TAATAGCACATAATGGTTTTTGTTGTTGTTGTTTTAATGTAGCCCTTA
CCTGGATATACATAGTCTGCAATCACCAAAGTATAATATCTTGTAAGGCT
ATATTTTTAAAGCATATTTTTCTTGAGCATTAAATTATCCTAAATGGT
AATATATTGTGGATAAGTCTGGGCTTATTGGACATAATACATATTTGGGT
TGGTACTGGTTGAATCCTTCAGTTAACTGCTTTGTTGCTTTTTGCAAGAT
TTTTTATCTTAAACATGTCAGGCATCTTAAGTCACCTTTATACTGTTTTG
TTCCTCTGAGTTTCTTTCAGTATGTTATACAAATGCCAGACATAACATGT
AGCAGCCATACTTGCATGGAAACTGACTACACATACATAATACTGCATTT
TATTGTAAGGTTTTCACATTAATACAGCAATTACCCTGACTAAATTGAGT

TTTGTGATATATGGAAAACTTCATTGTAAGAGAATCTTGCATACAATGTT

GACATATTAACATCCAAAATAAAGCATCTGTGTACAAGCTGA

As used herein the term "BCL2" has its general meaning in the art and refers to B-cell CLL/lymphoma 2 gene. A typical cDNA sequence of BCL2 is represented by SEQ ID NO:13.

(BCL2_homo sapiens)
SEQ ID NO: 13
ACCACCTCCTTCTCCCCACCCCTCGCCGCACCACACACAGCGCGGGCTTC

TAGCGCTCGGCACCGGCGGGCCAGGCGCGTCCTGCCTTCATTTATCCAGC

AGCTTTTCGGAAAATGCATTTGCTGTTCGGAGTTTAATCAGAAGAGGATT

CCTGCCTCCGTCCCCGGCTCCTTCATCGTCCCCTCTCCCCTGTCTCTCTC

CTGGGGAGGCGTGAAGCGGTCCCGTGGATAGAGATTCATGCCTGTGCCCG

CGCGTGTGTGCGCGCGTGTAAATTGCCGAGAAGGGGAAAACATCACAGGA

CTTCTGCGAATACCGGACTGAAAATTGTAATTCATCTGCCGCCGCCGCTG

CCTTTTTTTTTTCTCGAGCTCTTGAGATCTCCGGTTGGGATTCCTGCGGA

TTGACATTTCTGTGAAGCAGAAGTCTGGGAATCGATCTGGAAATCCTCCT

AATTTTTACTCCCTCTCCCCGCGACTCCTGATTCATTGGGAAGTTTCAAA

TCAGCTATAACTGGAGAGTGCTGAAGATTGATGGGATCGTTGCCTTATGC

ATTTGTTTTGGTTTTACAAAAAGGAAACTTGACAGAGGATCATGCTGTAC

TTAAAAAATACAACATCACAGAGGAAGTAGACTGATATTAACAATACTTA

CTAATAATAACGTGCCTCATGAAATAAAGATCCGAAAGGAATTGGAATAA

AAATTTCCTGCATCTCATGCCAAGGGGAAACACCAGAATCAAGTGTTCC

GCGTGATTGAAGACACCCCCTCGTCCAAGAATGCAAAGCACATCCAATAA

AATAGCTGGATTATAACTCCTCTTCTTTCTCTGGGGGCCGTGGGGTGGGA

GCTGGGGCGAGAGGTGCCGTTGGCCCCCGTTGCTTTTCCTCTGGGAAGGA

TGGCGCACGCTGGGAGAACAGGGTACGATAACCGGGAGATAGTGATGAAG

TACATCCATTATAAGCTGTCGCAGAGGGGCTACGAGTGGGATGCGGGAGA

TGTGGGCGCCGCGCCCCGGGGGCCGCCCCGCACCGGGCATCTTCTCCT

CCCAGCCCGGGCACACGCCCCATCCAGCCGCATCCCGGGACCCGGTCGCC

AGGACCTCGCCGCTGCAGACCCCGGCTGCCCCCGGCGCCGCCGCGGGGCC

TGCGCTCAGCCCGGTGCCACCTGTGGTCCACCTGACCCTCCGCCAGGCCG

GCGACGACTTCTCCCGCCGCTACCGCCGCGACTTCGCCGAGATGTCCAGC

CAGCTGCACCTGACGCCCTTCACCGCGCGGGACGCTTTGCCACGGTGGT

GGAGGAGCTCTTCAGGGACGGGGTGAACTGGGGGAGGATTGTGGCCTTCT

TTGAGTTCGGTGGGGTCATGTGTGTGGAGAGCGTCAACCGGGAGATGTCG

CCCCTGGTGGACAACATCGCCCTGTGGATGACTGAGTACCTGAACCGGCA

CCTGCACACCTGGATCCAGGATAACGGAGGCTGGGATGCCTTTGTGGAAC

TGTACGGCCCCAGCATGCGGCCTCTGTTTGATTTCTCCTGGCTGTCTCTG

AAGACTCTGCTCAGTTTGGCCCTGGTGGGAGCTTGCATCACCCTGGGTGC

CTATCTGGGCCACAAGTGAAGTCAACATGCCTGCCCCAAACAAATATGCA

AAAGGTTCACTAAAGCAGTAGAAATAATATGCATTGTCAGTGATGTACCA

TGAAACAAAGCTGCAGGCTGTTTAAGAAAAAATAACACACATATAAACAT

CACACACACAGACAGACACACACACACAACAATTAACAGTCTTCAGGC

AAAACGTCGAATCAGCTATTTACTGCCAAAGGGAAATATCATTTATTTTT

TACATTATTAAGAAAAAAAGATTTATTTATTTAAGACAGTCCCATCAAAA

CTCCTGTCTTTGGAAATCCGACCACTAATTGCCAAGCACCGCTTCGTGTG

GCTCCACCTGGATGTTCTGTGCCTGTAAACATAGATTCGCTTTCCATGTT

GTTGGCCGGATCACCATCTGAAGAGCAGACGGATGGAAAAAGGACCTGAT

CATTGGGGAAGCTGGCTTTCTGGCTGCTGGAGGCTGGGGAGAAGGTGTTC

ATTCACTTGCATTTCTTTGCCCTGGGGGCTGTGATATTAACAGAGGGAGG

GTTCCTGTGGGGGGAAGTCCATGCCTCCCTGGCCTGAAGAAGAGACTCTT

TGCATATGACTCACATGATGCATACCTGGTGGGAGGAAAAGAGTTGGGAA

CTTCAGATGGACCTAGTACCCACTGAGATTTCCACGCCGAAGGACAGCGA

TGGGAAAAATGCCCTTAAATCATAGGAAAGTATTTTTTTAAGCTACCAAT

TGTGCCGAGAAAAGCATTTTAGCAATTTATACAATATCATCCAGTACCTT

AAGCCCTGATTGTGTATATTCATATATTTTGGATACGCACCCCCCAACTC

CCAATACTGGCTCTGTCTGAGTAAGAAACAGAATCCTCTGGAACTTGAGG

AAGTGAACATTTCGGTGACTTCCGCATCAGGAAGGCTAGAGTTACCCAGA

GCATCAGGCCGCCACAAGTGCCTGCTTTTAGGAGACCGAAGTCCGCAGAA

CCTGCCTGTGTCCCAGCTTGGAGGCCTGGTCCTGGAACTGAGCCGGGGCC

CTCACTGGCCTCCTCCAGGGATGATCAACAGGGCAGTGTGGTCTCCGAAT

GTCTGGAAGCTGATGGAGCTCAGAATTCCACTGTCAAGAAAGAGCAGTAG

AGGGGTGTGGCTGGGCCTGTCACCCTGGGGCCCTCCAGGTAGGCCCGTTT

TCACGTGGAGCATGGGAGCCACGACCCTTCTTAAGACATGTATCACTGTA

GAGGGAAGGAACAGAGGCCCTGGGCCCTTCCTATCAGAAGGACATGGTGA

AGGCTGGGAACGTGAGGAGAGGCAATGGCCACGGCCCATTTTGGCTGTAG

CACATGGCACGTTGGCTGTGTGGCCTTGGCCCACCTGTGAGTTTAAAGCA

AGGCTTTAAATGACTTTGGAGAGGGTCACAAATCCTAAAAGAAGCATTGA

AGTGAGGTGTCATGGATTAATTGACCCCTGTCTATGGAATTACATGTAAA

ACATTATCTTGTCACTGTAGTTTGGTTTTATTTGAAAACCTGACAAAAAA

AAAGTTCCAGGTGTGGAATATGGGGGTTATCTGTACATCCTGGGGCATTA

A

As used herein the term "MS4A1" has its general meaning in the art and refers to membrane-spanning 4-domains, subfamily A, member 1. A typical cDNA sequence of MS4A1 is represented by SEQ ID NO:14.

(MS4A1_homo sapiens)
SEQ ID NO: 14
ACCCTCCCAGTGTGCTTGAGAAACAAACTGCACCCACTGAACTCCGCAGC

TAGCATCCAAATCAGCCCTTGAGATTTGAGGCCTTGGAGACTCAGGAGTT

TTGAGAGCAAAATGACAACACCCAGAAATTCAGTAAATGGGACTTTCCCG

GCAGAGCCAATGAAAGGCCCTATTGCTATGCAATCTGGTCCAAAACCACT

CTTCAGGAGGATGTCTTCACTGGAACTTGTAATAGCTGGCATCGTTGAGA

-continued

```
ATGAATGGAAAAGAACGTGCTCCAGACCCAAATCTAACATAGTTCTCCTG

TCAGCAGAAGAAAAAAAAGAACAGACTATTGAAATAAAAGAAGAAGTGGT

TGGGCTAACTGAAACATCTTCCCAACCAAAGAATGAAGAAGACATTGAAA

TTATTCCAATCCAAGAAGAGGAAGAAGAAGAAACAGAGACGAACTTTCCA

GAACCTCCCCAAGATCAGGAATCCTCACCAATAGAAAATGACAGCTCTCC

TTAAGTGATTTCTTCTGTTTTCTGTTTCCTTTTTTAAACATTAGTGTTCA

TAGCTTCCAAGAGACATGCTGACTTTCATTTCTTGAGGTACTCTGCACAT

ACGCACCACATCTCTATCTGGCCTTTGCATGGAGTGACCATAGCTCCTTC

TCTCTTACATTGAATGTAGAGAATGTAGCCATTGTAGCAGCTTGTGTTGT

CACGCTTCTTCTTTTGAGCAACTTTCTTACACTGAAGAAAGGCAGAATGA

GTGCTTCAGAATGTGATTTCCTACTAACCTGTTCCTTGGATAGGCTTTTT

AGTATAGTATTTTTTTTTGTCATTTTCTCCATCAACAACCAGGGAGACTG

CACCTGATGGAAAAGATATATGACTGCTTCATGACATTCCTAAACTATCT

TTTTTTTATTCCACATCTACGTTTTTGG
```

As used herein, the term "target nucleic acid sequence" refers to a specific nucleic acid sequence of the gene for which the determination of the expression level is sought (i.e. NEK6, IRF4, IGHM, CCND1, LMO2, FOXP1, TNFRSF9, BCL6, TNFRSF13B, CCND2, MYC, MYBL1, BCL2, and MS4A1). According to the invention the target nucleic acid sequence consists of 2 segments which are substantially adjacent. As used herein, the term "substantially adjacent" is used in reference to nucleic acid molecules that are in close proximity to one another.

MLPA is a well known method for determining the level expressions genes in a multiplex assay performed in one single tube. The general protocol for MLPA is described in Schouten, J. P. et al., (2002) Nucl. Acid Res. 30, e57, on mplpa.com and also can be found U.S. Pat. No. 6,955,901, these references are incorporated herein by reference in their entirety. MLPA probes are designed that hybridizes to the target nucleic acid sequences specific for the genes of interest (i.e. NEK6, IRF4, IGHM, CCND1, LMO2, FOXP1, TNFRSF9, BCL6, TNFRSF13B, CCND2, MYC, MYBL1, BCL2, o MS4A1). Each probe is actually in two parts, both of which will hybridize to the target cDNA in close proximity to each other. Each part of the probe carries the sequence for one of the PCR primers. Only when the two parts of the MLPA probe are hybridize to the target DNA in close proximity to each other will the two parts be ligated together, and thus form a complete DNA template for the one pair of PCR primers used. Thus, with the RT-MLPA assay of the present invention, it is possible to perform a multiplex PCR reaction in which the expression levels of at least the 10genes are simultaneously quantified. The method is thus very sensitive. Moreover, MLPA reactions require small amount of cDNA. In contrast to e.g. FISH and BAC-arrays or even RT-PCR, the sequences detected are small (about 60nucleotides), and RT-MLPA is thus particularly adapted to the analysis of partially degraded RNA samples, for example obtained from formalin fixed paraffin embedded tissues. Compared to other techniques, an MLPA reaction is fast, cheap and very simple to perform. The equipment required is present in most molecular biology laboratories.

In some embodiments, the method of the present comprises the following steps of i) preparing a cDNA sample from the tumor tissue sample, ii) incubating the cDNA sample of step i) with a mixture of at least 10 different pairs of probes specific of a target nucleic acid sequence of NEK6, IRF4, IGHM, LMO2, FOXP1, TNFRSF9, BCL6, TNFRSF13B, CCND2 and MYBL1, iii) connecting (i.e. ligating) the first probe to the second probe of the pairs probes, iv) amplifying the ligated probes produced at step iii) and v) detecting and quantifying the amplicons produced at step iv).

In some embodiments, the cDNA sample is also incubated with a pair of probes specific for a target nucleic sequence of CCND1.

In some embodiments, the cDNA sample is also incubated with a pair of probes specific for a target nucleic sequence of MS4A1.

In some embodiments, the cDNA sample is also incubated with a pair of probes specific for a target nucleic sequence of MYC.

In some embodiments, the cDNA sample is also incubated with a pair of probes specific for a target nucleic sequence of BCL2.

In some embodiments, the method of the present comprises the following steps of i) preparing a cDNA sample from the tumor tissue sample, ii) incubating the cDNA sample of step i) with a mixture of at least 14 different pairs of probes specific of a target nucleic acid sequences of NEK6, IRF4, IGHM, LMO2, FOXP1, TNFRSF9, BCL6, TNFRSF13B, CCND2 and MYBL1, iii) connecting (i.e. ligating) the first probe to the second probe of the pairs probes, iv) amplifying the ligated probes produced at step iii) and v) detecting and quantifying the amplicons produced at step iv).

Typically, the cDNA sample is prepared as follows. mRNA contained in the tumor tissue sample is extracted according to standard methods, for example using lytic enzymes or chemical solutions or extracted by nucleic-acid-binding resins following the manufacturer's instructions. Then cDNA synthesis is performed according to standard methods involving reverse transcriptase. In some embodiments, random hexamer primers (instead of gene specific primers) are used for the cDNA synthesis. Random hexamers primers are well known in the art and are typically commercially available from FISCHER.

According to the invention, the pair of probes consists of:
  a first probe having
    a target specific region (L) complementary to the first segment of the target nucleic acid sequence and
    a tail region (TL) at the 5' extremity of the target specific region (L) which is non-complementary to said target nucleic acid sequence,
  a second probe having
    a target specific region (R) complementary to the second segment of the target nucleic acid sequence and; and
    a tail region (TR) at the 3' extremity of the target specific region (R) which is non-complementary to said target nucleic acid sequence As used herein, "probe" refers to a known sequence of a nucleic acid that is capable of selectively binding to a target nucleic acid sequence. More specifically, the term "probe" refers to an oligonucleotide designed to be sufficiently complementary to a sequence of one strand of a nucleic acid that is to be probed such that the probe and nucleic acid strand will hybridise under selected stringency conditions. Typically, the probes of the present invention are chemically synthesised. According to the invention the first probes and the second probes are able to form a litigated probe after the ligation step (step iii)) as explained herein after. As used herein a "ligated probe" refers to the end product of a ligation reaction between the pair of probes. Accordingly, the probes are in a sufficient proximity to allow the 3' end of the first probe that is brought into juxtaposition with the 5' end of the second probe so that they may be ligated by a ligase enzyme. In other words, the 5' end and the 3' end of the two probes, the first one hybridising to the first segment and the second probe to the second segment, are sufficiently near each other to allow connection of the ends of both probes to one another. In some embodiments, the 5' terminal end of the target specific region (R) is phosphorylated to allow ligation as described herein after.

In some embodiments, the target specific regions (L) and (R) of the pair of probes of the present invention long enough to allow hybridization at elevated temperatures (e.g. 60° C.). Typically, the length of the complementary region is at least 20 nucleotides.

In some embodiments, the target specific regions (L) and (R) of the pair of probes of the present invention are designed across exon-exon boundaries to avoid unwanted amplifications from genomic DNA during the step iv).

In some embodiments, the target specific regions (L) and (R) of the pair of probes specific for NEK6 are designed across exon 2 and exon 3 in SEQ ID NO: 1.

In some embodiments, the target specific regions (L) and (R) of the pair of probes specific for IRF4 are designed across exon 6 and exon 7 in SEQ ID NO: 2.

In some embodiments, the target specific regions (L) and (R) of the pair of probes specific for IGHM are designed across exon 2 and exon 3 in SEQ ID NO: 3.

In some embodiments, the target specific regions (L) and (R) of the pair of probes specific for CCND1 are designed across exon 3 and exon 4 in SEQ ID NO: 4.

In some embodiments, the target specific regions (L) and (R) of the pair of probes specific for LMO2 are designed across exon 5 and exon 6 in SEQ ID NO: 5.

In some embodiments, the target specific regions (L) and (R) of the pair of probes specific for FOXP1 are designed across exon 10 and exon 11 in SEQ ID NO: 6.

In some embodiments, the target specific regions (L) and (R) of the pair of probes specific for TNFRSF9 are designed across exon 3 and exon 4 in SEQ ID NO: 7.

In some embodiments, the target specific regions (L) and (R) of the pair of probes specific for BCL6 are designed across exon 3 and exon 4 in SEQ ID NO: 8.

In some embodiments, the target specific regions (L) and (R) of the pair of probes specific for TNFRSF13B are designed across exon 2 and exon 3 in SEQ ID NO: 9.

In some embodiments, the target specific regions (L) and (R) of the pair of probes specific for CCND2 are designed across exon 1 and exon 2 in SEQ ID NO: 10.

In some embodiments, the target specific regions (L) and (R) of the pair of probes specific for MYC are designed across exon 1 and exon 2 in SEQ ID NO: 11.

In some embodiments, the target specific regions (L) and (R) of the pair of probes specific for MYBL1 are designed across exon 10 and exon 11 in SEQ ID NO: 12.

In some embodiments, the target specific regions (L) and (R) of the pair of probes specific for BCL2 are designed across exon 1 and exon 2 in SEQ ID NO: 13.

In some embodiments, the target specific regions (L) and (R) of the pair of probes specific for MS4A1 are designed across exon 5 and exon 6 in SEQ ID NO: 14.

In some embodiments, the pair of probes specific for NEK6 consists of a first probe having its target specific region (L) as set forth by SEQ ID NO:15 (CCTGTGCATC-CTCCTGACCCACAG) and a second probe having its target specific region (R) as set forth by SEQ ID NO:16 (AGGCATCCCAACACGCTGTCTTT).

In some embodiments, the pair of probes specific for IRF4 consists of a first probe having its target specific region (L) as set forth by SEQ ID NO:17 (CTGCCGAAGCCTTG-GCGTTCTCAG) and a second probe having its target specific region (R) as set forth by SEQ ID NO:18 (ACT-GCCGGCTGCACATCTGCCTGTA).

In some embodiments, the pair of probes specific for IGHM consists of a first probe having its target specific region (L) as set forth by SEQ ID NO:19 (GCGTCCTC-CATGTGTGGCCCCG) and a second probe having its target specific region (R) as set forth by SEQ ID NO:20 (AT-CAAGACACAGCCATCCGGGTCTTC).

In some embodiments, the pair of probes specific for CCND1 consists of a first probe having its target specific region (L) as set forth by SEQ ID NO:21 (ACCTTCGTT-GCCCTCTGTGCCACAG) and a second probe having its target specific region (R) as set forth by SEQ ID NO:22 (ATGTGAAGTTCATTTCCAATCCGCCCT).

In some embodiments, the pair of probes specific for LMO2 consists of a first probe having its target specific region (L) as set forth by SEQ ID NO:23 (CGGAAGCTCT-GCCGGAGAGACTATCTCAG) and a second probe having its target specific region (R) as set forth by SEQ ID NO:24 (GCTTTTTGGGCAAGACGGTCTCTGC).

In some embodiments, the pair of probes specific for FOXP1 consists of a first probe having its target specific region (L) as set forth by SEQ ID NO:25 (CCCTTCCCCT-TCAACCTCTTGCTCAAG) and a second probe having its target specific region (R) as set forth by SEQ ID NO:26 (GCATGATTCCAACAGAACTGCAGCAGC).

In some embodiments, the pair of probes specific for TNFRSF9 consists of a first probe having its target specific region (L) as set forth by SEQ ID NO:27 (GGACCTGT-GACATATGCAGGCAGTGTAAAG) and a second probe having its target specific region (R) as set forth by SEQ ID NO:28 (GTGTTTTCAGGACCAGGAAGGAGTGTTCC).

In some embodiments, the pair of probes specific for BCL6 consists of a first probe having its target specific region (L) as set forth by SEQ ID NO:29 (CATAAAACG-GTCCTCATGGCCTGCAG) and a second probe having its target specific region (R) as set forth by SEQ ID NO:30 (TGGCCTGTTCTATAGCATCTTTACAGACCAGTTG).

In some embodiments, the pair of probes specific for TNFRSF13B consists of a first probe having its target specific region (L) as set forth by SEQ ID NO:31 (GCG-CACCTGTGCAGCCTTCTGCA) and a second probe having its target specific region (R) as set forth by SEQ ID NO:32 (GGTCACTCAGCTGCCGCAAGGAGC).

In some embodiments, the pair of probes specific for CCND2 consists of a first probe having its target specific region (L) as set forth by SEQ ID NO:33 (GACCTTCAT-TGCTCTGTGTGCCACCG) and a second probe having its target specific region (R) as set forth by SEQ ID NO:34 (ACTTTAAGTTTGCCATGTACCCACCGTCGA).

In some embodiments, the pair of probes specific for MYC consists of a first probe having its target specific region (L) as set forth by SEQ ID NO:35 (TCGGGTAGTG-GAAAACCAGCAGCCTC) and a second probe having its target specific region (R) as set forth by SEQ ID NO:36 (CCGCGACGATGCCCCTCAACGTTA).

In some embodiments, the pair of probes specific for MYBL1 consists of a first probe having its target specific region (L) as set forth by SEQ ID NO:37 (CCAGAATTT-GCAGAGACTCTAGAACTTATTGAATCT) and a second probe having its target specific region (R) as set forth by SEQ ID NO:38 (GATCCTGTAGCATGGAGTGACGT-TACCAGTTTT).

In some embodiments, the pair of probes specific for BCL2 consists of a first probe having its target specific region (L) as set forth by SEQ ID NO:39 (CCTGGATC-CAGGATAACGGAGGCTGG) and a second probe having its target specific region (R) as set forth by SEQ ID NO:40 (GATGCCTTTGTGGAACTGTACGGCC).

In some embodiments, the pair of probes specific for MS4A1 consists of a first probe having its target specific region (L) as set forth by SEQ ID NO:41 (TTCTTCAT-GAGGGAATCTAAGACTTTGGGG) and a second probe having its target specific region (R) as set forth by SEQ ID NO:42 (GCTGTCCAGATTATGAATGGGCTCTTCCAC).

According to the invention, the tail region TR and the reverse complement sequence or the tail region TL of the probes are designed so as to be capable of hybridizing with a primer.

In some embodiments, the tail regions (TL) and (TR) can be of any size, and typically comprises a nucleic acid sequence with a length of at least 15 nucleotides.

In some embodiments, the tail region (TL) of the first probes are identical for each pair of probes and the tail regions (TR) of the second probe are also identical for each pair of probes so that the amplification of the primer assemblies during the step iv) is carried out with only one pair of primers and thus excluding any bias in the amplification of the probes due to sequence differences in the primers.

In some embodiments, the pairs of probes of the present invention comprise first probes having the same tail region (TL) as set forth by SEQ ID NO:43 (GTGCCAG-CAAGATCCAATCTAGA).

In some embodiments, the pairs of probes of the present invention comprise second probes having the same tail region (TR) as set forth by SEQ ID NO: 44 (TCCAAC-CCTTAGGGAACCC).

In some embodiments, the probes of the present invention comprise a spacer region placed between the target specific region and the tail region. The spacer region can be of any size, and typically comprises a nucleic acid with a length of at least 1 nucleotide (e.g. A, C, T or G). By varying the size of the spacer region one can easily design probes that comprise the same hybridisation capacity (wherein the length of complementarity region with the target nucleic acid sequence and the CG/AT content are adjusted to each other), while still being able to discriminate the resulting amplicons by size. In some embodiments, the spacer region comprises a plurality of trinucleotides repeats (e.g. TAC repeats). The spacer regions are of particular interest in the multiplex amplification as explained herein after to allow the discrimination of the different amplicons that can result from said amplification. Discrimination will be indeed achieved since the size of each amplicon that can occur is different.

In some embodiments, the spacer region is selected from the group consisting of TAC (SEQ ID NO: 45), TACT (SEQ ID NO:46), TACTA (SEQ ID NO:47), TACTACT (SEQ ID NO:48), TACTACTACT (SEQ ID NO:49), TACTAC-TACTA (SEQ ID NO:50), TACTACTACTAC (SEQ ID NO:51), TACTACTACTACTA (SEQ ID NO:52), and TAC-TACTACTACTACT (SEQ ID NO:53).

In some embodiments, the pair of probes specific for NEK6 consists of a first probe which is SEQ ID NO:54 (GTGCCAGCAAGATCCAATCTAGACCTGTGCATC-CTCCTGACCCACAG) and a second probe which is SEQ ID NO:55 (AGGCATCCCAACACGCTGTCTTTTC-CAACCCTTAGGGAACCC).

In some embodiments, the pair of probes specific for IRF4 consists of a first probe which is SEQ ID NO:56 (GTGC-CAGCAAGATCCAATCTAGATCTGCCGAAGCCTTG-GCGTTCTCAG) and a second probe which is SEQ ID NO:57 (ACTGCCGGCTGCACATCTGCCTGTATC-CAACCCTTAGGGAACCC).

In some embodiments, the pair of probes specific for IGHM consists of a first probe which is SEQ ID NO:58 (GTGCCAGCAAGATCCAATCTAGATGCGTCCTCCAT-GTGTGGCCCCG) and a second probe which is SEQ ID NO:59 (ATCAAGACACAGCCATCCGGGTCTTCTAC-TATCCAACCCTTAGGGAACCC).

In some embodiments, the pair of probes specific for CCND1 consists of a first probe which is SEQ ID NO:60 (GTGCCAGCAAGATCCAATCTAGATACCTTCGTTGC-CCTCTGTGCCACAG) and a second probe which is SEQ ID NO:61 (ATGTGAAGTTCATTTCCAATCCGCCCT-TACTTCCAACCCTTAGGGAACCC).

In some embodiments, the pair of probes specific for LMO2 consists of a first probe which is SEQ ID NO:62 (GTGCCAGCAAGATCCAATCTAGACGGAAGCTCT-GCCGGAGAGACTATCTCAG) and a second probe which is SEQ ID NO:63 (GCTTTTTGGGCAAGACGGTCTCT-GCTACTATCCAACCCTTAGGGAACCC).

In some embodiments, the pair of probes specific for FOXP1 consists of a first probe which is SEQ ID NO:64 (GTGCCAGCAAGATCCAATCTAGACCCTTCCCCT-TCAACCTCTTGCTCAAG) and a second probe which is SEQ ID NO:65 (GCATGATTCCAACAGAACTGCAGCA-GCTACTACTACTCCAACCCTTAGGGAACCC).

In some embodiments, the pair of probes specific for TNFRSF9 consists of a first probe which is SEQ ID NO:66 (GTGCCAGCAAGATCCAATCTAGATACGGACCTGT-GACATATGCAGGCAGTGTAAAG) and a second probe which is SEQ ID NO:67 (GTGTTTTCAGGACCAG-GAAGGAGTGTTCCTACTCCAACCCT-TAGGGAACCC).

In some embodiments, the pair of probes specific for BCL6 consists of a first probe which is SEQ ID NO:68 (GTGCCAGCAAGATCCAATCTAGATACTACT-CATAAAACGGTCCTCATGGCCTGCAG) and a second probe which is SEQ ID NO:69 (TGGCCTGTTCTATAG-CATCTTTACAGACCAGTTGTCCAACCCT-TAGGGAACCC).

In some embodiments, the pair of probes specific for TNFRSF13B consists of a first probe which is SEQ ID NO:70 (GTGCCAGCAAGATCCAATCTAGATACTAC-TACTAGCGCACCTGTGCAGCCTTCTGCA) and a second probe which is SEQ ID NO:71 (GGTCACTCAGCT-GCCGCAAGGAGCTACTACTACTACTCCAACCCTTAGGGAACCC).

In some embodiments, the pair of probes specific for CCND2 consists of a first probe which is SEQ ID NO:72 (GTGCCAGCAAGATCCAATCTAGATACTACTGACCT-TCATTGCTCTGTGTGCCACCG) and a second probe which is SEQ ID NO:73 (ACTTTAAGTTTGCCATGTAC-CCACCGTCGATACTACTATCCAACCCT-TAGGGAACCC).

In some embodiments, the pair of probes specific for MYC consists of a first probe which is SEQ ID NO:74 (GTGCCAGCAAGATCCAATCTAGATACTACTACT-TCGGGTAGTGGAAAACCAGCAGCCTC) and a second probe which is SEQ ID NO:75 (CCGCGACGATGCCCCT-CAACGTTATACTACTACTACTATCCAACCCT-TAGGGAACCC).

In some embodiments, the pair of probes specific for MYBL1 consists of a first probe which is SEQ ID NO:76 (GTGCCAGCAAGATCCAATCTAGACCAGAATTT-GCAGAGACTCTAGAACTTATTGAATCT) and a second probe which is SEQ ID NO:77 (GATCCTGTAGCATG-GAGTGACGTTACCAGTTTTTACTACTTCCAACCCT-TAGGGAACCC).

In some embodiments, the pair of probes specific for BCL2 consists of a first probe which is SEQ ID NO:78 (GTGCCAGCAAGATCCAATCTAGATACTACTACTAC-CCTGGATCCAGGATAACGGAGGCTGG) and a second probe which is SEQ ID NO:79 (GATGCCTTTGTG-GAACTGTACGGCCTACTACTACTACTACTTCCAAC-CCTTAGGGAACCC).

In some embodiments, the pair of probes specific for MS4A1 consists of a first probe which is SEQ ID NO:80 (GTGCCAGCAAGATCCAATCTAGATACTACTACTAT-TCTTCATGAGGGAATCTAAGACTTTGGGG) and a second probe which is SEQ ID NO:81 (GCTGTCCAGATTAT-GAATGGGCTCTTCCACTACTACTACTATCCAACCCTTAGGGAACCC).

In some embodiments, the cDNA sample is also incubating with a mixture of competitor probes.

As used herein the term "competitor probe" refers to a probe specific for the target nucleic acid sequence wherein said probe does not contain a tail region as defined above. The competitor probe is suitable for normalizing the amplification signals of the target nucleic acid sequence during the amplification step of the present invention.

In some embodiments, the cDNA sample is also incubated with at least one competitor probe specific for NEK6 or IRF4.

In some embodiments, the cDNA sample is incubated with a competitor probe specific for NEK6. In some embodiments, the cDNA sample is incubated with a competitor probe specific for NEK6 which is SEQ ID NO:82 (AG-GCATCCAACACGCTGTCTTT).

In some embodiments, the cDNA sample is incubated with a competitor probe specific for IGHM. In some embodiments, the cDNA sample is incubated with a competitor probe specific for IGHM which is SEQ ID NO:83 (ATCAAGACACAGCCATCCGGGTCTTC).

In some embodiments, the cDNA sample is incubated with the pairs of probes specific for the five GCB genes (LMO2, MYBL1, BCL6, NEK6, TNFRSF9) and the five ABC genes (IRF4, FOXP1, IGHM, TNFRSF13B, CCND2) and 2 competitor probes for NEK6 and IGHM.

In some embodiments, the cDNA sample is incubated with the pairs of probes specific for the five GCB genes (LMO2, MYBL1, BCL6, NEK6, TNFRSF9), the five ABC genes (IRF4, FOXP1, IGHM, TNFRSF13B, CCND2), the 2 prognostic genes (MYC and BCL2) and the 2 control genes (CCND1 and MS4A1) and the 2 competitor probes for NEK6 and IGHM.

In some embodiments, the cDNA sample is incubated with the nucleic acid sequences SEQ ID NO:54-73 (probes specific for LMO2, MYBL1, BCL6, NEK6, TNFRSF9, IRF4, FOXP1, IGHM, TNFRSF13B, CCND2, MYC, BCL2, CCND1 and MS4A1) and with the nucleic acids SEQ ID NO:82-83 (competitor probes for NEK6 and IGHM).

Typically, the probes of the same pair of probes are present in the mixture in substantially equal amounts, although the said amounts can differ from one another, e.g. dependent on the hybridisation characteristics of the target specific regions with the target nucleic acid sequence.

Typically, the amount of probes in the mixture is less than 10 femtomoles. In some embodiments, the amount of the probed in the mixture is about 3 fentomoles.

In some embodiments, the molar ratio between the probes and the corresponding competitor probe ranges from 1 to 4.

According to the invention, the cDNA sample is incubated with the pairs of probes and optionally with the competitor probes for a sufficient time for allowing hybridization of the probes to the 14 target nucleic acid sequences.

Typically, hybridizing the probes to the target nucleic acid sequences is faster in buffers of high ionic strength. The salt concentration of the buffer has to be reduced however to less than approximately 150 mM after the hybridization reaction for optimal ligase activity. Inclusion of certain chemicals such as polyethyleenglycol polymers or proteins such as BSA may increase both the ligation activity as well as the probed hybridisation speed and do not interfere below certain limits with the ligation and amplification reactions. According to the invention, it is possible to obtain a so called "one-tube reaction" by careful selection of the hybridisation, ligation and amplification reaction conditions.

The duration of the probe hybridization is very important. Some probes will hybridise faster than others. This is due to a difference in length of the hybridising sequence; the presence or absence of regions with a high % G/C (GC-clamps); secondary structure of the probes and/or the target nucleic acid sequence etc. According to the invention, care has to be taken that either hybridisation of each probe is complete, or that hybridisation of none of the probes is complete. Hybridization of the probes to the target nucleic acid sequences is concentration dependent and is typically performed in a small volume in the order of 8 µL. and at temperatures of 50-65° C. in order to prevent hybridization of probes to non specific targets. In order to prevent evaporation the use of a thermocycler with heated lid is preferred.

In some embodiments, the cDNA sample is incubated with the pairs of probes and optionally with the competitor probed for of about 60 min but longer time can also convenient.

Typically, the ligation step iii) is performed with a thermostable nucleic acid ligase active at temperatures of 50° C. or higher, but capable of being rapidly inactivated above approximately 95° C. Once probes are connected it is preferred that essentially no connecting activity is present during amplification since this is not required and can only introduce ambiguity in the method. Since the subsequently amplification steps usually require repeated denaturation of template nucleic acid at temperatures above 95° C. it is preferred to remove the connecting activity through said heat incubation. In order to prevent hybridisation of probes to sequences only partially complementary it is particularly recommended to perform the ligation reaction at temperatures of at least 50° C. The present invention therefore in one aspect provides a method wherein ligation of probes annealed to a target nucleic acid is performed by a thermostable nucleic acid ligation enzyme, i.e. with an activity optimum higher than at least 50° C., under suitable conditions, wherein at least 95% of the ligation activity of the said ligation enzyme is inactivated by incubating for example said sample for 10 minutes at a temperature of approximately 95° C.

Typically, the ligase is selected from the group consisting of DNA ligases. DNA ligases are enzymes capable of forming a covalent phosphate link between two oligonucleotides bound at adjacent sites on a complementary strand. These enzymes use either NAD or ATP as a cofactor to seal nicks in ds DNA. Alternatively chemical autoligation of modified DNA-ends can be used to ligate two oligonucleotides bound at adjacent sites on a complementary strand (Xu, Y. & Kool, E. T. (1999), Nucleic Acid Res. 27, 875-881). Both chemical as well as enzymatic ligation is much more efficient on perfectly matched probe-target nucleic acid complexes compared to complexes in which one or both of the oligonucleotides form a mismatch with the target nucleic acid at, or close to the ligation site (Wu, D. Y. & Wallace, R. B. (1989) Gene, 76, 245-254; Xu, Y. & Kool, E. T. (1999), Nucleic Acid Res. 27, 875-881).

In some embodiments, a ligase is used that remains active at 50-65° C. for prolonged times, but which can be easily inactivated at the higher temperatures used during a PCR reaction. The only ligases commercially available at the moment are enzymes that function only at temperatures below 50° C. such as the DNA ligase encoded by E. coli and by phage T4, and thermostable enzymes that have a half-life of more than 30 minutes at temperatures of 95° C. such as the DNA ligase encoded by Thermus aquaticus. For example, the ligase is "Ligase 65" which is commercially available from MRC Holland. Ligase-65 is active at 60-65° C. In contrast to Tth- and Taq DNA ligase however, the activity of ligase-65 is destroyed more than 90% by incubation in the optimum reaction buffer for 10 minutes at 95° C.

The ligation step is usually carried out in a relatively small volume of 40 μl, although larger volumes, as well as increase of volume of the reaction mixture in subsequent reaction steps are tolerated.

In some embodiments, the duration of the ligation step ranges from 10 min to 30 min. Typically, the duration of the step is about 15 min.

According to the invention, amplification is initiated by incubating the sample with an amount of a first primer (U1) specific for the tail region (TL) and an amount of a second primer (U2) specific for the tail region (TR).

As used herein, the term "primer" refers to an oligonucleotide, whether occurring naturally as in a purified restriction digest or produced synthetically, which is capable of acting as a point of initiation of nucleic acid sequence synthesis when placed under conditions in which synthesis of a primer extension product which is complementary to a nucleic acid strand is induced, i.e. in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand.

In some embodiments, the pair of primers is ILLU1 (SEQ ID NO: 84) (GGGTTCCCTAAGGGTTGGA) and ILLU2 (SEQ ID NO: 85) (GTGCCAGCAAGATCCAATCTAGA).

Typically, the primer (e.g. ILLU2) of the present invention is labelled at its 5' end with a fluorophore. Suitable fluorophores include, but are not limited to, 5- or 6-carboxyfluorescein (FAM™); ALEXA FLUOR®405, 430, 488, 532, 546, 555, 568, 594, 633, 647 , or 660; Cy2; Cy3; Cy3.5; Cy5; Cy5.5; Cy7; hydroxycoumarin; methoxycoumarin; aminocoumarin; fluorescein; HEX; R-phycoerythrin; rhodamine Red-X; ROX; Red 613; TEXAS RED®; allophycocyanin; TruRed; BODIPY® 630/650; BODIPY® 650/665; BODIPY®-FL; BODIPY®-R6G; BODIPY®-TMR; BODIPY®-TRX; carboxyfluorescein; CASCADE BLUE®; 6-JOE; Lissamine rhodamine B; OREGON GREEN® 488, 500 , or 514; PACIFIC BLUE®; REG; Rhodamine Green; SpectrumAqua; TAMRA; TET; and Tetramethylrhodamine.

As used herein, "amplification" refers to the increase in the number of copies of a particular nucleic acid. Copies of a particular nucleic acid made in vitro in an amplification reaction are called "amplicons" or "amplification products".

Accordingly, following the ligation reaction, the ligated probed can be amplified with the use of two primers, dNTP's and a polymerase, one primer being complementary to one of the sequence tail region and the other primer corresponding in sequence to the second tail region.

As explained above, although it is possible for the first probe of different pair of probes to have different tail region sequences, implicating that a plurality of different first primers are to be used in the amplification step it is highly preferred that the first tail regions of the first probes of the different pair of probes are identical, so that only one first primer has to be used in the amplification reaction. A bias in the amplification due to a difference in the sequence of different primers used for the amplification can thus be completely avoided, resulting in a substantially uniform amplification for all probe assemblies. According to the invention it is however also possible that a number of first nucleic acid probes comprise the same tail region, whereas first probes belonging to another pair of probes may comprise another first tail region.

The preferred method for amplification is PCR. The typical conditions include a sufficiently long elongation time and the presence of a higher concentration of Taq polymerase than in ordinary PCR reactions. Other amplification methods than PCR such as NASBA or 3SR (Guatelli et al., Proc. Natl. Acad. Sci. USA 87:1874-1878, 1990) can also be used in combination with the current invention.

In some embodiments, the ligase and the polymerase are added simultaneously and wherein the ligase is active at moderate temperatures and is inactivated at high temperatures whereas the polymerase is activated only after the heating step.

As the buffer composition during the ligation reaction is very similar to a standard PCR buffer, it is possible to use the complete volume of the ligation reaction and start the amplification reaction by the addition of primers, dNTP's, a small amount of a non-ionic detergent such as 0.01% triton X-100 and a heat stable polymerase such as Taq polymerase. The presence of other compounds such as betaine, are known to improve some multiplex PCR amplification reactions and do not severely inhibit the ligation reaction.

For most experiments it is advantageous to use PCR conditions that prevent a bias in the amplification of some amplicons. Important in this respect is that the concentrations of the amplicons during the later stages of the amplification reaction do not reach very high concentrations. This can be accomplished by using only low amounts of one of the PCR primers. A bias in the amplification of some amplicons will be due to faster renaturation kinetics of some amplicons after each denaturation cycle and displacement of PCR primers by the complementary strand of the amplicon. Important in this respect is also the nature of the first nucleotide following the PCR primer, G or C being the preferred first nucleotides. This displacement can be reduced when using PCR primers containing one or more LNA residues at their 3' end. LNA (Locked Nucleic Acids) residues have an improved thermostability of duplexes towards complementary DNA strands (Wahlestedt, C. Et al. Proc. Natl. Acad. Sci. USA 97, 5633-38).

In some embodiments, it is advantageous to use PCR conditions that promote the amplification of rare templates as compared to the amplification of more abundant templates in order to obtain amplifications of almost equal intensity for the different nucleic acid target sequences. These PCR conditions typically include: (1) The use of higher salt concentrations which promote the hybridization of complementary strands and reduce the polymerase activity; (2) High concentrations of primers (3) Reduced hybridization/extension temperatures during the last PCR-cycles; (4) Additives to the PCR buffer such as betaine and DMSO.

Typically, the molar ratio between the primer and the probe is preferably at least 200, more preferably at least 500, even more preferably at least 1000 and most preferably at least 2000. The higher the said ratio, the more different primer sets for the detection of a corresponding number of different amplicons can be used. However, as indicated above, unspecific amplification reactions as a result of high primer concentrations is to be avoided. Thereto, the primer concentration preferably is below 50 pMoles, more preferably below 20 pMoles in a reaction volume of 10-100 µl. The amplification step is usually performed in a volume of 20-150 µl; for this, the optionally smaller volume of the reaction mixture in the ligation step is usually completed to the desired volume for the amplification by adding the additional ingredients for the amplification reaction.

In some embodiments, the duration of the amplification step ranges from 60 min to 120 min. Typically, the duration of the step is about 90 min.

Any method well known in the art can be used for detecting and quantifying the amount of the amplicons. Typically, fluorescent primers are used along with a fluorescent detection system. Detection of fluorescence during the thermal cycling process can be performed for instance with the use of a capillary electrophoresis analyzer. In capillary electrophoresis, the lengths of amplicons are examined by allowing them to migrate through a thin tube filled with gel and measuring a period of time required for the sample to migrate a certain distance (e.g., to the end of a capillary). Upon capillary electrophoresis, it is usual to detect the amplicon using a fluorescence signal detector that is installed at the end of a capillary. Apparatuses for carrying out capillary electrophoresis are well-known. Many references are available describing the basic apparatus and several capillary electrophoresis instruments are commercially available, e.g., from Applied Biosystems (Foster City, Calif.). Exemplary references describing capillary electrophoresis apparatus and their operation include Jorgenson, Methods 4:179-90 (1992); Colburn et al., Applied Biosystems Research News, issue 1 (winter 1990); and the like.

In some embodiments, the duration of the step for detecting and quantifying the amplicons ranges from 15 min to 45 min. Typically, the duration of the step is about 30 min.

In some embodiments, the method of the present invention further comprises a step consisting of calculating a score which represents the probability that the DLBCL belongs to a particular class (ABC vs GCB).

As described in the EXAMPLE, the score may result from an adaptation of the Linear Predictor Score (LPS) defined by Wright et al (Wright et al. Proc Natl Acad Sci USA. 2003 Aug. 19; 100(17):9991-6) and a Bayesian predictor. The skilled artisan can indeed adopt the assumption that the distributions of the scores within the GCB and ABC groups follow normal distributions, which allows estimating the probability for each case to belong to one or the other subtype. To balance the over-weighting of the most highly expressed genes (a marginal phenomenon in heavily normalized and log-transformed values used in Wright's publication which is no longer negligible with the linear scaled values manipulated here), scaling factors can be applied to account for the differences in expression ranges between the different genes by dividing all t statistics by the mean expression of their corresponding genes in the training series.

In some embodiments, the score (LPS) is calculated via the formula:

$$LPS(X) = \sum_{g \in G} \left( \frac{t_g}{m_g} * X_g \right) \text{ wherein } X_g = \frac{H_g}{\frac{1}{n} * \sum_{j \in J} H_j}$$

and wherein G represents the set of 10 GCB-ABC genes, J represents the set of n=14 measured genes, $t_g$ represents the t statistics generated by a t-test for the difference in expression of gene g between GCB and ABC cases in the training series, $m_g$ represents the arithmetic mean of gene expressions for gene g in the training series and $X_g$ represents the gene expression of gene g in the considered sample. The gene expression $X_g$ of gene g in a given sample is computed as the maximal height $H_g$ of the fluorescence peak measured for gene g divided by the arithmetic mean of the 14 peaks measured for the considered sample.

In some embodiments, the $t_g$ and $m_g$ values are defined according to Table A:

TABLE A

| Gene (g) | $t_g$ | $m_g$ |
|---|---|---|
| NEK6 | −6.09456 | 0.37762 |
| MYBL1 | −4.00549 | 0.30712 |
| LMO2 | −8.80942 | 0.79006 |
| TACI | 4.46992 | 0.41455 |
| TNFRSF9 | −2.50028 | 0.34052 |
| BCL6 | −3.16453 | 0.44348 |
| CCND2 | 2.7198 | 0.70859 |
| IRF4 | 5.35073 | 1.95678 |
| IGHM | 5.0939 | 2.87208 |
| FOXP1 | 2.67211 | 1.63401 |

In some embodiments, the method of the present invention further comprises the steps of comparing the score (LPS) with scores obtained with the same method in a training series of GCB and ABC cases classified by a reference method, and compute for each sample the likelihood to belong to the GCB and ABC groups:

$$P(X \in ABC) = \frac{\Phi(LPS(X), \hat{\mu}_{ABC}, \hat{\sigma}^2_{ABC})}{\Phi(LPS(X), \hat{\mu}_{ABC}, \hat{\sigma}^2_{ABC}) + \Phi(LPS(X), \hat{\mu}_{GCB}, \hat{\sigma}^2_{GCB})}$$

$$P(X \in GCB) = 1 - P(X \in ABC)$$

wherein $\Phi(x, \mu, \sigma^2)$ represents the probability density function of a normal distribution of mean µ and standard deviation $\sigma^2$, $\mu_{ABC}$ and $\mu_{GCB}$ represent respectively the arithmetic means of the LPS scores in the ABC and GCB cases of the training series, $\sigma^2_{ABC}$ and $\sigma^2_{GCB}$ represent respectively the standard deviations of the LPS scores in the ABC and GCB cases of the training series. Samples for which the probability to belong to the ABC group is higher than a predetermined confidence threshold (e.g. 90%) are finally classified ABC, and respectively for the GCB group. Samples that fail to classify as one of these two groups are termed "unclassified". In some embodiments, the μ and σ² values are determined as described in Table B:

TABLE B

|  | ABC | GCB |
|---|---|---|
| μ | 18.72886 | −33.53634 |
| σ² | 10.21838 | 18.12447 |

The method of the present invention is thus particularly suitable for determining whether a subject is eligible or not to a treatment. Treatments of DLBCL are well known in the art (Mark Roschewski, Louis M. Staudt and Wyndham H. Wilson. Diffuse large B-cell lymphoma—treatment approaches in the molecular era. Nat. Rev. Clin. Oncol. 11, 12-23 (2014)). Basal treatment includes administering the subject with cyclophosphamide, doxorubicin, vincristine, prednisone and ritxumimab (R-CHOP) or with etoposide, doxorubicin, cyclophosphamide, vincristine, prednisone and rituximab (DA-EPOCH-R). Subjects with GCB DLBCL have better prognoses than those with ABC DLBCL when treated with R-CHOP or with DA-EPOCH-R. Histone-lysine N-methyltransferase EZH2 (EZH2) inhibitors (e.g. GSK126 and E11 E7438) could be particularly suitable for the treatment of GCB DLBCL. Inhibitors of PI3K/Akt/mTOR pathway (e.g. LY294002, Everolimus, temsirolimus, Idelalisib also known as CAL-101 or MK-2206) could be particularly suitable for the treatment of GCB DLBCL. BCL2 inhibitors (e.g. Navitoclax (ABT-263), ABT-199, or ABT-737) could be particularly suitable for the treatment of GCB DLBCL. BCL6 inhibitors (e.g. small-molecule inhibitor 79-6) could be particularly suitable for the treatment of GCB DLBCL. Inhibitors of NF-κB pathway could be particularly suitable for the treatment of ABC DLBCL. Inhibitors of NF-κB pathway typically include but are not limited to inhibitors of the IκB kinase (IKK) and inhibitors of proteasome (e.g. Bortezomib, Carfilzomib). For instance Bortezomib plus DA-EPOCH (or R-CHOP) resulted in higher response rates and survival in patients with ABC DLBCL compared with GCB DLBCL. Lenalidomide, could also be particularly suitable for the treatment of ABC DLBCL. Ibrutinib, formerly PCI-32765, which is an oral small-molecule inhibitor that selectively and irreversibly inhibits Bruton tyrosine kinase (BTK) through covalent binding via cysteine-481 could be also particularly suitable for the treatment of ABC DLBCL. Enzastaurin or Sotrastaurin which is are inhibitors of PKC-β could be particularly suitable for the treatment of ABC DLBCL. Inhibitors of JAK-1 and JAK-2 (e.g. Ruxolitinib) could also be particularly suitable for the treatment of ABC DLBCL.

In some embodiments, the method of the present invention is not only particularly suitable for classifying the subject's DLBCL into a GCB-DLBCL or into a ABC-DLBCL but also can also be suitable for determining whether the subject will achieve a response with an anti-CD20antibody if the expression level of MS4A1is included in the RT-MPLPA assay. Examples of antibodies specific for CD20 antigen include: "C2B8" which is now called "Rituximab" ("RITUXAN®") (U.S. Pat. No. 5,736,137, expressly incorporated herein by reference), a chimaeric pan-B antibody targeting CD20; the yttrium-[90]-labeled 2B8murine antibody designated "Y2B8" or "Ibritumomab Tiuxetan" ZEVALIN®(U.S. Pat. No. 5,736,137, expressly incorporated herein by reference), a murine IgG1 kappa mAb covalently linked to MX-DTPA for chelating to yttrium-[90]; murine IgG2a "B1," also called "Tositumomab," optionally labeled with radioactive 131 1 to generate the "I 31I-B1" antibody (iodine 131tositumomab, BEXXAR™) (U.S. Pat. No. 5,595,721, expressly incorporated herein by reference); murine monoclonal antibody "1F5" (Press et al. Blood 69(2):584-591(1987) and variants thereof including "framework patched" or humanized 1 F5 (W 003/002607, Leung, S.; ATCC deposit HB-96450); murine 2H7and chimeric 2H7antibody (U.S. Pat. No. 5,677,180, expressly incorporated herein by reference); humanized 2H7, also known as ocrelizumab (PRO-70769); Ofatumumab (ARZERRA®), a fully human IgG1against a novel epitope on CD20huMax-CD20(GENMAB®, Denmark; WO2004/035607(U.S. 10/687,799, expressly incorporated herein by reference)); AME-133(ocaratuzumab; Applied Molecular Evolution), a fully-humanized and optimized IgG1 mAb against CD20; A20antibody or variants thereof such as chimeric or humanized A20 antibody (cA20, hA20, respectively) (U.S. 10/366,709, expressly incorporated herein by reference, IMMUNOMEDICS®); and monoclonal antibodies L27, G28-2, 93-1B3, B-CI or NU-B2available from the International Leukocyte Typing Workshop (Valentine et al, In: Leukocyte Typing III (McMichael, Ed., p. 440, Oxford University Press (1987)). Further, suitable antibodies include e.g. antibody GA101(obinutuzumab), a third generation humanized anti-CD20-antibody of BIOGEN IDEC®/GENENTECH®/ ROCHE®. Moreover, BLX-301of Biolex Therapeutics, a humanized anti CD20with optimized glycosylation or Veltuzumab (hA20), a 2nd-generation humanized anti-CD20antibody of IMMUNO-MEDICS® or DXL625, derivatives of veltuzumab, such as the bispecific hexavalent antibodies of IBC Pharmaceuticals (IMMUNOMEDICS®) which are comprised of a divalent anti-CD20 IgG of veltuzumab and a pair of stabilized dimers of Fab derived from milatuzumab, an anti-CD20mAb enhanced with InNexus' Dynamic Cross Linking technology, of Inexus Biotechnology both are humanized anti-CD20antibodies are suitable. Further suitable antibodies are BM-ca (a humanized anti-CD20antibody (Int J Oncol. 201 1Feb;38(2):335-44)), C2H7(a chimeric anti-CD20antibody (Mol Immunol. 2008May;45(10):2861-8)), PRO131921(a third generation anti-CD20antibody developed by GENENTECH®), Reditux (a biosimilar version of rituximab developed by Dr Reddy's), PBO-326(a biosimilar version of rituximab developed by Probiomed), a biosimilar version of rituximab developed by Zenotech, TL-01 1(a biosimilar version of rituximab developed by TEVA®), CMAB304(a biosimilar version of rituximab developed by Shanghai CP Guojian), GP-2013(a biosimilar version of rituximab developed by SANDOZ® (NOVARTIS®)), SAIT-101(a biosimilar version of rituximab developed by SAMSUNG BIOLOGICS®), a biosimilar version of rituximab developed by INTAS BIOPHARMACEUTICALS®, CT-P10(a biosimilar version of rituximab developed by CELLTRION®), a biosimilar version of rituximab developed by BIOCAD®, Ublituximab (LFB-R603, a transgenically produced mAb targeting CD20 developed by GTC Biotherapeutics (LFB Biotechnologies)), PF-05280586 (presumed to be a biosimilar version of rituximab developed by PFIZER®), Lymphomun (Bi-20, a trifunctional anti-CD20and anti-CD3antibody, developed by Trion Pharma), a biosimilar version of rituximab developed by Natco Pharma, a biosimilar version of rituximab developed by iBio, a biosimilar version of rituximab developed by Gedeon Richter/Stada, a biosimilar version of rituximab developed by Curaxys, a biosimilar version of rituximab developed by Coherus Biosciences/ DAIICHI SANKYO®, a biosimilar version of rituximab developed by BIOXPRESS®, BT-D004(a biosimilar version of rituximab developed by Protheon), AP-052(a biosimilar version of rituximab developed by Aprogen), a biosimilar version of ofatumumab developed by BIOXPRESS®, MG-1 106(a biosimilar version of rituximab developed by Green Cross), IBI-301(a humanized monoclonal antibody against CD20developed by Innovent Biologies), BVX-20(a humanized mAb against the CD20developed by VACCINEX®), 20-C2-2b (a bispecific mAb-IFNalpha that targets CD20and human leukocyte antigen-DR (HLA-DR) developed by IMMUNOMEDICS®), MEDI-552 (developed by MEDLMMUNE®/ ASTRAZENECA®), the anti-CD20/streptavidin conjugates developed by NeoRx (now Poniard Pharmaceuticals), the 2nd generation anti-CD20human antibodies developed by Favrille (now MMRGIobal), TRU-015, an anti-CD20 antibody fragment developed by Trubion/ EMERGENT BIOSOLUTIONS®.

The method of the present invention is particularly suitable for predicting the survival time of the subject when the assay also comprises means for determining the expression of MYC and/or BCL2. In some embodiments, the expression level(s) of MYC and/or BCL2 is (are) compared with their respective predetermined reference values wherein when the expression level(s) MYC and/or BCL6 is (are) higher than their respective predetermined reference values, it is concluded that the subject will have a poor prognosis (i.e. the duration of the disease-free survival (DFS) or the overall survival (OS) or both).

The present invention also relates to a kit for performing the method of the present invention.

In some embodiments, the kit comprises 14 pairs of probes specific for the 14 target nucleic sequences of NEK6, IRF4, IGHM, CCND1, LMO2, FOXP1, TNFRSF9, BCL6, TNFRSF13B, CCND2, MYC, MYBL1, BCL2, and MS4A1, wherein each pair of probes consists of:
a first probe having
a target specific region (L) complementary to the first segment of the target nucleic acid sequence and
a tail region (TL) at the 3' extremity of the target specific region (L) which is non-complementary to said target nucleic acid sequence,
a second probe having
a target specific region (R) complementary to the second segment of the target nucleic acid sequence and,
a tail region (TR) at the 5' extremity of the target specific region (R) which is non-complementary to said target nucleic acid sequence In some embodiments, the kit comprises a pair of probes specific for NEK6 which consists of a first probe having its target specific region (L) as set forth by SEQ ID NO:15 (CCTGTGCATCCTCCTGACCCACAG) and a second probe having its target specific region (R) as set forth by SEQ ID NO:16 (AGGCATCCCAACACGCTGTCTTT).

In some embodiments, the kit comprises a pair of probes specific for IRF4 which consists of a first probe having its target specific region (L) as set forth by SEQ ID NO:17 (CTGCCGAAGCCTTGGCGTTCTCAG) and a second probe having its target specific region (R) as set forth by SEQ ID NO:18 (ACTGCCGGCTGCACATCTGCCTGTA).

In some embodiments, the kit comprises a pair of probes specific for IGHM which consists of a first probe having its target specific region (L) as set forth by SEQ ID NO:19 (GCGTCCTCCATGTGTGGCCCCG) and a second probe having its target specific region (R) as set forth by SEQ ID NO:20 (ATCAAGACACAGCCATCCGGGTCTTC).

In some embodiments, the kit of the present invention comprises a pair of probes specific for CCND1 which consists of a first probe having its target specific region (L) as set forth by SEQ ID NO:21 (ACCTTCGTTGCCCTCT-GTGCCACAG) and a second probe having its target specific region (R) as set forth by SEQ ID NO:22 (ATGT-GAAGTTCATTTCCAATCCGCCCT).

In some embodiments, the kit of the present invention comprises a pair of probes specific for LMO2 which consists of a first probe having its target specific region (L) as set forth by SEQ ID NO:23 (CGGAAGCTCTGCCGGAGA-GACTATCTCAG) and a second probe having its target specific region (R) as set forth by SEQ ID NO:24 (GCTTTTTGGGCAAGACGGTCTCTGC).

In some embodiments, the kit of the present invention comprises a pair of probes specific for FOXP1 which consists of a first probe having its target specific region (L) as set forth by SEQ ID NO:25 (CCCTTCCCCTTCAAC-CTCTTGCTCAAG) and a second probe having its target specific region (R) as set forth by SEQ ID NO:26 (GCAT-GATTCCAACAGAACTGCAGCAGC).

In some embodiments, the kit of the present invention comprises a pair of probes specific for TNFRSF9 which consists of a first probe having its target specific region (L) as set forth by SEQ ID NO:27 (GGACCTGTGACATAT-GCAGGCAGTGTAAAG) and a second probe having its target specific region (R) as set forth by SEQ ID NO:28 (GTGTTTTCAGGACCAGGAAGGAGTGTTCC).

In some embodiments, the kit of the present invention comprises a pair of probes specific for BCL6 which consists of a first probe having its target specific region (L) as set forth by SEQ ID NO:29 (CATAAAACGGTCCTCATGGC-CTGCAG) and a second probe having its target specific region (R) as set forth by SEQ ID NO:30 (TGGCCTGT-TCTATAGCATCTTTACAGACCAGTTG).

In some embodiments, the kit of the present invention comprises a pair of probes specific for TNFRSF13B which consists of a first probe having its target specific region (L) as set forth by SEQ ID NO:31 (GCGCACCTGTGCAGC-CTTCTGCA) and a second probe having its target specific region (R) as set forth by SEQ ID NO:32 (GGTCACTCA-GCTGCCGCAAGGAGC).

In some embodiments, the kit of the present invention comprises a pair of probes specific for CCND2 which consists of a first probe having its target specific region (L) as set forth by SEQ ID NO:33 (GACCTTCATTGCTCTGT-GTGCCACCG) and a second probe having its target specific region (R) as set forth by SEQ ID NO:34 (ACTT-TAAGTTTGCCATGTACCCACCGTCGA).

In some embodiments, the kit of the present invention comprises a pair of probes specific for MYC which consists of a first probe having its target specific region (L) as set forth by SEQ ID NO:35 (TCGGGTAGTGGAAAACCA-GCAGCCTC) and a second probe having its target specific region (R) as set forth by SEQ ID NO:36 (CCGCGACGAT-GCCCCTCAACGTTA).

In some embodiments, the kit of the present invention comprises a pair of probes specific for MYBL1 which consists of a first probe having its target specific region (L) as set forth by SEQ ID NO:37 (CCAGAATTTGCAGA-GACTCTAGAACTTATTGAATCT) and a second probe having its target specific region (R) as set forth by SEQ ID NO:38 (GATCCTGTAGCATGGAGTGACGTTACCA-GTTTT).

In some embodiments, the kit of the present invention comprises a pair of probes specific for BCL2 which consists of a first probe having its target specific region (L) as set forth by SEQ ID NO:39 (CCTGGATCCAGGATAACG-GAGGCTGG) and a second probe having its target specific region (R) as set forth by SEQ ID NO:40 (GATGCCTTT-GTGGAACTGTACGGCC).

In some embodiments, kit of the present invention comprises a pair of probes specific for MS4A1 which consists of a first probe having its target specific region (L) as set forth by SEQ ID NO:41 (TTCTTCAT-GAGGGAATCTAAGACTTTGGGG) and a second probe having its target specific region (R) as set forth by SEQ ID NO:42 (GCTGTCCAGATTATGAATGGGCTCTTCCAC).

In some embodiments, the kit of the present invention comprises a pair of probes specific for NEK6 which consists of a first probe which is SEQ ID NO:53 (GTGCCAG-CAAGATCCAATCTAGACCTGTGCATCCTCCTGAC-CCACAG) and a second probe which is SEQ ID NO:55 (AGGCATCCCAACACGCTGTCTTTTCCAACCCT-TAGGGAACCC).

In some embodiments, the kit of the present invention comprises a pair of probes specific for IRF4 which consists of a first probe which is SEQ ID NO:56 (GTGCCAG-CAAGATCCAATCTAGATCTGCCGAAGCCTTGGCGT-TCTCAG) and a second probe which is SEQ ID NO:57 (ACTGCCGGCTGCACATCTGCCTGTATCCAACCCT-TAGGGAACCC).

In some embodiments, the kit of the present invention comprises a pair of probes specific for IGHM which consists of a first probe which is SEQ ID NO:58 (GTGCCAG-CAAGATCCAATCTAGATGCGTCCTCCATGTGTGGC-CCCG) and a second probe which is SEQ ID NO:59 (ATCAAGACACAGCCATCCGGGTCTTCTACTATC-CAACCCTTAGGGAACCC).

In some embodiments, the kit of the present invention comprises a pair of probes specific for CCND1 which consists of a first probe which is SEQ ID NO:60 (GTGC-CAGCAAGATCCAATCTAGATACCTTCGTTGCCCTCT-GTGCCACAG) and a second probe which is SEQ ID NO:61 (ATGTGAAGTTCATTTCCAATCCGCCCTTACT-TCCAACCCTTAGGGAACCC).

In some embodiments, the kit of the present invention comprises a pair of probes specific for LMO2 which consists of a first probe which is SEQ ID NO:62 (GTGCCAG-CAAGATCCAATCTAGACGGAAGCTCTGCCGGAGA-GACTATCTCAG) and a second probe which is SEQ ID NO:63 (GCTTTTTGGGCAAGACGGTCTCTGCTAC-TATCCAACCCTTAGGGAACCC).

In some embodiments, the kit of the present invention comprises a pair of probes specific for FOXP1 which consists of a first probe which is SEQ ID NO:64 (GTGC-CAGCAAGATCCAATCTAGACCCTTCCCCTTCAAC-CTCTTGCTCAAG) and a second probe which is SEQ ID NO:65 (GCATGATTCCAACAGAACTGCAGCAGCTAC-TACTACTCCAACCCTTAGGGAACCC).

In some embodiments, the kit of the present invention comprises a pair of probes specific for TNFRSF9 which consists of a first probe which is SEQ ID NO:66 (GTGC-CAGCAAGATCCAATCTAGATACGGACCTGT-GACATATGCAGGCAGTGTAAAG) and a second probe which is SEQ ID NO:67 (GTGTTTTCAGGACCAG-GAAGGAGTGTTCCTACTCCAACCCT-TAGGGAACCC).

In some embodiments, the kit of the present invention comprises a pair of probes specific for BCL6 which consists of a first probe which is SEQ ID NO:68 (GTGCCAG-CAAGATCCAATCTAGATACTACTCATAAAACGGTC-CTCATGGCCTGCAG) and a second probe which is SEQ ID NO:69 (TGGCCTGTTCTATAGCATCTTTACAGAC-CAGTTGTCCAACCCTTAGGGAACCC).

In some embodiments, the kit of the present invention comprises a pair of probes specific for TNFRSF13B which consists of a first probe which is SEQ ID NO:70 (GTGC-CAGCAAGATCCAATCTAGATACTACTACTAGCG-CACCTGTGCAGCCTTCTGCA) and a second probe which is SEQ ID NO:71 (GGTCACTCAGCTGCCG-CAAGGAGCTACTACTACTACTCCAACCCT-TAGGGAACCC).

In some embodiments, the kit of the present invention comprises a pair of probes specific for CCND2 which consists of a first probe which is SEQ ID NO:72 (GTGC-CAGCAAGATCCAATCTAGATACTACTGACCTTCATT-GCTCTGTGTGCCACCG) and a second probe which is SEQ ID NO:73 (ACTTTAAGTTTGCCATGTACCCAC-CGTCGATACTACTATCCAACCCTTAGGGAACCC).

In some embodiments, the kit of the present invention comprises a pair of probes specific for MYC which consists of a first probe which is SEQ ID NO:74 (GTGCCAG-CAAGATCCAATCTAGATACTACTACTTCGGG-TAGTGGAAAACCAGCAGCCTC) and a second probe which is SEQ ID NO:75 (CCGCGACGATGCCCCT-CAACGTTATACTACTACTACTATCCAACCCT-TAGGGAACCC).

In some embodiments, the kit of the present invention comprises a pair of probes specific for MYBL1 which consists of a first probe which is SEQ ID NO:76 (GTGC-CAGCAAGATCCAATCTAGACCAGAATTTGCAGA-GACTCTAGAACTTATTGAATCT) and a second probe which is SEQ ID NO:77 (GATCCTGTAGCATGGAGT-GACGTTACCAGTTTTTACTACTTCCAACCCT-TAGGGAACCC).

In some embodiments, the kit of the present invention comprises a pair of probes specific for BCL2 which consists of a first probe which is SEQ ID NO:78 (GTGCCAG-CAAGATCCAATCTAGATACTACTACTACCCTGGATC-CAGGATAACGGAGGCTGG) and a second probe which is SEQ ID NO:79 (GATGCCTTTGTGGAACTGTACGGC-CTACTACTACTACTTCCAACCCT-TAGGGAACCC).

In some embodiments, the kit of the present invention comprises a pair of probes specific for MS4A1 which consists of a first probe which is SEQ ID NO:80 (GTGC-CAGCAAGATCCAATCTAGATACTACTACTATTCT-TCATGAGGGAATCTAAGACTTTGGGG) and a second probe which is SEQ ID NO:81 (GCTGTCCAGATTAT-GAATGGGCTCTTCCACTACTACTACTATCCAACCCT-TAGGGAACCC).

In some embodiments, the kit of the present invention comprises at least one competitor probe specific for specific for NEK6 or IRF4.

In some embodiments, the kit of the present invention comprises a competitor probe specific for NEK6 which is SEQ ID NO:82 (AGGCATCCCAACACGCTGTCTTT).

In some embodiments, the kit of the present invention comprises a competitor probe specific for IGHM which is SEQ ID NO:83 (ATCAAGACACAGCCATC-CGGGTCTTC).

In some embodiments the probes SEQ ID NO:54-73 and the competitor probes SEQ ID NO:82-83.

In some embodiments, the kit of the present invention comprises the random hexamer primers suitable for the cDNA synthesis as above described.

In some embodiments, the kit of the present invention comprises any mean suitable for performing the ligation step. In particular the kit of the invention comprises a ligase as above described.

In some embodiments, the kit of the present invention comprises any means suitable for performing the amplification step as above described. In particular, the kit of the present invention comprises at least one pair of primers as above described. In some embodiments, the pair of primers is ILLU1 (SEQ ID NO: 84) (GGGTTCCCTAAGGGT-TGGA) and ILLU2 (SEQ ID NO: 85) (GTGCCAG-CAAGATCCAATCTAGA). The kit of the present invention may further comprises buffer, dNTP's, detergents, a polymerase such as Taq polymerase or any further agent such as betaine.

In some embodiments, the kit of the invention comprises any means for calculating the score as above described. In particular, the kit of the present invention may further comprise a software suitable for calculating the score as above described and optionally interpreting the results so as to determine how the DLCL of the subject shall be classified.

The present invention relates to software that can be implemented on any system (e.g. a computer) for calculating the score as above described and optionally interpreting the results so as to determine how the DLCL of the subject shall be classified.

The invention will be further illustrated by the following figures and examples. However, these examples and figures should not be interpreted in any way as limiting the scope of the present invention.

FIGURES

FIG. 1A and B: Description of the analyzed cohorts.

General structure and overlaps between the different cohorts are indicated, along with their main characteristics (sample count, material type, GEP standard when available). Cohorts from our institution (A) are separated from the external cohort (B) to highlight their independence.

Figure 2:
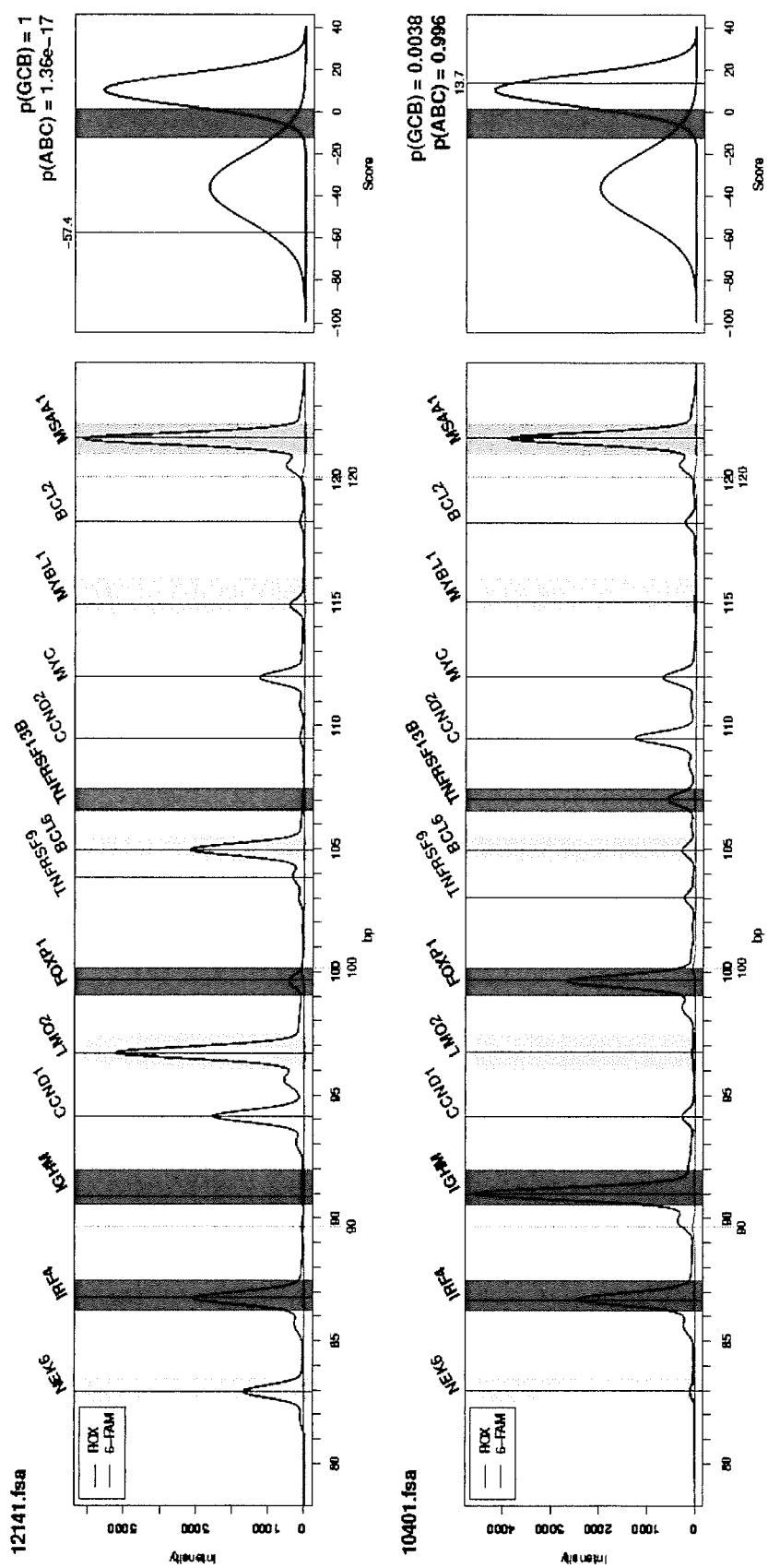

FIG. 2: Representative RT-MLPA profiles.

RT-MLPA profiles generated by the dedicated software are presented for two representative samples (GCB in the upper panel, ABC in the lower panel). For each sample, a fragment-analysis profile (intensity of fluorescence as a function of the PCR fragment sizes) is provided in the left panel, with intervals scanned for gene-related peaks highlighted by various colors (blue for ABC-related genes, orange for GCB-related genes, green for the MS4A1 internal control, and grey for other diagnostically or prognostically relevant genes). Size markers, as used for alignment of profiles and fragment size estimation (ROX channel), are displayed using dotted lines indicating their theoretical size. The right panel illustrates the prediction made by the RT-MLPA predictor, showing the superposition of the score of the sample on the theoretic distributions of scores in the ABC and GCB subgroups.

Figure 3A:
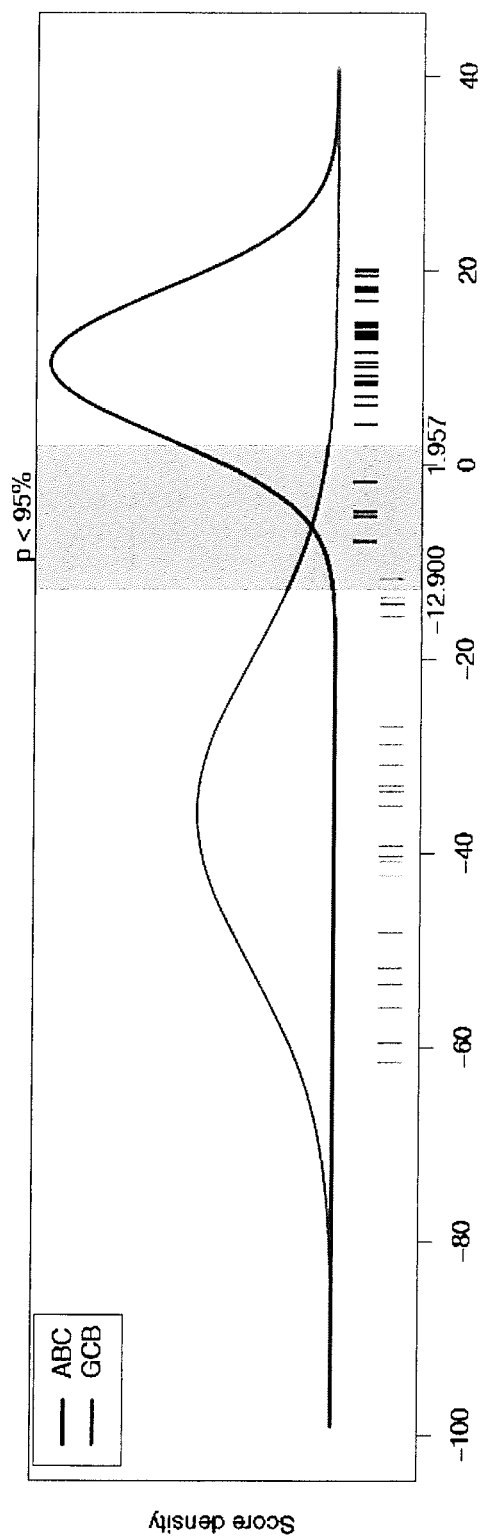
Figure 3B:
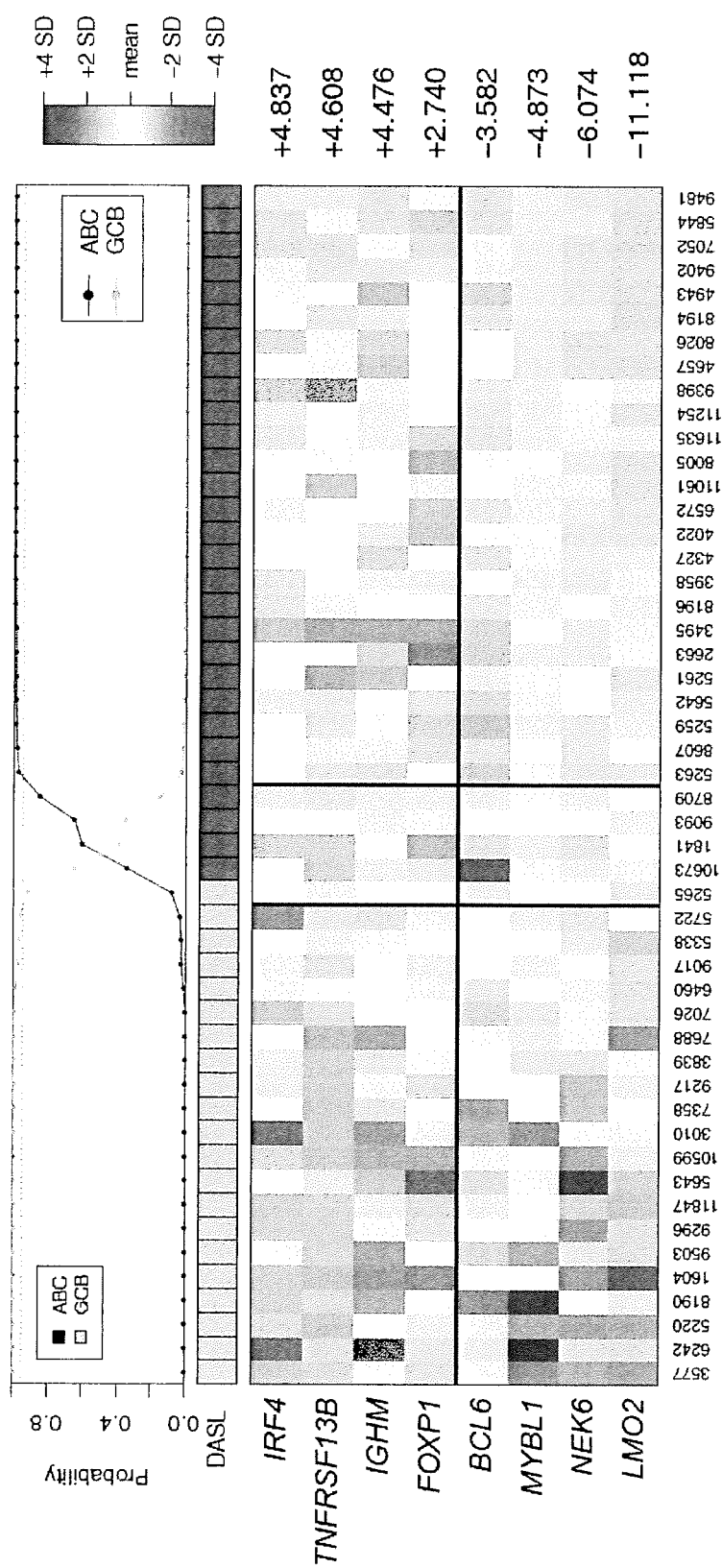
Figure 3C:
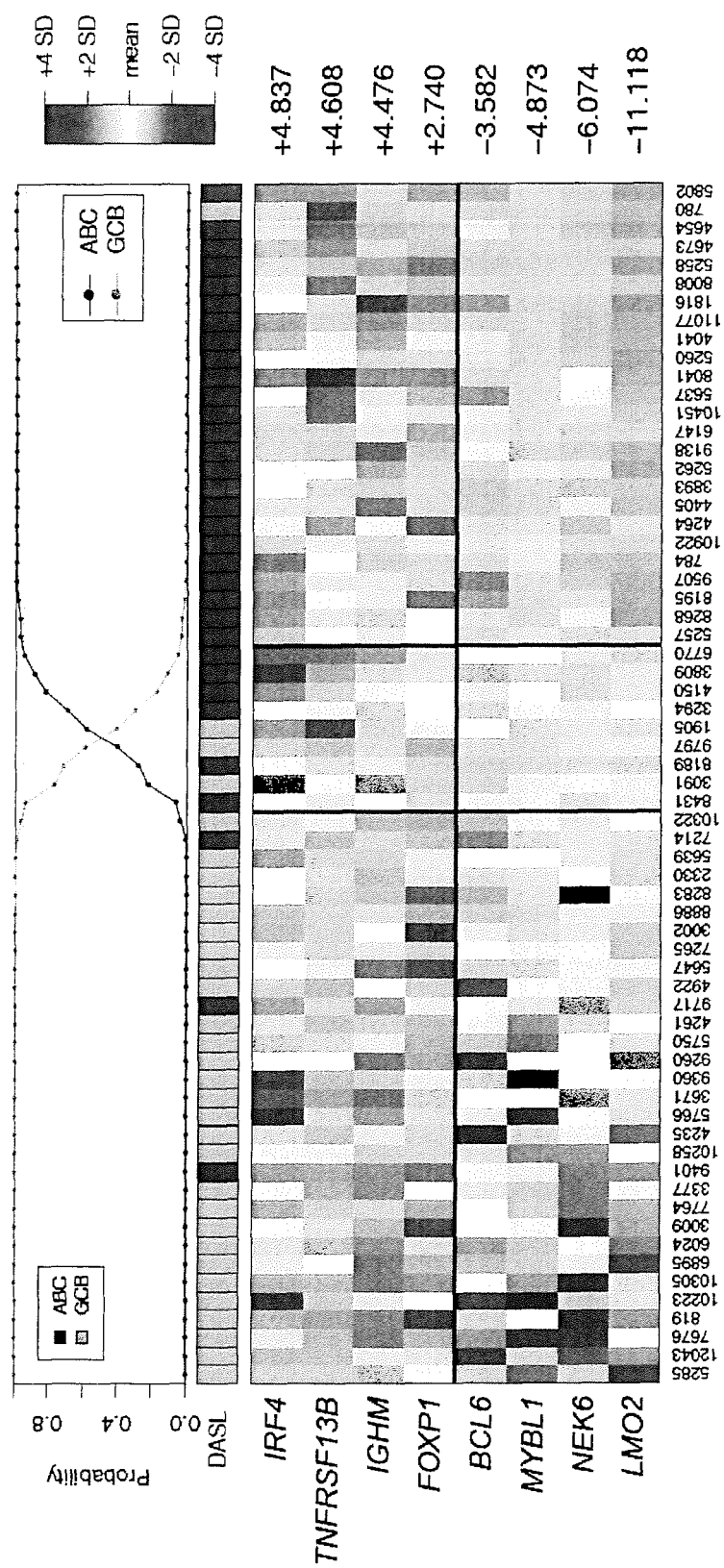

FIG. 3A-C: RT-MLPA predictor training and validation.

(A) The scores of the GCB and ABC samples of the training series are presented as vertical bars, beneath the estimated density functions used in the prediction model. (B) and (C) present the expression of the 8 genes included in the GCB-ABC predictor in the training (B) and validation (C) series as heat maps, along with the expected classes computed using the DASL technology (middle panel) and the predicted probability to belong to each of the groups (top panel). Samples (columns) are ordered by ascending RT-MLPA scores, while genes (rows) are ordered by their discriminating power (t statistics displayed on the right). Black vertical bars split samples according to the group they are predicted to belong to (GCB, unclassified and ABC from left to right).

Figure 4:
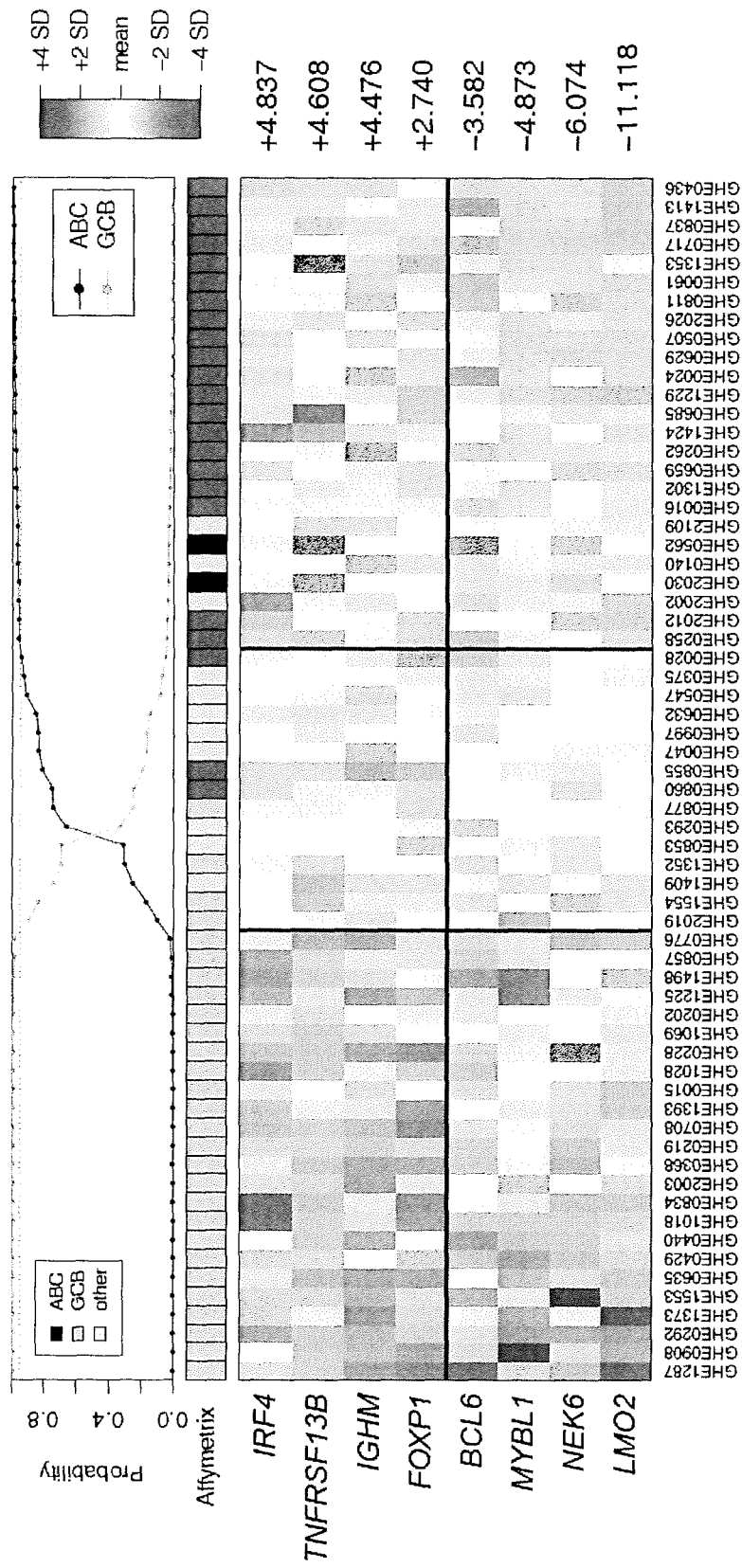

FIG. 4: RT-MLPA predictor independent validation on Affymetrix samples

The expression of the 8 genes included in the GCB-ABC predictor in an independent series of 64 frozen samples is presented as a heat map, along with the expected classes computed using Affymetrix U133+2 arrays (middle panel) and the predicted probability of belonging to each of the groups (top panel). Samples (columns) are ordered by ascending RT-MLPA scores, while genes (rows) are ordered by their discriminating power (t statistics displayed on the right). Black vertical bars split samples according to the group they are predicted to belong to (GCB, unclassified and ABC from left to right).

Figure 5A:
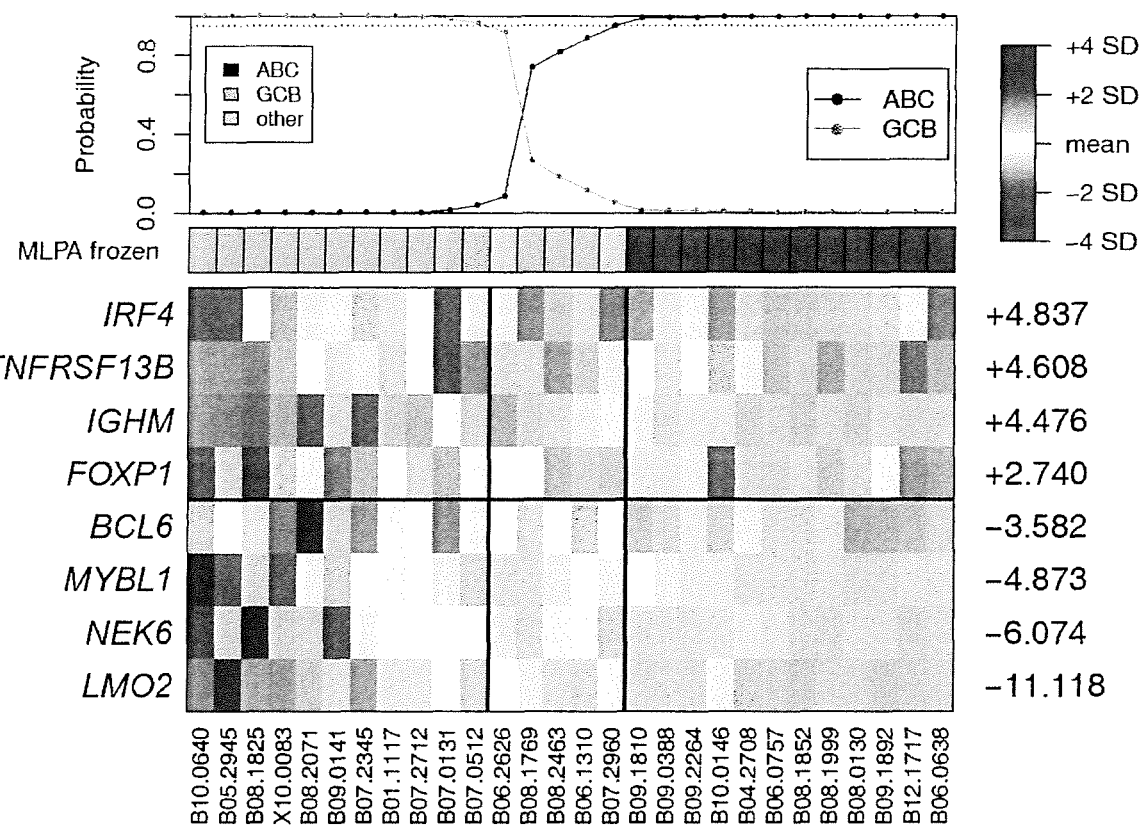

FIG. 5A and B: RT-MLPA predictor performances in FFPE samples.

The expression of the 8 genes included in the GCB-ABC predictor in a series of 28 FFPE samples is presented as a heat map, along with the expected classes computed using the DASL technology on matching frozen samples (middle panel) and the predicted probability of belonging to each of the groups (top panel). The samples (columns) are ordered by ascending RT-MLPA scores, while the genes (rows) are ordered by their discriminating power (t statistics displayed on the right). The black vertical bars split samples according to the group they are predicted to belong to (GCB, unclassified and ABC from left to right).

Figure 6:
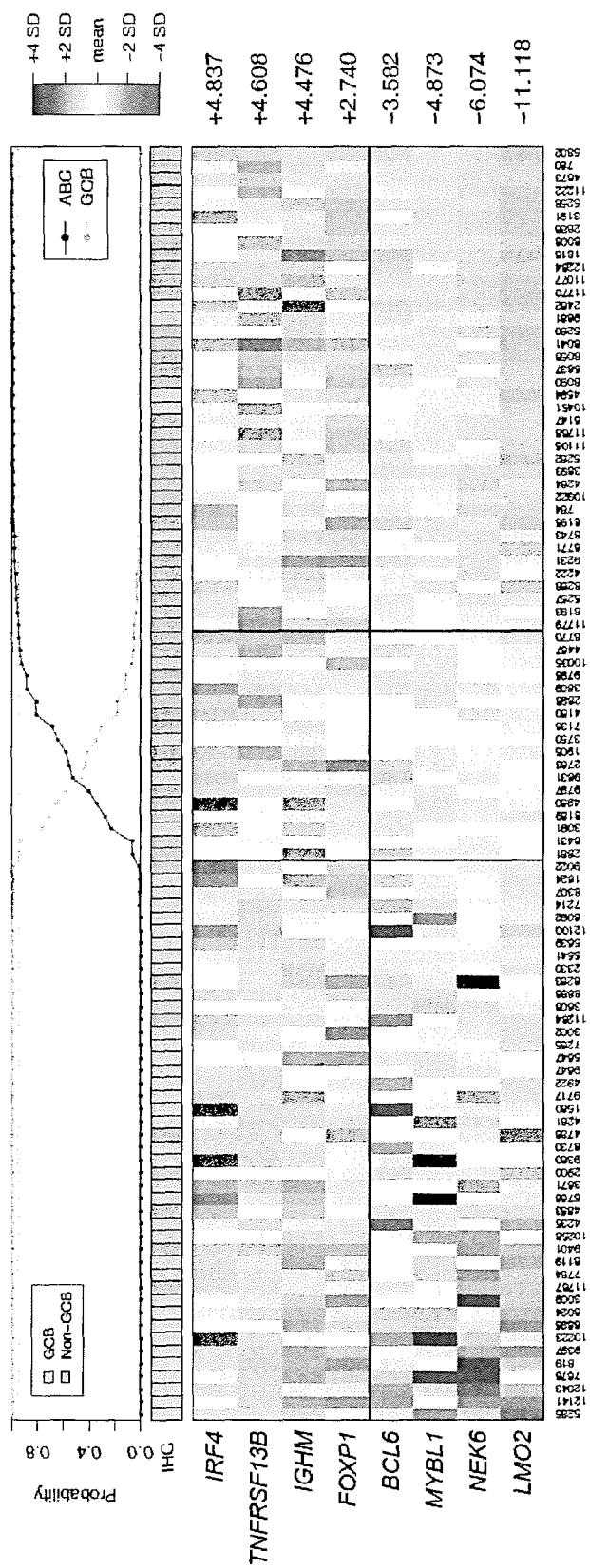

FIG. 6: RT-MLPA predictor performances as compared to IHC.

The expression of the 8 genes included in the GCB-ABC predictor in a series of 100 frozen samples is presented as a heat map, along with Hans' immunohistochemical algorithm results (middle panel), and the predicted probability of belonging to each of the groups (top panel). Samples (columns) are ordered by ascending RT-MLPA scores, while genes (rows) are ordered by their discriminating power (t statistics displayed on the right). Black vertical bars split samples according to the group they are predicted to belong to (GCB, unclassified and ABC from left to right).

FIG. 7A-E: Patient outcomes according to RT-MLPA-based grouping.

Progression-free (left column) and overall survival (right column) of a series of 135 patients treated with a combination of rituximab and chemotherapy are presented according to various grouping factors: GCB-ABC subgroup, as predicted by RT-MLPA (A), LMO2 (B), BCL6 (C) and TNFRSF13B (D) expressions as measured by RT-MLPA according to their respective medians, MYC+ BCL2+ against the rest of the cohort (E), defined by an RT-MLPA expression higher than 1.284 for MYC and 0.256 for BCL2. Raw log-rank p-values are displayed on the respective legend panels.

Figure 8:
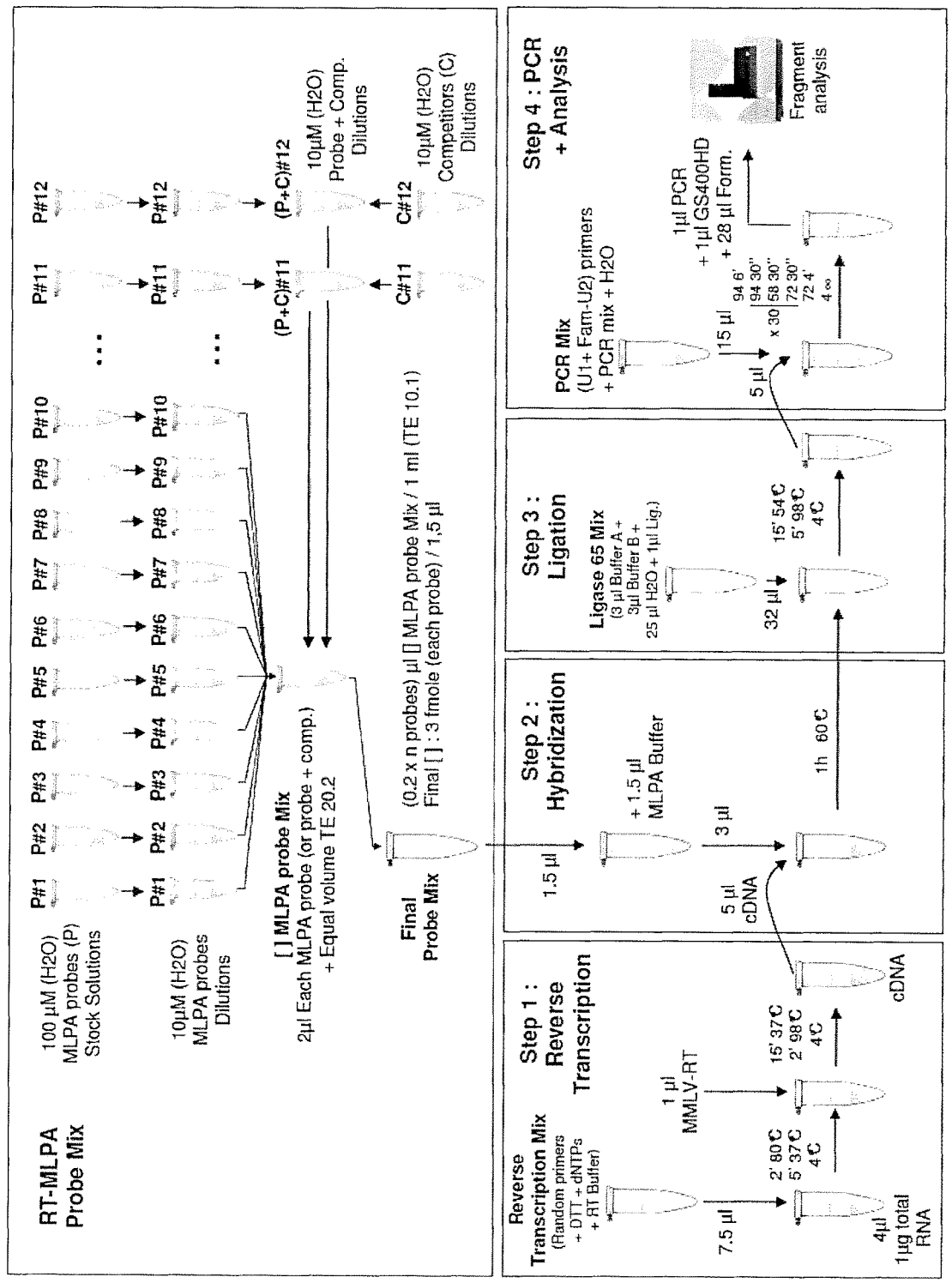

FIG. 8: Workflow of the RT-MLPA experimental procedure.

The procedure for the preparation of the RT-MLPA probes and competitor mix is described in the upper panel. Following this protocol, the final mix allows testing more then 600 samples, and the concentrated mix more than 6000 samples. The experimental workflow, which consists of four steps, specifically, Reverse transcription, Hybridization, Ligation and PCR/analysis, is detailed in the lower panel.

FIG. 9A-C: Reproducibility and robustness of the RT-MLPA predictor.

The RT-MLPA scores obtained for 10 replicates of two frozen samples (RNA 9260 and 9402, GCB and ABC respectively) are plotted on their modelized distributions in the GCB and ABC subgroups (A). The same representation is shown (B) for the 12 serial dilutions of sample 9402, with an obvious outlier (12th dilution, corresponding to less than 1 ng of RNA) highlighted in red. Raw (C) and normalized (D) peak heights for the 14 genes included in the RT-MLPA predictor in the 12 serial dilutions of sample 9402 are also depicted, along with the scores and predicted probabilities to belong to the ABC subgroup (E).

EXAMPLE

Materials and Methods
Patients

A total of 259 DLBCL patients were included in this study (FIG. 1 and Table S1). All samples were obtained after receiving patient consent and this study was approved by our institutional review board. A first series of 195 patients from a single institution (Centre Henri Becquerel, Rouen, France) was used to train and validate the GCB/ABC classifier. A GCB/ABC classification previously determined using a DASL assay (cDNA-mediated Annealing, Selection, extension and Ligation method)[18] was available for 115 patients. An immunohistochemical classification was available for 100 cases, and survival data for 135 of them. A second series of 64 patients included in the GHEDI study program conducted by the LYSA group and previously analyzed by gene expression profile arrays (Affymetrix U133A+2) was used as an external validation set[19]. For all patients, the inclusion criteria were de novo DLBCL with available RNA extracted from frozen lymph node biopsies at the time of diagnosis. The diagnoses were determined according to the WHO 2008 criteria by expert pathologists[1]. Primary mediastinal diffuse large B-cell lymphomas and T-cell rich DLBCLs were excluded.

RNA Extraction

Total RNA was extracted from frozen biopsy fragments using the RNA NOW kit (Biogentex, Seabrook, Tex.). The RNA samples were subsequently stored at −80° C. in water. For 30 cases, RNA samples were extracted from formalin-fixed paraffin-embedded (FFPE) biopsies using the Absolutely RNA FFPE Kit (Agilent Technologies, La Jolla, Calif., USA).

Immunohistochemistry

To build tissue microarrays (TMA) (Alphelys, Plaisir, France), three representative cores (0.6 mm) of FFPE tissues were used for each case. Immunohistochemical staining was performed on 4 μm sections using standard procedures. Antigen retrieval was performed on PTLink (DAKO, Glostrup, Denmark) with a pH 9 buffer. CD10 (clone 56C6, 1/50e, DAKO, Glostrup, Denmark), BCL6 (clone PGB6P, 1/10e, DAKO, Glostrup, Denmark) and MUM1 (clone MUM1p, 1/100e, DAKO, Glostrup, Denmark) were stained using an AUTOSTAINER Link48 (DAKO, Glostrup, Denmark) with the envision flex system. GCB and non-GCB phenotypes were defined using the decision tree with indicated cut-offs established by Hans and colleagues[20].

RT-MLPA Probe Design and Mix

The RT-MLPA probes that were used are listed in Table 1. To avoid unwanted amplifications of genomic DNA, all the probes were designed across exon-exon boundaries. They are made of a gene specific region complementary to the cDNA target and of a tail to allow the final PCR amplification. All 5' probes have a common tail at their 5' end (GTGCCAGCAAGATCCAATCTAGA; SEQ ID NO: 43), which corresponded to the universal primer, U1. All 3' probes have a different common tail at their 3' end (TC-CAACCCTTAGGGAACCC; SEQ ID NO: 44), which is complementary to the universal primer, U2. Additional spacers (TAC repeats) were inserted between the tails and the gene specific regions to allow the separation and the identification of the PCR products according to their size. The 3' probes were ordered with phosphorylated 5' ends to allow for the ligation reactions. All the RT-MLPA probes used in this study were synthetic oligonucleotides, ordered at the lowest purification grade (HPSF) and at the minimal synthesis scale (0.01 μmol for the left probes and 0.05 μmol for the right phosphorylated probes) (Eurofins MWG Operon, Ebersberg, Germany). For two genes, we also designed competitor probes identical to the MLPA probes, but without the PCR tails, which were used to normalize the amplification signals.

To prepare the MLPA probe mix, 10 μM dilutions of each probe and competitors were prepared in Tris 10 mM and EDTA 1 mM. The two competitors were mixed with their corresponding probes at a 1 (MLPA probe) to 4 (competitor) ratio for the IGHM and NEK6 genes. Then, 2 μl of each probe dilution (n=26) or (probe+competitor mix dilution) (n=2) dilution were mixed together to obtain a final volume of 56 μl. An equal volume of 1× TE was then added to obtain a volume of 112 μl. The final dilution was obtained by diluting 11.2 μl of the concentrated probe mix in a final volume of 1 ml Tris 10 mM and EDTA 1 mM buffer.

RT-MLPA Procedure

The RT-MLPA protocol was adapted from Eldering et al[17]. A schematic workflow of the experimental procedure is provided in FIG. 8. The most important modifications we made were the use of random hexamer primers instead of gene specific primers for cDNA synthesis, the reduction of the hybridization step from 16 to 1 hour, and the use of synthetic oligonucleotides as MLPA probes.

All RT-MLPA reactions were performed in 200 μl tubes in a thermocycler with a heated lid. Approximately one microgram of total RNAs obtained from DLBCL biopsies were first diluted in 4 μl RNAse-free water and kept on ice. After the addition of 7.5 μl of reverse transcription mix (2.5 μl 5× RT-MMLV Buffer, 1 μl DTT 100 mM, 2 μl dNTPs 10 mM and 2 μl random primers 100 μM), the samples were heated for 1 min at 80° C. to melt the secondary structure of the mRNA, incubated for 5 min at 37° C. to allow the hybridization of the random primers and cooled at 4° C. Next, 1 μl of MMLV-Reverse transcriptase was added, and the samples were incubated for 15 min at 37° C. to synthesize the cDNA, heated for 2 min at 98° C. to inactivate the enzyme and cooled at 4° C. Then, 5 μl of cDNA was transferred into a new tube, and 3 μl of a RT-MLPA probe mix (1.5 μl SALSA-MLPA Buffer+1.5 μl final dilution probe mix) were added. The samples were heated for 2 min at 95° C. and incubated for 1 h at 60° C. to allow the annealing of the MLPA probes to their cDNA targets. The ligation of the annealed oligonucleotides was performed by cooling all samples at 56° C., adding 32 μl of a ligation mix (3 μl SALSA-Ligase 65 Buffer A, 3 μL SALSA-Ligase Buffer B, 25 μl RNAse Free Water, 1 μl SALSA-Ligase 65), and incubating the mixed samples for 15 min at 56° C. The ligase enzyme was next inactivated by heating for 5 min at 98° C. For the final PCR amplification, 5 μl of each ligation product were added to 15 μl of a PCR mix (10 μl Thermo Scientific Extensor Hi-Fidelity PCR Master Mix; Thermo Scientific, 1 μl 10 μM primer U1, 1 μl 10 μM FAM-labeled primer U2, 3 μl RNAse free water). The amplification was performed with the following program: 6 min 94° C.; 35 cycles (30 sec 94° C., 30 sec 58° C., 30 sec 72° C.); 4 min 72° C.; cooled down to 16° C.

For data analysis, 1 µl of each PCR product was mixed with 1 µl of GeneScan-400 HD ROX size standard and 28 µl formamide, denatured for 3 min at 95° C., and loaded onto an ABI3130 capillary electrophoresis analyzer in GeneScan mode (Applied Biosystems, Warrington, UK). The migration settings were as follows: Pre Run Voltage 15 kV; Pre Run Time 180 sec; Injection Voltage 1 kV; Injection Time 3 sec (reduced to 1 sec when fluorescence signals were off-scale), Run Voltage 10 kV; Run Time 180 sec.

Data Processing

To facilitate the interpretation of the results, interfaced software was developed to handle the entire analysis process, from the raw fragment analyzer files (.fsa) to the sample calls and GCB/ABC probabilities. This software, which can be freely downloaded from bioinformatics.ovsa.fr/MLPA, provides a graphical representation of the profile and of the GCB/ABC classification (FIG. 2), and a table of normalized gene expressions. It consists in a Tcl-tk user interface built upon an R package (R core team, .r-project.org), both of which are freely distributed under the GNU Public License 3.

Each channel of the electrophoresis profiles is first corrected for time-related biases, using a LOWESS transformation of the signals over time. To estimate the sizes of the peaks in base pairs, the profiles are then aligned using the 50, 60, 90, 100 and 120 bp size standards. The ROX profile is smoothed using a Nadaraya-Watson Gaussian kernel, and the time indexes of local maxima are used to fit a linear model converting time indexes into base pairs. The heights of the different peaks are next measured by looking for the FAM signal maxima in size intervals that are predefined in base pairs. Both the gene and size standard windows were tuned from the graphical profiles, and made available in the software's design file (version 1.8.5). To minimize RNA quantity bias, all expression values are finally divided by the mean of all genes measured in the sample, and the base 2 logarithms of these ratios plus 1 are used as normalized expression values.

Survival Analysis

Survival analysis was restricted to the 135 patients diagnosed between 2001 and 2011 at the Centre Henri Becquerel who were treated by a combination of rituximab and chemotherapy. It was performed using the "survival" package (2.37.4) for the R software, considering an alpha risk of 5% as a significance threshold. Overall survival (OS) was computed from the day of treatment to death from any cause, or right-censored at last follow-up. Progression-free survival (PFS) was computed from the day of treatment to either disease progression, relapse or death from any cause, or right-censored at last follow-up. The survival rates were estimated using the Kaplan-Meier method providing 95% confidence intervals, and significant differences between groups were assessed by the log-rank test ($\alpha$=5%). Continuous univariate analyses were performed using Cox proportional hazards regression models, and the likelihood ratio test p values and derived False Discovery Rates are reported[21]. All combinations of thresholds were tested for PFS significance of the MYC+BCL2+ subgroup, focusing on the couple of values that led to the most significant segmentation of patients[22].

Statistical Analysis

Prediction accuracies and unclassified proportions are reported with 95% confidence intervals (CI) estimated by the "exact" binomial computation method, as implemented in the binom R package (version 1.1-1).

Results

Gene Selection

The candidate genes for inclusion into the GCB/ABC predictor were selected according to their differential expression in two independent series of Affymetrix U133+2 arrays. The first series consisted of 203 arrays made available by Lenz et al[23] in the GEO database (GSE11318). The second consisted of an independent series of 225 arrays classified into the GCB or ABC subtypes, following the recommendations of Wrights and col.[24] and a signature of 24 genes[19]. A LIMMA model was built for each series using R (2.15.1, LIMMA package version 3.12.3) to discriminate two groups using single-channel arrays. Genes with at least one probeset FDR $<10^{-12}$ in both series were selected for RT-MLPA testing, beginning with the lowest p-values. The 16 markers obtained from this initial selection are listed in Table 2.

Different combinations of genes were then tested to finalize the design and those expressed at the most comparable levels were selected. We finally retained four GCB (LMO2, MYBL1, BCL6, NEK6) and four ABC (IRF4, FOXP1, IGHM, TNFRSF13B) markers. For two genes expressed at very high levels in some samples (NEK6 and IGHM), competitor probes were used to reduce the height of the corresponding peaks in the RT-MLPA profiles. We finally included the MYC, BCL2 and TNFRSF9 genes, which were shown to be prognostic in DLBCLs, and the CCND1, CCND2 and MS4A1 (encoding CD20) genes as controls. Representative RT-MLPA profiles are presented in FIG. 2 and all gene expression values are detailed in Table S2.

Class Prediction Model

The classification of samples as GCB or ABC was achieved using an adaptation of the Linear Predictor Score (LPS) defined by Wright et al.[24] and a Bayesian predictor. We adopted the same assumption that the distributions of the scores within the GCB and ABC groups followed normal distributions (FIG. 3A), which allowed the estimation of the probability for each case of belonging to one or the other subtype. Scaling factors were applied to balance the over-weighting of the most highly expressed genes, a marginal phenomenon in heavily normalized values used in Wright's publication which is no longer negligible with the values manipulated here. To account for the differences in expression ranges, the T statistics that were used as gene-specific coefficients were thus further divided by the mean expressions of the corresponding genes in the training series. This correction also allowed the avoidance of the "shift and scale" normalization to Lymphochip's ranges that was suggested by the authors to adapt their model to other platforms, which may lead to incorrect calls in series with GCB/ABC distributions distinct from the original Lymphochip series. Finally, the confidence threshold to consider a sample either as GCB or ABC was changed from 90% (as recommended by the authors) to 95%, for better specificity.

The Bayesian predictor was developed using a training series of 50 randomly selected DLBCL cases previously characterized in our laboratory using a Veracode Illumina DASL assay (FIG. 1, Cohort #1) and a 17 genes signature (FIG. 3B)[18]. As expected, the average expressions of the eight GCB/ABC discriminant genes were significantly different between the two subtypes in this series (Table 2). The predictor classified 90% of the cases within the expected subtypes (20 GCB and 25 ABC), while 10% (1 GCB and 4 ABC) were considered unclassified (95% CIs [78%, 97%] and [3%, 22%] respectively). In a second independent validation series of 65 patients (from the same institution and characterized using the same Veracode Illumina DASL assay; FIG. 1, Cohort #2), 80% of the cases were classified within the expected subtypes (24 ABC and 28 GCB), 13.8% were considered unclassified (3 GCB and 6 ABC) and four were misclassified (95% CIs [68%, 89%] and [7%, 25%] respectively; FIG. 3C). When focusing on samples classified by both techniques, 93% of agreement is reached in this second series (95% CI [82%, 98%]).

Reproducibility Assessment

We next performed ten independent repeats for two samples (RNA 9402 and 9260, ABC and GCB respectively). As shown in FIG. 9A, the calculated scores remained highly stable (average −32.75, standard deviation 0.41 for the sample 9260, average 17.88, standard deviation 0.32 for the sample 9402). To address further the robustness of the assay, we also tested 12 serial ½ dilutions of the same samples (9402), from 400 ng to less than 1 ng of RNA. As shown in FIG. 9C, the raw fluorescence peak heights for the 14 genes remained stable from 400 to 12 ng of RNA, resulting in a high stability of the normalized expression values (FIG. 9D), scores (average 17.84, standard deviation 0.26; FIG. 9B and E) and GCB/ABC probabilities (FIG. 9E).

Validation on an Independent Cohort of Frozen Samples

We next applied this predictor to a second independent validation series of 64 patients from the GHEDI study (FIG. 1, Cohort#4), classified within the GCB or ABC subtypes using Affymetrix U133+2 gene expression data and a Bayesian predictor based on a 24 gene expression signature as previously described[24]. This series comprised 28 GCB, 25 ABC, and 11 unclassified cases. As shown in FIG. 4, the RT-MLPA assay classified 84.4% (95% CI [73%, 92%]) of these cases within the expected subtypes (24/28 GCB, 22/25 ABC and 8/11 unclassified). 4 GCB and 3 ABC cases were considered unclassifiable, accounting for 13.2% (95% CI [5%, 25%]) of samples classified by the reference technique. Finally 3 previously unclassified cases were misclassified into the ABC subtype. When focusing on samples classified by both techniques, none of the 46 remaining sample was in contradiction between this assay and the Affymetrix U133+2 "gold standard" (95% CI [92%, 100%]).

Validation on FFPE Samples

Figure 5B:
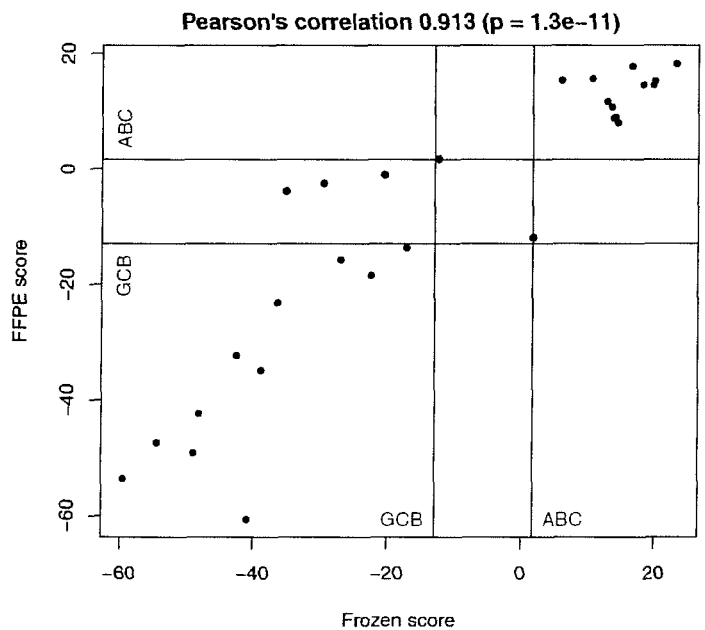

To test further the robustness of this assay, we next compared the results obtained from paired frozen and FFPE biopsies. Thirty RNA samples extracted from FFPE archival materials from the CHB cohort were tested. Except for two extraction failures, interpretable profiles were obtained for all 28 remaining cases. As shown in FIG. 5A, the RT-MLPA assay classified 25 (89.3%) of the FFPE samples within the expected subtypes (11/14 GCB, 12/12 ABC and 2/2 unclassified), while 3 GCB cases were considered unclassified. The statistically significant (p=1.2e-11) Pearson's correlation between frozen and FFPE samples is illustrated in FIG. 5B.

Extended Series of Samples

We next included 80 additional independent frozen samples, all from the Centre Henri Becquerel, and for which neither DASL nor Affymetrix classification was available (FIG. 1, Cohort #3). The resulting extended series of 195 cases allowed us to test for the correlations between the RT-MLPA GCB/ABC classification, IHC (100 cases) and survival (135 cases). Excluding the 50 samples of the training cohort, the RT-MLPA predictor classified 63 of the 145 remaining cases into the GCB subtype (43.4%), 56 into the ABC subtype (38.6%), and 26 were considered unclassifiable (17.9%). These proportions correspond to the repartition which is typically observed in DLBCL populations.

Comparison with Immunochemistry

For 100 cases (54 in the validation Cohort #1 and 46 in the Cohort #3), the GC/non-GC origin had been addressed by IHC at diagnosis using the Hans algorithm, implemented in our department of pathology in 2005[20]. To avoid artifacts, only cases with positive CD10 internal controls were considered interpretable. In this series, IHC and RT-MLPA were in agreement for 36/44 GCB cases (81.8%) and 32/38 ABC cases (84.2%). The last 18 cases, considered unclassified by RT-MLPA, distributed within the GCB (4 cases) and non-GCB (14 cases) subtypes defined by IHC (FIG. 6). These results are in agreement with what is typically observed between Affymetrix classifications and the Hans algorithm, which identifies GCB cases but does not differentiate unclassified cases from ABC cases (both referred as non-GCB cases)[20].

Survival Analysis

Figure 7A:
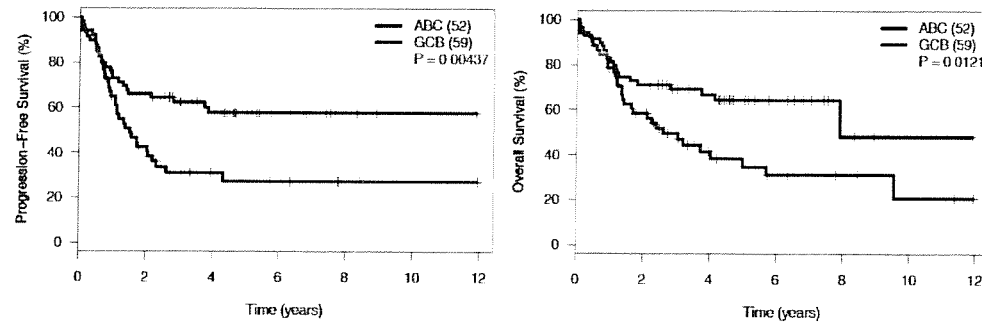
Figure 7B:
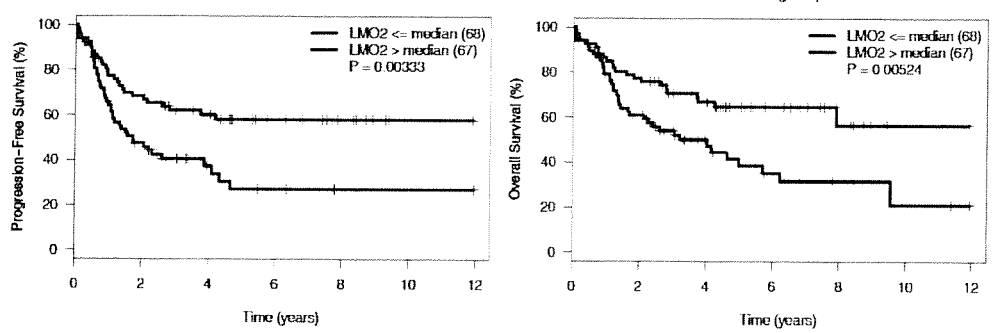
Figure 7C:
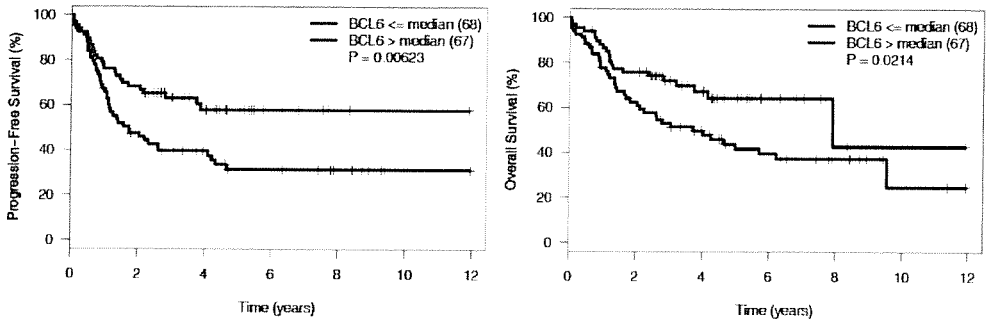
Figure 7D:
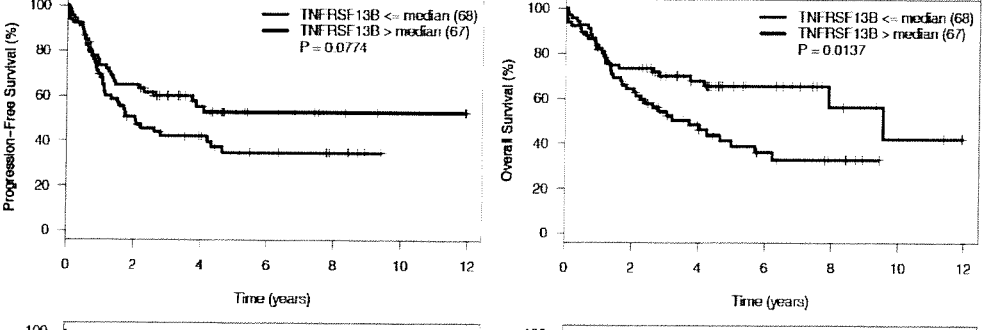

To evaluate the prognostic value of this assay, we next focused on the 135 patients diagnosed between 2001 and 2011 at the Centre Henri Becquerel who were treated by a combination of rituximab and chemotherapy. As expected, ABC cases were significantly associated with a poorer PFS (p=0.004) and OS (p=0.012) (FIG. 7A). Continuous univariate analysis also confirmed that the expression of several individual genes within this MLPA signature were significantly associated with prognosis (Table S3). As expected, high LMO2 (FDR=0.006 and 0.012 in PFS and OS, respectively) and BCL6 (FDR=0.019 in PFS) expressions were found to be associated with a better prognosis. Similarly, low TNFRSF13B expression was linearly correlated with a better prognosis (FDR=0.036 and 0.012 in PFS and OS, respectively). Simplification toward two-group models classifying patients according to the median expression of the considered gene led to similar results (FIG. 7B-D).

Figure 7E:
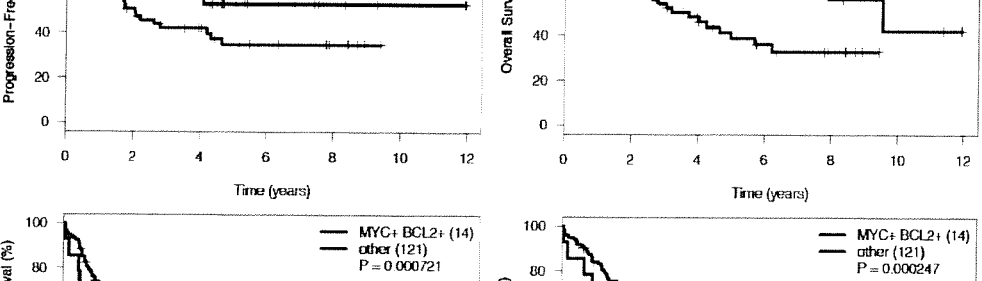

To further illustrate the ability of this assay to retrieve well-established prognosis factors, the survival of MYC+ BCL2+ patients was compared to the rest of the series. Following previously described methods[22], the expression thresholds were set at values (0.256 for BCL2, 1.284 for MYC) that lead to the most significant segmentation of patients in PFS. In total, 14 patients were classified as MYC+ BCL2+, and showed a particularly poor outcome in OS (27% [11-66] versus 67% [58-76] at 3 years, p=0.0002) and PFS (14% [4-52] versus 56% [47-66] at 3 years, p=0.0007) (FIG. 7E).

Discussion

Here, we describe a rapid and robust RT-MLPA assay which allows an accurate classification of GCB and ABC DLBCL. This easy to use method allows the rapid evaluation of the relative expression of 14 genes in a single reaction. It only requires a thermocycler, a capillary sequencer and basic molecular biology reagents, and can thus be implemented in many laboratories[17]. Its simplicity and flexibility allows testing from a single to up to 40 samples in parallel, making it particularly suitable for a routine diagnosis workflow. Furthermore, with the few adaptations we made, the whole procedure can be achieved in less than one day, making it a rapid and inexpensive alternative (with a reagent cost of less than 5 dollars/sample) to the current methods of GCB and ABC DLBCL stratification.

In the independent validation series we tested, none of the RT-MLPA calls was in contradiction with the current gold standard (Affymetrix arrays) and only a few samples moved from or to the "unclassified" group. Several well known prognostic factors were also found to be significant when determined by RT-MLPA, including the GCB/ABC classification[25], LMO2 and BCL6 gene expressions (Alizadeh et al, 2011a) and MYC-BCL2 co-expression (Johnson et al, 2012), further confirming the validity of this assay.

The proportions of unclassifiable or "Type III" samples we observed (13.8% and 13.2% of the two frozen validation cohorts) are slightly higher than the 9% originally described with the gold standard[24] and the 7% reported by the same laboratory using the Nanostring technology[16]. It should be noted however that the confidence threshold used for decision making was raised from the 90% originally published to the more ubiquitous 95%, which can explain this small increase. Nevertheless these proportions are consistent with the performances obtained using other gene expression based methods: 16%[15] or 20%[13]. The same problem was also reported with Hans' IHC algorithm[8-10] as CD10 and BCL6 reliable interpretation cannot always be achieved. Whether this "Type III" subgroup corresponds to an independent biological entity or to a heteroclite collection of atypical tumours is still an open question. However, the discrepancies observed in our series regarding these lymphomas, as well as the lack of consensus observed in the literature concerning their prognostic value[14,24], tend to support the later hypothesis.

When compared to other GEP methods, RT-MLPA is associated with a relatively poor dynamic range[26]. This characteristic impacted the development of the classifier as some genes, such as MME (encoding CD10), one of the best markers of the GCB subtype, could not be incorporated into the final design. On the other hand, RT-MLPA also proved to be efficient in evaluating the expression of other highly discriminant markers, such as LMO2, which is particularly difficult to evaluate by IHC. Furthermore, even though GCB and ABC DLBCLs differ by the expression of thousands of genes[4], the flexibility of RT-MLPA allowed us to easily and rapidly test multiple combinations of markers to reach a satisfactory design. Another important advantage of RT-MLPA over most others GEP methods is that as only short cDNA fragments are necessary for the correct binding and ligation of the gene specific oligonucleotide probes. It is thus less impacted by the use of low RNA concentration and RNA degradation, and constitutes as such an interesting alternative for testing FFPE biopsies. It could thus be used for the retrospective analysis of archival collections and for the inclusion of patients in prospective clinical trials, as only a few institutions routinely collect frozen biopsy materials.

In conclusion, the robust and cost effective RT-MLPA assay we describe, with its simple workflow and its short turn-around time, could be used in many laboratories without requiring the acquisition of any dedicated platform. It could then challenge IHC and other quantitative GEP assays to enable the stratification of DLBCL patients in prospective clinical trials, and ultimately facilitate the generalization of GCB/ABC DLBCL targeted therapies.

TABLE 1

Sequences of the RT-MLPA oligonucleotides.
The sequences of the forward and 5' phosphorylated reverse primers are presented with the symbol of the gene assessed, along with the 3 oligonucleotides used as competitors. The underlined sequence is designed to hybridize with PCR primers for a common amplification, while the rest of the sequence is a combination of a gene-specific sequence and spacer.

5' RT-MLPA probes

| Name | Sequence |
|---|---|
| NEK6_E2L (SEQ ID NO: 54) | 5'-<u>GTGCCAGCAAGATCCAATCTAGA</u>CCTGTGCATCCTCCTGACCCACAG-3' |
| IRF4_E6L (SEQ ID NO: 56) | 5'-<u>GTGCCAGCAAGATCCAATCTAGA</u>TCTGCCGAAGCCTTGGCGTTCTCAG-3' |
| IGHM_E2L (SEQ ID NO: 58) | 5'-<u>GTGCCAGCAAGATCCAATCTAGA</u>TGCGTCCTCCATGTGTGGCCCCG-3' |
| CCND1_E3L (SEQ ID NO: 60) | 5'-<u>GTGCCAGCAAGATCCAATCTAGA</u>TACCTTCGTTGCCCTCTGTGCCACAG-3' |
| LMO2_E5L (SEQ ID NO: 62) | 5'-<u>GTGCCAGCAAGATCCAATCTAGA</u>CGGAAGCTCTGCCGGAGAGACTATCTCAG-3' |
| FOXP1_E10L (SEQ ID NO: 64) | 5'-<u>GTGCCAGCAAGATCCAATCTAGA</u>CCCTTCCCCTTCAACCTCTTGCTCAAG-3' |
| TNFRSF9_E2L (SEQ ID NO: 66) | 5'-<u>GTGCCAGCAAGATCCAATCTAGA</u>TACGGACCTGTGACATATGCAGGCAGTGTAAAG-3' |
| BCL6_E3L (SEQ ID NO: 68) | 5'-<u>GTGCCAGCAAGATCCAATCTAGA</u>TACTACTCATAAAACGGTCCTCATGGCCTGCAG-3' |
| TNFRSF13B_E2L (SEQ ID NO: 70) | 5'-<u>GTGCCAGCAAGATCCAATCTAGA</u>TACTACTACTAGCGCACCTGTGCAGCCTTCTGCA-3' |
| CCND2_E1L (SEQ ID NO: 72) | 5'-<u>GTGCCAGCAAGATCCAATCTAGA</u>TACTACTGACCTTCATTGCTCTGTGTGCCACCG-3' |
| MYC_E1L (SEQ ID NO: 74) | 5'-<u>GTGCCAGCAAGATCCAATCTAGA</u>TACTACTACTTCGGGTAGTGGAAAACCAGCAGCCTC-3' |
| MYBL1_E10L (SEQ ID NO: 76) | 5'-<u>GTGCCAGCAAGATCCAATCTAGA</u>CCAGAATTTGCAGAGACTCTAGAACTTATTGAATCT-3' |
| BCL2_E1L (SEQ ID NO: 78) | 5'-<u>GTGCCAGCAAGATCCAATCTAGA</u>TACTACTACTACCCTGGATCCAGGATAACGGAGGCTGG-3' |

TABLE 1-continued

Sequences of the RT-MLPA oligonucleotides.
The sequences of the forward and 5' phosphorylated reverse primers are presented with the symbol of the gene assessed, along with the 3 oligonucleotides used as competitors. The underlined sequence is designed to hybridize with PCR primers for a common amplification, while the rest of the sequence is a combination of a gene-specific sequence and spacer.

| | |
|---|---|
| MS4A1_E5F (SEQ ID NO: 80) | 5'-<u>GTGCCAGCAAGATCCAATCTAGA</u>TACTACTACTATTCTTCATGAGGGAATCTAAGACTTTGGGG-3' |

3' RT-MLPA probes

| | |
|---|---|
| NEK6_E3R (SEQ ID NO: 55) | 5'-Pho-AGGCATCCCAACACGCTGTCTTT<u>TCCAACCCTTAGGGAACCC</u>-3' |
| IRF4_E7R (SEQ ID NO: 57) | 5'-Pho-ACTGCCGGCTGCACATCTGCCTGTA<u>TCCAACCCTTAGGGAACCC</u>-3' |
| IGHM_E3R (SEQ ID NO: 59) | 5'-Pho-ATCAAGACACAGCCATCCGGGTCTTCTACTA<u>TCCAACCCTTAGGGAACCC</u>-3' |
| CCND1_E4R (SEQ ID NO: 61) | 5'-Pho-ATGTGAAGTTCATTTCCAATCCGCCCTTACT<u>TCCAACCCTTAGGGAACCC</u>-3' |
| LMO2_E6R (SEQ ID NO: 63) | 5'-Pho-GCTTTTTGGGCAAGACGGTCTCTGCTACTA<u>TCCAACCCTTAGGGAACCC</u>-3' |
| FOXP1_E11R (SEQ ID NO: 65) | 5'-Pho-GCATGATTCCAACAGAACTGCAGCAGCTACTACTAC<u>TCCAACCCTTAGGGAACCC</u>-3' |
| TNFRSF9_E3R (SEQ ID NO: 67) | 5'-Pho-GTGTTTTCAGGACCAGGAAGGAGTGTTCCTAC<u>TCCAACCCTTAGGGAACCC</u>-3' |
| BCL6_E4R (SEQ ID NO: 69) | 5'-Pho-TGGCCTGTTCTATAGCATCTTTACAGACCAGTTG<u>TCCAACCCTTAGGGAACCC</u>-3' |
| TNFRSF13B_E3R (SEQ ID NO: 71) | 5'-Pho-GGTCACTCAGCTGCCGCAAGGAGCTACTACTACTAC<u>TCCAACCCTTAGGGAACCC</u>-3' |
| CCND2_E2R (SEQ ID NO: 73) | 5'-Pho-ACTTTAAGTTTGCCATGTACCCACCGTCGATACTACTA<u>TCCAACCCTTAGGGAACCC</u>-3' |
| MYC_E2R (SEQ ID NO: 75) | 5'-Pho-CCGCGACGATGCCCCTCAACGTTATACTACTACTACTA<u>TCCAACCCTTAGGGAACCC</u>-3' |
| MYBL1_E11R (SEQ ID NO: 77) | 5'-Pho-GATCCTGTAGCATGGAGTGACGTTACCAGTTTTTACTACT<u>TCCAACCCTTAGGGAACCC</u>-3' |
| BCL2_E2R (SEQ ID NO: 79) | 5'-Pho-GATGCCTTTGTGGAACTGTACGGCCTACTACTACTACTACT<u>TCCAACCCTTAGGGAACCC</u>-3' |
| MS4A1_E6R (SEQ ID NO: 81) | 5'-Pho-GCTGTCCAGATTATGAATGGGCTCTTCCACTACTACTACTA<u>TCCAACCCTTAGGGAACCC</u>-3' |

Competitors

| | |
|---|---|
| NEK6_comp (SEQ ID NO: 82) | 5'-AGGCATCCCAACACGCTGTCTTT-3' |
| IGHM_comp (SEQ ID NO: 83) | 5'-ATCAAGACACAGCCATCCGGGTCTTC-3' |

TABLE 2

Candidate genes considered for inclusion in the RT-MLPA predictor.
GCB and ABC discriminating genes (reported as False Discovery Rates from two distinct LIMMA analyses) in two independent series of Affymetrix U133 + 2 arrays (GHEDI and Lenz et al.) were considered for inclusion in the predictor. The considered Affymetrix probeset, as well as the final decision to retain the gene (+) or not according to its performances in RT-MLPA, are indicated.

| Gene | Probeset | High in | GHEDI FDR | Lenz FDR | RT-MLPA | RT-MLPA FDR |
|---|---|---|---|---|---|---|
| BATF | 205965_at | ABC | $1.95 \times 10^{-11}$ | $1.05 \times 10^{-35}$ | | |
| CCND2 | 200953_s_at | ABC | $1.12 \times 10^{-6}$ | $8.92 \times 10^{-14}$ | | |
| FOXP1 | 224838_at | ABC | $5.97 \times 10^{-28}$ | $1.35 \times 10^{-28}$ | + | $9.98 \times 10^{-3}$ |
| FUT8 | 203988_s_at | ABC | $5.19 \times 10^{-15}$ | $4.71 \times 10^{-26}$ | | |
| IGHM | 209374_s_at | ABC | $1.62 \times 10^{-10}$ | $2.29 \times 10^{-21}$ | + | $9.93 \times 10^{-5}$ |
| IRF4 | 204562_at | ABC | $3.92 \times 10^{-14}$ | $2.55 \times 10^{-17}$ | + | $9.93 \times 10^{-5}$ |
| LIMD1 | 222762_x_at | ABC | $3.28 \times 10^{-16}$ | $2.00 \times 10^{-34}$ | | |
| SH3BP5 | 201811_x_at | ABC | $1.19 \times 10^{-22}$ | $9.98 \times 10^{-25}$ | | |
| SLA | 203761_at | ABC | $5.10 \times 10^{-17}$ | $5.64 \times 10^{-31}$ | | |
| TNFRSF13B | 207641_at | ABC | $3.40 \times 10^{-11}$ | $4.44 \times 10^{-20}$ | + | $9.93 \times 10^{-5}$ |
| BCL6 | 203140_at | GCB | $5.13 \times 10^{-6}$ | $2.00 \times 10^{-34}$ | + | $8.93 \times 10^{-4}$ |
| LMO2 | 204249_s_at | GCB | $1.25 \times 10^{-10}$ | $1.32 \times 10^{-23}$ | + | $1.90 \times 10^{-10}$ |
| MME | 203434_s_at | GCB | $1.36 \times 10^{-5}$ | $6.08 \times 10^{-21}$ | | |
| MYBL1 | 213906_at | GCB | $8.44 \times 10^{-10}$ | $2.23 \times 10^{-27}$ | + | $1.12 \times 10^{-4}$ |
| NEK6 | 223158_s_at | GCB | $1.06 \times 10^{-10}$ | $7.01 \times 10^{-29}$ | + | $1.03 \times 10^{-5}$ |
| TNFRSF9 | 207536_s_at | GCB | $9.81 \times 10^{-4}$ | $6.39 \times 10^{-2}$ | | |

TABLE S1

Full sample list.

The characteristics of the 317 samples analyzed in this paper, identified by their RNA and Patient unique IDs. When available, reference GCB-ABC classification as evaluated by Affymetrix, DASL or IHC is provided along with the final (MLPA) classification. The raw scores and probabilities of belonging to the ABC subgroup are also provided, as computed by the RT-MLPA predictor (probability of belonging to the GCB subgroup can be computed as the complement to 1).

| Material | Cohort | RNA | Patient | Affymetrix | DASL | DASL.score | IHC | OS.time (years) | OS.event | PFS.time (years) | PFS.event | MLPA | MLPA.score | MLPA.p (ABC) |
|---|---|---|---|---|---|---|---|---|---|---|---|---|---|---|
| frozen | dilutions | 9402_D01 | UPN1633 | | | | | | | | | ABC | 17.559 | 9.98E-01 |
| frozen | dilutions | 9402_D02 | UPN1633 | | | | | | | | | ABC | 18.308 | 9.98E-01 |
| frozen | dilutions | 9402_D03 | UPN1633 | | | | | | | | | ABC | 17.937 | 9.98E-01 |
| frozen | dilutions | 9402_D04 | UPN1633 | | | | | | | | | ABC | 17.793 | 9.98E-01 |
| frozen | dilutions | 9402_D05 | UPN1633 | | | | | | | | | ABC | 17.687 | 9.98E-01 |
| frozen | dilutions | 9402_D06 | UPN1633 | | | | | | | | | ABC | 17.758 | 9.98E-01 |
| frozen | dilutions | 9402_D07 | UPN1633 | | | | | | | | | ABC | 17.152 | 9.97E-01 |
| frozen | dilutions | 9402_D08 | UPN1633 | | | | | | | | | ABC | 17.487 | 9.97E-01 |
| frozen | dilutions | 9402_D09 | UPN1633 | | | | | | | | | ABC | 16.461 | 9.97E-01 |
| frozen | dilutions | 9402_D10 | UPN1633 | | | | | | | | | ABC | 16.818 | 9.97E-01 |
| frozen | dilutions | 9402_D11 | UPN1633 | | | | | | | | | ABC | 16.238 | 9.97E-01 |
| frozen | dilutions | 9402_D12 | UPN1633 | | | | | | | | | ABC | 12.679 | 9.96E-01 |
| FFPE | FFPE | B01.1117 | UPN1001 | | | | | | | | | GCB | −23.148 | 1.54E-04 |
| FFPE | FFPE | B04.2708 | UPN1291 | | | | | | | | | ABC | 11.634 | 9.95E-01 |
| FFPE | FFPE | B05.2945 | UPN1389 | | | | | | | | | GCB | −53.532 | 9.41E-16 |
| FFPE | FFPE | B06.0638 | UPN1411 | | | | | | | | | ABC | 18.094 | 9.98E-01 |
| FFPE | FFPE | B06.0757 | UPN1415 | | | | | | | | | ABC | 14.390 | 9.97E-01 |
| FFPE | FFPE | B06.1310 | UPN1434 | | | | | | | | | other | −0.937 | 8.90E-01 |
| FFPE | FFPE | B06.2626 | UPN1474 | | | | | | | | | other | −11.896 | 8.10E-02 |
| FFPE | FFPE | B07.0131 | UPN1485 | | | | | | | | | GCB | −15.802 | 1.17E-02 |
| FFPE | FFPE | B07.0512 | UPN1497 | | | | | | | | | GCB | −13.605 | 3.62E-02 |
| FFPE | FFPE | B07.2345 | UPN1549 | | | | | | | | | GCB | −32.380 | 2.29E-07 |
| FFPE | FFPE | B07.2712 | UPN1560 | | | | | | | | | GCB | −18.459 | 2.67E-03 |
| FFPE | FFPE | B07.2960 | UPN1569 | | | | | | | | | other | 1.728 | 9.50E-01 |
| FFPE | FFPE | B08.0130 | UPN1574 | | | | | | | | | ABC | 15.298 | 9.97E-01 |
| FFPE | FFPE | B08.1825 | UPN1580 | | | | | | | | | GCB | −49.048 | 9.42E-14 |
| FFPE | FFPE | B08.1769 | UPN1627 | | | | | | | | | other | −3.877 | 7.39E-01 |
| FFPE | FFPE | B08.1852 | UPN1633 | | | | | | | | | ABC | 14.493 | 9.97E-01 |
| FFPE | FFPE | B08.1999 | UPN1637 | | | | | | | | | ABC | 15.061 | 9.97E-01 |
| FFPE | FFPE | B08.2071 | UPN1639 | | | | | | | | | GCB | −42.454 | 4.99E-11 |
| FFPE | FFPE | B08.2463 | UPN1647 | | | | | | | | | other | −2.575 | 8.21E-01 |
| FFPE | FFPE | B09.0141 | UPN1684 | | | | | | | | | GCB | −34.849 | 3.30E-08 |
| FFPE | FFPE | B09.0388 | UPN1691 | | | | | | | | | ABC | 8.677 | 9.91E-01 |
| FFPE | FFPE | B09.1810 | UPN1737 | | | | | | | | | ABC | 7.888 | 9.89E-01 |
| FFPE | FFPE | B09.1892 | UPN1741 | | | | | | | | | ABC | 15.512 | 9.97E-01 |
| FFPE | FFPE | B09.2264 | UPN1750 | | | | | | | | | ABC | 8.806 | 9.91E-01 |
| FFPE | FFPE | B10.0146 | UPN1768 | | | | | | | | | ABC | 10.632 | 9.94E-01 |
| FFPE | FFPE | B10.0640 | UPN1787 | | | | | | | | | GCB | −60.672 | 3.49E-19 |
| FFPE | FFPE | X10.0083 | UPN1801 | | | | | | | | | GCB | −47.320 | 5.16E-13 |
| FFPE | FFPE | B12.1717 | UPN1911 | | | | | | | | | ABC | 17.609 | 9.98E-01 |
| frozen | LYSA | GHE0015 | GHE0015 | GCB | | | | | | | | GCB | −26.420 | 1.75E-05 |
| frozen | LYSA | GHE0016 | GHE0016 | ABC | | | | | | | | ABC | 4.158 | 9.74E-01 |
| frozen | LYSA | GHE0024 | GHE0024 | ABC | | | | | | | | ABC | 7.561 | 9.89E-01 |
| frozen | LYSA | GHE0028 | GHE0028 | ABC | | | | | | | | other | 1.586 | 9.48E-01 |

TABLE S1-continued

Full sample list.
The characteristics of the 317 samples analyzed in this paper, identified by their RNA and Patient unique IDs. When available, reference GCB-ABC classification as evaluated by Affymetrix, DASL or IHC is provided along with the final (MLPA) classification. The raw scores and probabilities of belonging to the ABC subgroup are also provided, as computed by the RT-MLPA predictor (probability of belonging to the GCB subgroup can be computed as the complement to 1).

| Material | Cohort | RNA | Patient | Affymetrix | DASL | DASL.score | IHC | OS.time (years) | OS.event | PFS.time (years) | PFS.event | MLPA | MLPA.score | MLPA.p (ABC) |
|---|---|---|---|---|---|---|---|---|---|---|---|---|---|---|
| frozen | LYSA | GHE0047 | GHE0047 | other | | | | | | | | other | −2.286 | 8.35E−01 |
| frozen | LYSA | GHE0061 | GHE0061 | ABC | | | | | | | | ABC | 9.757 | 9.93E−01 |
| frozen | LYSA | GHE0140 | GHE0140 | other | | | | | | | | ABC | 3.532 | 9.70E−01 |
| frozen | LYSA | GHE0202 | GHE0202 | GCB | | | | | | | | GCB | −19.790 | 1.22E−03 |
| frozen | LYSA | GHE0219 | GHE0219 | GCB | | | | | | | | GCB | −27.557 | 7.94E−06 |
| frozen | LYSA | GHE0228 | GHE0228 | GCB | | | | | | | | GCB | −21.441 | 4.50E−04 |
| frozen | LYSA | GHE0258 | GHE0258 | ABC | | | | | | | | ABC | 2.531 | 9.60E−01 |
| frozen | LYSA | GHE0262 | GHE0262 | ABC | | | | | | | | ABC | 5.615 | 9.82E−01 |
| frozen | LYSA | GHE0292 | GHE0292 | GCB | | | | | | | | GCB | −44.127 | 1.07E−11 |
| frozen | LYSA | GHE0293 | GHE0293 | other | | | | | | | | other | −4.798 | 6.65E−01 |
| frozen | LYSA | GHE0368 | GHE0368 | GCB | | | | | | | | GCB | −30.089 | 1.29E−06 |
| frozen | LYSA | GHE0375 | GHE0375 | other | | | | | | | | other | 0.447 | 9.27E−01 |
| frozen | LYSA | GHE0429 | GHE0429 | GCB | | | | | | | | GCB | −35.412 | 2.10E−08 |
| frozen | LYSA | GHE0436 | GHE0436 | ABC | | | | | | | | ABC | 15.539 | 9.97E−01 |
| frozen | LYSA | GHE0440 | GHE0440 | GCB | | | | | | | | GCB | −34.923 | 3.11E−08 |
| frozen | LYSA | GHE0507 | GHE0507 | ABC | | | | | | | | ABC | 7.684 | 9.89E−01 |
| frozen | LYSA | GHE0547 | GHE0547 | other | | | | | | | | other | −0.071 | 9.15E−01 |
| frozen | LYSA | GHE0562 | GHE0562 | ABC | | | | | | | | ABC | 3.471 | 9.69E−01 |
| frozen | LYSA | GHE0629 | GHE0629 | ABC | | | | | | | | ABC | 7.597 | 9.89E−01 |
| frozen | LYSA | GHE0632 | GHE0632 | other | | | | | | | | other | −1.969 | 8.50E−01 |
| frozen | LYSA | GHE0635 | GHE0635 | GCB | | | | | | | | GCB | −35.976 | 1.32E−08 |
| frozen | LYSA | GHE0659 | GHE0659 | ABC | | | | | | | | ABC | 5.195 | 9.80E−01 |
| frozen | LYSA | GHE0685 | GHE0685 | ABC | | | | | | | | ABC | 6.618 | 9.86E−01 |
| frozen | LYSA | GHE0708 | GHE0708 | GCB | | | | | | | | GCB | −27.290 | 9.57E−06 |
| frozen | LYSA | GHE0717 | GHE0717 | ABC | | | | | | | | ABC | 10.833 | 9.94E−01 |
| frozen | LYSA | GHE0776 | GHE0776 | GCB | | | | | | | | GCB | −15.686 | 1.24E−02 |
| frozen | LYSA | GHE0811 | GHE0811 | ABC | | | | | | | | ABC | 9.167 | 9.92E−01 |
| frozen | LYSA | GHE0834 | GHE0834 | GCB | | | | | | | | GCB | −33.168 | 1.25E−07 |
| frozen | LYSA | GHE0837 | GHE0837 | ABC | | | | | | | | ABC | 12.755 | 9.96E−01 |
| frozen | LYSA | GHE0853 | GHE0853 | other | | | | | | | | other | −8.507 | 2.98E−01 |
| frozen | LYSA | GHE0855 | GHE0855 | ABC | | | | | | | | other | −2.843 | 8.06E−01 |
| frozen | LYSA | GHE0857 | GHE0857 | GCB | | | | | | | | GCB | −16.082 | 1.01E−02 |
| frozen | LYSA | GHE0860 | GHE0860 | ABC | | | | | | | | other | −3.716 | 7.50E−01 |
| frozen | LYSA | GHE0877 | GHE0877 | other | | | | | | | | other | −3.776 | 7.46E−01 |
| frozen | LYSA | GHE0908 | GHE0908 | GCB | | | | | | | | GCB | −44.859 | 5.42E−12 |
| frozen | LYSA | GHE0997 | GHE0997 | other | | | | | | | | ABC | −2.302 | 8.35E−01 |
| frozen | LYSA | GHE1018 | GHE1018 | GCB | | | | | | | | GCB | −34.597 | 4.04E−08 |
| frozen | LYSA | GHE1028 | GHE1028 | ABC | | | | | | | | GCB | −22.667 | 2.09E−04 |
| frozen | LYSA | GHE1069 | GHE1069 | GCB | | | | | | | | GCB | −19.875 | 1.16E−03 |
| frozen | LYSA | GHE1225 | GHE1225 | GCB | | | | | | | | GCB | −17.685 | 4.15E−03 |
| frozen | LYSA | GHE1229 | GHE1229 | ABC | | | | | | | | ABC | 7.207 | 9.88E−01 |
| frozen | LYSA | GHE1287 | GHE1287 | GCB | | | | | | | | GCB | −48.593 | 1.48E−13 |
| frozen | LYSA | GHE1302 | GHE1302 | ABC | | | | | | | | ABC | 4.331 | 9.75E−01 |
| frozen | LYSA | GHE1352 | GHE1352 | GCB | | | | | | | | other | −8.586 | 2.91E−01 |
| frozen | LYSA | GHE1353 | GHE1353 | ABC | | | | | | | | ABC | 9.731 | 9.93E−01 |
| frozen | LYSA | GHE1373 | GHE1373 | GCB | | | | | | | | GCB | −39.420 | 7.32E−10 |

TABLE S1-continued

Full sample list.
The characteristics of the 317 samples analyzed in this paper, identified by their RNA and Patient unique IDs. When available, reference GCB-ABC classification as evaluated by Affymetrix, DASL or IHC is provided along with the final (MLPA) classification. The raw scores and probabilities of belonging to the ABC subgroup are also provided, as computed by the RT-MLPA predictor (probability of belonging to the GCB subgroup can be computed as the complement to 1).

| Material | Cohort | RNA | Patient | Affymetrix | DASL | DASL.score | IHC | OS.time (years) | PFS.time (years) | OS.event | PFS.event | MLPA | MLPA.score | MLPA.p (ABC) |
|---|---|---|---|---|---|---|---|---|---|---|---|---|---|---|
| frozen | LYSA | GHE1393 | GHE1393 | GCB | | | | | | | | GCB | −26.683 | 1.46E−05 |
| frozen | LYSA | GHE1409 | GHE1409 | other | | | | | | | | other | −9.193 | 2.38E−01 |
| frozen | LYSA | GHE1413 | GHE1413 | ABC | | | | | | | | ABC | 13.527 | 9.96E−01 |
| frozen | LYSA | GHE1424 | GHE1424 | ABC | | | | | | | | ABC | 5.913 | 9.83E−01 |
| frozen | LYSA | GHE1498 | GHE1498 | GCB | | | | | | | | GCB | −17.476 | 4.67E−03 |
| frozen | LYSA | GHE1553 | GHE1553 | GCB | | | | | | | | GCB | −38.138 | 2.19E−09 |
| frozen | LYSA | GHE1554 | GHE1554 | other | | | | | | | | other | −10.272 | 1.60E−01 |
| frozen | LYSA | GHE2002 | GHE2002 | other | | | | | | | | ABC | 2.866 | 9.64E−01 |
| frozen | LYSA | GHE2003 | GHE2003 | GCB | | | | | | | | GCB | −30.308 | 1.09E−06 |
| frozen | LYSA | GHE2012 | GHE2012 | ABC | | | | | | | | ABC | 2.695 | 9.62E−01 |
| frozen | LYSA | GHE2019 | GHE2019 | GCB | | | | | | | | other | −11.509 | 9.61E−02 |
| frozen | LYSA | GHE2026 | GHE2026 | ABC | | | | | | | | ABC | 7.649 | 9.89E−01 |
| frozen | LYSA | GHE2030 | GHE2030 | ABC | | | | | | | | ABC | 2.960 | 9.65E−01 |
| frozen | LYSA | GHE2109 | GHE2109 | other | | | | | | | | ABC | 3.627 | 9.70E−01 |
| frozen | additional | 1560 | UPN0958 | | | | GCB | 11.91 | 11.91 | FALSE | FALSE | GCB | −29.883 | 1.50E−06 |
| frozen | additional | 1572 | UPN0962 | | | | | 11.36 | 1.35 | FALSE | TRUE | ABC | 17.211 | 9.97E−01 |
| frozen | additional | 1624 | UPN0968 | | | | GCB | | | | | GCB | −16.294 | 8.96E−03 |
| frozen | additional | 2462 | UPN1025 | | | | GCB | 9.52 | 1.17 | TRUE | TRUE | ABC | 13.738 | 9.96E−01 |
| frozen | additional | 2686 | UPN1035 | | | | Non-GCB | 7.80 | 7.80 | FALSE | FALSE | ABC | 15.295 | 9.97E−01 |
| frozen | additional | 2763 | UPN1161 | | | | Non-GCB | 9.31 | 9.31 | FALSE | FALSE | other | −5.828 | 5.69E−01 |
| frozen | additional | 2881 | UPN1170 | | | | Non-GCB | 2.04 | 0.80 | TRUE | TRUE | other | −12.649 | 5.73E−02 |
| frozen | additional | 2900 | UPN1084 | | | | Non-GCB | | | | | GCB | −36.003 | 1.30E−08 |
| frozen | additional | 3191 | UPN2036 | | | | GCB | 1.20 | 0.69 | TRUE | TRUE | ABC | 15.911 | 9.97E−01 |
| frozen | additional | 3235 | UPN1209 | | | | | 7.54 | 7.54 | FALSE | FALSE | GCB | −47.321 | 5.16E−13 |
| frozen | additional | 3247 | UPN1211 | | | | | 4.02 | 1.55 | TRUE | TRUE | ABC | 4.438 | 9.76E−01 |
| frozen | additional | 3454 | UPN1232 | | | | | 6.22 | 1.00 | TRUE | TRUE | other | 1.409 | 9.45E−01 |
| frozen | additional | 3608 | UPN1252 | | | | GCB | 8.92 | 8.92 | FALSE | FALSE | GCB | −24.767 | 5.34E−05 |
| frozen | additional | 3750 | UPN1260 | | | | GCB | 8.42 | 8.42 | FALSE | FALSE | other | −5.032 | 6.44E−01 |
| frozen | additional | 4258 | UPN0966 | | | | | 3.04 | 1.71 | TRUE | TRUE | ABC | 16.789 | 9.97E−01 |
| frozen | additional | 4594 | UPN1336 | | | | GCB | 1.10 | 0.75 | TRUE | TRUE | ABC | 12.204 | 9.95E−01 |
| frozen | additional | 4853 | UPN0891 | | | | Non-GCB | | | | | GCB | −38.281 | 1.94E−09 |
| frozen | additional | 5719 | UPN1402 | | | | | 5.71 | 1.71 | TRUE | TRUE | ABC | 19.872 | 9.98E−01 |
| frozen | additional | 6771 | UPN1473 | | | | Non-GCB | 2.60 | 2.60 | TRUE | TRUE | ABC | 6.194 | 9.84E−01 |
| frozen | additional | 7136 | UPN1490 | | | | Non-GCB | 4.64 | 4.64 | TRUE | TRUE | other | −4.446 | 6.95E−01 |
| frozen | additional | 7280 | UPN1164 | | | | | 4.16 | 3.86 | TRUE | TRUE | GCB | −16.573 | 7.70E−03 |
| frozen | additional | 8056 | UPN2037 | | | | Non-GCB | 3.21 | 1.50 | TRUE | TRUE | ABC | 12.668 | 9.96E−01 |
| frozen | additional | 8090 | UPN1547 | | | | Non-GCB | | | | | ABC | 12.207 | 9.95E−01 |

TABLE S1-continued

Full sample list.
The characteristics of the 317 samples analyzed in this paper, identified by their RNA and Patient unique IDs. When available, reference GCB-ABC classification as evaluated by Affymetrix, DASL or IHC is provided along with the final (MLPA) classification. The raw scores and probabilities of belonging to the ABC subgroup are also provided, as computed by the RT-MLPA predictor (probability of belonging to the GCB subgroup can be computed as the complement to 1).

| Material | Cohort | RNA | Patient | Affymetrix | DASL | DASL.score | IHC | OS.time (years) | PFS.time (years) | OS.event | PFS.event | MLPA | MLPA.score | MLPA.p (ABC) |
|---|---|---|---|---|---|---|---|---|---|---|---|---|---|---|
| frozen | additional | 8119 | UPN1549 | | | | GCB | 0.90 | 0.90 | TRUE | TRUE | GCB | -42.555 | 4.55E-11 |
| frozen | additional | 8307 | UPN0856 | | | | GCB | | | | | GCB | -16.390 | 8.51E-03 |
| frozen | additional | 8743 | UPN2038 | | | | GCB | 5.74 | 5.74 | FALSE | FALSE | ABC | 6.473 | 9.85E-01 |
| frozen | additional | 9022 | UPN1597 | | | | Non-GCB | 4.65 | 4.65 | FALSE | FALSE | GCB | -15.969 | 1.07E-02 |
| frozen | additional | 9083 | UPN1603 | | | | | 1.26 | 0.95 | TRUE | TRUE | GCB | -42.679 | 4.07E-11 |
| frozen | additional | 9231 | UPN1561 | | | | Non-GCB | | | | | ABC | 5.673 | 9.82E-01 |
| frozen | additional | 9397 | UPN1630 | | | | GCB | | | | | GCB | -49.660 | 5.10E-14 |
| frozen | additional | 9795 | UPN1654 | | | | Non-GCB | | | | | other | -0.874 | 8.92E-01 |
| frozen | additional | 9831 | UPN1657 | | | | GCB | 0.67 | 0.67 | FALSE | FALSE | other | -6.265 | 5.25E-01 |
| frozen | additional | 9881 | UPN1662 | | | | GCB | 4.99 | 4.32 | TRUE | TRUE | ABC | 13.348 | 9.96E-01 |
| frozen | additional | 10035 | UPN1565 | | | | GCB | | | | | other | 0.510 | 9.29E-01 |
| frozen | additional | 10401 | UPN1691 | | | | | 0.96 | 0.96 | FALSE | FALSE | ABC | 13.737 | 9.96E-01 |
| frozen | additional | 10823 | UPN1718 | | | | | 3.96 | 3.96 | FALSE | FALSE | ABC | 14.966 | 9.97E-01 |
| frozen | additional | 11105 | UPN1741 | | | | | 0.68 | 0.50 | TRUE | TRUE | ABC | 10.482 | 9.94E-01 |
| frozen | additional | 11222 | UPN0841 | | | | Non-GCB | | | | | ABC | 17.459 | 9.97E-01 |
| frozen | additional | 11284 | UPN1753 | | | | Non-GCB | 0.19 | 0.13 | TRUE | TRUE | GCB | -24.883 | 4.94E-05 |
| frozen | additional | 11767 | UPN0707 | | | | Non-GCB | | | | | GCB | -43.936 | 1.28E-11 |
| frozen | additional | 11768 | UPN0445 | | | | Non-GCB | | | | | ABC | 10.466 | 9.94E-01 |
| frozen | additional | 11770 | UPN0810 | | | | Non-GCB | | | | | ABC | 13.625 | 9.96E-01 |
| frozen | additional | 11779 | UPN0373 | | | | Non-GCB | | | | | ABC | 1.793 | 9.51E-01 |
| frozen | additional | 11887 | UPN1789 | | | | | 2.48 | 2.48 | FALSE | FALSE | ABC | 7.641 | 9.89E-01 |
| frozen | additional | 12003 | UPN1800 | | | | | 2.55 | 2.55 | FALSE | FALSE | GCB | -31.670 | 3.94E-07 |
| frozen | additional | 12100 | UPN1805 | | | | GCB | 3.37 | 3.37 | FALSE | FALSE | GCB | -21.441 | 4.50E-04 |
| frozen | additional | 12141 | UPN1806 | | | | GCB | | 0.65 | TRUE | TRUE | GCB | -57.438 | 1.36E-17 |
| frozen | additional | 12284 | UPN1814 | | | | Non-GCB | 1.17 | | | | ABC | 14.451 | 9.97E-01 |
| frozen | additional | 12422 | UPN1827 | | | | | 3.02 | 3.02 | FALSE | FALSE | GCB | -37.225 | 4.72E-09 |
| frozen | additional | 12547 | UPN1838 | | | | | 0.01 | 0.01 | TRUE | TRUE | ABC | 9.080 | 9.92E-01 |
| frozen | additional | 12621 | UPN1841 | | | | | 2.43 | 2.43 | FALSE | FALSE | GCB | -36.585 | 8.03E-09 |
| frozen | additional | 12639 | UPN1842 | | | | | 2.62 | 2.69 | TRUE | TRUE | other | -11.558 | 9.41E-02 |
| frozen | additional | 12757 | UPN1849 | | | | | 2.69 | 2.69 | FALSE | FALSE | GCB | -24.791 | 5.25E-05 |
| frozen | additional | 12766 | UPN1850 | | | | | 2.78 | 2.78 | FALSE | FALSE | GCB | -51.481 | 8.00E-15 |
| frozen | additional | 12855 | UPN1455 | | | | | 6.82 | 4.08 | TRUE | TRUE | other | -5.154 | 6.33E-01 |
| frozen | additional | 12861 | UPN1861 | | | | | 2.22 | 2.22 | FALSE | FALSE | other | -4.139 | 7.19E-01 |
| frozen | additional | 12984 | UPN1865 | | | | | 2.31 | 2.31 | FALSE | FALSE | ABC | 2.188 | 9.56E-01 |
| frozen | additional | 12986 | UPN1866 | | | | | 0.08 | 0.05 | TRUE | TRUE | GCB | -27.776 | 6.81E-06 |

TABLE S1-continued

Full sample list.
The characteristics of the 317 samples analyzed in this paper, identified by their RNA and Patient unique IDs. When available, reference GCB-ABC classification as evaluated by Affymetrix, DASL or IHC is provided along with the final (MLPA) classification. The raw scores and probabilities of belonging to the ABC subgroup are also provided, as computed by the RT-MLPA predictor (probability of belonging to the GCB subgroup can be computed as the complement to 1).

| Material | Cohort | RNA | Patient | Affymetrix | DASL | DASL.score | IHC | OS.time (years) | PFS.time (years) | OS.event | PFS.event | MLPA | MLPA.score | MLPA.p (ABC) |
|---|---|---|---|---|---|---|---|---|---|---|---|---|---|---|
| frozen | additional | 13016 | UPN1868 | | | | | 2.73 | 2.73 | FALSE | FALSE | ABC | 12.123 | 9.95E-01 |
| frozen | additional | 13062 | UPN1871 | | | | | 2.60 | 2.60 | FALSE | FALSE | other | -5.904 | 5.61E-01 |
| frozen | additional | 13274 | UPN1887 | | | | | 1.59 | 1.29 | TRUE | TRUE | GCB | -31.208 | 5.59E-07 |
| frozen | additional | 13519 | UPN1899 | | | | | 2.30 | 1.68 | FALSE | TRUE | other | -5.117 | 6.37E-01 |
| frozen | additional | 13761 | UPN1911 | | | | | 1.43 | 1.11 | TRUE | TRUE | ABC | 16.505 | 9.97E-01 |
| frozen | additional | 13959 | UPN1920 | | | | | 2.20 | 2.20 | FALSE | FALSE | GCB | -27.542 | 8.03E-06 |
| frozen | additional | 14186 | UPN1938 | | | | | 2.11 | 2.11 | FALSE | FALSE | ABC | 2.709 | 9.62E-01 |
| frozen | additional | 14341 | UPN1948 | | | | | 0.45 | 0.45 | TRUE | TRUE | ABC | 17.675 | 9.98E-01 |
| frozen | additional | 14347 | UPN1798 | | | | | 2.87 | 1.44 | FALSE | TRUE | GCB | -16.772 | 6.90E-03 |
| frozen | additional | 2898 | UPN0914 | | | | Non-GCB | | | | | other | -2.693 | 8.14E-01 |
| frozen | additional | 4222 | UPN1306 | | | | Non-GCB | 3.72 | 2.04 | TRUE | TRUE | ABC | 4.359 | 9.76E-01 |
| frozen | additional | 4467 | UPN1324 | | | | Non-GCB | 4.25 | 4.20 | FALSE | FALSE | other | 1.238 | 9.42E-01 |
| frozen | additional | 4788 | UPN1359 | | | | Non-GCB | 7.42 | 7.42 | FALSE | FALSE | GCB | -34.014 | 6.41E-08 |
| frozen | additional | 4950 | UPN1372 | | | | Non-GCB | 2.79 | 2.79 | FALSE | FALSE | other | -8.156 | 3.31E-01 |
| frozen | additional | 5541 | UPN1396 | | | | GCB | 6.54 | 1.39 | FALSE | TRUE | GCB | -22.444 | 2.40E-04 |
| frozen | additional | 6092 | UPN1434 | | | | GCB | 0.88 | 0.50 | TRUE | TRUE | GCB | -20.530 | 7.86E-04 |
| frozen | additional | 8193 | UPN0285 | | | | Non-GCB | | | | | ABC | 2.422 | 9.59E-01 |
| frozen | additional | 8730 | UPN1586 | | | | GCB | 3.75 | 3.75 | TRUE | TRUE | GCB | -34.945 | 3.06E-08 |
| frozen | additional | 9647 | UPN1178 | | | | GCB | | | | | GCB | -29.031 | 2.78E-06 |
| frozen | additional | 10181 | UPN1675 | | | | | 4.04 | 4.04 | FALSE | FALSE | GCB | -38.852 | 1.19E-09 |
| frozen | additional | 10724 | UPN1703 | | | | | 3.76 | 3.76 | FALSE | FALSE | other | -9.166 | 2.41E-01 |
| frozen | additional | 11573 | UPN1773 | | | | | 3.01 | 3.01 | FALSE | FALSE | GCB | -39.515 | 6.74E-10 |
| frozen | validation | 9260 | UPN1622 | | GCB | -7.352 | | 4.43 | 4.43 | FALSE | FALSE | GCB | -33.227 | 1.19E-07 |
| frozen | replicates | 9260_R02 | UPN1622 | | | | | | | | | GCB | -33.139 | 1.27E-07 |
| frozen | replicates | 9260_R03 | UPN1622 | | | | | | | | | GCB | -32.411 | 2.24E-07 |
| frozen | replicates | 9260_R04 | UPN1622 | | | | | | | | | GCB | -33.155 | 1.26E-07 |
| frozen | replicates | 9260_R05 | UPN1622 | | | | | | | | | GCB | -33.275 | 1.15E-07 |
| frozen | replicates | 9260_R06 | UPN1622 | | | | | | | | | GCB | -32.721 | 1.76E-07 |
| frozen | replicates | 9260_R07 | UPN1622 | | | | | | | | | GCB | -32.956 | 1.47E-07 |
| frozen | replicates | 9260_R08 | UPN1622 | | | | | | | | | GCB | -32.131 | 2.77E-07 |
| frozen | replicates | 9260_R09 | UPN1622 | | | | | | | | | GCB | -33.453 | 9.97E-08 |
| frozen | replicates | 9260_R10 | UPN1622 | | | | | | | | | GCB | -32.972 | 1.45E-07 |
| frozen | training | 9402 | UPN1633 | | ABC | 14.158 | | 0.59 | 0.56 | TRUE | TRUE | ABC | 18.084 | 9.98E-01 |
| frozen | replicates | 9402_R02 | UPN1633 | | | | | | | | | ABC | 17.725 | 9.98E-01 |
| frozen | replicates | 9402_R03 | UPN1633 | | | | | | | | | ABC | 17.901 | 9.98E-01 |
| frozen | replicates | 9402_R04 | UPN1633 | | | | | | | | | ABC | 17.124 | 9.97E-01 |
| frozen | replicates | 9402_R05 | UPN1633 | | | | | | | | | ABC | 17.731 | 9.98E-01 |
| frozen | replicates | 9402_R06 | UPN1633 | | | | | | | | | ABC | 18.256 | 9.98E-01 |
| frozen | replicates | 9402_R07 | UPN1633 | | | | | | | | | ABC | 17.444 | 9.97E-01 |
| frozen | replicates | 9402_R08 | UPN1633 | | | | | | | | | ABC | 17.734 | 9.98E-01 |

TABLE S1-continued

Full sample list.

The characteristics of the 317 samples analyzed in this paper, identified by their RNA and Patient unique IDs. When available, reference GCB-ABC classification as evaluated by Affymetrix, DASL or IHC is provided along with the final (MLPA) classification. The raw scores and probabilities of belonging to the ABC subgroup are also provided, as computed by the RT-MLPA predictor (probability of belonging to the GCB subgroup can be computed as the complement to 1).

| Material | Cohort | RNA | Patient | Affymetrix | DASL | DASL.score | IHC | OS.time (years) | PFS.time (years) | OS.event | PFS.event | MLPA | MLPA.score | MLPA.p (ABC) |
|---|---|---|---|---|---|---|---|---|---|---|---|---|---|---|
| frozen | replicates | 9402_R09 | UPN1633 | | | | | | | | | ABC | 17.606 | 9.98E-01 |
| frozen | replicates | 9402_R10 | UPN1633 | | | | | | | | | ABC | 17.599 | 9.98E-01 |
| frozen | training | 1841 | UPN1010 | | ABC | 6.555 | | 8.72 | 8.72 | FALSE | FALSE | other | −5.508 | 6.00E-01 |
| frozen | training | 2663 | UPN1149 | | ABC | 12.958 | | 6.36 | 6.36 | FALSE | FALSE | ABC | 8.438 | 9.91E-01 |
| frozen | training | 3495 | UPN1028 | | ABC | 11.192 | | | | | | ABC | 8.903 | 9.91E-01 |
| frozen | training | 3958 | UPN1281 | | ABC | 13.045 | | 8.44 | 8.44 | FALSE | FALSE | ABC | 10.389 | 9.94E-01 |
| frozen | training | 4022 | UPN1291 | | ABC | 12.335 | | 0.93 | 0.48 | TRUE | TRUE | ABC | 12.813 | 9.96E-01 |
| frozen | training | 4327 | UPN1313 | | ABC | 10.142 | | 7.78 | 7.78 | FALSE | FALSE | ABC | 11.460 | 9.95E-01 |
| frozen | training | 4657 | UPN0943 | | ABC | 12.310 | | | | | | ABC | 14.496 | 9.97E-01 |
| frozen | training | 4943 | UPN1370 | | ABC | 17.298 | | 0.47 | 0.46 | TRUE | TRUE | ABC | 17.806 | 9.98E-01 |
| frozen | training | 5259 | UPN0497 | | ABC | 9.512 | | | | | | ABC | 6.762 | 9.86E-01 |
| frozen | training | 5261 | UPN0526 | | ABC | 8.168 | | | | | | ABC | 8.155 | 9.90E-01 |
| frozen | training | 5263 | UPN0721 | | ABC | 6.295 | | | | | | ABC | 4.015 | 9.73E-01 |
| frozen | training | 5642 | UPN0466 | | ABC | 12.579 | | | | | | ABC | 8.046 | 9.90E-01 |
| frozen | training | 5844 | UPN1415 | | ABC | 11.168 | | 1.38 | 0.86 | TRUE | TRUE | ABC | 19.686 | 9.98E-01 |
| frozen | training | 6572 | UPN1465 | | ABC | 9.940 | | 1.16 | 0.88 | TRUE | TRUE | ABC | 12.970 | 9.96E-01 |
| frozen | training | 7052 | UPN1486 | | ABC | 17.700 | | 1.78 | 1.78 | FALSE | FALSE | ABC | 19.242 | 9.98E-01 |
| frozen | training | 8005 | UPN1540 | | ABC | 10.242 | | 1.34 | 0.85 | TRUE | TRUE | ABC | 13.203 | 9.96E-01 |
| frozen | training | 8026 | UPN1541 | | ABC | 15.877 | | 0.90 | 0.73 | TRUE | TRUE | ABC | 16.699 | 9.97E-01 |
| frozen | training | 8194 | UPN0878 | | ABC | 13.199 | | | | | | ABC | 17.650 | 9.98E-01 |
| frozen | training | 8196 | UPN0937 | | ABC | 11.665 | | | | | | ABC | 9.857 | 9.93E-01 |
| frozen | training | 8607 | UPN1574 | | ABC | 12.665 | | 2.12 | 0.63 | TRUE | TRUE | ABC | 5.932 | 9.83E-01 |
| frozen | training | 8709 | UPN1583 | | ABC | 9.113 | | 1.30 | 0.54 | TRUE | TRUE | other | −1.899 | 8.53E-01 |
| frozen | training | 9093 | UPN1604 | | ABC | 9.430 | | 0.05 | 0.05 | TRUE | TRUE | other | −4.985 | 6.49E-01 |
| frozen | training | 9398 | UPN1631 | | ABC | 6.036 | | 0.93 | 0.93 | TRUE | TRUE | ABC | 14.197 | 9.96E-01 |
| frozen | training | 9481 | UPN1637 | | ABC | 12.831 | | 2.25 | 2.20 | TRUE | TRUE | ABC | 19.840 | 9.98E-01 |
| frozen | training | 10673 | UPN1296 | | ABC | 10.370 | | 3.29 | 3.29 | FALSE | FALSE | other | −8.056 | 3.41E-01 |
| frozen | training | 11061 | UPN1732 | | ABC | 12.801 | | 3.53 | 1.31 | FALSE | TRUE | ABC | 12.960 | 9.96E-01 |
| frozen | training | 11254 | UPN1750 | | ABC | 14.058 | | 1.69 | 1.12 | TRUE | TRUE | ABC | 14.046 | 9.96E-01 |
| frozen | training | 11635 | UPN1768 | | ABC | 12.207 | | 0.04 | 0.04 | TRUE | TRUE | ABC | 13.520 | 9.96E-01 |
| frozen | training | 1604 | UPN0964 | | GCB | −6.562 | | | | | | GCB | −51.942 | 4.97E-15 |
| frozen | training | 3010 | UPN0602 | | GCB | −6.902 | | | | | | GCB | −35.210 | 2.47E-08 |
| frozen | training | 3577 | UPN1251 | | GCB | −6.146 | | 8.34 | 8.34 | FALSE | FALSE | GCB | −61.664 | 1.10E-19 |
| frozen | training | 3839 | UPN0853 | | GCB | −6.034 | | | | | | GCB | −31.067 | 6.21E-07 |
| frozen | training | 5220 | UPN1386 | | GCB | −7.046 | | 7.03 | 0.96 | FALSE | TRUE | GCB | −55.994 | 6.68E-17 |
| frozen | training | 5265 | UPN0987 | | GCB | −0.037 | | | | | | other | −11.930 | 7.98E-02 |
| frozen | training | 5338 | UPN1392 | | GCB | −0.042 | | 1.82 | 1.14 | TRUE | TRUE | GCB | −14.479 | 2.33E-02 |
| frozen | training | 5643 | UPN0494 | | GCB | −4.501 | | | | | | GCB | −40.421 | 3.06E-10 |
| frozen | training | 5722 | UPN1404 | | GCB | −1.630 | | 6.33 | 6.33 | FALSE | FALSE | GCB | −13.816 | 3.26E-02 |
| frozen | training | 6242 | UPN1443 | | GCB | −8.608 | | 4.60 | 4.60 | FALSE | FALSE | GCB | −59.637 | 1.14E-18 |
| frozen | training | 6460 | UPN1458 | | GCB | 0.659 | | 5.75 | 5.75 | FALSE | FALSE | GCB | −15.810 | 1.16E-02 |
| frozen | training | 7026 | UPN1485 | | GCB | −5.099 | | 2.81 | 2.81 | TRUE | TRUE | GCB | −27.192 | 1.03E-05 |
| frozen | training | 7358 | UPN1505 | | GCB | −7.208 | | 5.41 | 5.41 | FALSE | FALSE | GCB | −33.746 | 7.92E-08 |
| frozen | training | 7688 | UPN1525 | | GCB | −3.601 | | 3.53 | 3.53 | FALSE | FALSE | GCB | −29.054 | 2.73E-06 |
| frozen | training | 8190 | UPN0235 | | GCB | −6.507 | | | | | | GCB | −53.620 | 8.57E-16 |
| frozen | training | 9017 | UPN1596 | | GCB | −1.494 | | 4.70 | 4.70 | FALSE | FALSE | GCB | −14.522 | 2.28E-02 |

TABLE S1-continued

Full sample list.

The characteristics of the 317 samples analyzed in this paper, identified by their RNA and Patient unique IDs. When available, reference GCB-ABC classification as evaluated by Affymetrix, DASL or IHC is provided along with the final (MLPA) classification. The raw scores and probabilities of belonging to the ABC subgroup are also provided, as computed by the RT-MLPA predictor (probability of belonging to the GCB subgroup can be computed as the complement to 1).

| Material | Cohort | RNA | Patient | Affymetrix | DASL | DASL.score | IHC | OS.time (years) | PFS.time (years) | OS.event | PFS.event | MLPA | MLPA.score | MLPA.p (ABC) |
|---|---|---|---|---|---|---|---|---|---|---|---|---|---|---|
| frozen | training | 9217 | UPN1614 | | GCB | -6.946 | | 4.59 | 4.59 | FALSE | FALSE | GCB | -33.149 | 1.26E-07 |
| frozen | training | 9296 | UPN1623 | | GCB | -2.870 | | 4.30 | 4.30 | FALSE | FALSE | GCB | -42.449 | 5.01E-11 |
| frozen | training | 9503 | UPN1639 | | GCB | -3.785 | | 4.35 | 4.35 | FALSE | FALSE | GCB | -48.289 | 2.00E-13 |
| frozen | training | 10599 | UPN1378 | | GCB | -7.147 | | 7.89 | 2.15 | TRUE | TRUE | GCB | -39.372 | 7.63E-10 |
| frozen | training | 11847 | UPN1787 | | GCB | -0.574 | | 2.68 | 2.68 | FALSE | FALSE | GCB | -40.977 | 1.87E-10 |
| frozen | validation | 1816 | UPN1003 | | ABC | 13.384 | | 11.95 | 11.95 | FALSE | FALSE | ABC | 14.743 | 9.97E-01 |
| frozen | validation | 3294 | UPN1217 | | ABC | 9.614 | Non-GCB | 2.80 | 1.24 | TRUE | TRUE | other | -4.388 | 7.00E-01 |
| frozen | validation | 3893 | UPN1275 | | ABC | 11.262 | Non-GCB | | | | | ABC | 10.173 | 9.93E-01 |
| frozen | validation | 4041 | UPN1290 | | ABC | 8.329 | Non-GCB | 7.79 | 7.79 | FALSE | FALSE | ABC | 14.054 | 9.96E-01 |
| frozen | validation | 4150 | UPN1297 | | ABC | 12.353 | Non-GCB | | | | | other | -2.558 | 8.21E-01 |
| frozen | validation | 4405 | UPN1318 | | ABC | 9.141 | Non-GCB | 0.36 | 0.36 | TRUE | TRUE | ABC | 9.728 | 9.93E-01 |
| frozen | validation | 4673 | UPN1344 | | ABC | 13.771 | Non-GCB | | | | | ABC | 17.647 | 9.98E-01 |
| frozen | validation | 5258 | UPN0430 | | ABC | 11.769 | Non-GCB | | | | | ABC | 16.703 | 9.97E-01 |
| frozen | validation | 5260 | UPN0522 | | ABC | 16.317 | Non-GCB | | | | | ABC | 13.279 | 9.96E-01 |
| frozen | validation | 5262 | UPN0591 | | ABC | 12.010 | Non-GCB | | | | | ABC | 10.143 | 9.93E-01 |
| frozen | validation | 5637 | UPN0301 | | ABC | 11.695 | Non-GCB | | | | | ABC | 12.642 | 9.96E-01 |
| frozen | validation | 5802 | UPN1411 | | ABC | 13.726 | Non-GCB | 1.36 | 0.69 | TRUE | TRUE | ABC | 23.087 | 9.98E-01 |
| frozen | validation | 6147 | UPN1437 | | ABC | 13.294 | Non-GCB | 0.07 | 0.07 | TRUE | TRUE | ABC | 10.970 | 9.94E-01 |
| frozen | validation | 6770 | UPN1474 | | ABC | 6.151 | Non-GCB | 5.48 | 5.48 | FALSE | FALSE | other | 1.551 | 9.47E-01 |
| frozen | validation | 8008 | UPN1449 | | ABC | 12.457 | Non-GCB | 1.66 | 1.07 | TRUE | TRUE | ABC | 14.695 | 9.97E-01 |
| frozen | validation | 8041 | UPN1542 | | ABC | 11.859 | Non-GCB | 0.52 | 0.52 | FALSE | FALSE | ABC | 12.950 | 9.96E-01 |
| frozen | validation | 8195 | UPN0934 | | ABC | 9.857 | Non-GCB | | | | | ABC | 7.114 | 9.87E-01 |
| frozen | validation | 8268 | UPN1559 | | ABC | 9.418 | Non-GCB | 0.74 | 0.49 | TRUE | TRUE | ABC | 3.556 | 9.70E-01 |
| frozen | validation | 8431 | UPN1569 | | ABC | 10.088 | Non-GCB | | | | | other | -12.476 | 6.21E-02 |
| frozen | validation | 9138 | UPN1608 | | ABC | 7.868 | Non-GCB | 4.21 | 2.32 | FALSE | TRUE | ABC | 10.201 | 9.93E-01 |
| frozen | validation | 9401 | UPN1632 | | ABC | 4.812 | Non-GCB | 4.50 | 4.50 | FALSE | FALSE | GCB | -39.447 | 7.15E-10 |
| frozen | validation | 9507 | UPN1635 | | ABC | 5.529 | Non-GCB | 2.40 | 2.06 | TRUE | TRUE | ABC | 8.131 | 9.90E-01 |
| frozen | validation | 10451 | UPN1694 | | ABC | 11.282 | GCB | 1.21 | 1.07 | TRUE | TRUE | ABC | 11.721 | 9.95E-01 |
| frozen | validation | 10922 | UPN1721 | | ABC | 12.097 | Non-GCB | 3.05 | 3.05 | FALSE | FALSE | ABC | 8.390 | 9.90E-01 |

TABLE S1-continued

Full sample list.

The characteristics of the 317 samples analyzed in this paper, identified by their RNA and Patient unique IDs. When available, reference GCB-ABC classification as evaluated by Affymetrix, DASL or IHC is provided along with the final (MLPA) classification. The raw scores and probabilities of belonging to the ABC subgroup are also provided, as computed by the RT-MLPA predictor (probability of belonging to the GCB subgroup can be computed as the complement to 1).

| Material | Cohort | RNA | Patient | Affymetrix | DASL | DASL.score | IHC | OS.time (years) | PFS.time (years) | OS.event | PFS.event | MLPA | MLPA.score | MLPA.p (ABC) |
|---|---|---|---|---|---|---|---|---|---|---|---|---|---|---|
| frozen | validation | 11077 | UPN1737 | | ABC | 15.220 | GCB | | | | | ABC | 14.407 | 9.97E-01 |
| frozen | validation | 784 | UPN0660 | | ABC | 6.618 | Non-GCB | 3.33 | 3.33 | FALSE | FALSE | ABC | 8.417 | 9.91E-01 |
| frozen | validation | 3809 | UPN1265 | | ABC | 9.141 | Non-GCB | 7.88 | 7.88 | FALSE | FALSE | other | -1.083 | 8.85E-01 |
| frozen | validation | 4264 | UPN0188 | | ABC | 11.465 | Non-GCB | | | | | ABC | 9.126 | 9.92E-01 |
| frozen | validation | 4654 | UPN0822 | | ABC | 10.375 | Non-GCB | | | | | ABC | 18.277 | 9.98E-01 |
| frozen | validation | 5257 | UPN0456 | | ABC | 9.489 | | | | | | ABC | 3.363 | 9.68E-01 |
| frozen | validation | 7214 | UPN1497 | | ABC | 4.536 | GCB | | | | | GCB | -17.306 | 5.13E-03 |
| frozen | validation | 8189 | UPN0106 | | ABC | 4.687 | Non-GCB | | | | | other | -8.815 | 2.71E-01 |
| frozen | validation | 9717 | UPN1647 | | ABC | 7.130 | GCB | 0.67 | 0.57 | TRUE | TRUE | GCB | -29.693 | 1.72E-06 |
| frozen | validation | 819 | UPN0722 | | GCB | -8.051 | GCB | | | | | GCB | -50.666 | 1.85E-14 |
| frozen | validation | 1905 | UPN0941 | | GCB | -0.640 | Non-GCB | | | | | other | -5.785 | 5.73E-01 |
| frozen | validation | 3002 | UPN0935 | | GCB | -8.759 | GCB | | | | | GCB | -25.261 | 3.84E-05 |
| frozen | validation | 3009 | UPN0776 | | GCB | -6.980 | GCB | | | | | GCB | -45.043 | 4.56E-12 |
| frozen | validation | 3377 | UPN1013 | | GCB | -5.342 | GCB | | | | | GCB | -39.527 | 6.67E-10 |
| frozen | validation | 3671 | UPN1001 | | GCB | -4.828 | GCB | | | | | GCB | -36.497 | 8.64E-09 |
| frozen | validation | 4261 | UPN0488 | | GCB | -7.597 | GCB | | | | | GCB | -32.137 | 2.76E-07 |
| frozen | validation | 4922 | UPN1368 | | GCB | -5.247 | GCB | 6.82 | 6.82 | FALSE | FALSE | GCB | -29.325 | 2.25E-06 |
| frozen | validation | 5285 | UPN1389 | | GCB | -6.337 | GCB | 6.74 | 6.74 | FALSE | FALSE | GCB | -59.611 | 1.18E-18 |
| frozen | validation | 5639 | UPN0304 | | GCB | -5.714 | GCB | | | | | GCB | -21.368 | 4.70E-04 |
| frozen | validation | 5647 | UPN0801 | | GCB | -7.328 | GCB | | | | | GCB | -27.562 | 7.91E-06 |
| frozen | validation | 6024 | UPN1429 | | GCB | -6.637 | GCB | 0.76 | 0.76 | TRUE | TRUE | GCB | -47.417 | 4.70E-13 |
| frozen | validation | 6895 | UPN1478 | | GCB | -8.357 | GCB | 5.17 | 5.17 | FALSE | FALSE | GCB | -47.993 | 2.67E-13 |
| frozen | validation | 7265 | UPN1499 | | GCB | -4.377 | GCB | 0.42 | 0.21 | TRUE | TRUE | GCB | -26.525 | 1.63E-05 |
| frozen | validation | 7676 | UPN1524 | | GCB | -4.818 | GCB | 5.06 | 5.06 | FALSE | FALSE | GCB | -53.819 | 6.94E-16 |
| frozen | validation | 7764 | UPN1528 | | GCB | -8.238 | GCB | 5.33 | 5.33 | FALSE | FALSE | GCB | -43.536 | 1.86E-11 |
| frozen | validation | 8283 | UPN1560 | | GCB | -3.768 | GCB | 0.17 | 0.17 | TRUE | TRUE | GCB | -22.614 | 2.16E-04 |
| frozen | validation | 9360 | UPN1627 | | GCB | -3.007 | Non-GCB | 4.25 | 4.25 | FALSE | FALSE | GCB | -35.253 | 2.38E-08 |
| frozen | validation | 10258 | UPN1684 | | GCB | 0.734 | GCB | 3.53 | 3.53 | FALSE | FALSE | GCB | -38.969 | 1.08E-09 |
| frozen | validation | 10305 | UPN1580 | | GCB | -4.477 | GCB | 1.19 | 0.29 | TRUE | TRUE | GCB | -49.006 | 9.82E-14 |
| frozen | validation | 12043 | UPN1801 | | GCB | -6.563 | GCB | | | | | GCB | -54.519 | 3.29E-16 |
| frozen | validation | 780 | UPN0699 | | GCB | -1.919 | Non-GCB | | | | | ABC | 19.367 | 9.98E-01 |
| frozen | validation | 2330 | UPN1094 | | GCB | 0.252 | GCB | 9.41 | 9.41 | FALSE | FALSE | GCB | -22.534 | 2.27E-04 |
| frozen | validation | 3091 | UPN1190 | | GCB | 0.417 | GCB | 7.70 | 7.70 | FALSE | FALSE | other | -9.335 | 2.27E-01 |
| frozen | validation | 4235 | UPN1308 | | GCB | -0.947 | GCB | 0.99 | 0.47 | TRUE | TRUE | GCB | -38.282 | 1.94E-09 |
| frozen | validation | 5750 | UPN1454 | | GCB | -2.366 | | 0.81 | 0.64 | TRUE | TRUE | GCB | -32.739 | 1.74E-07 |
| frozen | validation | 5766 | UPN1407 | | GCB | -2.369 | GCB | | | | | GCB | -36.752 | 7.00E-09 |

TABLE S1-continued

Full sample list.

The characteristics of the 317 samples analyzed in this paper, identified by their RNA and Patient unique IDs. When available, reference GCB-ABC classification as evaluated by Affymetrix, DASL or IHC is provided along with the final (MLPA) classification. The raw scores and probabilities of belonging to the ABC subgroup are also provided, as computed by the RT-MLPA predictor (probability of belonging to the GCB subgroup can be computed as the complement to 1).

| Material | Cohort | RNA | Patient | Affymetrix | DASL | DASL.score | IHC | OS.time (years) | OS.event | PFS.time (years) | PFS.event | MLPA | MLPA.score | MLPA.p (ABC) |
|---|---|---|---|---|---|---|---|---|---|---|---|---|---|---|
| frozen | validation | 8886 | UPN1587 | | GCB | 0.074 | GCB | | | | | GCB | −24.264 | 7.44E−05 |
| frozen | validation | 9797 | UPN1652 | | GCB | −0.071 | Non-GCB | 4.02 | FALSE | 4.02 | FALSE | other | −7.488 | 3.98E−01 |
| frozen | validation | 10223 | UPN1680 | | GCB | −0.079 | GCB | 1.09 | TRUE | 0.56 | TRUE | GCB | −49.276 | 7.50E−14 |
| frozen | validation | 10322 | UPN1687 | | GCB | 0.456 | GCB | 0.11 | TRUE | 0.11 | TRUE | GCB | −13.770 | 3.34E−02 |

TABLE S2

Gene expression measured by RT-MLPA.
The sample-normalized values of the expression of the 14 genes measured by RT-MLPA in the diverse cohorts analyzed throughout this paper, including the training, validation, external and FFPE series.

| Sample | NEK6 | IRF4 | IGHM | CCND1 | LMO2 | FOXP1 | TNFRSF9 | BCL6 | TNFRSF13B | CCND2 | MYC | MYBL1 | BCL2 | MS4A1 |
|---|---|---|---|---|---|---|---|---|---|---|---|---|---|---|
| 10035 | 0.378 | 1.439 | 1.669 | 0.215 | 0.504 | 2.214 | 0.305 | 0.450 | 0.539 | 0.040 | 0.878 | 0.046 | 0.377 | 2.117 |
| 10181 | 0.374 | 0.982 | 1.319 | 0.847 | 1.913 | 0.671 | 0.885 | 0.960 | 0.101 | 0.017 | 0.510 | 0.242 | 0.063 | 2.472 |
| 10223 | 0.740 | 0.290 | 1.950 | 1.095 | 0.463 | 1.248 | 0.537 | 1.471 | 0.083 | 0.051 | 1.504 | 1.836 | 0.108 | 0.634 |
| 10258 | 0.932 | 1.244 | 0.708 | 0.799 | 0.900 | 0.938 | 1.192 | 0.818 | 0.276 | 0.358 | 0.756 | 0.906 | 0.340 | 2.379 |
| 10305 | 1.369 | 1.955 | 0.080 | 1.142 | 1.110 | 0.633 | 0.661 | 0.654 | 0.042 | 0.490 | 1.239 | 0.832 | 0.153 | 1.898 |
| 10322 | 0.608 | 1.075 | 2.661 | 0.869 | 0.912 | 0.724 | 0.554 | 0.136 | 0.260 | 1.058 | 1.073 | 0.188 | 0.320 | 1.231 |
| 10401 | 0.116 | 1.571 | 2.237 | 0.278 | 0.070 | 1.652 | 0.243 | 0.285 | 0.542 | 1.018 | 0.646 | 0.044 | 0.244 | 2.058 |
| 10451 | 0.180 | 1.684 | 1.875 | 0.854 | 0.212 | 1.584 | 0.265 | 0.417 | 0.932 | 1.153 | 1.336 | 0.093 | 0.622 | 1.152 |
| 10599 | 1.082 | 0.942 | 0.298 | 1.580 | 1.120 | 0.662 | 0.368 | 0.678 | 0.040 | 1.069 | 2.153 | 0.306 | 0.821 | 1.333 |
| 10673 | 0.118 | 1.664 | 1.050 | 0.722 | 0.351 | 1.722 | 1.659 | 1.506 | 0.051 | 1.004 | 1.300 | 0.088 | 0.211 | 0.789 |
| 10724 | 0.098 | 0.157 | 0.038 | 2.792 | 0.430 | 0.825 | 0.067 | 0.092 | 0.047 | 2.057 | 2.045 | 0.171 | 0.205 | 0.042 |
| 10823 | 0.063 | 1.572 | 3.380 | 0.417 | 0.095 | 0.272 | 0.176 | 0.101 | 0.471 | 0.794 | 0.323 | 0.056 | 0.039 | 0.402 |
| 10922 | 0.121 | 1.757 | 2.216 | 1.118 | 0.279 | 1.546 | 0.610 | 0.340 | 0.517 | 0.854 | 1.112 | 0.145 | 0.540 | 0.872 |
| 11061 | 0.181 | 1.683 | 1.850 | 0.595 | 0.086 | 1.575 | 0.436 | 0.577 | 0.980 | 1.291 | 1.175 | 0.091 | 0.946 | 0.990 |
| 11077 | 0.021 | 2.065 | 2.897 | 0.226 | 0.109 | 1.755 | 0.257 | 0.241 | 0.127 | 0.196 | 0.697 | 0.050 | 0.070 | 0.495 |
| 11105 | 0.266 | 1.801 | 1.554 | 0.489 | 0.175 | 0.697 | 0.254 | 0.089 | 0.820 | 2.144 | 1.540 | 0.069 | 0.572 | 1.225 |
| 11222 | 0.049 | 1.246 | 1.957 | 0.097 | 0.080 | 1.919 | 0.278 | 0.324 | 1.044 | 1.219 | 0.825 | 0.072 | 0.243 | 1.978 |
| 11254 | 0.188 | 1.860 | 2.311 | 0.465 | 0.094 | 1.552 | 0.140 | 0.154 | 0.526 | 1.360 | 1.312 | 0.040 | 0.230 | 0.988 |
| 11284 | 0.096 | 2.087 | 0.792 | 0.364 | 1.300 | 1.605 | 0.558 | 1.575 | 0.128 | 0.566 | 0.563 | 0.246 | 0.054 | 1.779 |
| 11573 | 0.721 | 1.188 | 0.320 | 1.377 | 1.616 | 1.321 | 0.887 | 0.773 | 0.066 | 0.757 | 1.473 | 0.271 | 0.119 | 1.723 |
| 11635 | 0.152 | 1.979 | 2.300 | 0.231 | 0.317 | 1.919 | 0.274 | 0.107 | 0.623 | 0.048 | 1.625 | 0.030 | 0.156 | 0.802 |
| 11767 | 0.822 | 0.851 | 0.947 | 0.307 | 1.559 | 1.088 | 0.711 | 0.986 | 0.106 | 0.794 | 0.516 | 0.442 | 0.699 | 2.420 |
| 11768 | 0.081 | 1.363 | 2.046 | 0.056 | 0.284 | 2.114 | 0.189 | 0.800 | 0.989 | 0.875 | 0.787 | 0.080 | 0.559 | 1.433 |
| 11770 | 0.034 | 1.185 | 1.886 | 0.106 | 0.065 | 2.094 | 0.192 | 0.883 | 0.992 | 1.231 | 0.905 | 0.047 | 0.464 | 1.588 |
| 11779 | 0.189 | 1.637 | 0.649 | 0.415 | 0.460 | 2.067 | 0.896 | 0.858 | 1.125 | 0.648 | 0.765 | 0.213 | 0.170 | 1.955 |
| 11847 | 0.856 | 0.854 | 1.099 | 1.102 | 1.572 | 0.886 | 0.604 | 0.730 | 0.101 | 0.602 | 0.788 | 0.325 | 0.268 | 2.412 |
| 11887 | 0.162 | 1.452 | 2.345 | 0.309 | 0.135 | 1.674 | 0.661 | 0.892 | 0.602 | 0.187 | 1.089 | 0.066 | 0.248 | 1.624 |
| 12003 | 0.192 | 1.308 | 1.118 | 0.861 | 1.937 | 1.881 | 0.513 | 1.169 | 0.271 | 0.269 | 1.207 | 0.130 | 0.020 | 1.249 |
| 12043 | 1.067 | 0.839 | 1.067 | 0.770 | 1.557 | 1.049 | 0.608 | 1.462 | 0.065 | 0.266 | 1.202 | 0.638 | 0.104 | 1.943 |
| 12100 | 0.274 | 0.348 | 1.570 | 0.154 | 0.139 | 1.567 | 0.317 | 2.133 | 0.054 | 0.132 | 1.765 | 0.508 | 0.192 | 1.865 |
| 12141 | 0.975 | 1.458 | 0.033 | 1.291 | 1.992 | 0.302 | 0.242 | 1.488 | 0.048 | 0.101 | 0.776 | 0.299 | 0.107 | 2.167 |
| 12284 | 0.089 | 1.956 | 2.346 | 0.945 | 0.173 | 1.444 | 0.239 | 0.113 | 0.693 | 0.223 | 1.312 | 0.167 | 0.235 | 1.246 |
| 12422 | 0.627 | 0.938 | 0.018 | 0.323 | 0.255 | 1.565 | 0.670 | 1.306 | 0.063 | 0.284 | 0.623 | 1.307 | 0.844 | 2.583 |
| 12547 | 0.243 | 1.794 | 1.963 | 0.951 | 0.299 | 0.962 | 0.725 | 0.224 | 0.811 | 1.057 | 0.909 | 0.085 | 0.324 | 1.804 |
| 12621 | 0.438 | 1.010 | 1.906 | 0.430 | 1.439 | 1.183 | 0.373 | 1.233 | 0.143 | 0.175 | 0.723 | 0.592 | 0.670 | 1.974 |
| 12639 | 0.460 | 2.196 | 0.249 | 1.200 | 0.673 | 0.875 | 1.156 | 0.447 | 0.422 | 0.976 | 0.985 | 0.237 | 0.472 | 1.881 |
| 12757 | 0.641 | 0.876 | 1.012 | 0.829 | 0.830 | 1.743 | 0.227 | 1.363 | 0.227 | 0.989 | 1.839 | 0.149 | 0.248 | 1.544 |
| 12766 | 0.317 | 0.651 | 0.718 | 0.100 | 2.202 | 1.412 | 0.205 | 1.363 | 0.026 | 0.045 | 0.094 | 0.492 | 0.058 | 2.564 |
| 12855 | 0.336 | 0.929 | 2.584 | 1.115 | 0.370 | 1.422 | 0.764 | 0.317 | 0.070 | 0.796 | 0.763 | 0.313 | 0.292 | 1.489 |
| 12861 | 0.115 | 1.450 | 2.039 | 0.396 | 0.406 | 2.020 | 0.560 | 1.206 | 0.171 | 0.221 | 0.910 | 0.162 | 0.613 | 1.476 |
| 12984 | 0.038 | 1.276 | 2.743 | 0.924 | 0.440 | 1.558 | 0.366 | 0.851 | 0.298 | 0.298 | 1.032 | 0.071 | 0.079 | 0.966 |
| 12986 | 0.638 | 1.417 | 0.630 | 1.549 | 1.111 | 1.805 | 0.955 | 1.022 | 0.039 | 0.032 | 1.265 | 0.153 | 0.169 | 1.579 |
| 13016 | 0.047 | 1.918 | 2.548 | 0.128 | 0.350 | 1.585 | 0.095 | 0.213 | 0.440 | 1.382 | 0.744 | 0.014 | 0.043 | 1.048 |
| 13062 | 0.348 | 1.468 | 1.777 | 0.603 | 0.557 | 1.446 | 0.890 | 0.655 | 0.300 | 1.301 | 1.206 | 0.114 | 0.294 | 1.623 |
| 13274 | 0.391 | 0.487 | 1.344 | 0.874 | 0.757 | 1.603 | 0.308 | 0.986 | 0.048 | 0.513 | 1.640 | 0.914 | 0.798 | 1.914 |
| 13519 | 0.164 | 1.518 | 1.191 | 0.576 | 0.586 | 2.183 | 1.240 | 0.742 | 0.321 | 0.933 | 0.844 | 0.194 | 0.425 | 1.447 |
| 13761 | 0.096 | 1.028 | 3.055 | 0.366 | 0.015 | 1.021 | 0.000 | 0.000 | 0.498 | 1.687 | 0.070 | 0.000 | 0.098 | 1.334 |
| 13959 | 0.611 | 0.076 | 1.177 | 0.158 | 0.046 | 1.492 | 0.403 | 1.957 | 0.060 | 0.150 | 1.398 | 0.615 | 0.647 | 2.352 |
| 14186 | 0.146 | 1.902 | 1.049 | 0.190 | 0.531 | 2.119 | 0.208 | 0.580 | 0.627 | 0.265 | 1.361 | 0.080 | 0.145 | 2.011 |
| 14341 | 0.060 | 1.828 | 2.935 | 0.100 | 0.045 | 1.701 | 0.133 | 0.258 | 0.446 | 0.532 | 0.647 | 0.007 | 0.205 | 0.657 |
| 14347 | 0.620 | 1.065 | 2.207 | 0.886 | 0.739 | 0.933 | 0.763 | 0.116 | 0.594 | 0.766 | 0.136 | 0.669 | 2.006 |
| 1560 | 0.147 | 0.168 | 2.485 | 0.177 | 1.150 | 0.995 | 0.344 | 2.281 | 0.055 | 0.051 | 0.914 | 0.100 | 0.171 | 1.346 |
| 1572 | 0.016 | 1.542 | 3.421 | 0.059 | 0.000 | 1.241 | 0.002 | 0.112 | 0.190 | 0.276 | 0.400 | 0.004 | 0.036 | 0.243 |
| 1604 | 1.159 | 2.168 | 0.064 | 1.615 | 2.195 | 0.455 | 0.262 | 0.449 | 0.021 | 0.175 | 1.664 | 0.203 | 0.038 | 0.212 |
| 1624 | 0.504 | 2.611 | 0.186 | 0.891 | 1.335 | 0.620 | 0.332 | 0.053 | 0.497 | 0.043 | 2.361 | 0.085 | 0.279 | 0.346 |
| 1816 | 0.067 | 1.275 | 3.592 | 0.110 | 0.033 | 0.600 | 0.033 | 0.024 | 0.188 | 0.178 | 0.497 | 0.010 | 0.064 | 0.114 |
| 1841 | 0.825 | 2.178 | 2.029 | 0.815 | 0.898 | 0.663 | 0.173 | 0.079 | 0.918 | 0.607 | 1.569 | 0.002 | 0.000 | 0.923 |
| 1905 | 0.187 | 2.069 | 0.724 | 0.094 | 1.164 | 1.145 | 0.085 | 0.539 | 1.058 | 0.057 | 2.465 | 0.064 | 0.128 | 1.137 |
| 2330 | 0.477 | 1.289 | 0.484 | 2.481 | 1.276 | 1.050 | 0.495 | 0.285 | 0.175 | 0.706 | 1.910 | 0.096 | 0.166 | 0.438 |
| 2462 | 0.050 | 0.705 | 3.366 | 0.097 | 0.094 | 1.388 | 0.053 | 0.078 | 0.291 | 0.753 | 1.037 | 0.008 | 0.062 | 0.224 |
| 2663 | 0.075 | 1.314 | 2.799 | 1.030 | 0.403 | 0.329 | 0.033 | 0.018 | 0.437 | 1.876 | 0.982 | 0.015 | 0.113 | 0.811 |
| 2686 | 0.030 | 1.349 | 2.168 | 0.175 | 0.051 | 2.123 | 0.122 | 0.232 | 0.467 | 0.964 | 0.651 | 0.032 | 0.249 | 2.014 |
| 2763 | 0.187 | 0.867 | 3.149 | 1.108 | 0.842 | 0.144 | 0.027 | 0.064 | 0.058 | 0.643 | 1.601 | 0.049 | 0.065 | 0.418 |
| 2881 | 0.559 | 1.519 | 0.059 | 2.171 | 0.912 | 1.419 | 0.167 | 0.000 | 0.416 | 0.323 | 1.962 | 0.065 | 0.189 | 1.476 |
| 2898 | 0.222 | 0.786 | 1.947 | 0.187 | 0.942 | 1.467 | 0.466 | 0.621 | 1.087 | 0.252 | 0.444 | 0.023 | 0.154 | 2.513 |
| 2900 | 0.581 | 1.476 | 1.493 | 0.380 | 1.575 | 1.070 | 0.704 | 1.113 | 0.457 | 0.172 | 0.869 | 0.533 | 0.156 | 1.945 |
| 3002 | 0.577 | 0.806 | 1.392 | 0.261 | 1.365 | 0.226 | 0.332 | 0.740 | 0.631 | 0.252 | 0.875 | 0.088 | 0.580 | 2.834 |
| 3009 | 1.352 | 1.265 | 0.532 | 0.983 | 1.529 | 0.391 | 0.421 | 0.533 | 0.209 | 1.254 | 1.465 | 0.222 | 0.918 | 1.715 |
| 3010 | 0.228 | 0.057 | 0.074 | 0.053 | 0.399 | 1.091 | 0.204 | 1.148 | 0.065 | 0.102 | 2.636 | 1.269 | 0.985 | 2.055 |
| 3091 | 0.278 | 0.659 | 2.688 | 0.613 | 1.006 | 1.750 | 0.126 | 0.217 | 0.304 | 0.505 | 1.112 | 0.173 | 0.128 | 1.364 |
| 3191 | 0.030 | 2.386 | 0.986 | 0.059 | 0.033 | 2.132 | 0.066 | 0.520 | 0.646 | 0.025 | 1.580 | 0.000 | 0.089 | 1.683 |
| 3235 | 1.336 | 1.407 | 0.165 | 0.821 | 1.271 | 0.872 | 0.135 | 0.553 | 0.018 | 0.311 | 1.453 | 0.553 | 0.173 | 2.470 |
| 3247 | 0.178 | 0.721 | 2.477 | 0.591 | 0.083 | 1.444 | 0.460 | 0.370 | 0.382 | 0.374 | 1.151 | 0.264 | 0.151 | 2.191 |

TABLE S2-continued

Gene expression measured by RT-MLPA.
The sample-normalized values of the expression of the 14 genes measured by RT-MLPA in the diverse cohorts analyzed throughout this paper, including the training, validation, external and FFPE series.

| Sample | NEK6 | IRF4 | IGHM | CCND1 | LMO2 | FOXP1 | TNFRSF9 | BCL6 | TNFRSF13B | CCND2 | MYC | MYBL1 | BCL2 | MS4A1 |
|---|---|---|---|---|---|---|---|---|---|---|---|---|---|---|
| 3294 | 0.229 | 1.454 | 2.297 | 0.876 | 0.740 | 1.307 | 0.724 | 0.248 | 0.294 | 0.993 | 1.267 | 0.204 | 0.266 | 1.249 |
| 3377 | 0.990 | 1.499 | 0.233 | 0.739 | 0.968 | 1.316 | 0.568 | 0.806 | 0.045 | 0.445 | 1.326 | 0.698 | 0.111 | 2.341 |
| 3454 | 0.134 | 1.432 | 0.535 | 1.105 | 0.462 | 2.277 | 0.292 | 0.264 | 0.495 | 1.413 | 1.793 | 0.152 | 0.283 | 1.062 |
| 3495 | 0.091 | 2.295 | 0.059 | 1.316 | 0.356 | 0.566 | 0.038 | 0.048 | 1.145 | 2.278 | 1.450 | 0.208 | 0.772 | 0.025 |
| 3577 | 1.078 | 0.822 | 1.226 | 1.445 | 1.854 | 0.885 | 0.608 | 0.681 | 0.090 | 0.037 | 1.242 | 1.166 | 0.329 | 1.329 |
| 3608 | 0.651 | 1.399 | 2.018 | 1.034 | 1.110 | 1.210 | 0.717 | 0.222 | 0.417 | 0.609 | 0.845 | 0.720 | 0.147 | 1.586 |
| 3671 | 0.865 | 0.523 | 0.019 | 1.295 | 1.119 | 0.944 | 0.424 | 0.542 | 0.006 | 0.034 | 1.549 | 0.286 | 1.534 | 2.409 |
| 3750 | 0.250 | 1.356 | 2.007 | 0.918 | 0.675 | 1.578 | 0.387 | 0.450 | 0.326 | 1.340 | 1.271 | 0.180 | 0.343 | 1.316 |
| 3809 | 0.098 | 2.524 | 0.834 | 0.318 | 1.102 | 1.021 | 0.291 | 0.145 | 0.767 | 0.474 | 0.872 | 0.023 | 0.114 | 2.210 |
| 3839 | 0.725 | 1.148 | 0.954 | 0.921 | 0.959 | 1.595 | 0.326 | 0.485 | 0.042 | 0.462 | 1.056 | 0.667 | 1.274 | 2.067 |
| 3893 | 0.029 | 1.323 | 2.427 | 0.056 | 0.203 | 1.665 | 0.030 | 0.156 | 0.133 | 0.034 | 0.939 | 0.014 | 0.105 | 2.454 |
| 3958 | 0.083 | 1.944 | 2.262 | 0.284 | 0.346 | 1.670 | 0.157 | 0.379 | 0.548 | 0.631 | 0.612 | 0.048 | 0.373 | 1.742 |
| 4022 | 0.069 | 1.685 | 2.351 | 0.294 | 0.156 | 2.007 | 0.260 | 0.329 | 0.538 | 0.915 | 0.758 | 0.126 | 0.327 | 1.291 |
| 4041 | 0.030 | 1.912 | 2.687 | 0.239 | 0.146 | 1.469 | 0.222 | 0.402 | 0.487 | 0.573 | 1.113 | 0.066 | 0.020 | 1.084 |
| 4150 | 0.075 | 2.106 | 1.217 | 0.322 | 0.459 | 1.325 | 0.382 | 0.381 | 0.103 | 2.073 | 1.901 | 0.306 | 0.136 | 0.299 |
| 4222 | 0.064 | 1.555 | 2.567 | 0.185 | 0.638 | 1.685 | 0.247 | 0.302 | 0.581 | 0.162 | 1.072 | 0.179 | 0.073 | 1.516 |
| 4235 | 0.259 | 1.072 | 1.097 | 0.337 | 1.792 | 0.968 | 0.603 | 1.750 | 0.071 | 0.139 | 0.696 | 0.069 | 0.057 | 2.360 |
| 4258 | 0.025 | 1.332 | 2.191 | 0.054 | 0.031 | 1.660 | 0.078 | 0.103 | 0.552 | 0.786 | 0.762 | 0.018 | 0.162 | 2.467 |
| 4261 | 0.687 | 1.641 | 0.650 | 1.144 | 0.835 | 1.851 | 0.527 | 0.698 | 0.067 | 0.051 | 1.161 | 0.899 | 0.289 | 1.861 |
| 4264 | 0.000 | 1.214 | 1.259 | 0.166 | 0.412 | 2.264 | 0.350 | 0.305 | 0.813 | 0.138 | 0.893 | 0.095 | 0.116 | 2.500 |
| 4327 | 0.109 | 1.618 | 2.768 | 0.777 | 0.293 | 1.487 | 0.504 | 0.116 | 0.484 | 0.728 | 1.052 | 0.090 | 0.321 | 0.438 |
| 4405 | 0.226 | 1.661 | 3.135 | 0.597 | 0.158 | 0.961 | 0.258 | 0.168 | 0.185 | 0.202 | 1.227 | 0.020 | 0.122 | 0.327 |
| 4467 | 0.280 | 1.859 | 2.312 | 1.146 | 1.048 | 1.054 | 0.127 | 0.073 | 1.011 | 0.682 | 1.479 | 0.050 | 0.233 | 0.103 |
| 4594 | 0.190 | 2.170 | 2.232 | 0.128 | 0.044 | 1.895 | 0.114 | 0.430 | 0.439 | 0.093 | 1.575 | 0.119 | 0.277 | 0.757 |
| 4654 | 0.029 | 1.607 | 2.614 | 0.168 | 0.089 | 1.812 | 0.359 | 0.417 | 0.904 | 0.054 | 1.294 | 0.073 | 0.082 | 1.018 |
| 4657 | 0.000 | 1.687 | 3.013 | 0.071 | 0.038 | 1.465 | 0.097 | 0.521 | 0.304 | 0.022 | 0.984 | 0.019 | 0.076 | 1.053 |
| 4673 | 0.056 | 1.891 | 2.246 | 0.313 | 0.223 | 1.841 | 0.206 | 0.219 | 0.857 | 1.435 | 0.937 | 0.014 | 0.065 | 0.776 |
| 4788 | 0.549 | 1.960 | 1.476 | 0.754 | 1.845 | 0.626 | 0.289 | 0.417 | 0.087 | 0.606 | 1.402 | 0.304 | 0.127 | 1.553 |
| 4853 | 0.667 | 0.647 | 0.537 | 0.326 | 1.358 | 1.289 | 0.446 | 0.966 | 0.342 | 0.476 | 1.605 | 0.511 | 0.522 | 2.394 |
| 4922 | 0.260 | 0.928 | 1.452 | 0.428 | 1.340 | 1.728 | 0.474 | 1.435 | 0.042 | 0.375 | 1.283 | 0.224 | 0.374 | 1.871 |
| 4943 | 0.063 | 1.234 | 3.093 | 0.160 | 0.075 | 1.371 | 0.049 | 0.030 | 0.590 | 1.360 | 0.720 | 0.023 | 0.088 | 0.542 |
| 4950 | 0.123 | 2.629 | 0.096 | 0.774 | 1.083 | 1.793 | 0.088 | 0.701 | 0.440 | 0.071 | 1.243 | 0.000 | 0.198 | 1.472 |
| 5220 | 1.128 | 0.957 | 1.853 | 0.699 | 1.734 | 1.047 | 0.244 | 0.682 | 0.018 | 0.397 | 0.665 | 0.988 | 1.234 | 1.140 |
| 5257 | 0.091 | 1.848 | 1.064 | 0.384 | 0.385 | 1.286 | 1.107 | 0.231 | 0.337 | 1.279 | 0.883 | 0.119 | 0.220 | 2.346 |
| 5258 | 0.114 | 1.076 | 2.709 | 0.131 | 0.064 | 2.157 | 0.098 | 0.210 | 0.675 | 0.595 | 0.877 | 0.022 | 0.127 | 1.260 |
| 5259 | 0.060 | 1.503 | 2.083 | 0.102 | 0.319 | 1.893 | 0.218 | 1.040 | 0.743 | 0.043 | 0.996 | 0.042 | 0.158 | 1.921 |
| 5260 | 0.031 | 1.322 | 2.309 | 0.157 | 0.052 | 1.656 | 0.213 | 0.350 | 0.451 | 1.547 | 1.096 | 0.052 | 0.447 | 1.567 |
| 5261 | 0.335 | 1.687 | 0.402 | 0.556 | 0.165 | 1.294 | 0.531 | 0.253 | 1.099 | 1.060 | 0.891 | 0.111 | 0.267 | 2.622 |
| 5262 | 0.178 | 1.219 | 2.719 | 0.163 | 0.046 | 1.742 | 0.120 | 0.232 | 0.354 | 0.164 | 1.791 | 0.168 | 0.067 | 1.116 |
| 5263 | 0.033 | 1.563 | 2.634 | 0.052 | 0.185 | 1.386 | 0.169 | 0.974 | 0.181 | 0.121 | 0.791 | 0.112 | 0.142 | 1.926 |
| 5265 | 0.378 | 1.568 | 1.474 | 0.727 | 1.158 | 1.241 | 1.126 | 0.234 | 0.663 | 0.331 | 1.826 | 0.213 | 0.166 | 1.422 |
| 5285 | 0.721 | 0.937 | 0.589 | 0.484 | 2.095 | 1.191 | 0.753 | 0.913 | 0.129 | 0.634 | 0.845 | 1.009 | 1.139 | 1.461 |
| 5338 | 0.103 | 1.608 | 2.179 | 0.527 | 1.477 | 1.391 | 0.448 | 0.480 | 0.671 | 0.228 | 0.996 | 0.352 | 0.424 | 1.244 |
| 5541 | 0.540 | 1.083 | 2.302 | 0.874 | 1.134 | 1.735 | 0.308 | 0.298 | 0.148 | 0.659 | 1.019 | 0.505 | 0.513 | 1.079 |
| 5637 | 0.271 | 1.463 | 2.067 | 0.466 | 0.154 | 0.758 | 0.024 | 0.000 | 0.923 | 0.638 | 2.588 | 0.077 | 0.389 | 0.861 |
| 5639 | 0.207 | 0.702 | 2.447 | 0.042 | 1.200 | 1.082 | 0.075 | 0.643 | 0.113 | 1.424 | 2.035 | 0.374 | 0.433 | 0.259 |
| 5642 | 0.363 | 1.867 | 1.723 | 0.232 | 0.255 | 0.966 | 0.062 | 0.070 | 0.738 | 1.900 | 1.894 | 0.081 | 0.308 | 0.957 |
| 5643 | 1.547 | 1.659 | 0.532 | 1.194 | 1.489 | 0.285 | 0.352 | 0.072 | 0.250 | 1.014 | 1.961 | 0.084 | 1.184 | 0.486 |
| 5647 | 0.534 | 1.373 | 0.016 | 0.902 | 0.980 | 0.399 | 0.471 | 0.220 | 0.272 | 1.081 | 2.790 | 0.614 | 0.416 | 1.093 |
| 5719 | 0.033 | 1.926 | 2.267 | 0.102 | 0.075 | 2.095 | 0.120 | 0.259 | 0.873 | 0.583 | 0.758 | 0.082 | 0.945 | 0.746 |
| 5722 | 0.032 | 0.365 | 2.691 | 0.687 | 0.807 | 1.630 | 0.597 | 0.559 | 0.193 | 0.108 | 1.037 | 0.607 | 0.068 | 1.559 |
| 5750 | 0.327 | 0.908 | 1.888 | 0.133 | 1.144 | 1.912 | 0.302 | 0.972 | 0.178 | 0.041 | 1.541 | 0.978 | 0.523 | 1.278 |
| 5766 | 0.501 | 0.207 | 0.328 | 0.712 | 0.415 | 1.012 | 0.562 | 0.757 | 0.172 | 0.242 | 2.532 | 1.395 | 0.161 | 2.063 |
| 5802 | 0.034 | 2.163 | 2.306 | 0.056 | 0.031 | 2.015 | 0.022 | 0.071 | 0.835 | 0.524 | 1.179 | 0.033 | 0.775 | 0.220 |
| 5844 | 0.134 | 2.028 | 2.687 | 0.176 | 0.051 | 1.973 | 0.095 | 0.083 | 0.638 | 0.495 | 0.539 | 0.034 | 0.102 | 0.724 |
| 6024 | 0.485 | 1.078 | 0.263 | 0.332 | 1.659 | 1.018 | 0.378 | 1.146 | 0.077 | 0.408 | 0.940 | 0.726 | 0.413 | 2.597 |
| 6092 | 0.380 | 1.078 | 2.068 | 0.577 | 0.456 | 1.436 | 0.635 | 0.458 | 0.088 | 0.762 | 0.880 | 1.056 | 0.851 | 1.773 |
| 6147 | 0.090 | 1.764 | 2.013 | 0.252 | 0.299 | 1.968 | 0.667 | 0.363 | 0.655 | 0.084 | 1.269 | 0.084 | 0.395 | 1.523 |
| 6242 | 0.748 | 0.214 | 0.079 | 0.978 | 1.263 | 1.791 | 0.819 | 0.765 | 0.109 | 0.183 | 0.408 | 1.747 | 0.200 | 2.252 |
| 6460 | 0.155 | 1.757 | 2.049 | 0.418 | 1.259 | 1.623 | 0.362 | 0.799 | 0.602 | 0.301 | 1.064 | 0.457 | 0.123 | 1.158 |
| 6572 | 0.113 | 1.784 | 1.940 | 0.168 | 0.119 | 1.953 | 0.423 | 0.176 | 0.464 | 0.588 | 1.719 | 0.083 | 0.483 | 1.296 |
| 6770 | 0.194 | 2.221 | 0.188 | 1.097 | 0.266 | 1.015 | 0.532 | 0.581 | 0.905 | 2.064 | 1.112 | 0.332 | 0.419 | 0.954 |
| 6771 | 0.113 | 1.021 | 2.221 | 0.424 | 0.095 | 1.906 | 0.667 | 0.362 | 0.223 | 1.215 | 0.643 | 0.188 | 0.475 | 1.854 |
| 6895 | 0.558 | 1.574 | 0.136 | 0.337 | 1.960 | 0.784 | 0.790 | 1.038 | 0.409 | 0.111 | 1.073 | 0.684 | 0.385 | 2.128 |
| 7026 | 0.575 | 0.781 | 1.884 | 0.827 | 1.182 | 1.222 | 0.794 | 0.936 | 0.843 | 0.642 | 1.305 | 0.647 | 0.168 | 1.359 |
| 7052 | 0.023 | 2.052 | 2.079 | 0.139 | 0.066 | 1.847 | 0.175 | 0.308 | 0.807 | 0.925 | 1.133 | 0.039 | 0.165 | 1.328 |
| 7136 | 0.347 | 1.640 | 2.298 | 0.771 | 0.441 | 1.413 | 0.952 | 0.485 | 0.327 | 0.017 | 0.667 | 0.359 | 0.259 | 1.721 |
| 7214 | 0.185 | 1.109 | 2.300 | 0.188 | 1.152 | 1.879 | 0.355 | 1.239 | 0.028 | 0.136 | 0.324 | 0.010 | 0.151 | 1.853 |
| 7265 | 0.281 | 1.140 | 1.014 | 0.756 | 1.374 | 1.759 | 0.530 | 0.530 | 0.147 | 0.897 | 1.276 | 0.460 | 0.295 | 2.005 |
| 7280 | 0.207 | 1.313 | 2.369 | 0.869 | 0.319 | 1.717 | 0.309 | 0.652 | 0.085 | 0.197 | 1.395 | 1.159 | 0.085 | 0.919 |
| 7358 | 0.985 | 1.298 | 0.951 | 1.029 | 0.886 | 1.424 | 0.456 | 1.214 | 0.047 | 1.008 | 1.230 | 0.317 | 0.152 | 1.854 |
| 7676 | 1.205 | 1.144 | 0.137 | 1.195 | 0.805 | 0.755 | 0.897 | 1.138 | 0.059 | 0.476 | 1.184 | 1.256 | 0.640 | 1.980 |
| 7688 | 0.579 | 1.485 | 0.103 | 1.089 | 1.936 | 1.162 | 0.801 | 0.673 | 1.004 | 0.225 | 1.792 | 0.038 | 0.250 | 1.173 |

TABLE S2-continued

Gene expression measured by RT-MLPA.
The sample-normalized values of the expression of the 14 genes measured by RT-MLPA in the diverse cohorts analyzed throughout this paper, including the training, validation, external and FFPE series.

| Sample | NEK6 | IRF4 | IGHM | CCND1 | LMO2 | FOXP1 | TNFRSF9 | BCL6 | TNFRSF13B | CCND2 | MYC | MYBL1 | BCL2 | MS4A1 |
|---|---|---|---|---|---|---|---|---|---|---|---|---|---|---|
| 7764 | 0.987 | 0.795 | 2.174 | 0.807 | 1.488 | 0.721 | 0.445 | 0.621 | 0.127 | 0.641 | 0.673 | 0.663 | 0.875 | 1.588 |
| 780 | 0.069 | 1.668 | 2.416 | 0.331 | 0.148 | 1.656 | 0.294 | 0.218 | 1.042 | 0.766 | 1.276 | 0.041 | 0.345 | 1.037 |
| 784 | 0.006 | 0.584 | 2.414 | 0.314 | 0.163 | 1.707 | 0.495 | 0.266 | 0.403 | 0.064 | 0.850 | 0.154 | 0.168 | 2.466 |
| 8005 | 0.074 | 1.275 | 2.041 | 0.087 | 0.051 | 2.139 | 0.085 | 0.320 | 0.629 | 0.262 | 0.555 | 0.144 | 0.227 | 2.353 |
| 8008 | 0.140 | 1.553 | 2.299 | 0.685 | 0.229 | 1.880 | 0.424 | 0.307 | 0.922 | 0.941 | 0.708 | 0.053 | 0.274 | 1.208 |
| 8026 | 0.000 | 2.096 | 2.785 | 0.114 | 0.147 | 1.372 | 0.123 | 0.471 | 0.633 | 0.752 | 0.663 | 0.025 | 0.082 | 0.754 |
| 8041 | 0.377 | 2.192 | 0.126 | 0.304 | 0.094 | 2.131 | 0.098 | 0.274 | 1.251 | 1.125 | 1.780 | 0.082 | 0.256 | 0.873 |
| 8056 | 0.083 | 1.221 | 2.275 | 0.246 | 0.101 | 1.778 | 0.352 | 0.646 | 0.849 | 0.477 | 0.578 | 0.081 | 0.354 | 2.077 |
| 8090 | 0.107 | 1.471 | 1.646 | 0.349 | 0.266 | 2.152 | 0.276 | 0.252 | 1.072 | 1.788 | 0.894 | 0.232 | 0.268 | 0.930 |
| 8119 | 0.383 | 0.879 | 0.107 | 0.624 | 1.773 | 1.669 | 0.775 | 0.809 | 0.201 | 0.046 | 1.111 | 0.650 | 0.259 | 2.342 |
| 8189 | 0.139 | 1.242 | 1.089 | 0.194 | 1.287 | 1.751 | 0.174 | 0.192 | 0.577 | 1.010 | 0.547 | 0.016 | 0.095 | 2.618 |
| 819 | 1.276 | 1.924 | 0.184 | 0.773 | 1.583 | 0.333 | 0.218 | 0.886 | 0.015 | 0.280 | 1.703 | 0.383 | 0.115 | 1.928 |
| 8190 | 0.520 | 0.864 | 0.269 | 0.921 | 1.065 | 1.160 | 0.268 | 1.268 | 0.120 | 0.331 | 0.995 | 1.649 | 0.139 | 2.360 |
| 8193 | 0.160 | 1.824 | 1.742 | 0.503 | 0.808 | 1.755 | 0.240 | 0.283 | 1.035 | 0.348 | 1.183 | 0.244 | 0.119 | 1.675 |
| 8194 | 0.111 | 1.691 | 2.344 | 0.604 | 0.081 | 1.525 | 0.102 | 0.135 | 0.785 | 1.284 | 1.350 | 0.036 | 0.296 | 1.019 |
| 8195 | 0.141 | 0.637 | 1.996 | 3.149 | 0.085 | 0.478 | 0.023 | 0.031 | 0.290 | 0.548 | 0.707 | 0.010 | 0.109 | 0.667 |
| 8196 | 0.221 | 1.998 | 1.774 | 0.508 | 0.301 | 1.277 | 0.127 | 0.179 | 0.680 | 1.901 | 0.908 | 0.046 | 0.140 | 1.471 |
| 8268 | 0.250 | 2.069 | 2.312 | 0.288 | 0.049 | 1.247 | 0.159 | 0.321 | 0.559 | 0.449 | 1.133 | 0.643 | 0.303 | 1.499 |
| 8283 | 1.166 | 1.435 | 0.542 | 1.519 | 0.966 | 0.454 | 0.862 | 0.078 | 0.644 | 0.688 | 2.203 | 0.086 | 0.795 | 0.971 |
| 8307 | 0.347 | 1.768 | 1.606 | 0.697 | 1.224 | 2.190 | 0.238 | 0.719 | 0.159 | 0.324 | 0.767 | 0.103 | 0.121 | 1.435 |
| 8431 | 0.144 | 1.453 | 1.609 | 0.791 | 1.015 | 1.639 | 1.054 | 0.697 | 0.231 | 0.017 | 0.580 | 0.191 | 0.360 | 2.150 |
| 8607 | 0.085 | 1.508 | 2.247 | 0.268 | 0.446 | 1.863 | 0.447 | 0.163 | 0.667 | 0.528 | 0.889 | 0.336 | 0.342 | 1.700 |
| 8709 | 0.127 | 1.103 | 2.330 | 0.412 | 0.471 | 1.656 | 0.569 | 0.732 | 0.176 | 0.900 | 1.046 | 0.099 | 0.174 | 1.792 |
| 8730 | 0.486 | 0.904 | 0.734 | 0.475 | 0.982 | 1.108 | 0.715 | 1.509 | 0.089 | 0.064 | 1.937 | 0.520 | 0.159 | 2.191 |
| 8743 | 0.067 | 1.846 | 2.519 | 0.092 | 0.508 | 1.992 | 0.211 | 0.675 | 0.462 | 0.502 | 0.479 | 0.017 | 0.067 | 1.109 |
| 8886 | 0.230 | 0.837 | 2.114 | 0.086 | 1.044 | 1.902 | 0.169 | 0.962 | 0.134 | 0.030 | 1.084 | 0.637 | 0.524 | 1.827 |
| 9017 | 0.437 | 1.778 | 1.802 | 0.616 | 1.204 | 1.663 | 0.359 | 0.363 | 0.161 | 0.348 | 1.084 | 0.054 | 0.231 | 1.782 |
| 9022 | 0.148 | 2.811 | 1.363 | 1.109 | 1.213 | 0.758 | 0.255 | 0.695 | 0.124 | 0.093 | 0.696 | 0.270 | 0.137 | 1.167 |
| 9083 | 0.633 | 1.245 | 2.162 | 1.081 | 1.295 | 1.303 | 0.637 | 0.915 | 0.286 | 0.302 | 0.773 | 1.286 | 0.334 | 0.339 |
| 9093 | 0.317 | 1.682 | 1.129 | 1.312 | 0.297 | 1.124 | 0.689 | 0.615 | 0.390 | 0.645 | 1.374 | 0.324 | 0.581 | 2.039 |
| 9138 | 0.039 | 0.978 | 3.257 | 0.173 | 0.127 | 1.818 | 0.174 | 0.444 | 0.079 | 0.070 | 0.175 | 0.000 | 0.000 | 1.001 |
| 9217 | 0.994 | 1.122 | 2.168 | 1.549 | 1.115 | 0.882 | 0.475 | 0.481 | 0.046 | 0.675 | 0.919 | 0.482 | 0.796 | 0.974 |
| 9231 | 0.056 | 1.534 | 3.471 | 0.433 | 0.511 | 0.373 | 0.084 | 0.112 | 0.116 | 0.144 | 0.602 | 0.022 | 0.000 | 0.072 |
| 9260 | 0.330 | 1.394 | 0.077 | 0.183 | 1.534 | 1.946 | 0.386 | 1.571 | 0.426 | 0.090 | 0.715 | 0.265 | 0.306 | 2.142 |
| 9260_R02 | 0.300 | 1.444 | 0.056 | 0.178 | 1.518 | 2.044 | 0.345 | 1.540 | 0.357 | 0.043 | 0.656 | 0.298 | 0.296 | 2.127 |
| 9260_R03 | 0.256 | 1.371 | 0.061 | 0.171 | 1.574 | 2.018 | 0.358 | 1.540 | 0.404 | 0.096 | 0.689 | 0.248 | 0.301 | 2.140 |
| 9260_R04 | 0.292 | 1.440 | 0.044 | 0.147 | 1.559 | 2.005 | 0.367 | 1.586 | 0.363 | 0.053 | 0.667 | 0.238 | 0.272 | 2.129 |
| 9260_R05 | 0.290 | 1.393 | 0.052 | 0.146 | 1.564 | 2.025 | 0.360 | 1.614 | 0.364 | 0.062 | 0.677 | 0.223 | 0.280 | 2.112 |
| 9260_R06 | 0.255 | 1.405 | 0.051 | 0.146 | 1.568 | 2.013 | 0.367 | 1.644 | 0.359 | 0.043 | 0.653 | 0.202 | 0.245 | 2.130 |
| 9260_R07 | 0.272 | 1.420 | 0.056 | 0.183 | 1.560 | 2.031 | 0.369 | 1.604 | 0.347 | 0.069 | 0.676 | 0.227 | 0.283 | 2.094 |
| 9260_R08 | 0.263 | 1.434 | 0.053 | 0.165 | 1.545 | 2.034 | 0.351 | 1.595 | 0.355 | 0.049 | 0.660 | 0.210 | 0.249 | 2.134 |
| 9260_R09 | 0.284 | 1.399 | 0.045 | 0.179 | 1.567 | 2.021 | 0.365 | 1.624 | 0.360 | 0.068 | 0.684 | 0.231 | 0.291 | 2.089 |
| 9260_R10 | 0.313 | 1.421 | 0.054 | 0.148 | 1.553 | 2.023 | 0.370 | 1.585 | 0.362 | 0.063 | 0.695 | 0.212 | 0.291 | 2.109 |
| 9296 | 1.153 | 0.877 | 1.274 | 1.380 | 1.327 | 0.948 | 0.680 | 0.566 | 0.087 | 0.911 | 1.662 | 0.490 | 0.589 | 1.253 |
| 9360 | 0.395 | 0.321 | 2.339 | 0.624 | 0.930 | 1.148 | 0.646 | 0.880 | 0.052 | 0.239 | 0.669 | 1.119 | 0.101 | 2.090 |
| 9397 | 0.897 | 1.927 | 0.109 | 1.017 | 1.904 | 0.715 | 0.589 | 0.701 | 0.035 | 0.424 | 0.833 | 0.500 | 0.342 | 1.960 |
| 9398 | 0.272 | 2.182 | 2.236 | 0.613 | 0.336 | 1.442 | 0.103 | 0.190 | 1.076 | 0.179 | 1.329 | 0.057 | 0.276 | 0.862 |
| 9401 | 0.967 | 2.036 | 0.204 | 1.789 | 1.636 | 0.553 | 0.304 | 0.447 | 0.009 | 0.029 | 1.451 | 0.179 | 0.231 | 1.631 |
| 9402_D01 | 0.048 | 1.701 | 2.530 | 0.071 | 0.078 | 1.805 | 0.086 | 0.291 | 0.663 | 0.686 | 1.210 | 0.027 | 0.193 | 1.253 |
| 9402_D02 | 0.045 | 1.693 | 2.591 | 0.054 | 0.071 | 1.767 | 0.081 | 0.265 | 0.665 | 0.678 | 1.206 | 0.007 | 0.175 | 1.222 |
| 9402_D03 | 0.065 | 1.733 | 2.512 | 0.080 | 0.093 | 1.759 | 0.110 | 0.248 | 0.718 | 0.697 | 1.275 | 0.023 | 0.155 | 1.225 |
| 9402_D04 | 0.053 | 1.689 | 2.592 | 0.051 | 0.061 | 1.782 | 0.094 | 0.310 | 0.665 | 0.638 | 1.170 | 0.023 | 0.176 | 1.230 |
| 9402_D05 | 0.079 | 1.638 | 2.629 | 0.038 | 0.027 | 1.699 | 0.098 | 0.304 | 0.640 | 0.691 | 1.213 | 0.011 | 0.141 | 1.292 |
| 9402_D06 | 0.057 | 1.708 | 2.743 | 0.062 | 0.114 | 1.618 | 0.058 | 0.290 | 0.717 | 0.669 | 1.095 | 0.015 | 0.072 | 1.077 |
| 9402_D07 | 0.043 | 1.502 | 2.907 | 0.085 | 0.063 | 1.696 | 0.048 | 0.162 | 0.428 | 0.484 | 1.078 | 0.000 | 0.159 | 1.122 |
| 9402_D08 | 0.042 | 1.818 | 2.921 | 0.101 | 0.033 | 1.557 | 0.042 | 0.210 | 0.366 | 0.510 | 1.059 | 0.000 | 0.000 | 0.898 |
| 9402_D09 | 0.281 | 1.554 | 3.081 | 0.044 | 0.000 | 1.635 | 0.035 | 0.000 | 0.457 | 0.381 | 0.894 | 0.000 | 0.061 | 0.798 |
| 9402_D10 | 0.257 | 1.656 | 3.177 | 0.015 | 0.000 | 1.474 | 0.000 | 0.000 | 0.428 | 0.199 | 0.854 | 0.000 | 0.000 | 0.834 |
| 9402_D11 | 0.154 | 1.497 | 3.209 | 0.074 | 0.000 | 1.597 | 0.000 | 0.269 | 0.427 | 0.284 | 0.839 | 0.000 | 0.051 | 0.500 |
| 9402_D12 | 0.676 | 1.381 | 3.220 | 0.000 | 0.000 | 1.564 | 0.000 | 0.000 | 0.739 | 0.118 | 0.377 | 0.000 | 0.000 | 0.941 |
| 9402 | 0.061 | 1.773 | 2.464 | 0.095 | 0.098 | 1.709 | 0.107 | 0.270 | 0.786 | 0.749 | 1.242 | 0.037 | 0.207 | 1.252 |
| 9402_R02 | 0.055 | 1.667 | 2.575 | 0.074 | 0.072 | 1.835 | 0.099 | 0.251 | 0.656 | 0.692 | 1.213 | 0.036 | 0.182 | 1.153 |
| 9402_R03 | 0.059 | 1.719 | 2.486 | 0.084 | 0.087 | 1.737 | 0.102 | 0.285 | 0.747 | 0.736 | 1.250 | 0.028 | 0.198 | 1.279 |
| 9402_R04 | 0.060 | 1.708 | 2.482 | 0.081 | 0.085 | 1.785 | 0.100 | 0.302 | 0.687 | 0.719 | 1.238 | 0.037 | 0.195 | 1.293 |
| 9402_R05 | 0.068 | 1.717 | 2.506 | 0.066 | 0.070 | 1.731 | 0.100 | 0.272 | 0.700 | 0.735 | 1.256 | 0.027 | 0.199 | 1.290 |
| 9402_R06 | 0.057 | 1.721 | 2.543 | 0.050 | 0.060 | 1.762 | 0.090 | 0.280 | 0.702 | 0.696 | 1.205 | 0.022 | 0.180 | 1.256 |
| 9402_R07 | 0.048 | 1.688 | 2.562 | 0.063 | 0.079 | 1.721 | 0.103 | 0.307 | 0.675 | 0.708 | 1.211 | 0.026 | 0.184 | 1.282 |
| 9402_R08 | 0.065 | 1.721 | 2.524 | 0.064 | 0.068 | 1.715 | 0.103 | 0.287 | 0.693 | 0.714 | 1.238 | 0.022 | 0.187 | 1.300 |
| 9402_R09 | 0.060 | 1.704 | 2.543 | 0.080 | 0.083 | 1.783 | 0.091 | 0.269 | 0.681 | 0.691 | 1.205 | 0.030 | 0.184 | 1.242 |
| 9402_R10 | 0.050 | 1.685 | 2.568 | 0.080 | 0.074 | 1.820 | 0.092 | 0.266 | 0.632 | 0.668 | 1.199 | 0.025 | 0.181 | 1.218 |
| 9481 | 0.048 | 1.865 | 2.713 | 0.265 | 0.086 | 1.596 | 0.106 | 0.102 | 0.733 | 0.049 | 1.335 | 0.045 | 0.381 | 0.831 |
| 9503 | 0.691 | 1.257 | 0.235 | 0.367 | 1.324 | 1.435 | 0.596 | 0.974 | 0.095 | 0.347 | 0.913 | 1.104 | 0.502 | 2.338 |
| 9507 | 0.023 | 1.995 | 2.001 | 0.094 | 0.106 | 1.691 | 0.274 | 1.239 | 0.544 | 0.065 | 1.435 | 0.058 | 0.037 | 1.475 |

TABLE S2-continued

Gene expression measured by RT-MLPA.
The sample-normalized values of the expression of the 14 genes measured by RT-MLPA in the diverse cohorts analyzed throughout this paper, including the training, validation, external and FFPE series.

| Sample | NEK6 | IRF4 | IGHM | CCND1 | LMO2 | FOXP1 | TNFRSF9 | BCL6 | TNFRSF13B | CCND2 | MYC | MYBL1 | BCL2 | MS4A1 |
|---|---|---|---|---|---|---|---|---|---|---|---|---|---|---|
| 9647 | 0.611 | 0.950 | 1.860 | 0.603 | 0.985 | 1.530 | 0.588 | 0.800 | 0.091 | 0.021 | 0.675 | 0.607 | 1.233 | 1.900 |
| 9717 | 0.861 | 2.034 | 0.225 | 1.026 | 1.314 | 1.120 | 0.603 | 0.485 | 0.153 | 0.857 | 0.767 | 0.140 | 0.495 | 2.059 |
| 9795 | 0.301 | 1.606 | 2.079 | 0.419 | 0.628 | 1.749 | 0.395 | 0.181 | 0.185 | 0.083 | 1.269 | 0.038 | 0.221 | 2.004 |
| 9797 | 0.200 | 0.906 | 2.209 | 0.268 | 1.036 | 1.954 | 0.254 | 0.848 | 0.713 | 0.214 | 0.694 | 0.047 | 0.174 | 1.870 |
| 9831 | 0.127 | 2.103 | 1.936 | 0.439 | 0.619 | 1.597 | 0.522 | 1.216 | 0.548 | 0.130 | 0.697 | 0.356 | 0.148 | 1.349 |
| 9881 | 0.200 | 1.679 | 2.377 | 0.790 | 0.248 | 1.676 | 0.417 | 0.220 | 0.918 | 0.585 | 0.750 | 0.113 | 0.549 | 1.156 |
| B01.1117 | 0.348 | 0.691 | 0.950 | 1.282 | 0.949 | 1.124 | 0.186 | 0.922 | 0.194 | 0.077 | 1.718 | 0.275 | 0.637 | 2.421 |
| B04.2708 | 0.131 | 1.277 | 2.859 | 0.275 | 0.067 | 1.408 | 0.105 | 0.474 | 0.448 | 0.922 | 0.923 | 0.033 | 0.125 | 1.371 |
| B05.2945 | 0.516 | 0.223 | 0.528 | 1.075 | 2.089 | 0.825 | 0.445 | 0.723 | 0.047 | 1.073 | 0.770 | 0.665 | 1.079 | 2.096 |
| B06.0638 | 0.041 | 1.632 | 2.287 | 0.287 | 0.078 | 1.576 | 0.040 | 0.174 | 0.653 | 1.011 | 1.323 | 0.043 | 0.360 | 0.433 |
| B06.0757 | 0.108 | 1.387 | 2.737 | 0.403 | 0.090 | 1.418 | 0.134 | 0.325 | 0.629 | 1.383 | 1.086 | 0.041 | 0.102 | 0.888 |
| B06.1310 | 0.212 | 0.674 | 2.354 | 0.504 | 0.196 | 0.771 | 0.171 | 0.241 | 0.121 | 1.721 | 1.251 | 0.241 | 0.648 | 2.015 |
| B06.2626 | 0.421 | 1.095 | 0.660 | 1.891 | 0.482 | 1.061 | 0.260 | 0.793 | 0.151 | 2.635 | 1.109 | 0.029 | 0.041 | 0.373 |
| B07.0131 | 0.285 | 0.179 | 2.125 | 0.521 | 0.648 | 0.705 | 0.286 | 1.630 | 0.873 | 0.893 | 1.403 | 0.299 | 0.050 | 1.904 |
| B07.0512 | 0.256 | 0.756 | 2.727 | 0.831 | 1.061 | 1.011 | 0.018 | 0.546 | 0.000 | 0.527 | 0.796 | 0.000 | 0.364 | 1.892 |
| B07.2345 | 0.176 | 0.638 | 0.210 | 0.808 | 1.384 | 1.515 | 0.473 | 1.601 | 0.268 | 0.039 | 1.792 | 0.220 | 0.101 | 2.198 |
| B07.2712 | 0.352 | 1.014 | 0.823 | 1.715 | 0.938 | 0.850 | 0.413 | 0.682 | 0.305 | 0.891 | 2.051 | 0.175 | 0.138 | 1.820 |
| B07.2960 | 0.056 | 1.612 | 2.232 | 1.317 | 0.416 | 1.477 | 0.605 | 0.715 | 0.256 | 0.023 | 1.308 | 0.118 | 0.184 | 1.337 |
| B08.0130 | 0.093 | 1.253 | 2.864 | 0.337 | 0.122 | 0.838 | 0.072 | 0.027 | 0.592 | 1.066 | 1.588 | 0.004 | 0.149 | 1.227 |
| B08.1769 | 0.076 | 0.328 | 2.811 | 1.443 | 0.366 | 1.026 | 0.307 | 1.135 | 0.177 | 0.241 | 0.913 | 0.035 | 0.000 | 1.585 |
| B08.1825 | 1.176 | 0.873 | 0.366 | 1.360 | 1.320 | 0.311 | 0.487 | 1.014 | 0.006 | 0.540 | 1.193 | 0.396 | 0.212 | 2.505 |
| B08.1852 | 0.062 | 1.334 | 2.838 | 0.121 | 0.047 | 0.861 | 0.068 | 0.310 | 0.574 | 1.029 | 1.846 | 0.034 | 0.254 | 0.782 |
| B08.1999 | 0.032 | 1.311 | 2.707 | 0.352 | 0.112 | 1.476 | 0.070 | 0.370 | 0.680 | 0.059 | 1.838 | 0.049 | 0.255 | 1.030 |
| B08.2071 | 0.523 | 0.778 | 0.152 | 0.422 | 1.195 | 1.003 | 0.412 | 2.582 | 0.405 | 0.645 | 1.058 | 0.285 | 0.315 | 1.745 |
| B08.2463 | 0.181 | 0.532 | 2.588 | 0.623 | 0.243 | 1.529 | 0.220 | 0.845 | 0.027 | 0.078 | 1.270 | 0.090 | 0.450 | 1.972 |
| B09.0141 | 0.849 | 1.072 | 1.163 | 1.338 | 0.971 | 0.550 | 0.772 | 1.239 | 0.221 | 0.730 | 1.203 | 0.408 | 0.315 | 2.049 |
| B09.0388 | 0.100 | 0.728 | 2.633 | 0.693 | 0.186 | 1.319 | 0.177 | 0.259 | 0.513 | 1.301 | 0.854 | 0.108 | 0.135 | 1.856 |
| B09.1810 | 0.092 | 1.485 | 2.286 | 0.601 | 0.180 | 1.306 | 0.205 | 0.135 | 0.319 | 1.541 | 1.496 | 0.211 | 0.205 | 1.377 |
| B09.1892 | 0.094 | 1.199 | 2.610 | 0.112 | 0.042 | 1.004 | 0.014 | 0.052 | 0.578 | 2.058 | 1.377 | 0.020 | 0.140 | 1.001 |
| B09.2264 | 0.089 | 1.093 | 2.508 | 0.452 | 0.133 | 1.278 | 0.159 | 0.412 | 0.407 | 1.693 | 1.391 | 0.078 | 0.168 | 1.274 |
| B10.0146 | 0.099 | 1.549 | 2.514 | 0.334 | 0.377 | 1.786 | 0.175 | 0.187 | 0.588 | 0.077 | 1.944 | 0.076 | 0.178 | 0.509 |
| B10.0640 | 0.913 | 0.194 | 0.562 | 1.206 | 1.484 | 0.436 | 0.411 | 1.208 | 0.037 | 0.542 | 0.940 | 1.069 | 0.255 | 2.513 |
| B12.1717 | 0.021 | 0.810 | 2.769 | 0.123 | 0.073 | 1.635 | 0.058 | 0.117 | 0.792 | 1.072 | 1.342 | 0.052 | 0.206 | 1.313 |
| X10.0083 | 0.546 | 0.509 | 0.786 | 0.791 | 1.393 | 0.855 | 0.346 | 1.649 | 0.111 | 0.492 | 1.746 | 0.666 | 0.130 | 2.104 |
| GHE0015 | 0.378 | 0.961 | 0.726 | 1.039 | 1.203 | 1.450 | 1.134 | 1.362 | 0.404 | 0.852 | 0.855 | 0.169 | 0.135 | 2.031 |
| GHE0016 | 0.168 | 1.033 | 1.909 | 0.284 | 0.303 | 1.654 | 0.493 | 0.574 | 0.565 | 0.416 | 1.009 | 0.074 | 0.153 | 2.483 |
| GHE0024 | 0.231 | 1.615 | 2.687 | 0.497 | 0.215 | 1.127 | 0.725 | 0.298 | 0.344 | 0.046 | 0.511 | 0.065 | 0.177 | 1.920 |
| GHE0028 | 0.194 | 1.463 | 0.975 | 0.614 | 0.444 | 2.020 | 0.655 | 0.468 | 0.537 | 0.756 | 0.555 | 0.077 | 0.266 | 2.424 |
| GHE0047 | 0.136 | 1.128 | 2.574 | 0.339 | 0.380 | 1.538 | 0.463 | 1.047 | 0.397 | 0.573 | 0.610 | 0.228 | 0.196 | 1.677 |
| GHE0061 | 0.100 | 1.405 | 2.379 | 0.338 | 0.177 | 1.696 | 0.448 | 0.428 | 0.463 | 0.325 | 0.655 | 0.082 | 0.246 | 2.098 |
| GHE0140 | 0.122 | 1.271 | 2.730 | 0.424 | 0.287 | 1.084 | 0.756 | 0.669 | 0.361 | 0.654 | 0.676 | 0.122 | 0.157 | 1.699 |
| GHE0202 | 0.238 | 1.002 | 1.294 | 0.393 | 0.867 | 1.201 | 0.602 | 1.232 | 0.165 | 1.003 | 0.523 | 0.222 | 0.246 | 2.619 |
| GHE0219 | 0.470 | 1.628 | 0.521 | 0.783 | 0.920 | 1.063 | 0.854 | 1.453 | 0.137 | 1.229 | 0.956 | 0.292 | 0.186 | 2.035 |
| GHE0228 | 0.550 | 1.865 | 0.061 | 0.732 | 0.910 | 0.622 | 1.343 | 0.543 | 0.031 | 0.659 | 0.755 | 0.114 | 0.175 | 2.650 |
| GHE0258 | 0.164 | 1.682 | 1.863 | 0.387 | 0.226 | 1.875 | 0.639 | 1.529 | 0.808 | 0.042 | 0.181 | 0.110 | 0.154 | 1.740 |
| GHE0262 | 0.094 | 1.103 | 2.969 | 0.486 | 0.334 | 1.273 | 0.498 | 0.501 | 0.288 | 0.512 | 0.626 | 0.032 | 0.078 | 1.476 |
| GHE0292 | 0.522 | 0.533 | 0.287 | 0.242 | 1.361 | 0.963 | 0.916 | 1.316 | 0.058 | 0.040 | 0.570 | 0.578 | 0.578 | 2.864 |
| GHE0293 | 0.156 | 1.107 | 1.866 | 0.609 | 0.694 | 1.628 | 0.521 | 0.503 | 0.335 | 0.646 | 0.853 | 0.150 | 0.218 | 2.348 |
| GHE0368 | 0.513 | 1.471 | 0.141 | 0.434 | 0.810 | 0.791 | 0.463 | 1.506 | 0.056 | 0.195 | 0.474 | 0.319 | 0.155 | 2.947 |
| GHE0375 | 0.205 | 1.111 | 1.828 | 0.510 | 0.380 | 1.668 | 0.653 | 0.695 | 0.516 | 0.845 | 0.786 | 0.111 | 0.296 | 2.259 |
| GHE0429 | 0.470 | 0.757 | 1.436 | 0.424 | 1.065 | 0.986 | 0.745 | 1.514 | 0.165 | 0.677 | 0.560 | 0.596 | 0.613 | 2.332 |
| GHE0436 | 0.067 | 1.733 | 2.441 | 0.096 | 0.072 | 1.589 | 0.164 | 0.531 | 0.728 | 0.730 | 1.123 | 0.034 | 0.208 | 1.502 |
| GHE0440 | 0.451 | 1.195 | 0.163 | 0.270 | 0.944 | 1.544 | 0.803 | 1.723 | 0.078 | 0.382 | 0.587 | 0.502 | 0.475 | 2.450 |
| GHE0507 | 0.061 | 1.666 | 2.339 | 0.161 | 0.177 | 1.356 | 0.264 | 0.791 | 0.349 | 0.978 | 0.891 | 0.015 | 0.044 | 1.943 |
| GHE0547 | 0.198 | 1.105 | 2.457 | 0.368 | 0.557 | 1.304 | 0.480 | 0.702 | 0.561 | 0.194 | 0.414 | 0.050 | 0.121 | 2.289 |
| GHE0562 | 0.017 | 1.473 | 1.387 | 0.176 | 0.741 | 1.291 | 0.177 | 0.356 | 0.986 | 1.304 | 0.803 | 0.133 | 0.134 | 2.472 |
| GHE0629 | 0.036 | 1.535 | 1.637 | 0.277 | 0.195 | 1.766 | 0.611 | 0.762 | 0.499 | 1.839 | 1.244 | 0.039 | 0.162 | 1.311 |
| GHE0632 | 0.255 | 0.944 | 2.143 | 0.118 | 0.472 | 1.606 | 0.281 | 0.741 | 0.669 | 0.512 | 0.708 | 0.202 | 0.121 | 2.372 |
| GHE0635 | 0.386 | 0.946 | 0.073 | 0.432 | 1.175 | 0.792 | 0.817 | 1.038 | 0.014 | 0.233 | 0.644 | 0.520 | 0.117 | 3.053 |
| GHE0659 | 0.033 | 1.632 | 2.015 | 0.191 | 0.193 | 1.855 | 0.310 | 0.803 | 0.352 | 0.199 | 1.121 | 0.184 | 0.196 | 2.024 |
| GHE0685 | 0.085 | 1.569 | 1.301 | 0.151 | 0.345 | 1.962 | 0.324 | 1.054 | 1.120 | 0.147 | 0.968 | 0.115 | 0.189 | 2.152 |
| GHE0708 | 0.411 | 1.838 | 0.340 | 0.404 | 0.934 | 0.636 | 0.897 | 1.293 | 0.072 | 0.032 | 0.717 | 0.313 | 0.239 | 2.720 |
| GHE0717 | 0.042 | 1.492 | 1.947 | 0.185 | 0.129 | 1.806 | 0.293 | 0.444 | 0.391 | 1.277 | 1.196 | 0.030 | 0.271 | 1.901 |
| GHE0776 | 0.508 | 1.460 | 0.094 | 0.706 | 1.206 | 1.778 | 0.739 | 0.553 | 0.917 | 0.041 | 1.006 | 0.089 | 0.234 | 2.348 |
| GHE0811 | 0.027 | 1.330 | 2.600 | 0.356 | 0.245 | 1.434 | 0.263 | 0.468 | 0.550 | 0.442 | 0.536 | 0.147 | 0.149 | 2.059 |
| GHE0834 | 0.481 | 0.146 | 2.008 | 0.238 | 1.202 | 0.702 | 0.460 | 1.111 | 0.044 | 0.212 | 0.544 | 0.351 | 0.144 | 2.767 |
| GHE0837 | 0.060 | 1.486 | 2.191 | 0.175 | 0.097 | 1.720 | 0.176 | 0.817 | 0.801 | 0.721 | 0.915 | 0.024 | 0.251 | 1.897 |
| GHE0853 | 0.368 | 1.215 | 1.682 | 0.949 | 0.574 | 1.968 | 0.370 | 1.101 | 0.428 | 0.801 | 0.755 | 0.107 | 0.183 | 1.775 |
| GHE0855 | 0.111 | 1.665 | 0.125 | 0.553 | 0.598 | 2.025 | 1.027 | 0.884 | 0.737 | 0.053 | 1.519 | 0.105 | 0.711 | 1.783 |
| GHE0857 | 0.196 | 0.538 | 2.042 | 0.270 | 0.481 | 1.744 | 0.794 | 1.463 | 0.095 | 0.378 | 0.588 | 0.374 | 0.100 | 2.202 |
| GHE0860 | 0.049 | 1.660 | 1.970 | 0.208 | 0.664 | 1.822 | 0.457 | 0.826 | 0.283 | 0.250 | 0.610 | 0.189 | 0.389 | 2.030 |
| GHE0877 | 0.180 | 1.018 | 1.783 | 0.352 | 0.402 | 1.877 | 0.671 | 0.793 | 0.256 | 1.035 | 0.669 | 0.175 | 0.259 | 2.217 |
| GHE0908 | 0.395 | 1.224 | 0.289 | 0.285 | 1.291 | 0.743 | 0.315 | 1.420 | 0.060 | 0.172 | 0.710 | 0.893 | 0.157 | 2.826 |

TABLE S2-continued

Gene expression measured by RT-MLPA.
The sample-normalized values of the expression of the 14 genes measured by RT-MLPA in the diverse cohorts analyzed throughout this paper, including the training, validation, external and FFPE series.

| Sample | NEK6 | IRF4 | IGHM | CCND1 | LMO2 | FOXP1 | TNFRSF9 | BCL6 | TNFRSF13B | CCND2 | MYC | MYBL1 | BCL2 | MS4A1 |
|---|---|---|---|---|---|---|---|---|---|---|---|---|---|---|
| GHE0997 | 0.182 | 1.369 | 1.231 | 0.556 | 0.557 | 1.401 | 1.085 | 0.618 | 0.623 | 0.830 | 1.063 | 0.146 | 0.260 | 2.318 |
| GHE1018 | 0.447 | 0.189 | 2.177 | 0.276 | 1.101 | 0.760 | 0.588 | 1.471 | 0.085 | 0.045 | 0.886 | 0.480 | 0.092 | 2.391 |
| GHE1028 | 0.182 | 0.413 | 1.906 | 0.261 | 0.872 | 0.956 | 0.289 | 1.492 | 0.057 | 0.097 | 0.067 | 0.216 | 0.312 | 2.852 |
| GHE1069 | 0.303 | 0.828 | 2.332 | 0.190 | 0.953 | 1.388 | 0.347 | 0.826 | 0.049 | 0.152 | 0.436 | 0.359 | 0.081 | 2.427 |
| GHE1225 | 0.099 | 1.920 | 0.016 | 0.226 | 0.780 | 2.071 | 0.407 | 1.254 | 0.617 | 0.247 | 1.466 | 0.669 | 0.274 | 1.609 |
| GHE1229 | 0.023 | 0.934 | 2.108 | 0.169 | 0.054 | 1.979 | 0.374 | 1.251 | 0.575 | 0.796 | 0.870 | 0.019 | 0.140 | 1.930 |
| GHE1287 | 0.483 | 1.638 | 0.033 | 0.466 | 1.640 | 0.582 | 0.637 | 1.948 | 0.067 | 0.216 | 1.247 | 0.456 | 0.248 | 1.971 |
| GHE1302 | 0.169 | 1.355 | 1.966 | 0.561 | 0.344 | 1.807 | 0.386 | 0.772 | 0.623 | 0.934 | 0.810 | 0.056 | 0.137 | 1.930 |
| GHE1352 | 0.086 | 1.447 | 1.385 | 0.195 | 0.749 | 1.561 | 0.333 | 1.356 | 0.725 | 0.059 | 0.920 | 0.218 | 0.086 | 2.376 |
| GHE1353 | 0.077 | 1.376 | 2.271 | 0.097 | 0.456 | 2.016 | 0.216 | 0.729 | 1.030 | 0.045 | 0.834 | 0.039 | 0.062 | 1.719 |
| GHE1373 | 0.142 | 0.764 | 0.032 | 0.200 | 1.665 | 1.009 | 0.285 | 1.167 | 0.274 | 0.130 | 1.130 | 0.555 | 0.491 | 2.810 |
| GHE1393 | 0.385 | 0.687 | 2.064 | 0.286 | 1.186 | 0.732 | 0.597 | 0.997 | 0.258 | 0.380 | 0.468 | 0.360 | 0.253 | 2.558 |
| GHE1409 | 0.160 | 1.401 | 0.730 | 0.300 | 0.962 | 1.770 | 0.703 | 1.150 | 0.873 | 0.387 | 0.622 | 0.056 | 0.134 | 2.415 |
| GHE1413 | 0.106 | 1.537 | 1.799 | 0.185 | 0.081 | 1.712 | 0.535 | 0.294 | 0.636 | 0.040 | 0.888 | 0.037 | 0.307 | 2.511 |
| GHE1424 | 0.195 | 2.167 | 0.783 | 0.219 | 0.214 | 1.178 | 0.360 | 0.955 | 0.933 | 0.508 | 1.448 | 0.055 | 0.085 | 2.225 |
| GHE1498 | 0.222 | 0.490 | 2.244 | 0.233 | 0.097 | 1.291 | 0.365 | 1.710 | 0.070 | 0.321 | 1.027 | 0.671 | 0.080 | 2.156 |
| GHE1553 | 0.761 | 1.704 | 0.264 | 0.457 | 1.109 | 1.086 | 0.769 | 1.630 | 0.106 | 0.807 | 1.087 | 0.354 | 0.777 | 1.788 |
| GHE1554 | 0.459 | 1.353 | 1.985 | 0.835 | 0.256 | 1.677 | 0.766 | 1.296 | 0.041 | 0.754 | 1.073 | 0.172 | 0.188 | 1.430 |
| GHE2002 | 0.329 | 0.374 | 2.185 | 0.400 | 0.125 | 1.501 | 0.574 | 0.533 | 0.577 | 0.370 | 2.215 | 0.098 | 0.426 | 1.528 |
| GHE2003 | 0.262 | 0.882 | 0.091 | 1.025 | 1.063 | 1.167 | 0.595 | 1.066 | 0.100 | 0.636 | 1.769 | 0.474 | 0.105 | 2.438 |
| GHE2012 | 0.027 | 0.690 | 1.846 | 1.759 | 0.115 | 1.877 | 0.217 | 0.921 | 0.404 | 0.360 | 0.290 | 0.185 | 0.135 | 2.174 |
| GHE2019 | 0.201 | 1.092 | 2.147 | 0.158 | 0.653 | 1.512 | 0.372 | 0.922 | 0.532 | 0.018 | 0.615 | 0.528 | 0.165 | 2.324 |
| GHE2026 | 0.127 | 1.489 | 1.788 | 0.115 | 0.261 | 1.855 | 0.148 | 0.734 | 0.690 | 0.675 | 0.741 | 0.034 | 0.090 | 2.324 |
| GHE2030 | 0.042 | 1.425 | 1.525 | 0.227 | 0.654 | 1.516 | 0.306 | 0.661 | 0.917 | 0.751 | 0.638 | 0.084 | 0.201 | 2.498 |
| GHE2109 | 0.142 | 1.247 | 2.328 | 0.395 | 0.335 | 1.507 | 0.619 | 0.799 | 0.727 | 0.620 | 0.646 | 0.189 | 0.119 | 1.936 |

TABLE S3

Univariate survival analysis of the genes included in the RT-MLPA predictor.
The individual power of 8 genes measured by RT-MLPA to predict the overall and progression-free survival of 135 patients treated with a combination of Rituximab and chemotherapy was assessed using univariate Cox models. Raw p-values of the subsequent likelihood-ratio tests, as well as the corresponding False Discovery Rates (FDR) and Hazard Ratios (HR), are presented for each of them.

| Gene | Progression-Free Survival | | | Overal Survival | | |
|---|---|---|---|---|---|---|
| | p | FDR | HR | p | FDR | HR |
| LMO2 | 0.000736 | 0.005884* | 0.457253 | 0.002983 | 0.011932* | 0.485042 |
| BCL6 | 0.004633 | 0.018531* | 0.423641 | 0.036193 | 0.070998 | 0.521272 |
| TNFRSF13B | 0.013549 | 0.036130* | 2.549328 | 0.002057 | 0.011932* | 3.452999 |
| FOXP1 | 0.026251 | 0.052502 | 1.841605 | 0.037758 | 0.070998 | 1.809569 |
| IGHM | 0.133880 | 0.178506 | 1.212521 | 0.768369 | 0.768369 | 1.039949 |
| NEK6 | 0.126099 | 0.178506 | 0.545349 | 0.130903 | 0.174537 | 0.533563 |
| IRF4 | 0.161656 | 0.184750 | 1.342991 | 0.044374 | 0.070998 | 1.585370 |
| MYBL1 | 0.436523 | 0.436523 | 0.767482 | 0.611616 | 0.698989 | 0.834771 |

*FDR <5%, considered significant

REFERENCES

Throughout this application, various references describe the state of the art to which this invention pertains. The disclosures of these references are hereby incorporated by reference into the present disclosure.

1. Swerdlow S H, International Agency for Research on Cancer, World Health Organization: WHO classification of tumours of haematopoietic and lymphoid tissues. Lyon, France, International Agency for Research on Cancer, 2008.

2. Coiffier B: Rituximab therapy in malignant lymphoma. Oncogene 2007, 26:3603-3613.

3. Coiffier B, Thieblemont C, Van Den Neste E, Lepeu G, Plantier I, Castaigne S, Lefort S, Marit G, Macro M, Sebban C, Belhadj K, Bordessoule D, Fermé C, Tilly H: Long-term outcome of patients in the LNH-98.5 trial, the first randomized study comparing rituximab-CHOP to standard CHOP chemotherapy in DLBCL patients: a study by the Groupe d'Etudes des Lymphomes de l'Adulte. Blood 2010, 116: 2040-2045.

4. Alizadeh A A, Eisen M B, Davis R E, Ma C, Lossos I S, Rosenwald A, Boldrick J C, Sabet H, Tran T, Yu X, Powell J I, Yang L, Marti G E, Moore T, Hudson J Jr, Lu L, Lewis D B, Tibshirani R, Sherlock G, Chan W C, Greiner T C, Weisenburger D D, Armitage J O, Warnke R, Levy R, Wilson W, Greyer M R, Byrd J C, Botstein D, Brown P O, Staudt L M: Distinct types of diffuse large B-cell lymphoma identified by gene expression profiling. Nature 2000, 403: 503-511.

5. Shaffer A L 3rd, Young R M, Staudt L M: Pathogenesis of human B cell lymphomas. Annu Rev Immunol 2012, 30:565-610.

6. Barton S, Hawkes E A, Wotherspoon A, Cunningham D: Are We Ready To Stratify Treatment for Diffuse Large B-Cell Lymphoma Using Molecular Hallmarks? The Oncologist 2012, 17:1562-1573.

7. Roschewski M, Staudt L M, Wilson W H: Diffuse large B-cell lymphoma-treatment approaches in the molecular era. Nat Rev Clin Oncol 2014, 11:12-23.

8. De Jong D, Rosenwald A, Chhanabhai M, Gaulard P, Klapper W, Lee A, Sander B, Thorns C, Campo E, Molina T, Norton A, Hagenbeek A, Horning S, Lister A, Raemaekers J, Gascoyne R D, Salles G, Weller E, Lunenburg Lymphoma Biomarker Consortium: Immunohistochemical prognostic markers in diffuse large B-cell lymphoma: validation of tissue microarray as a prerequisite for broad clinical applications—a study from the Lunenburg Lymphoma Biomarker Consortium. J Clin Oncol 2007, 25:805-812.

9. Salles G, de Jong D, Xie W, Rosenwald A, Chhanabhai M, Gaulard P, Klapper W, Calaminici M, Sander B, Thorns C, Campo E, Molina T, Lee A, Pfreundschuh M, Horning S, Lister A, Sehn L H, Raemaekers J, Hagenbeek A, Gascoyne R D, Weller E: Prognostic significance of immunohistochemical biomarkers in diffuse large B-cell lymphoma: a study from the Lunenburg Lymphoma Biomarker Consortium. Blood 2011, 117:7070-7078.

10. Gutiérrez-Garcia G, Cardesa-Salzmann T, Climent F, González-Barca E, Mercadal S, Mate J L, Sancho J M, Arenillas L, Serrano S, Escoda L, Martinez S, Valera A, Martinez A, Jares P, Pinyol M, Garcia-Herrera A, Martinez-Trillos A, Gine E, Villamor N, Campo E, Colomo L, Lopez-Guillermo A: Gene-expression profiling and not immunophenotypic algorithms predicts prognosis in patients with diffuse large B-cell lymphoma treated with immunochemotherapy. Blood 2011, 117:4836-4843.

11. Lossos I S, Czerwinski D K, Alizadeh A A, Wechser M A, Tibshirani R, Botstein D, Levy R: Prediction of survival in diffuse large-B-cell lymphoma based on the expression of six genes. N Engl J Med 2004, 350:1828-1837.

12. Alizadeh A A, Gentles A J, Alencar A J, Liu C L, Kohrt H E, Houot R, Goldstein M J, Zhao S, Natkunam Y, Advani R H, Gascoyne R D, Briones J, Tibshirani R J, Myklebust J H, Plevritis S K, Lossos I S, Levy R: Prediction of survival in diffuse large B-cell lymphoma based on the expression of 2 genes reflecting tumor and microenvironment. Blood 2011, 118:1350-1358.

13. Rimsza L M, Wright G, Schwartz M, Chan W C, Jaffe E S, Gascoyne R D, Campo E, Rosenwald A, Ott G, Cook J R, Tubbs R R, Braziel R M, Delabie J, Miller T P, Staudt L M: Accurate classification of diffuse large B-cell lymphoma into germinal center and activated B-cell subtypes using a nuclease protection assay on formalin-fixed, paraffin-embedded tissues. Clin Cancer Res 2011, 17:3727-3732.

14. Barrans S L, Crouch S, Care M A, Worrillow L, Smith A, Patmore R, Westhead D R, Tooze R, Roman E, Jack A S: Whole genome expression profiling based on paraffin embedded tissue can be used to classify diffuse large B-cell lymphoma and predict clinical outcome. Br J Haematol 2012, 159:441-453.

15. Masqué-Soler N, Szczepanowski M, Kohler C W, Spang R, Klapper W:
Molecular classification of mature aggressive B-cell lymphoma using digital multiplexed gene expression on formalin-fixed paraffin-embedded biopsy specimens. Blood 2013, 122:1985-1986.

16. Scott D W, Wright G W, Williams P M, Lih C-J, Walsh W, Jaffe E S, Rosenwald A, Campo E, Chan W C, Connors J M, Smeland E B, Mottok A, Braziel R M, Ott G, Delabie J, Tubbs R R, Cook J R, Weisenburger D D, Greiner T C, Glinsmann-Gibson B J, Fu K, Staudt L M, Gascoyne R D, Rimsza L M: Determining cell-of-origin subtypes of diffuse large B-cell lymphoma using gene expression in formalin-fixed paraffin-embedded tissue. Blood 2014, 123:1214-1217.

17. Eldering E, Spek C A, Aberson H L, Grummels A, Derks I A, de Vos A F, McElgunn C J, Schouten J P: Expression profiling via novel multiplex assay allows rapid assessment of gene regulation in defined signalling pathways. Nucleic Acids Res 2003, 31:e153.

18. Bohers E, Mareschal S, Bouzelfen A, Marchand V, Ruminy P, Maingonnat C, Ménard A-L, Etancelin P, Bertrand P, Dubois S, Alcantara M, Bastard C, Tilly H, Jardin F:
Targetable activating mutations are very frequent in GCB and ABC diffuse large B-cell lymphoma. Genes Chromosomes Cancer 2014, 53:144-153.

19. Jardin F, Mareschal S, Figeac M, Jais J-P, Leroy K, Copie-Bergman C, Salles G A, Coiffier B, Delarue R, Peyrade F, Bosly A, Ketterer N, Haioun C, Tilly H, Molina T J: Integrated Analysis of High-Resolution Gene Expression and Copy Number Profiling Identified Biallelic Deletion of CDKN2A/2B Tumor Suppressor Locus As the Most Frequent and Unique Genomic Abnormality in Diffuse Large B-Cell Lymphoma (DLBCL) with Strong Prognostic Value in Both GCB and ABC Subtypes and Not Overcome by a Dose-Intensive Immunochemotherapy Regimen Plus Rituximab. Results of a Prospective GELA Clinical Trial Program. ASH Annual Meeting Abstracts 2012, 120:415.

20. Hans C P, Weisenburger D D, Greiner T C, Gascoyne R D, Delabie J, Ott G, Müller-Hermelink H K, Campo E, Braziel R M, Jaffe E S, Pan Z, Farinha P, Smith L M, Falini B, Banham A H, Rosenwald A, Staudt L M, Connors J M, Armitage J O, Chan W C: Confirmation of the molecular classification of diffuse large B-cell lymphoma by immunohistochemistry using a tissue microarray. Blood 2004, 103: 275-282.

21. Benjamini Y, Hochberg Y: Controlling the False Discovery Rate: A Practical and Powerful Approach to Multiple Testing. Journal of the Royal Statistical Society Series B (Methodological) 1995, 57:289-300.

22. Johnson N A, Slack G W, Savage K J, Connors J M, Ben-Neriah S, Rogic S, Scott D W, Tan K L, Steidl C, Sehn L H, Chan W C, Iqbal J, Meyer P N, Lenz G, Wright G, Rimsza L M, Valentino C, Brunhoeber P, Grogan T M, Braziel R M, Cook J R, Tubbs R R, Weisenburger D D, Campo E, Rosenwald A, Ott G, Delabie J, Holcroft C, Jaffe E S, Staudt L M, Gascoyne R D: Concurrent expression of MYC and BCL2 in diffuse large B-cell lymphoma treated with rituximab plus cyclophosphamide, doxorubicin, vincristine, and prednisone. J Clin Oncol 2012, 30:3452-3459.

23. Lenz G, Wright G, Dave S S, Xiao W, Powell J, Zhao H, Xu W, Tan B, Goldschmidt N, Iqbal J, Vose J, Bast M, Fu K, Weisenburger D D, Greiner T C, Armitage J O, Kyle A, May L, Gascoyne R D, Connors J M, Troen G, Holte H, Kvaloy S, Dierickx D, Verhoef G, Delabie J, Smeland E B, Jares P, Martinez A, Lopez-Guillermo A, Montserrat E, Campo E, Braziel R M, Miller T P, Rimsza L M, Cook J R, Pohlman B, Sweetenham J, Tubbs R R, Fisher R I, Hartmann E, Rosenwald A, Ott G, Muller-Hermelink H-K, Wrench D, Lister T A, Jaffe E S, Wilson W H, Chan W C, Staudt L M, Lymphoma/Leukemia Molecular Profiling Project: Stromal gene signatures in large-B-cell lymphomas. N Engl J Med 2008, 359:2313-2323.

24. Wright G, Tan B, Rosenwald A, Hurt E H, Wiestner A, Staudt L M: A gene expression-based method to diagnose clinically distinct subgroups of diffuse large B cell lymphoma. Proc Natl Acad Sci USA 2003, 100:9991-9996.

25. Lenz G, Wright G, Dave S S, Xiao W, Powell J, Zhao H, Xu W, Tan B, Goldschmidt N, Iqbal J, Vose J, Bast M, Fu K, Weisenburger D D, Greiner T C, Armitage J O, Kyle A, May L, Gascoyne R D, Connors J M, Troen G, Holte H, Kvaloy S, Dierickx D, Verhoef G, Delabie J, Smeland E B, Jares P, Martinez A, Lopez-Guillermo A, Montserrat E, Campo E, Braziel R M, Miller T P, Rimsza L M, Cook J R, Pohlman B, Sweetenham J, Tubbs R R, Fisher R I, Hartmann E, Rosenwald A, Ott G, Muller-Hermelink H-K, Wrench D, Lister T A, Jaffe E S, Wilson W H, Chan W C, Staudt L M: Stromal gene signatures in large-B-cell lymphomas. N Engl J Med 2008, 359:2313-2323.

26. Patrinos G P: Molecular diagnostics. Amsterdam, Academic Press, 2010.

The invention claimed is:

1. A method for classifying a diffuse large B-cell lymphoma (DLBCL) of a subject into a germinal center B cell-like (GCB)-DLBCL or into a activated B-Cell like (ABC)-DLBCL comprising:
determining an expression level of at least 10 genes in a tumor tissue sample obtained from the subject by performing a Reverse Transcriptase Multiplex Ligation dependent Probe Amplification (RT-MLPA) assay wherein the at least 10 genes are selected from the group consisting of NEK6, IRF4, IGHM, LMO2, FOXP1, TNFRSF9, BCL6, TNFRSF13B, CCND2 and MYBL1, said RT-LMPA assay including the steps of
i) preparing a cDNA sample from the tumor tissue sample,
ii) incubating the cDNA sample of step i) with a mixture of at least 10 different pairs of probes, wherein each pair of probes is specific for a target nucleic acid sequence of a gene selected from the group consisting of NEK6, IRF4, IGHM, LMO2, FOXP1, TNFRSF9, BCL6, TNFRSF13B, CCND2, MYBL1, and wherein each pair of probes includes a first probe and a second probe,
wherein the first probe comprises
a target specific region (L) complementary to a first segment of the target nucleic acid sequence, and
a tail region (TL) at the 5' extremity of the target specific region (L) which is non-complementary to said target nucleic acid sequence,
wherein the second probe comprises
a target specific region (R) complementary to a second segment of the target nucleic acid sequence; and
a tail region (TR) at the 3' extremity of the target specific region (R) which is non-complementary to said target nucleic acid sequence,
wherein one or more of the pair of probes specific for a target nucleic acid sequence is selected from the group consisting of:

a) a pair of probes specific for NEK6 comprising a first probe which is SEQ ID NO:54 (GTGCCAGCAAGATCCAATCTAGACCTGTGCATCCTCCTGACCCACAG) and a second probe which is SEQ ID NO:55 (AGGCATCCAACACGCTGTCTTTTCCAACCCTTAGGGAACCC);
b) a pair of probes specific for IRF4comprising a first probe which is SEQ ID NO:56 (GTGCCAGCAAGATCCAATCTAGATCTGCCGAAGCCTTGGCGTTCTCAG) and a second probe which is SEQ ID NO:57 (ACTGCCGGCTGCACATCTGCCTGTATCCAACCCTTAGGGAACCC);
c) a pair of probes specific for IGHM comprising a first probe which is SEQ ID NO:58 (GTGCCAGCAAGATCCAATCTAGATGCGTCCTCCATGTGTGGCCCCG) and a second probe which is SEQ ID NO:59 (ATCAAGACACAGCCATCCGGGTCTTCTACTATCCAACCCTTAGGGAACC);
d) a pair of probes specific for LMO2comprising a first probe which is SEQ ID NO:62 (GTGCCAGCAAGATCCAATCTAGACGGAAGCTCTGCCGGAGAGACTATCTCAG) and a second probe which is SEQ ID NO:63 (GCTTTTTGGGCAAGACGGTCTCTGCTACTATCCAACCCTTAGGGAACCC);
e) a pair of probes specific for FOXP1comprising a first probe which is SEQ ID No:64 (GTGCCAGCAAGATCCAATCTAGACCCTTCCCCTTCAACCTCTTGCTCAAG) and a second probe which is SEQ ID NO:65 (GCATGATTCCAACAGAACTGCAGCAGCTACTACTACTCCAACCCTTAGGGAACCC);
f) a pair of probes specific for TNFRSF9 comprising a first probe which is SEQ ID NO:66 (GTGCCAGCAAGATCCAATCTAGATACGGACCTGTGACATATGCAGGCAGTGTAAAG) and a second probe which is SEQ ID NO:67

(GTGTTTTCAGGACCAGGAAGGAGTGTTC-CTACTCCAACCCTTAGGGAACCC);
g) a pair of probes specific for BCL6 comprising a first probe which is SEQ ID NO:68 (GTGCCA-GCAAGATCCAATCTAGATACTACT-CATAAAACGGTCCTCATGGCCTGCAG) and a second probe which is SEQ ID NO:69 (TGGC-TGTTCTATAGCATCTTTACAGACCAGTT-GTCCAACCCTTAGGGAACCC)
h) a pair of probes specific for TNFRSF13B comprising a first probe which is SEQ ID NO:70 (GTGCCAGCAAGATCCAATCTAGATACTAC-TACTAGCGCACCTGTGCAGCCTTCTGCA) and a second probe which is SEQ ID NO:71 (GGTCACTCAGCTGCCGCAAGGAGCTAC-TACTACTACTCCAACCCTTAGGGAACCC);
i) a pair of probes specific for CCND2 comprising a first probe which is SEQ ID NO:72 (GTGCCA-GCAAGATCCAATCTAGATACTACTGACCT-TCATTGCTCTGTGTGCCACCG) and a second probe which is SEQ ID NO:73 (ACTTTAAGTTT-GCCATGTACCCACCGTCGATACTACTATC-CAACCCTTAGGGAACCC); and
j) a pair of probes specific for MYBL1 comprising a first probe which is SEQ ID NO:76 (GTGCCA-GCAAGATCCAATCTAGACCAGAATTTGCA-GAGACTCTAGAACTTATTGAATCT) and a second probe which is SEQ ID NO:77 (GATC-CTGTAGCATGGAGTGACGTTACCAGTTTT-TACTACTTCCAACCCTTAGGGAACCC);
iii) ligating the first probe to the second probe of each pair of probes,
iv) amplifying ligated probes produced at step iii), and
v) detecting and quantifying amplicons produced at step iv),
based on the expression level determined in the determining step, calculating, for the DLBCL, a probability of belonging to an ABC class and a probability of belonging to a GCB class;
classifying the DLBCL as an ABC when the probability of belonging to the ABC class is higher than a predetermined ABC confidence threshold, or
classifying the DLBCL as a GCB when the probability of belonging to a GCB-DLBCL class is higher than a predetermined GCB-DLBCL confidence threshold.

2. A method for classifying a diffuse large B-cell lymphoma (DLBCL) of a subject into a germinal center B cell-like (GCB)-DLBCL or into a activated B-Cell like (ABC)-DLBCL comprising:
determining an expression level of at least 10 genes in a tumor tissue sample obtained from the subject by performing a Reverse Transcriptase Multiplex Ligation dependent Probe Amplification (RT-MLPA) assay wherein the at least 10 genes are selected from the group consisting of NEK6, IRF4, IGHM, LMO2, FOXP1, TNFRSF9, BCL6, TNFRSF13B, CCND2and MYBL1, said RT-LMPA assay including the steps of
i) preparing a cDNA sample from the tumor tissue sample,
ii) incubating the cDNA sample of step i) with a mixture of at least 10different pairs of probes, wherein each pair of probes is specific for a target nucleic acid sequence of a gene selected from the group consisting of NEK6, IRF4, IGHM, LMO2, FOXP1, TNFRSF9, BCL6, TNFRSF13B, CCND2, MYBL1, and wherein each pair of probes includes a first probe and a second probe, wherein the cDNA sample is also incubated with a competitor probe specific for NEK6 which is SEQ ID NO:82 (AG-GCATCCCAACACGCTGTCTTT)),
iii) ligating the first probe to the second probe of each pair of probes,
iv) amplifying ligated probes produced at step iii), and
v) detecting and quantifying amplicons produced at step iv),
based on the expression level determined in the determining step, calculating, for the DLBCL, a probability of belonging to an ABC class and a probability of belonging to a GCB class;
classifying the DLBCL as an ABC when the probability of belonging to the ABC class is higher than a predetermined ABC confidence threshold, or
classifying the DLBCL as a GCB when the probability of belonging to a GCB-DLBCL class is higher than a predetermined GCB-DLBCL confidence threshold.

3. A method for classifying a diffuse large B-cell lymphoma (DLBCL) of a subject into a germinal center B cell-like (GCB)-DLBCL or into a activated B-Cell like (ABC)-DLBCL comprising:
determining an expression level of at least 10 genes in a tumor tissue sample obtained from the subject by performing a Reverse Transcriptase Multiplex Ligation dependent Probe Amplification (RT-MLPA) assay wherein the at least 10 genes are selected from the group consisting of NEK6, IRF4, IGHM, LMO2, FOXP1, TNFRSF9, BCL6, TNFRSF13B, CCND2and MYBL1, said RT-LMPA assay including the steps of
i) preparing a cDNA sample from the tumor tissue sample,
ii) incubating the cDNA sample of step i) with a mixture of at least 10 different pairs of probes, wherein each pair of probes is specific for a target nucleic acid sequence of a gene selected from the group consisting of NEK6, IRF4, IGHM, LMO2, FOXP1, TNFRSF9, BCL6, TNFRSF13B, CCND2, MYBL1, and wherein each pair of probes includes a first probe and a second probe, wherein the cDNA sample is also incubated with a competitor probe specific for IGHM which is SEQ ID NO:83 (AT-CAAGACACAGCCATCCGGGTCTTC)),
iii) ligating the first probe to the second probe of each pair of probes,
iv) amplifying ligated probes produced at step iii), and
v) detecting and quantifying amplicons produced at step iv),
based on the expression level determined in the determining step, calculating, for the DLBCL, a probability of belonging to an ABC class and a probability of belonging to a GCB class;
classifying the DLBCL as an ABC when the probability of belonging to the ABC class is higher than a predetermined ABC confidence threshold, or
classifying the DLBCL as a GCB when the probability of belonging to a GCB-DLBCL class is higher than a predetermined GCB-DLBCL confidence threshold.

4. A method of treating diffuse large B-cell lymphoma (DLBCL) in a subject in need thereof, comprising
i) classifying a diffuse large B-cell lymphoma (DLBCL) of a subject into a germinal center B cell-like (GCB)-DLBCL or into an activated B-cell like (ABC)-DLBCL by
a) determining an expression level of at least 10 genes in a tumor tissue sample obtained from the subject by performing a Reverse Transcriptase Multiplex Ligation dependent Probe Amplification (RT-MLPA) assay wherein the at least 10 genes are selected from the group consisting of NEK6, IRF4, IGHM, LMO2, FOXP1, TNFRSF9, BCL6, TNFRSF13B, CCND2, and MYBL1,
- b) based on the expression level determined in determining step a), calculating, for the DLBCL, a probability of belonging to an ABC class and a probability of belonging to a GCB class;
- c) classifying the DLBCL as an ABC when the probability of belonging to the ABC class is higher than a predetermined ABC confidence threshold, or
- d) classifying the DLBCL as a GCB when the probability of belonging to a GCB-DLBCL class is higher than a predetermined GCB-DLBCL confidence threshold; and ii) treating the subject for ABC-DLBCL when the DLBCL is classified as an ABC, or treating the subject for GCB-DLBCL when the DLBCL is classified as an GCB.

5. A method of determining an expression level of at least 10 genes in a tumor tissue sample obtained from a subject having diffuse large B-cell lymphoma (DLBCL), comprising the step of performing a Reverse Transcriptase Multiplex Ligation dependent Probe Amplification (RT-MLPA) assay to amplify at least 10 genes are selected from the group consisting of NEK6, IRF4, IGHM, LMO2, FOXP1, TNFRSF9, BCL6, TNFRSF13B, CCND2 and MYBL1.

6. The method of claim 5, wherein the method further includes amplification of at least one additional gene selected from the group consisting of CCND1, MS4A1, MYC, and BCL2.

7. An analysis method, comprising the steps of:
- obtaining a tumor tissue sample from a subject having a tumor; and
- performing a reverse transcriptase multiplex ligation dependent probe
- amplification (RT-MLPA) on the tumor tissue sample to determine an expression level of NEK6, IRF4, IGHM, LMO2. FOXP1, TNFRSF9, BCL6, TNFRSF13B, CCND2 and MYBL1.

* * * * *